(12) United States Patent
Ghosh et al.

(10) Patent No.: US 10,544,208 B2
(45) Date of Patent: Jan. 28, 2020

(54) **EXPRESSION OF A SINGLE CHAIN ANTIBODY AGAINST *SALMONELLA* IN *LACTOBACILLUS***

(71) Applicant: Sambuddha Ghosh, Pune (IN)

(72) Inventors: Sambuddha Ghosh, Pune (IN);
Sanjiban Kumar Banerjee, Pune (IN);
Manisha Pravin Sabnis, Pune (IN)

(73) Assignee: SAMBUDDHA GHOSH, Pune (IN)

( * ) Notice: Subject to any disclaimer, the term of this patent is extended or adjusted under 35 U.S.C. 154(b) by 47 days.

(21) Appl. No.: 15/129,661

(22) PCT Filed: Mar. 27, 2015

(86) PCT No.: PCT/IB2015/000407
§ 371 (c)(1),
(2) Date: Sep. 27, 2016

(87) PCT Pub. No.: WO2015/145250
PCT Pub. Date: Oct. 1, 2015

(65) Prior Publication Data
US 2017/0152305 A1 Jun. 1, 2017

(30) Foreign Application Priority Data
Mar. 27, 2014 (IN) .......................... 1100/MUM/2014

(51) Int. Cl.
| | |
|---|---|
| *C07K 16/12* | (2006.01) |
| *C07K 14/335* | (2006.01) |
| *A23K 20/10* | (2016.01) |
| *A23L 33/17* | (2016.01) |
| *A23L 3/00* | (2006.01) |
| *C12R 1/225* | (2006.01) |

(52) U.S. Cl.
CPC .......... *C07K 16/1235* (2013.01); *A23K 20/10* (2016.05); *A23L 3/00* (2013.01); *A23L 33/17* (2016.08); *C07K 14/335* (2013.01); *C12R 1/225* (2013.01); *A23V 2002/00* (2013.01); *C07K 2317/14* (2013.01); *C07K 2317/22* (2013.01); *C07K 2317/565* (2013.01); *C07K 2317/569* (2013.01); *C07K 2317/622* (2013.01); *C07K 2319/00* (2013.01)

(58) Field of Classification Search
None
See application file for complete search history.

(56) References Cited

FOREIGN PATENT DOCUMENTS

WO    WO 2015/145250 A2    10/2015

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS, vol. 109 No. 31, pp. 12272-12273).*
International Search Report and Written Opinion received in PCT Application No. PCT/IB2015/00047 dated Nov. 26, 2015.
El Khattabi et al., "Llama Single-Chain Antibody That Blocks Lipopolysaccharide Binding and Singaling: Prospects for Therapeutic Applications," *Clin Vaccine Immunol*, 13(10):1079-1086 (2006).
Helmuth, et al., "Epidemiology of Virulence-Associated Plasmids and Outer Membrane Protein Patterns Within Seven Common *Salmonella* Serotypes," *Infect Immun*, 48(1):175-182 (1985).
Michael et al., "Immune Response to Parental and Rough Mutant Strains of *Salmonella minnesota*," *Infect Immun*, 33:784-787 (1981).
Isibasi, et al., "Protection against *Salmonella typhi* Infection in Mice after Immunization with Outer Membrane Proteins Isolated from *Salmonella typhi*, 9,12,d,Vi," *Infect Immunit*, 56(II): 2953-2959 (1988).
Liu, et al., "Immunogenicity and Cross-Protective Efficacy Induced by Outer Membrane Proteins from *Salmonella typhimurium* Mutants with Truncated LPS in Mice," *Int. J. of Mol. Sci.*, 17:416, 16 pgs. (2016).
Cho et al., "Proteomic Analysis of Outer Membrane Proteins in *Salmonella enterica Enteritidis*," *J. Microbiol. Biotechnol.*, 25(2):288-295 (2015).
Chalghoumi et al., "Production of Hen Egg Yolk Immunoglobulins Simultaneously Directed Against *Salmonella* enteritidis and *Salmonella typhimurium* in the Same Egg Yolk," *Poultry Science*, 87:32-40 (2008).
Biswas et al., "Cross-reactivity of anti-*Salmonella* egg-yolk antibodies to *Salmonella* serovars," *J. of Environ. Sci. and Health Part B*, 45:790-795 (2010).

* cited by examiner

*Primary Examiner* — Robert A Zeman
(74) *Attorney, Agent, or Firm* — Brinks Gilson & Lione

(57) ABSTRACT

The present disclosure relates to camel id antibodies that inhibit growth, and colonization of *Salmonella* serovars. The present disclosure also relates to a modified *Lactobacillus* as a delivery vehicle for controlling *Salmonella* in a host organism.

5 Claims, 4 Drawing Sheets

Specification includes a Sequence Listing.

EXPRESSION OF A SINGLE CHAIN ANTIBODY AGAINST *SALMONELLA* IN *LACTOBACILLUS*

The present patent document is a § 371 filing based on the International Application Serial No. PCT/IB2015/000407, filed Mar. 27, 2015, which claims the benefit of priority to Indian Patent Application No. 1100/MUM/2014, filed on Mar. 27, 2014, which are hereby incorporated by reference in their entirety.

FIELD OF INVENTION

The current disclosure relates to the field of microbiology and genetic engineering. The current disclosure provides recombinant chimeric proteins and antibodies directed against *Salmonella*.

BACKGROUND OF THE INVENTION

Fermented food products have been developed and used by mankind with the aid of lactic acid bacteria (LAB), which have been classified as probiotics and are categorized as generally recognized as safe (GRAS) by the United states Food & Drug Administration (USFDA). In addition to be considered as the powerhouses for the food industry, LAB continue to be the focus of considerable interest as probiotic organisms, since they have also been conferred with specific health promoting functions which they execute by modulating the gut environment of the host.

Their ability to adhere to certain areas of the gastrointestinal tract has created interests to tap the potential of such microbes as vehicles for the delivery of biologically active compounds & vaccines (Pouwels et al., *Int J Food Microbiol.*, 1998, 41, 155-157).

Most infectious organisms gain entry at the mucosal surfaces, there is a great deal of interest in developing vaccines that elicit effective mucosal immune responses against various pathogens. LAB, which are safe and non-pathogenic, are excellent mucosal delivery vehicles for heterologous antigens and therapeutic proteins. Many LABs produce extracellular polysaccharides and these have been extensively studied in terms of their biosynthesis, structure & function and engineering, including the importance of these molecules in host microbe interactions (Leeber et al., *Microbial Biotechnology*, 2011, 4(3), 368-374).

Camelids produce functional antibodies devoid of light chains of which the single N-terminal domain is fully capable of antigen binding and could be delivered on mucosal surfaces by the lactic acid bacteria for various therapeutic interventions. The unique physicochemical and pharmacological properties of these camelid heavy chain antibody (VHH) fragments have led to its prospective use as new generation therapeutic agents. The remarkable preference of VHH fragments to bind clefts and cavities on protein surfaces offers the possibility to develop selective therapeutics (Paalanen et al., *Eur J Pharm Sci.*, 2011, 42(4), 332-9) by activity modulation of cell surface proteins, such as receptors, ion channels involved in various biological activities (Wei et al., *PLoS ONE*, 2011, 6(12). Moreover, VHH fragment molecules recognize cryptic epitopes hidden deeply in clefts of various pathogens (Forsman et al., *J. Virol.*, 2008, 82(24), 12069-12081) and have high structural stability and solubility (Muyldermans et al., *Biochem Sci.*, 2001, 26, 230-235; Philipp et al., *Nat. Biotechnol.*, 2005, 23(9), 1126-1136).

Salmonellosis is the most common food borne disease and gastrointestinal infection across the world. *Salmonella* is the second major cause of food borne diseases in U.S., Europe & in the world causing as many as 1.3 billion cases of diseases annually. In addition to the health consequences, *Salmonella* species with about 2600 existing serovars are being identified belonging to six subspecies (Coburn et al., *Immunology and Cell Biology*, 2007, 85, 112-118; Ochman et al., *EXS*, 1994, 69, 479-493). Sub species are further sub divided into serovars that are differentiated by their flagellar, carbohydrate and lipopolysaccharide (LPS) structures. *S. enteric* species are typically orally acquired pathogens that cause one of the four major syndromes, Enteric fever (typhoid) enterocolitis/diarrhea, bacteremia and chronic asymptomatic carriage. The disease manifestation depends on both host susceptibility and the infectious. *S. enteric* serovar (Fierer et al., *J Clin Invest.*, 2001, 107, 775-780). Prominent inflammatory disease outcomes are a common feature of typhoid & enterocolitis. The various patho-biological outcomes of infection are mainly due to the interaction of the *Salmonella* species with host defence mechanisms at various tissues in different stages of infection. This results in significant host immunopathology, morbidity and mortality.

*Salmonella* is a significant pathogen for food producing animals and these animals are the primary source of salmonellosis. It is one of the most commonly isolated food borne pathogens associated with poultry, raw meats, eggs, milk and dairy products, fresh farm produce like fruits & vegetables etc. In recent years, the incidence of food borne outbreaks caused by the contamination of fresh fruits and vegetables has increased and become a great concern in industrialized countries.

The major types of vaccines used to control salmonellosis are the killed bacteria vaccine, subunit vaccines and live attenuated vaccines. Comparative analysis of live and killed vaccines revealed that killed vaccines are usually less effective as they comprise of surface antigens that give rise to inadequate protective immune response, they fail to elicit secretory immune response at the mucosal surfaces which is critical in inhibiting the colonization of the pathogens at the mucosal surface. Attempts to overcome all these shortcomings by the use of various adjuvants has led to only partial success (Smith, *J Hyg.*, 1956, 54, 419-432; Singh et al., *Haryana Vet.*, 2005, 44, 1-12; Baljer et al., *J Med Vet.*, 1986, 33, 206-212).

The utility of live vaccines in eradication of salmonellosis is limited, as there are multiple serovars of *Salmonella* and vaccines made from any one serovar do not confer cross protection against another serovar. The organisms are capable to adapt in different animal species whilst still maintaining their zoonotic and interspecies transfer potential. Moreover, effective vaccines against some host adapted and common serovars in the primary source of host have been developed but their use has led to the emergence of other serovars. This has been further compounded by the international trade and movement of animal and farm products which has led various serovars to cross continental boundaries. Thus, there is a need in the art to develop anti-*Salmonella* biological and it is desirable to develop and provide an alternative means for the control and management of enteropathogenic *Salmonella*, by therapy and/or prophylaxis.

EP1066375B1 relates to use of transformed *Lactobacillus* species as vaccine delivery vehicles.

US2008/0206233 A1 relates to heavy chain immunoglobulins or fragments thereof of the VHH or VNAR type or domain antibodies (dAbs) suitable for use in the management of infections, particularly of the gastrointestinal tract.

US2009/0226418 A1 relates to food products or pharmaceutical preparations comprising antibodies or antibody fragments which are active in the gut and probiotic microorganisms independent from their antibodies or antibody fragments.

SUMMARY OF THE INVENTION

An aspect of the present disclosure relates to a single chain antibody or a fragment thereof against *Salmonella* surface proteins, comprising of 3 complementarity determining regions.

An aspect of the present disclosure relates to a recombinant host cell expressing on the surface one or more chimeric proteins, wherein the chimeric protein comprises of (a) at least one single chain antibody or a fragment thereof against *Salmonella* surface proteins, comprising of 3 complementarity determining regions, and (b) at least one protein that is expressed on the surface of the recombinant host cell, wherein the surface protein expressed in the recombinant host cell is MuB or CnBP.

An aspect of the present disclosure relates to a recombinant DNA construct comprising a polynucleotide sequence encoding a single chain antibody or a fragment thereof against *Salmonella* surface proteins, comprising of three complementarity determining regions.

An aspect of the present disclosure relates to a recombinant DNA vector comprising a recombinant DNA construct comprising a polynucleotide sequence encoding a single chain antibody or a fragment thereof against *Salmonella* surface proteins, comprising of three complementarity determining regions.

An aspect of the present disclosure relates to a recombinant host cell comprising a recombinant DNA construct comprising a polynucleotide sequence encoding a single chain antibody or a fragment thereof against *Salmonella* surface proteins, comprising of three complementarity determining regions.

An aspect of the present disclosure relates to a recombinant host cell comprising a recombinant DNA vector comprising a recombinant DNA construct comprising a polynucleotide sequence encoding a single chain antibody or a fragment thereof against *Salmonella* surface proteins, comprising of three complementarity determining regions.

An aspect of the present disclosure relates to a chimeric protein comprising amino acid sequence selected from the group consisting of SEQ ID NO:93, 95, 97, 99, 101, 130, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, and 243.

An aspect of the present disclosure relates to a food product comprising a recombinant host cell comprising of a single chain antibody or a fragment thereof against *Salmonella* surface proteins, comprising of 3 complementarity determining regions.

An aspect of the present disclosure relates to a food product comprising a recombinant host cell comprising a recombinant DNA vector comprising a recombinant DNA construct comprising a polynucleotide sequence encoding a single chain antibody or a fragment thereof against *Salmonella* surface proteins, comprising of three complementarity determining regions.

An aspect of the present disclosure relates to a food product comprising a recombinant host cell comprising a recombinant DNA construct comprising a polynucleotide sequence encoding a single chain antibody or a fragment thereof against *Salmonella* surface proteins, comprising of three complementarity determining regions.

An aspect of the following disclosure relates to a formulation comprising a single chain antibody or a fragment thereof against *Salmonella* surface proteins, comprising of 3 complementarity determining regions, additionally consisting of a diluent, excipient or a carrier.

An aspect of the present disclosure relates to a method of inhibiting the growth of *Salmonella*, said method comprising contacting a food product comprising a single chain antibody or a fragment thereof with a sample containing *Salmonella*.

An aspect of the present disclosure relates to a method of inhibiting activity of *Salmonella*, said method comprising contacting a food product comprising a single chain antibody or a fragment thereof with sample containing *Salmonella*.

An aspect of the present disclosure relates to an isolated *Lactobacillus* strain, *Lactobacillus reuteri* 1LB7 deposited with Microbial Type Culture Collection and Gene Bank (MTCC) having accession number 5894 for management of enteric *Salmonella* population in animal husbandry.

This summary is not intended to identify essential features of the claimed subject matter nor is it intended for use in determining or limiting the scope of the claimed subject matter.

BRIEF DESCRIPTION OF ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

DETAILED DESCRIPTION OF THE INVENTION

Figure 1:
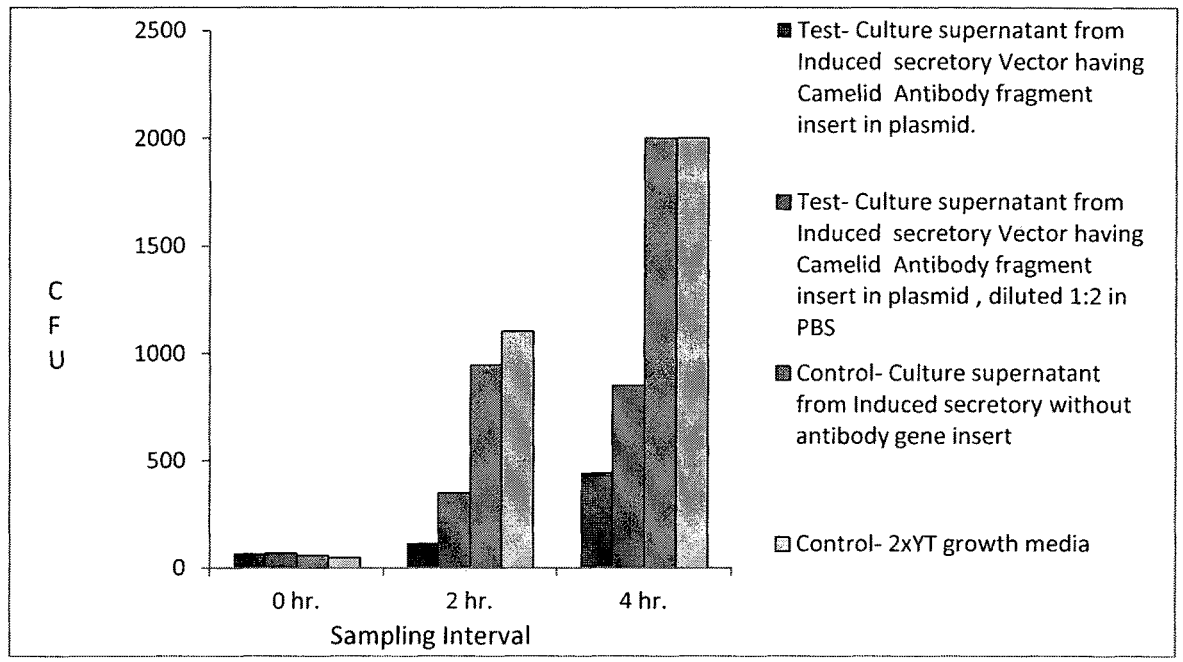
FIG. 1 depicts the effect of secreted anti-*Salmonella* camelid VHH antibody fragments in a milk based formulation on growth of *Salmonella*, in accordance with an embodiment of the present disclosure.

Those skilled in the art will be aware that the invention described herein is subject to variations and modifications other than those specifically described. It is to be understood that the invention described herein includes all such variations and modifications. The invention also includes all such steps, features, compositions and methods referred to or indicated in this specification, individually or collectively, and any and all combinations of any two or more of said steps or features.

Definitions

For convenience, before further description of the present invention, certain terms employed in the specification, examples are collected here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

As used in the specification and the claims, the singular forms "a", "an", and "the" include plural referents unless the context clearly dictates otherwise.

The present disclosure is not to be limited in scope by the specific embodiments described herein, which are intended for the purposes of exemplification only Functionally-equivalent processes and methods are clearly within the scope of the disclosure, as described herein.

Brief Description of Sequences

SEQ ID NO: 1 shows the CDR1 amino acid sequence of antibody A, I, J, K, and L.

SEQ ID NO: 2 shows the CDR2 amino acid sequence of antibody A.

SEQ ID NO: 3 shows the CDR3 amino acid sequence of antibody A, B, I, J, K, and L.

SEQ ID NO: 4 shows the CDR1 amino acid sequence of antibody B.

SEQ ID NO: 5 shows the CDR2 amino acid sequence of antibody B.

SEQ ID NO: 6 shows the CDR1 amino acid sequence of antibody C.

SEQ ID NO: 7 shows the CDR2 amino acid sequence of antibody C, E, F, and G.

SEQ ID NO: 8 shows the CDR3 amino acid sequence of antibody C, E, F, and G.

SEQ ID NO: 9 shows the CDR1 amino acid sequence of antibody D.

SEQ ID NO: 10 shows the CDR2 amino acid sequence of antibody D.

SEQ ID NO: 11 shows the CDR3 amino acid sequence of antibody D.

SEQ ID NO: 12 shows the CDR1 amino acid sequence of antibody E, F, and G.

SEQ ID NO: 13 shows the CDR1 amino acid sequence of antibody H, N, and O.

SEQ ID NO: 14 shows the CDR2 amino acid sequence of antibody H, N, and O.

SEQ ID NO: 15 shows the CDR3 amino acid sequence of antibody H, N, and O.

SEQ ID NO: 16 shows the CDR2 amino acid sequence of antibody I.

SEQ ID NO: 17 shows the CDR2 amino acid sequence of antibody J, and L.

SEQ ID NO: 18 shows the CDR2 amino acid sequence of antibody K.

SEQ ID NO: 19 shows the CDR1 amino acid sequence of antibody M.

SEQ ID NO: 20 shows the CDR2 amino acid sequence of antibody M.

SEQ ID NO: 21 shows the CDR3 amino acid sequence of antibody M.

SEQ ID NO: 22 shows the CDR1 amino acid sequence of antibody P.

SEQ ID NO: 23 shows the CDR2 amino acid sequence of antibody P.

SEQ ID NO: 24 shows the CDR3 amino acid sequence of antibody P.

SEQ ID NO: 25 shows the CDR1 amino acid sequence of antibody Q, R, and S.

SEQ ID NO: 26 shows the CDR2 amino acid sequence of antibody Q, R, and S.

SEQ ID NO: 27 shows the CDR3 amino acid sequence of antibody Q, R, and S.

SEQ ID NO: 28 shows the CDR1 nucleotide sequence of antibody A, I, J, K, and L.

SEQ ID NO: 29 shows the CDR2 nucleotide sequence of antibody A.

SEQ ID NO: 30 shows the CDR3 nucleotide sequence of antibody A, B, I, J, K, and L.

SEQ ID NO: 31 shows the CDR1 nucleotide sequence of antibody B.

SEQ ID NO: 32 shows the CDR2 nucleotide sequence of antibody B.

SEQ ID NO: 33 shows the CDR1 nucleotide sequence of antibody C.

SEQ ID NO: 34 shows the CDR2 nucleotide sequence of antibody C, E, F, and G.

SEQ ID NO: 35 shows the CDR3 nucleotide sequence of antibody C, E, F, and G.

SEQ ID NO: 36 shows the CDR1 nucleotide sequence of antibody D.

SEQ ID NO: 37 shows the CDR2 nucleotide sequence of antibody D.

SEQ ID NO: 38 shows the CDR3 nucleotide sequence of antibody D.

SEQ ID NO: 39 shows the CDR1 nucleotide sequence of antibody E, F, and G.

SEQ ID NO: 40 shows the CDR1 nucleotide sequence of antibody H, N, and O.

SEQ ID NO: 41 shows the CDR2 nucleotide sequence of antibody H, N, and O.

SEQ ID NO: 42 shows the CDR3 nucleotide sequence of antibody H, N, and O.

SEQ ID NO: 43 shows the CDR2 nucleotide sequence of antibody I.

SEQ ID NO: 44 shows the CDR2 nucleotide sequence of antibody J, and L.

SEQ ID NO: 45 shows the CDR2 nucleotide sequence of antibody K.

SEQ ID NO: 46 shows the CDR1 nucleotide sequence of antibody M.

SEQ ID NO: 47 shows the CDR2 nucleotide sequence of antibody M.

SEQ ID NO: 48 shows the CDR3 nucleotide sequence of antibody M.

SEQ ID NO: 49 shows the CDR1 nucleotide sequence of antibody P.

SEQ ID NO: 50 shows the CDR2 nucleotide sequence of antibody P.

SEQ ID NO: 51 shows the CDR3 nucleotide sequence of antibody P.

SEQ ID NO: 52 shows the CDR1 nucleotide sequence of antibody Q, R, and S.

SEQ ID NO: 53 shows the CDR2 nucleotide sequence of antibody Q, R, and S.

SEQ ID NO: 54 shows the CDR3 nucleotide sequence of antibody Q, R, and S.

SEQ ID NO: 55 shows the amino acid sequence of antibody A.

SEQ ID NO: 56 shows the nucleotide sequence of antibody A.

SEQ ID NO: 57 shows the amino acid sequence of antibody B.

SEQ ID NO: 58 shows the nucleotide sequence of antibody B.

SEQ ID NO: 59 shows the amino acid sequence of antibody C.

SEQ ID NO: 60 shows the nucleotide sequence of antibody C.

SEQ ID NO: 61 shows the amino acid sequence of antibody D.

SEQ ID NO: 62 shows the nucleotide sequence of antibody D.

SEQ ID NO: 63 shows the amino acid sequence of antibody E.

SEQ ID NO: 64 shows the nucleotide sequence of antibody E.

SEQ ID NO: 65 shows the amino acid sequence of antibody F.

SEQ ID NO: 66 shows the nucleotide sequence of antibody F.

SEQ ID NO: 67 shows the amino acid sequence of antibody G.

SEQ ID NO: 68 shows the nucleotide sequence of antibody G.

SEQ ID NO: 69 shows the amino acid sequence of antibody H.

SEQ ID NO: 70 shows the nucleotide sequence of antibody H.

SEQ ID NO: 71 shows the amino acid sequence of antibody I.

SEQ ID NO: 72 shows the nucleotide sequence of antibody I.

SEQ ID NO: 73 shows the amino acid sequence of antibody J.

SEQ ID NO: 74 shows the nucleotide sequence of antibody J.

SEQ ID NO: 75 shows the amino acid sequence of antibody K.

SEQ ID NO: 76 shows the nucleotide sequence of antibody K.

SEQ ID NO: 77 shows the amino acid sequence of antibody L.

SEQ ID NO: 78 shows the nucleotide sequence of antibody L.

SEQ ID NO: 79 shows the amino acid sequence of antibody M.

SEQ ID NO: 80 shows the nucleotide sequence of antibody M.

SEQ ID NO: 81 shows the amino acid sequence of antibody N.

SEQ ID NO: 82 shows the nucleotide sequence of antibody N.

SEQ ID NO: 83 shows the amino acid sequence of antibody O.

SEQ ID NO: 84 shows the nucleotide sequence of antibody O.

SEQ ID NO: 85 shows the amino acid sequence of antibody P.

SEQ ID NO: 86 shows the nucleotide sequence of antibody P.

SEQ ID NO: 87 shows the amino acid sequence of antibody Q.

SEQ ID NO: 88 shows the nucleotide sequence of antibody Q.

SEQ ID NO: 89 shows the amino acid sequence of antibody R.

SEQ ID NO: 90 shows the nucleotide sequence of antibody R.

SEQ ID NO: 91 shows the amino acid sequence of antibody S.

SEQ ID NO: 92 shows the nucleotide sequence of antibody S.

SEQ ID NO: 93, 131, and 169 shows the contiguous amino acid sequence within the chimeric protein comprising of antibody A and MuB.

SEQ ID NO: 94, 132, and 170 shows the contiguous nucleotide sequence within the nucleotide sequence encoding the chimeric protein comprising of antibody A and MuB.

SEQ ID NO: 95, 133, and 171 shows the contiguous amino acid sequence within the chimeric protein comprising of antibody B and MuB.

SEQ ID NO: 96, 134, and 172 shows the contiguous nucleotide sequence within the nucleotide sequence encoding the chimeric protein comprising of antibody B and MuB.

SEQ ID NO: 97, 135, and 173 shows the contiguous amino acid sequence within the chimeric protein comprising of antibody C and MuB.

SEQ ID NO: 98, 136, and 174 shows the contiguous nucleotide sequence within the nucleotide sequence encoding the chimeric protein comprising of antibody C and MuB.

SEQ ID NO: 99, 137, and 175 shows the contiguous amino acid sequence within the chimeric protein comprising of antibody D and MuB.

SEQ ID NO: 100, 138, and 176 shows the contiguous nucleotide sequence within the nucleotide sequence encoding the chimeric protein comprising of antibody D and MuB.

SEQ ID NO: 101, 139, and 177 shows the contiguous amino acid sequence within the chimeric protein comprising of antibody E and MuB.

SEQ ID NO: 102, 140 and 178 shows the contiguous nucleotide sequence within the nucleotide sequence encoding the chimeric protein comprising of antibody E and MuB.

SEQ ID NO: 103, 141, and 179 shows the contiguous amino acid sequence within the chimeric protein comprising of antibody F and MuB.

SEQ ID NO: 104, 142, and 180 shows the contiguous nucleotide sequence within the nucleotide sequence encoding the chimeric protein comprising of antibody F and MuB.

SEQ ID NO: 105, 143, and 181 shows the contiguous amino acid sequence within the chimeric protein comprising of antibody G and MuB.

SEQ ID NO: 106, 144, and 182 shows the contiguous nucleotide sequence within the nucleotide sequence encoding the chimeric protein comprising of antibody G and MuB.

SEQ ID NO: 107, 145, and 183 shows the contiguous amino acid sequence within the chimeric protein comprising of antibody H and MuB.

SEQ ID NO: 108, 146, and 184 shows the contiguous nucleotide sequence within the nucleotide sequence encoding the chimeric protein comprising of antibody H and MuB.

SEQ ID NO: 109, 147, and 185 shows the contiguous amino acid sequence within the chimeric protein comprising of antibody I and MuB.

SEQ ID NO: 110, 148, and 186 shows the contiguous nucleotide sequence within the nucleotide sequence encoding the chimeric protein comprising of antibody and MuB.

SEQ ID NO: 111, 149, and 187 shows the contiguous amino acid sequence within the chimeric protein comprising of antibody J and MuB.

SEQ ID NO: 112, 150, and 188 shows the contiguous nucleotide sequence within the nucleotide sequence encoding the chimeric protein comprising of antibody J and MuB.

SEQ ID NO: 113, 151, and 189 shows the contiguous amino acid sequence within the chimeric protein comprising of antibody K and MuB.

SEQ ID NO: 114, 152, and 190 shows the contiguous nucleotide sequence within the nucleotide sequence encoding the chimeric protein comprising of antibody K and MuB.

SEQ ID NO: 115, 153, and 191 shows the contiguous amino acid sequence within the chimeric protein comprising of antibody L and MuB.

SEQ ID NO: 116, 154, and 192 shows the contiguous nucleotide sequence within the nucleotide sequence encoding the chimeric protein comprising of antibody L and MuB.

SEQ ID NO: 117, 155, and 193 shows the contiguous amino acid sequence within the chimeric protein comprising of antibody M and MuB.

SEQ ID NO: 118, 156, and 194 shows the contiguous nucleotide sequence within the nucleotide sequence encoding the chimeric protein comprising of antibody M and MuB.

SEQ ID NO: 119, 157, and 195 shows the contiguous amino acid sequence within the chimeric protein comprising of antibody N and MuB.

SEQ ID NO: 120, 158, and 196 shows the contiguous nucleotide sequence within the nucleotide sequence encoding the chimeric protein comprising of antibody N and MuB.

SEQ ID NO: 121, 159, and 197 shows the contiguous amino acid sequence within the chimeric protein comprising of antibody O and MuB.

SEQ ID NO: 122, 160, and 198 shows the contiguous nucleotide sequence within the nucleotide sequence encoding the chimeric protein comprising of antibody O and MuB.

SEQ ID NO: 123, 161, and 199 shows the contiguous amino acid sequence within the chimeric protein comprising of antibody P and MuB.

SEQ ID NO: 124, 162, and 200 shows the contiguous nucleotide sequence within the nucleotide sequence encoding the chimeric protein comprising of antibody P and MuB.

SEQ ID NO: 125, 163, and 201 shows the contiguous amino acid sequence within the chimeric protein comprising of antibody Q and MuB.

SEQ ID NO: 126, 164, and 202 shows the contiguous nucleotide sequence within the nucleotide sequence encoding the chimeric protein comprising of antibody Q and MuB.

SEQ ID NO: 127, 165, and 203 shows the contiguous amino acid sequence within the chimeric protein comprising of antibody R and MuB.

SEQ ID NO: 128, 166, and 204 shows the contiguous nucleotide sequence within the nucleotide sequence encoding the chimeric protein comprising of antibody R and MuB.

SEQ ID NO: 129, 167, and 205 shows the contiguous amino acid sequence within the chimeric protein comprising of antibody S and MuB.

SEQ ID NO: 130, 168, and 206 shows the contiguous nucleotide sequence within the nucleotide sequence encoding the chimeric protein comprising of antibody S and MuB.

SEQ ID NO: 207 shows the contiguous amino acid sequence within the chimeric protein comprising of antibody A and CnBP.

SEQ ID NO: 208 shows the contiguous nucleotide sequence within the nucleotide sequence encoding the chimeric protein comprising of antibody A and CnBP.

SEQ ID NO: 209 shows the contiguous amino acid sequence within the chimeric protein comprising of antibody B and CnBP.

SEQ ID NO: 210 shows the contiguous nucleotide sequence within the nucleotide sequence encoding the chimeric protein comprising of antibody B and CnBP.

SEQ ID NO: 211 shows the contiguous amino acid sequence within the chimeric protein comprising of antibody C and CnBP.

SEQ ID NO: 212 shows the contiguous nucleotide sequence within the nucleotide sequence encoding the chimeric protein comprising of antibody C and CnBP.

SEQ ID NO: 213 shows the contiguous amino acid sequence within the chimeric protein comprising of antibody D and CnBP.

SEQ ID NO: 214 shows the contiguous nucleotide sequence within the nucleotide sequence encoding the chimeric protein comprising of antibody D and CnBP.

SEQ ID NO: 215 shows the contiguous amino acid sequence within the chimeric protein comprising of antibody E and CnBP.

SEQ ID NO: 216 shows the contiguous nucleotide sequence within the nucleotide sequence encoding the chimeric protein comprising of antibody E and CnBP.

SEQ ID NO: 217 shows the contiguous amino acid sequence within the chimeric protein comprising of antibody F and CnBP.

SEQ ID NO: 218 shows the contiguous nucleotide sequence within the nucleotide sequence encoding the chimeric protein comprising of antibody F and CnBP.

SEQ ID NO: 219 shows the contiguous amino acid sequence within the chimeric protein comprising of antibody G and CnBP.

SEQ ID NO: 220 shows the contiguous nucleotide sequence within the nucleotide sequence encoding the chimeric protein comprising of antibody G and CnBP.

SEQ ID NO: 221 shows the contiguous amino acid sequence within the chimeric protein comprising of antibody H and CnBP.

SEQ ID NO: 222 shows the contiguous nucleotide sequence within the nucleotide sequence encoding the chimeric protein comprising of antibody H and CnBP.

SEQ ID NO: 223 shows the contiguous amino acid sequence within the chimeric protein comprising of antibody I and CnBP.

SEQ ID NO: 224 shows the contiguous nucleotide sequence within the nucleotide sequence encoding the chimeric protein comprising of antibody I and CnBP.

SEQ ID NO: 225 shows the contiguous amino acid sequence within the chimeric protein comprising of antibody J and CnBP.

SEQ ID NO: 226 shows the contiguous nucleotide sequence within the nucleotide sequence encoding the chimeric protein comprising of antibody J and CnBP.

SEQ ID NO: 227 shows the contiguous amino acid sequence within the chimeric protein comprising of antibody K and CnBP.

SEQ ID NO: 228 shows the contiguous nucleotide sequence within the nucleotide sequence encoding the chimeric protein comprising of antibody K and CnBP.

SEQ ID NO: 229 shows the contiguous amino acid sequence within the chimeric protein comprising of antibody L and CnBP.

SEQ ID NO: 230 shows the contiguous nucleotide sequence within the nucleotide sequence encoding the chimeric protein comprising of antibody L and CnBP.

SEQ ID NO: 231 shows the contiguous amino acid sequence within the chimeric protein comprising of antibody M and CnBP.

SEQ ID NO: 232 shows the contiguous nucleotide sequence within the nucleotide sequence encoding the chimeric protein comprising of antibody M and CnBP.

SEQ ID NO: 233 shows the contiguous amino acid sequence within the chimeric protein comprising of antibody N and CnBP.

SEQ ID NO: 234 shows the contiguous nucleotide sequence within the nucleotide sequence encoding the chimeric protein comprising of antibody N and CnBP.

SEQ ID NO: 235 shows the contiguous amino acid sequence within the chimeric protein comprising of antibody O and CnBP.

SEQ ID NO: 236 shows the contiguous nucleotide sequence within the nucleotide sequence encoding the chimeric protein comprising of antibody O and CnBP.

SEQ ID NO: 237 shows the contiguous amino acid sequence within the chimeric protein comprising of antibody P and CnBP.

SEQ ID NO: 237 shows the contiguous nucleotide sequence within the nucleotide sequence encoding the chimeric protein comprising of antibody P and CnBP.

SEQ ID NO: 239 shows the contiguous amino acid sequence within the chimeric protein comprising of antibody Q and CnBP.

SEQ ID NO: 240 shows the contiguous nucleotide sequence within the nucleotide sequence encoding the chimeric protein comprising of antibody Q and CnBP.

SEQ ID NO: 241 shows the contiguous amino acid sequence within the chimeric protein comprising of antibody R and CnBP.

SEQ ID NO: 242 shows the contiguous nucleotide sequence within the nucleotide sequence encoding the chimeric protein comprising of antibody R and CnBP.

SEQ ID NO: 243 shows the contiguous amino acid sequence within the chimeric protein comprising of antibody S and CnBP.

SEQ ID NO: 244 shows the contiguous nucleotide sequence within the nucleotide sequence encoding the chimeric protein comprising of antibody S and CnBP.

SEQ ID NO: 245 shows the forward primer sequence for identification of *Lactobacillus*.

SEQ ID NO: 246 shows the reverse primer sequence for identification of *Lactobacillus*.

SEQ ID NO: 247 shows the forward primer sequence for identification of *Lactobacillus reuteri*.

SEQ ID NO: 248 shows the reverse primer sequence for identification of *Lactobacillus reuteri*.

SEQ ID NO: 249 shows the forward primer sequence for amplification of a 1.7 kb partial MuB gene fragment.

SEQ ID NO: 250 shows the reverse primer sequence for amplification of a 1.7 kb partial MuB gene fragment.

SEQ ID NO: 251 shows the forward primer sequence for amplification of the complete 1.08 kb CnBP gene.

SEQ ID NO: 252 shows the reverse primer sequence for amplification of the complete 1.08 kb CnBP gene.

SEQ ID NO: 253 shows the forward primer sequence for amplification of the 900 bp VHH large insert.

SEQ ID NO: 254 shows the reverse primer sequence for amplification of the 900 bp VHH large insert.

SEQ ID NO: 255 shows the forward primer sequence for the 4.7 kb MuB gene inverse PCR product.

SEQ ID NO: 256 shows the reverse primer sequence for the 4.7 kb MuB gene inverse PCR product.

SEQ ID NO: 257 shows the forward primer sequence for 400 bp VHH insert in to the MuB gene.

SEQ ID NO: 258 shows the reverse primer sequence for 400 bp VHH insert in to the MuB gene.

SEQ ID NO: 259 shows the forward primer sequence for the 1.7 kb *L. reuteri* MuB gene fragment without restriction sites.

SEQ ID NO: 260 shows the reverse primer sequence for the 1.7 kb *L. reuteri* MuB gene fragment without restriction sites.

SEQ ID NO: 261 shows the forward primer sequence for the 4.1 kb CnBP gene inverse PCR product.

SEQ ID NO: 262 shows the reverse primer sequence for the 4.1 kb CnBP gene inverse PCR product.

SEQ ID NO: 263 shows the forward primer sequence for the 400 bp VHH insert in to the CnBP gene.

SEQ ID NO: 264 shows the reverse primer sequence for the 400 bp VHH insert in to the CnBP gene.

SEQ ID NO: 265 shows the phosphoryalted forward primer sequence for the 1.4 kb CnBP gene.

SEQ ID NO: 266 shows the phosphoryalted reverse primer sequence for the 1.4 kb CnBP gene.

SEQ ID NO: 267 shows the forward primer sequence for the 1 kb nucleotide fragment encoding *Salmonella* FimH protein.

SEQ ID NO: 268 shows the reverse primer sequence for the 1 kb nucleotide fragment sequence encoding *Salmonella* FimH protein.

SEQ ID NO: 269 shows the forward primer sequence for the 1.1 kb nucleotide fragment encoding *Salmonella* OmPD protein.

SEQ ID NO: 270 shows the reverse primer sequence for the 1.1 kb nucleotide fragment encoding *Salmonella* OmPD protein.

SEQ ID NO: 271 shows the nucleotide sequence of the amplicon generated by primers as set forth in SEQ ID NO: 267 and 268.

SEQ ID NO: 272 shows the nucleotide sequence of the amplicon generated by primers as set forth in SEQ ID NO: 269 and 270.

In an embodiment of the present disclosure, there is provided a single chain antibody or a fragment thereof against *Salmonella* surface proteins, comprising of 3 complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a single chain antibody or a fragment thereof against *Salmonella* surface proteins, comprising of 3 complementarity determining regions encoded by a polynucleotide sequence selected from the group consisting of: (a) SEQ ID NO:28 for CDR1, SEQ ID NO:29 for CDR2, and SEQ ID NO:30 for CDR3; (b) SEQ ID NO:31 for CDR1, SEQ ID NO:32 for CDR2, and SEQ ID NO:30 for CDR3; (c) SEQ ID NO:33 for CDR1, SEQ ID NO:34 for CDR2, and SEQ ID NO:35 for CDR3; (d) SEQ ID NO:36 for CDR1, SEQ ID NO:37 for CDR2, and SEQ ID NO:38 for CDR3; (e) SEQ ID NO:39 for CDR1, SEQ ID NO:34 for CDR2, and SEQ ID NO:35 for CDR3; (f) SEQ ID NO:40 for CDR1, SEQ ID NO:41 for CDR2, and SEQ ID NO:42 for CDR3; (g) SEQ ID NO:28 for CDR1, SEQ ID NO:43 for CDR2, and SEQ ID NO:30 for CDR3; (h) SEQ ID NO:28 for CDR1, SEQ ID NO:44 for CDR2, and SEQ ID NO:30 for CDR3; (i) SEQ ID NO:28 for CDR1, SEQ ID NO:45 for CDR2, and SEQ ID NO:30 for CDR3; (j) SEQ ID NO:46 for CDR1, SEQ ID NO:47 for CDR2, and SEQ ID NO:48 for CDR3; (k) SEQ ID NO:49 for CDR1, SEQ ID NO:50 for CDR2, and SEQ ID NO:51 for CDR3; and (l) SEQ ID NO:52 for CDR1, SEQ ID NO:53 for CDR2, and SEQ ID NO:54 for CDR3.

In an embodiment of the present disclosure, there is provided a single chain antibody or a fragment thereof, designated antibody A, against whole cell *Salmonella*, having amino acid sequence as set forth in SEQ ID NO: 55 encoded by a polynucleotide sequence as set forth in SEQ ID NO: 56.

In an embodiment of the present disclosure, there is provided a single chain antibody or a fragment thereof, designated antibody B, against whole cell *Salmonella*, having amino acid sequence as set forth in SEQ ID NO: 57 encoded by a polynucleotide sequence as set forth in SEQ ID NO: 58.

In an embodiment of the present disclosure, there is provided a single chain antibody or a fragment thereof, designated antibody C, against whole cell *Salmonella*, having amino acid sequence as set forth in SEQ ID NO: 59 encoded by a polynucleotide sequence as set forth in SEQ ID NO: 60.

In an embodiment of the present disclosure, there is provided a single chain antibody or a fragment thereof, designated antibody D, against whole cell *Salmonella*, having amino acid sequence as set forth in SEQ ID NO: 61 encoded by a polynucleotide sequence as set forth in SEQ ID NO: 62.

In an embodiment of the present disclosure, there is provided a single chain antibody or a fragment thereof, designated antibody E, against whole cell *Salmonella*, having amino acid sequence as set forth in SEQ ID NO: 63 encoded by a polynucleotide sequence as set forth in SEQ ID NO: 64.

In an embodiment of the present disclosure, there is provided a single chain antibody or a fragment thereof, designated antibody E, against whole cell *Salmonella*, having amino acid sequence as set forth in SEQ ID NO: 65 encoded by a polynucleotide sequence as set forth in SEQ ID NO: 66.

In an embodiment of the present disclosure, there is provided a single chain antibody or a fragment thereof, designated antibody F, against whole cell *Salmonella*, having amino acid sequence as set forth in SEQ ID NO: 67 encoded by a polynucleotide sequence as set forth in SEQ ID NO: 68.

In an embodiment of the present disclosure, there is provided a single chain antibody or a fragment thereof, designated antibody G, against whole cell *Salmonella*, having amino acid sequence as set forth in SEQ ID NO: 69 encoded by a polynucleotide sequence as set forth in SEQ ID NO: 70.

In an embodiment of the present disclosure, there is provided a single chain antibody or a fragment thereof, designated antibody H, against whole cell *Salmonella*, having amino acid sequence as set forth in SEQ ID NO: 71 encoded by a polynucleotide sequence as set forth in SEQ ID NO: 72.

In an embodiment of the present disclosure, there is provided a single chain antibody or a fragment thereof, designated antibody I, against whole cell *Salmonella*, having amino acid sequence as set forth in SEQ ID NO: 73 encoded by a polynucleotide sequence as set forth in SEQ ID NO: 74.

In an embodiment of the present disclosure, there is provided a single chain antibody or a fragment thereof, designated antibody J, against whole cell *Salmonella*, having amino acid sequence as set forth in SEQ ID NO: 75 encoded by a polynucleotide sequence as set forth in SEQ ID NO: 76.

In an embodiment of the present disclosure, there is provided a single chain antibody or a fragment thereof, designated antibody K, against whole cell *Salmonella*, having amino acid sequence as set forth in SEQ ID NO: 77 encoded by a polynucleotide sequence as set forth in SEQ ID NO: 78.

In an embodiment of the present disclosure, there is provided a single chain antibody or a fragment thereof, designated antibody L, against whole cell *Salmonella*, having amino acid sequence as set forth in SEQ ID NO: 79 encoded by a polynucleotide sequence as set forth in SEQ ID NO: 80.

In an embodiment of the present disclosure, there is provided a single chain antibody or a fragment thereof, designated antibody M, against whole cell *Salmonella*, having amino acid sequence as set forth in SEQ ID NO: 81 encoded by a polynucleotide sequence as set forth in SEQ ID NO: 82.

In an embodiment of the present disclosure, there is provided a single chain antibody or a fragment thereof, designated antibody N, against whole cell *Salmonella*, having amino acid sequence as set forth in SEQ ID NO: 83 encoded by a polynucleotide sequence as set forth in SEQ ID NO: 84.

In an embodiment of the present disclosure, there is provided a single chain antibody or a fragment thereof, designated antibody O, against whole cell *Salmonella*, having amino acid sequence as set forth in SEQ ID NO: 85 encoded by a polynucleotide sequence as set forth in SEQ ID NO: 86.

In an embodiment of the present disclosure, there is provided a single chain antibody or a fragment thereof, designated antibody P, against whole cell *Salmonella*, having amino acid sequence as set forth in SEQ ID NO: 87 encoded by a polynucleotide sequence as set forth in SEQ ID NO: 88.

In an embodiment of the present disclosure, there is provided a single chain antibody or a fragment thereof, designated antibody Q, against whole cell *Salmonella*, having amino acid sequence as set forth in SEQ ID NO: 89 encoded by a polynucleotide sequence as set forth in SEQ ID NO: 90.

In an embodiment of the present disclosure, there is provided a single chain antibody or a fragment thereof, designated antibody R, against whole cell *Salmonella*, having amino acid sequence as set forth in SEQ ID NO: 91 encoded by a polynucleotide sequence as set forth in SEQ ID NO: 92.

In an embodiment of the present disclosure, there is provided a single chain antibody or a fragment thereof, designated antibody S, against whole cell *Salmonella*, having amino acid sequence as set forth in SEQ ID NO: 93 encoded by a polynucleotide sequence as set forth in SEQ ID NO: 94.

In an embodiment of the present disclosure, there is provided a single chain antibody or a fragment thereof having amino acid sequence as set forth in SEQ ID NO: 55, 57, 59, 63, 65, 67, 71, 73, 75, 77, or 79 that binds to FimH protein of *Salmonella*.

In an embodiment of the present disclosure, there is provided a single chain antibody or a fragment thereof encoded by a nucleotide sequence as set forth in SEQ ID NO: 56, 58, 60, 64, 66, 68, 72, 74, 76, 78, or 80 that binds to FimH protein of *Salmonella*.

In an embodiment of the present disclosure, there is provided a single chain antibody or a fragment thereof having amino acid sequence as set forth in SEQ ID NO: 61, 69, 81, 83, or 85 that binds to OmPD protein of *Salmonella*.

In an embodiment of the present disclosure, there is provided a single chain antibody or a fragment thereof encoded by a nucleotide sequence as set forth in SEQ ID NO: 62, 70, 82, 84 or 86 that binds to OmPD protein of *Salmonella*.

In an embodiment of the present disclosure, there is provided a single chain antibody or a fragment thereof having amino acid sequence as set forth in SEQ ID NO: 87, 89, or 91 that bind to whole cell *Salmonella*.

In an embodiment of the present disclosure, there is provided a single chain antibody or a fragment thereof encoded by a nucleotide sequence as set forth in SEQ ID NO: 88, 90, or 92 that binds to whole cell *Salmonella*.

In an embodiment of the present disclosure, there is provided a single chain antibody or a fragment thereof against *Salmonella* surface proteins, having amino acid sequence selected from the group consisting of SEQ ID NO: 55, 57, 59, 61, 63, 65, 67, 69, 71, 73, 75, 77, 79, 81, 83, 85, 87, 89, and 91.

In an embodiment of the present disclosure, there is provided a single chain antibody or a fragment thereof against *Salmonella* surface proteins, encoded by a polynucleotide sequence selected from the group consisting of SEQ ID NO:56, 58, 60, 62, 64, 66, 68, 70, 72, 74, 76, 78, 80, 82, 84, 86, 88, 90, and 92.

In an embodiment of the present disclosure, there is provided a single chain antibody or a fragment thereof against *Salmonella* surface proteins, having amino acid sequence as set forth in SEQ ID NO: 55, wherein the single chain antibody or a fragment thereof has 3 complementarity determining regions having amino acid sequence as set forth in SEQ ID NO: 1 for CDR1, SEQ ID NO: 2 for CDR2, and SEQ ID NO:3 for CDR3.

In an embodiment of the present disclosure, there is provided a single chain antibody or a fragment thereof against *Salmonella* surface proteins, having amino acid sequence as set forth in SEQ ID NO: 57, wherein the single chain antibody or a fragment thereof has 3 complementarity determining regions having amino acid sequence as set forth in SEQ ID NO: 4 for CDR1, SEQ ID NO:5 for CDR2, and SEQ ID NO:3 for CDR3.

In an embodiment of the present disclosure, there is provided a single chain antibody or a fragment thereof against *Salmonella* surface proteins, having amino acid sequence as set forth in SEQ ID NO: 59, wherein the single chain antibody or a fragment thereof has 3 complementarity determining regions having amino acid sequence as set forth in SEQ ID NO: 6 for CDR1, SEQ ID NO:7 for CDR2, and SEQ ID NO:8 for CDR3.

In an embodiment of the present disclosure, there is provided a single chain antibody or a fragment thereof against *Salmonella* surface proteins, having amino acid sequence as set forth in SEQ ID NO: 61, wherein the single chain antibody or a fragment thereof has 3 complementarity determining regions having amino acid sequence as set forth in SEQ ID NO: 9 for CDR1, SEQ ID NO:10 for CDR2, and SEQ ID NO:11 for CDR3.

In an embodiment of the present disclosure, there is provided a single chain antibody or a fragment thereof against *Salmonella* surface proteins, having amino acid sequence as set forth in SEQ ID NO: 63, wherein the single chain antibody or a fragment thereof has 3 complementarity determining regions having amino acid sequence as set forth in SEQ ID NO: 12 for CDR1, SEQ ID NO: 7 for CDR2, and SEQ ID NO:8 for CDR3.

In an embodiment of the present disclosure, there is provided a single chain antibody or a fragment thereof against *Salmonella* surface proteins, having amino acid sequence as set forth in SEQ ID NO: 65, wherein the single chain antibody or a fragment thereof has 3 complementarity determining regions having amino acid sequence as set forth in SEQ ID NO: 12 for CDR1, SEQ ID NO:7 for CDR2, and SEQ ID NO:8 for CDR3.

In an embodiment of the present disclosure, there is provided a single chain antibody or a fragment thereof against *Salmonella* surface proteins, having amino acid sequence as set forth in SEQ ID NO: 67, wherein the single chain antibody or a fragment thereof has 3 complementarity determining regions having amino acid sequence as set forth in SEQ ID NO: 12 for CDR1, SEQ ID NO: 7 for CDR2, and SEQ ID NO:8 for CDR3.

In an embodiment of the present disclosure, there is provided a single chain antibody or a fragment thereof against *Salmonella* surface proteins, having amino acid sequence as set forth in SEQ ID NO: 69, wherein the single chain antibody or a fragment thereof has 3 complementarity determining regions having amino acid sequence as set forth in SEQ ID NO:13 for CDR1, SEQ ID NO:14 for CDR2, and SEQ ID NO:15 for CDR3.

In an embodiment of the present disclosure, there is provided a single chain antibody or a fragment thereof against *Salmonella* surface proteins, having amino acid sequence as set forth in SEQ ID NO:71, wherein the single chain antibody or a fragment thereof has 3 complementarity determining regions having amino acid sequence as set forth in SEQ ID NO:1 for CDR1, SEQ ID NO:16 for CDR2, and SEQ ID NO:3 for CDR3.

In an embodiment of the present disclosure, there is provided a single chain antibody or a fragment thereof against *Salmonella* surface proteins, having amino acid sequence as set forth in SEQ ID NO:73, wherein the single chain antibody or a fragment thereof has 3 complementarity determining regions having amino acid sequence as set forth in SEQ ID NO:1 for CDR1, SEQ ID NO:17 for CDR2, and SEQ ID NO:3 for CDR3.

In an embodiment of the present disclosure, there is provided a single chain antibody or a fragment thereof against *Salmonella* surface proteins, having amino acid sequence as set forth in SEQ ID NO:75, wherein the single chain antibody or a fragment thereof has 3 complementarity determining regions having amino acid sequence as set forth in SEQ ID NO:1 for CDR1, SEQ ID NO:18 for CDR2, and SEQ ID NO:3 for CDR3.

In an embodiment of the present disclosure, there is provided a single chain antibody or a fragment thereof against *Salmonella* surface proteins, having amino acid sequence as set forth in SEQ ID NO:77, wherein the single chain antibody or a fragment thereof has 3 complementarity determining regions having amino acid sequence as set forth in SEQ ID NO:1 for CDR1, SEQ ID NO:17 for CDR2, and SEQ ID NO:3 for CDR3.

In an embodiment of the present disclosure, there is provided a single chain antibody or a fragment thereof against *Salmonella* surface proteins, having amino acid sequence as set forth in SEQ ID NO:79, wherein the single chain antibody or a fragment thereof has 3 complementarity determining regions having amino acid sequence as set forth in SEQ ID NO:19 for CDR1, SEQ ID NO:20 for CDR2, and SEQ ID NO:21 for CDR3.

In an embodiment of the present disclosure, there is provided a single chain antibody or a fragment thereof against *Salmonella* surface proteins, having amino acid sequence as set forth in SEQ ID NO:81, wherein the single chain antibody or a fragment thereof has 3 complementarity determining regions having amino acid sequence as set forth in SEQ ID NO:13 for CDR1, SEQ ID NO:14 for CDR2, and SEQ ID NO:15 for CDR3.

In an embodiment of the present disclosure, there is provided a single chain antibody or a fragment thereof against *Salmonella* surface proteins, having amino acid sequence as set forth in SEQ ID NO:83, wherein the single chain antibody or a fragment thereof has 3 complementarity determining regions having amino acid sequence as set forth in SEQ ID NO:13 for CDR1, SEQ ID NO:14 for CDR2, and SEQ ID NO:15 for CDR3.

In an embodiment of the present disclosure, there is provided a single chain antibody or a fragment thereof against *Salmonella* surface proteins, having amino acid sequence as set forth in SEQ ID NO:85, wherein the single chain antibody or a fragment thereof has 3 complementarity determining regions having amino acid sequence as set forth in SEQ ID NO:22 for CDR1, SEQ ID NO:23 for CDR2, and SEQ ID NO:24 for CDR3.

In an embodiment of the present disclosure, there is provided a single chain antibody or a fragment thereof against *Salmonella* surface proteins, having amino acid sequence as set forth in SEQ ID NO:87, wherein the single chain antibody or a fragment thereof has 3 complementarity determining regions having amino acid sequence as set forth in SEQ ID NO:25 for CDR1, SEQ ID NO:26 for CDR2, and SEQ ID NO:27 for CDR3.

In an embodiment of the present disclosure, there is provided a single chain antibody or a fragment thereof against *Salmonella* surface proteins, having amino acid sequence as set forth in SEQ ID NO:89, wherein the single chain antibody or a fragment thereof has 3 complementarity determining regions having amino acid sequence as set forth in SEQ ID NO:25 for CDR1, SEQ ID NO:26 for CDR2, and SEQ ID NO:27 for CDR3.

In an embodiment of the present disclosure, there is provided a single chain antibody or a fragment thereof against *Salmonella* surface proteins, having amino acid sequence as set forth in SEQ ID NO:91, wherein the single chain antibody or a fragment thereof has 3 complementarity determining regions having amino acid sequence as set forth in SEQ ID NO:25 for CDR1, SEQ ID NO:26 for CDR2, and SEQ ID NO:27 for CDR3.

In an embodiment of the present disclosure, there is provided a single chain antibody or a fragment thereof against *Salmonella* surface proteins, encoded by a polynucleotide sequence as set forth in SEQ ID NO:56, wherein the single chain antibody or a fragment thereof has 3 complementarity determining regions encoded by a polynucleotide sequence as set forth in SEQ ID NO:28 for CDR1, SEQ ID NO:29 for CDR2, and SEQ ID NO:30 for CDR3.

In an embodiment of the present disclosure, there is provided a single chain antibody or a fragment thereof against *Salmonella* surface proteins, encoded by a polynucleotide sequence as set forth in SEQ ID NO:58, wherein the single chain antibody or a fragment thereof has 3 complementarity determining regions encoded by a polynucleotide sequence as set forth in SEQ ID NO:31 for CDR1, SEQ ID NO:32 for CDR2, and SEQ ID NO:30 for CDR3.

In an embodiment of the present disclosure, there is provided a single chain antibody or a fragment thereof against *Salmonella* surface proteins, encoded by a polynucleotide sequence as set forth in SEQ ID NO:60, wherein the single chain antibody or a fragment thereof has 3 complementarity determining regions encoded by a polynucleotide sequence as set forth in SEQ ID NO:33 for CDR1, SEQ ID NO:34 for CDR2, and SEQ ID NO:35 for CDR3.

In an embodiment of the present disclosure, there is provided a single chain antibody or a fragment thereof against *Salmonella* surface proteins, encoded by a polynucleotide sequence as set forth in SEQ ID NO:62, wherein the single chain antibody or a fragment thereof has 3 complementarity determining regions encoded by a polynucleotide sequence as set forth in SEQ ID NO:36 for CDR1, SEQ ID NO:37 for CDR2, and SEQ ID NO:38 for CDR3.

In an embodiment of the present disclosure, there is provided a single chain antibody or a fragment thereof against *Salmonella* surface proteins, encoded by a polynucleotide sequence as set forth in SEQ ID NO:64, wherein the single chain antibody or a fragment thereof has 3 complementarity determining regions encoded by a polynucleotide sequence as set forth in SEQ ID NO:39 for CDR1, SEQ ID NO:34 for CDR2, and SEQ ID NO:35 for CDR3.

In an embodiment of the present disclosure, there is provided a single chain antibody or a fragment thereof against *Salmonella* surface proteins, encoded by a polynucleotide sequence as set forth in SEQ ID NO:66, wherein the single chain antibody or a fragment thereof has 3 complementarity determining regions encoded by a polynucleotide sequence as set forth in SEQ ID NO:39 for CDR1, SEQ ID NO:34 for CDR2, and SEQ ID NO:35 for CDR3.

In an embodiment of the present disclosure, there is provided a single chain antibody or a fragment thereof against *Salmonella* surface proteins, encoded by a polynucleotide sequence as set forth in SEQ ID NO:68, wherein the single chain antibody or a fragment thereof has 3 complementarity determining regions encoded by a polynucleotide sequence as set forth in SEQ ID NO:39 for CDR1, SEQ ID NO:34 for CDR2, and SEQ ID NO:35 for CDR3.

In an embodiment of the present disclosure, there is provided a single chain antibody or a fragment thereof against *Salmonella* surface proteins, encoded by a polynucleotide sequence as set forth in SEQ ID NO:70, wherein the single chain antibody or a fragment thereof has 3 complementarity determining regions encoded by a polynucleotide sequence as set forth in SEQ ID NO:40 for CDR1, SEQ ID NO:41 for CDR2, and SEQ ID NO:42 for CDR3.

In an embodiment of the present disclosure, there is provided a single chain antibody or a fragment thereof against *Salmonella* surface proteins, encoded by a polynucleotide sequence as set forth in SEQ ID NO:72, wherein the single chain antibody or a fragment thereof has 3 complementarity determining regions encoded by a polynucleotide sequence as set forth in SEQ ID NO:28 for CDR1, SEQ ID NO:43 for CDR2, and SEQ ID NO:30 for CDR3.

In an embodiment of the present disclosure, there is provided a single chain antibody or a fragment thereof against *Salmonella* surface proteins, encoded by a polynucleotide sequence as set forth in SEQ ID NO:74, wherein the single chain antibody or a fragment thereof has 3 complementarity determining regions encoded by a polynucleotide sequence as set forth in SEQ ID NO:28 for CDR1, SEQ ID NO:44 for CDR2, and SEQ ID NO:30 for CDR3.

In an embodiment of the present disclosure, there is provided a single chain antibody or a fragment thereof against *Salmonella* surface proteins, encoded by a polynucleotide sequence as set forth in SEQ ID NO:76, wherein the single chain antibody or a fragment thereof has 3 complementarity determining regions encoded by a polynucleotide sequence as set forth in SEQ ID NO:28 for CDR1, SEQ ID NO:45 for CDR2, and SEQ ID NO:30 for CDR3.

In an embodiment of the present disclosure, there is provided a single chain antibody or a fragment thereof against *Salmonella* surface proteins, encoded by a polynucleotide sequence as set forth in SEQ ID NO:78, wherein the single chain antibody or a fragment thereof has 3 complementarity determining regions encoded by a polynucleotide sequence as set forth in SEQ ID NO:28 for CDR1, SEQ ID NO:44 for CDR2, and SEQ ID NO:30 for CDR3.

In an embodiment of the present disclosure, there is provided a single chain antibody or a fragment thereof against *Salmonella* surface proteins, encoded by a polynucleotide sequence as set forth in SEQ ID NO:80, wherein the single chain antibody or a fragment thereof has 3 complementarity determining regions encoded by a polynucleotide sequence as set forth in SEQ ID NO:46 for CDR1, SEQ ID NO:47 for CDR2, and SEQ ID NO:48 for CDR3.

In an embodiment of the present disclosure, there is provided a single chain antibody or a fragment thereof against *Salmonella* surface proteins, encoded by a polynucleotide sequence as set forth in SEQ ID NO:82, wherein the single chain antibody or a fragment thereof has 3 complementarity determining regions encoded by a polynucleotide sequence as set forth in SEQ ID NO:40 for CDR1, SEQ ID NO:41 for CDR2, and SEQ ID NO:42 for CDR3.

In an embodiment of the present disclosure, there is provided a single chain antibody or a fragment thereof against *Salmonella* surface proteins, encoded by a polynucleotide sequence as set forth in SEQ ID NO:84, wherein the single chain antibody or a fragment thereof has 3 complementarity determining regions encoded by a polynucleotide sequence as set forth in SEQ ID NO:40 for CDR1, SEQ ID NO:41 for CDR2, and SEQ ID NO:42 for CDR3.

In an embodiment of the present disclosure, there is provided a single chain antibody or a fragment thereof against *Salmonella* surface proteins, encoded by a polynucleotide sequence as set forth in SEQ ID NO:86, wherein the single chain antibody or a fragment thereof has 3 complementarity determining regions encoded by a polynucleotide sequence as set forth in SEQ ID NO:49 for CDR1, SEQ ID NO:50 for CDR2, and SEQ ID NO:51 for CDR3.

In an embodiment of the present disclosure, there is provided a single chain antibody or a fragment thereof against *Salmonella* surface proteins, encoded by a polynucleotide sequence as set forth in SEQ ID NO:88, wherein the single chain antibody or a fragment thereof has 3 complementarity determining regions encoded by a polynucleotide sequence as set forth in SEQ ID NO:52 for CDR1, SEQ ID NO:53 for CDR2, and SEQ ID NO:54 for CDR3.

In an embodiment of the present disclosure, there is provided a single chain antibody or a fragment thereof against *Salmonella* surface proteins, encoded by a polynucleotide sequence as set forth in SEQ ID NO:90, wherein the single chain antibody or a fragment thereof has 3 complementarity determining regions encoded by a polynucleotide sequence as set forth in SEQ ID NO:52 for CDR1, SEQ ID NO:53 for CDR2, and SEQ ID NO:54 for CDR3.

In an embodiment of the present disclosure, there is provided a single chain antibody or a fragment thereof against *Salmonella* surface proteins, encoded by a polynucleotide sequence as set forth in SEQ ID NO:92, wherein the single chain antibody or a fragment thereof has 3 complementarity determining regions encoded by a polynucleotide sequence as set forth in SEQ ID NO:52 for CDR1, SEQ ID NO:53 for CDR2, and SEQ ID NO:54 for CDR3.

In an embodiment of the present disclosure, there is provided a single chain antibody or a fragment thereof that binds to *Salmonella*.

In an embodiment of the present disclosure, there is provided a single chain antibody or a fragment thereof that binds to FimH protein in *Salmonella*.

In an embodiment of the present disclosure, there is provided a single chain antibody or a fragment thereof having amino acid sequence selected from the group consisting of SEQ ID NO:55, 57, 59, 63, 65, 67, 71, 73, 75, 77, and 79, wherein said single chain antibody or a fragment thereof binds to FimH protein in *Salmonella*.

In an embodiment of the present disclosure, there is provided a single chain antibody or a fragment thereof encoded by a polynucleotide sequence selected from the group consisting of SEQ ID NO:56, 58, 60, 64, 66, 68, 72, 76, 78, and 80, wherein said single chain antibody or a fragment thereof binds to FimH protein in *Salmonella*.

In an embodiment of the present disclosure, there is provided a single chain antibody or a fragment thereof that binds to OmPD protein in *Salmonella*.

In an embodiment of the present disclosure, there is provided a single chain antibody or a fragment thereof having amino acid sequence selected from the group consisting of SEQ ID NO:61, 69, 81, 83, and 85, wherein said single chain antibody or a fragment thereof binds to OmPD protein in *Salmonella*.

In an embodiment of the present disclosure, there is provided a single chain antibody or a fragment thereof encoded by a polypeptide sequence selected from the group consisting of SEQ ID NO: 62, 70, 82, 84, and 86, wherein said single chain antibody or a fragment thereof binds to OmPD protein in *Salmonella*.

In an embodiment of the present disclosure, there is provided a single chain antibody or a fragment thereof that binds to a surface protein in *Salmonella*.

In an embodiment of the present disclosure, there is provided a recombinant host cell expressing on the surface one or more chimeric proteins, said chimeric protein comprising of: (a) at least one single chain antibody or a fragment thereof against *Salmonella* surface protein comprising of 3 complementarity determining regions, and (b) at least one surface protein that is expressed on the surface of the recombinant host cell, wherein the surface protein expressed in the recombinant host cell is MuB or CnBP.

In an embodiment of the present disclosure, the chimeric protein as described herein is encoded within the host genome.

In an embodiment of the present disclosure, there is provided a recombinant host cell as described herein, further comprising one or more exogenous nucleic acid sequences encoding another antibody or a fragment thereof against *Salmonella* surface proteins.

In an embodiment of the present disclosure, the protein expressed on the surface of the recombinant host cell is a chimeric protein comprising MuB, and a antibody or a fragment thereof as described herein.

In an embodiment of the present disclosure, the protein expressed on the surface of the recombinant host cell is a chimeric protein comprising CnBP, and an antibody or a fragment thereof as described herein.

In an embodiment of the present disclosure, the proteins expressed on the surface of the recombinant host cell are two different chimeric proteins, each comprising CnBP or MuB, and an antibody or a fragment thereof as described herein.

In an embodiment of the present disclosure, the recombinant host cell expressing on the surface one or more chimeric proteins is a member of the genera *Lactobacillus*.

In an embodiment of the present disclosure, the recombinant host cell expressing on the surface one or more chimeric proteins is selected from the group not limited to: *Lactobacillus acidophilus, Lactobacillus acidophilus* LAFTI L10, *Lactobacillus casei, Lactobacillus casei* LAFTI L26, *Lactobacillus acidophilus* DDS-1, *Lactobacillus acidophilus* LA-5, *Lactobacillus acidophilus* NCFM, *Lactobacillus acidophilus* CD 1285, *Lactobacillus casei* 431, *Lactobacillus casei* F19, *Lactobacillus casei* Shirota, *Lactobacillus paracasei, Lactobacillus paracasei* St11, *Lactobacillus johnsonii, Lactobacillus johnsonii* La1, *Lactobacillus lactis, Lactobacillus lactis* L1A, *Lactobacillus plantarum, Lactobacillus plantarum* 299v, *Lactobacillus reuteri, Lactobacillus reuteri* ATCC55730, *Lactobacillus rhamnosus, Lactobacillus rhamnosus* ATCC53013, *Lactobacillus rhamnosus* LB21, *Lactobacillus rhamnosus* GR-1, *Lactobacillus reuteri* RC-14, *Lactobacillus rhamnosus* R011, *Lactobacillus helveticus*, and *Lactobacillus helveticus* R0052.

In a preferred embodiment of the present disclosure, there is provided a recombinant host cell expressing on the surface one or more chimeric proteins, said recombinant host cell is *Lactobacillus reuteri*.

In an embodiment of the present disclosure, there is provided a recombinant DNA construct comprising a polynucleotide sequence encoding a single chain antibody or a fragment thereof against *Salmonella* surface proteins, comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a recombinant DNA construct comprising a polynucleotide sequence encoding a single chain antibody or a fragment thereof against *Salmonella* surface proteins, comprising of three complementarity determining regions encoded by a polynucleotide sequence selected from the group consisting of: (a) SEQ ID NO:28 for CDR1, SEQ ID NO:29 for CDR2, and SEQ ID NO:30 for CDR3; (b) SEQ ID NO:31 for CDR1, SEQ ID NO:32 for CDR2, and SEQ ID NO:30 for CDR3; (c) SEQ ID NO:33 for CDR1, SEQ ID NO:34 for CDR2, and SEQ ID NO:35 for CDR3; (d) SEQ ID NO:36 for CDR1, SEQ ID NO:37 for CDR2, and SEQ ID NO:38 for CDR3; (e) SEQ ID NO:39 for CDR1, SEQ ID NO:34 for CDR2, and SEQ ID NO:35 for CDR3; (f) SEQ ID NO:40 for CDR1, SEQ ID NO:41 for CDR2, and SEQ ID NO:42 for CDR3; (g) SEQ ID NO:28 for CDR1, SEQ ID NO:43 for CDR2, and SEQ ID NO:30 for CDR3; (h) SEQ ID NO:28 for CDR1, SEQ ID NO:44 for CDR2, and SEQ ID NO:30 for CDR3; (i) SEQ ID NO:28 for CDR1, SEQ ID NO:45 for CDR2, and SEQ ID NO:30 for CDR3; (j) SEQ ID NO:46 for CDR1, SEQ ID NO:47 for CDR2, and SEQ ID NO:48 for CDR3; (k) SEQ ID NO:49 for CDR1, SEQ ID NO:50 for CDR2, and SEQ ID NO:51 for CDR3; and (l) SEQ ID NO:52 for CDR1, SEQ ID NO:53 for CDR2, and SEQ ID NO:54 for CDR3.

In an embodiment of the present disclosure, there is provided a recombinant DNA vector comprising a recombinant DNA construct comprising a polynucleotide sequence encoding a single chain antibody or a fragment thereof against *Salmonella* surface proteins, comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a recombinant DNA vector comprising a recombinant DNA construct comprising a polynucleotide sequence encoding a single chain antibody or a fragment thereof against *Salmonella* surface proteins, comprising of three complementarity determining regions encoded by a polynucleotide sequence selected from the group consisting of: (a) SEQ ID NO:28 for CDR1, SEQ ID NO:29 for CDR2, and SEQ ID NO:30 for CDR3; (b) SEQ ID NO:31 for CDR1, SEQ ID NO:32 for CDR2, and SEQ ID NO:30 for CDR3; (c) SEQ ID NO:33 for CDR1, SEQ ID NO:34 for CDR2, and SEQ ID NO:35 for CDR3; (d) SEQ ID NO:36 for CDR1, SEQ ID NO:37 for CDR2, and SEQ ID NO:38 for CDR3; (e) SEQ ID NO:39 for CDR1, SEQ ID NO:34 for CDR2, and SEQ ID NO:35 for CDR3; (f) SEQ ID NO:40 for CDR1, SEQ ID NO:41 for CDR2, and SEQ ID NO:42 for CDR3; (g) SEQ ID NO:28 for CDR1, SEQ ID NO:43 for CDR2, and SEQ ID NO:30 for CDR3; (h) SEQ ID NO:28 for CDR1, SEQ ID NO:44 for CDR2, and SEQ ID NO:30 for CDR3; (i) SEQ ID NO:28 for CDR1, SEQ ID NO:45 for CDR2, and SEQ ID NO:30 for CDR3; (j) SEQ ID NO:46 for CDR1, SEQ ID NO:47 for CDR2, and SEQ ID NO:48 for CDR3; (k) SEQ ID NO:49 for CDR1, SEQ ID NO:50 for CDR2, and SEQ ID NO:51 for CDR3; and (l) SEQ ID NO:52 for CDR1, SEQ ID NO:53 for CDR2, and SEQ ID NO:54 for CDR3.

In an embodiment of the present disclosure, there is provided a recombinant host cell comprising a recombinant DNA construct comprising a polynucleotide sequence encoding a single chain antibody or a fragment thereof against *Salmonella* surface proteins, comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a recombinant host cell comprising a recombinant DNA construct comprising a polynucleotide sequence encoding a single chain antibody or a fragment thereof against *Salmonella* surface proteins, comprising of three complementarity determining regions encoded by a polynucleotide sequence selected from the group consisting of: (a) SEQ ID NO:28 for CDR1, SEQ ID NO:29 for CDR2, and SEQ ID NO:30 for CDR3; (b) SEQ ID NO:31 for CDR1, SEQ ID NO:32 for CDR2, and SEQ ID NO:30 for CDR3; (c) SEQ ID NO:33 for CDR1, SEQ ID NO:34 for CDR2, and SEQ ID NO:35 for CDR3; (d) SEQ ID NO:36 for CDR1, SEQ ID NO:37 for CDR2, and SEQ ID NO:38 for CDR3; (e) SEQ ID NO:39 for CDR1, SEQ ID NO:34 for CDR2, and SEQ ID NO:35 for CDR3; (f) SEQ ID NO:40 for CDR1, SEQ ID NO:41 for CDR2, and SEQ ID NO:42 for CDR3; (g) SEQ ID NO:28 for CDR1, SEQ ID NO:43 for CDR2, and SEQ ID NO:30 for CDR3; (h) SEQ ID NO:28 for CDR1, SEQ ID NO:44 for CDR2, and SEQ ID NO:30 for CDR3; (i) SEQ ID NO:28 for CDR1, SEQ ID NO:45 for CDR2, and SEQ ID NO:30 for CDR3; (j) SEQ ID NO:46 for CDR1, SEQ ID NO:47 for CDR2, and SEQ ID NO:48 for CDR3; (k) SEQ ID NO:49 for CDR1, SEQ ID NO:50 for CDR2, and SEQ ID NO:51 for CDR3; and (l) SEQ ID NO:52 for CDR1, SEQ ID NO:53 for CDR2, and SEQ ID NO:54 for CDR3.

In an embodiment of the present disclosure, the recombinant host cell comprising a recombinant DNA construct comprising a polynucleotide sequence encoding a single chain antibody or a fragment thereof against *Salmonella* surface proteins, comprising of three complementarity determining regions is selected from the group not limited to: *Lactobacillus acidophilus, Lactobacillus acidophilus* LAFTI L10, *Lactobacillus casei, Lactobacillus casei* LAFTI L26, *Lactobacillus acidophilus* DDS-1, *Lactobacillus acidophilus* LA-5, *Lactobacillus acidophilus* NCFM, *Lactobacillus acidophilus* CD 1285, *Lactobacillus casei* 431, *Lactobacillus casei* F19, *Lactobacillus casei* Shirota, *Lactobacillus paracasei, Lactobacillus paracasei* St11, *Lactobacillus johnsonii, Lactobacillus johnsonii* La1, *Lactobacillus lactis, Lactobacillus lactis* L1A, *Lactobacillus plantarum, Lactobacillus plantarum* 299v, *Lactobacillus reuteri, Lactobacillus reuteri* ATCC55730, *Lactobacillus rhamnosus, Lactobacillus rhamnosus* ATCC53013, *Lactobacillus rhamnosus* LB21, *Lactobacillus rhamnosus* GR-1, *Lactobacillus reuteri* RC-14, *Lactobacillus rhamnosus* R011, *Lactobacillus helveticus*, and *Lactobacillus helveticus* R0052.

In an embodiment of the present disclosure, there is provided a recombinant host cell comprising a recombinant DNA vector comprising a recombinant DNA construct comprising a polynucleotide sequence encoding a single chain antibody or a fragment thereof against *Salmonella* surface proteins, comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a recombinant host cell comprising a recombinant DNA vector comprising a recombinant DNA construct comprising a polynucleotide sequence encoding a single chain antibody or a fragment thereof against *Salmonella* surface proteins, comprising of three complementarity determining regions encoded by a polynucleotide sequence selected from the group consisting of: (a) SEQ ID NO:28 for CDR1, SEQ ID NO:29 for CDR2, and SEQ ID NO:30 for CDR3; (b) SEQ ID NO:31 for CDR1, SEQ ID NO:32 for CDR2, and SEQ ID NO:30 for CDR3; (c) SEQ ID NO:33 for CDR1, SEQ ID NO:34 for CDR2, and SEQ ID NO:35 for CDR3; (d) SEQ ID NO:36 for CDR1, SEQ ID NO:37 for CDR2, and SEQ ID NO:38 for CDR3; (e) SEQ ID NO:39 for CDR1, SEQ ID NO:34 for CDR2, and SEQ ID NO:35 for CDR3; (f) SEQ ID NO:40 for CDR1, SEQ ID NO:41 for CDR2, and SEQ ID NO:42 for CDR3; (g) SEQ ID NO:28 for CDR1, SEQ ID NO:43 for CDR2, and SEQ ID NO:30 for CDR3; (h) SEQ ID NO:28 for CDR1, SEQ ID NO:44 for CDR2, and SEQ ID NO:30 for CDR3; (i) SEQ ID NO:28 for CDR1, SEQ ID NO:45 for CDR2, and SEQ ID NO:30 for CDR3; (j) SEQ ID NO:46 for CDR1, SEQ ID NO:47 for CDR2, and SEQ ID NO:48 for CDR3; (k) SEQ ID NO:49 for CDR1, SEQ ID NO:50 for CDR2, and SEQ ID NO:51 for CDR3; and (l) SEQ ID NO:52 for CDR1, SEQ ID NO:53 for CDR2, and SEQ ID NO:54 for CDR3.

In an embodiment of the present disclosure, the recombinant host cell comprising a recombinant DNA vector comprising a recombinant DNA construct comprising a polynucleotide sequence encoding a single chain antibody or a fragment thereof against *Salmonella* surface proteins, comprising of three complementarity determining regions is selected from the group not limited to: *Lactobacillus acidophilus, Lactobacillus acidophilus* LAFTI L10, *Lactobacillus casei, Lactobacillus casei* LAFTI L26, *Lactobacillus acidophilus* DDS-1, *Lactobacillus acidophilus* LA-5, *Lactobacillus acidophilus* NCFM, *Lactobacillus acidophilus* CD 1285, *Lactobacillus casei* 431, *Lactobacillus casei* F19, *Lactobacillus casei* Shirota, *Lactobacillus paracasei, Lactobacillus paracasei* St11, *Lactobacillus johnsonii, Lactobacillus johnsonii* La1, *Lactobacillus lactis, Lactobacillus lactis* L1A, *Lactobacillus plantarum, Lactobacillus plantarum* 299v, *Lactobacillus reuteri, Lactobacillus reuteri* ATCC55730, *Lactobacillus rhamnosus, Lactobacillus rhamnosus* ATCC53013, *Lactobacillus rhamnosus* LB21, *Lactobacillus rhamnosus* GR-1, *Lactobacillus reuteri* RC-14, *Lactobacillus rhamnosus* R011, *Lactobacillus helveticus*, and *Lactobacillus helveticus* R0052.

In a preferred embodiment of the present disclosure, there is provided a recombinant host cell secreting a single chain antibody or a fragment thereof having amino acid sequence selected from the group consisting of SEQ ID NO: 55, 57, 59, 61, 63, 65, 67, 69, 71, 73, 75, 77, 79, 81, 83, 85, 87, 89, and 91, wherein the recombinant host cell is *Bacillus subtilis*.

In an embodiment of the present disclosure, there is provided a recombinant host cell expressing a single chain antibody or a fragment thereof encoded by a polynucleotide sequence selected from the group consisting of SEQ ID NO:56, 58, 60, 62, 64, 66, 68, 70, 72, 74, 76, 78, 80, 82, 84, 86, 88, 90, and 92, wherein the recombinant host cell secretes the said single chain antibody or a fragment thereof extracellularly.

In an embodiment of the present disclosure, there is provided a single chain antibody or a fragment thereof, said single chain antibody or a fragment thereof is a camelid antibody.

In an embodiment of the present disclosure, there is provided a chimeric protein having at least a contiguous amino acid sequence as set forth in SEQ ID NO: 93, 95, 97, 99, 101, 130, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, and 243.

In an embodiment of the present disclosure, there is provided a chimeric protein having at least a contiguous polynucleotide sequence as set forth in SEQ ID NO: 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, and 244.

In an embodiment of the present disclosure, there is provided a chimeric protein comprising of a single chain antibody or a fragment thereof against *Salmonella* surface proteins, comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a chimeric protein comprising of a single chain antibody or a fragment thereof against *Salmonella* surface proteins, comprising of three complementarity determining regions encoded by a polynucleotide sequence selected from the group consisting of: (a) SEQ ID NO:28 for CDR1, SEQ ID NO:29 for CDR2, and SEQ ID NO:30 for CDR3; (b) SEQ ID NO:31 for CDR1, SEQ ID NO:32 for CDR2, and SEQ ID NO:30 for CDR3; (c) SEQ ID NO:33 for CDR1, SEQ ID NO:34 for CDR2, and SEQ ID NO:35 for CDR3; (d) SEQ ID NO:36 for CDR1, SEQ ID NO:37 for CDR2, and SEQ ID NO:38 for CDR3; (e) SEQ ID NO:39 for CDR1, SEQ ID NO:34 for CDR2, and SEQ ID NO:35 for CDR3; (f) SEQ ID NO:40 for CDR1, SEQ ID NO:41 for CDR2, and SEQ ID NO:42 for. CDR3; (g) SEQ ID NO:28 for CDR1, SEQ ID NO:43 for CDR2, and SEQ ID NO:30 for CDR3; (h) SEQ ID NO:28 for CDR1, SEQ ID NO:44 for CDR2, and SEQ ID NO:30 for CDR3; (i) SEQ ID NO:28 for CDR1, SEQ ID NO:45 for CDR2, and SEQ ID NO:30 for CDR3; (j) SEQ ID NO:46 for CDR1, SEQ ID NO:47 for CDR2, and SEQ ID NO:48 for CDR3; (k) SEQ ID NO:49 for CDR1, SEQ ID NO:50 for CDR2, and SEQ ID NO:51 for CDR3; and (l) SEQ ID NO:52 for CDR1, SEQ ID NO:53 for CDR2, and SEQ ID NO:54 for CDR3.

In an embodiment of the present disclosure, there is provided a food product comprising a recombinant host cell comprising a recombinant DNA construct comprising a polynucleotide sequence encoding a single chain antibody or a fragment thereof against *Salmonella* surface proteins, comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a food product comprising a recombinant host cell comprising a recombinant DNA construct comprising a polynucleotide sequence encoding a single chain antibody or a fragment thereof against *Salmonella* surface proteins, comprising of three complementarity determining regions encoded by a polynucleotide sequence selected from the group consisting of: (a) SEQ ID NO:28 for CDR1, SEQ ID NO:29 for CDR2, and SEQ ID NO:30 for CDR3; (b) SEQ ID NO:31 for CDR1, SEQ ID NO:32 for CDR2, and SEQ ID NO:30 for CDR3; (c) SEQ ID NO:33 for CDR1, SEQ ID NO:34 for CDR2, and SEQ ID NO:35 for CDR3; (d) SEQ ID NO:36 for CDR1, SEQ ID NO:37 for CDR2, and SEQ ID NO:38 for CDR3; (e) SEQ ID NO:39 for CDR1, SEQ ID NO:34 for CDR2, and SEQ ID NO:35 for CDR3; (f) SEQ ID NO:40 for CDR1, SEQ ID NO:41 for CDR2, and SEQ ID NO:42 for CDR3; (g) SEQ ID NO:28 for CDR1, SEQ ID NO:43 for CDR2, and SEQ ID NO:30 for CDR3; (h) SEQ ID NO:28 for CDR1, SEQ ID NO:44 for CDR2, and SEQ ID NO:30 for CDR3; (i) SEQ ID NO:28 for CDR1, SEQ ID NO:45 for CDR2, and SEQ ID NO:30 for CDR3; (j) SEQ ID NO:46 for CDR1, SEQ ID NO:47 for CDR2, and SEQ ID NO:48 for CDR3; (k) SEQ ID NO:49 for CDR1, SEQ ID NO:50 for CDR2, and SEQ ID NO:51 for CDR3; and (l) SEQ ID NO:52 for CDR1, SEQ ID NO:53 for CDR2, and SEQ ID NO:54 for CDR3.

In an embodiment of the present disclosure, there is provided a food product comprising a recombinant host cell comprising a recombinant DNA vector comprising a recombinant DNA construct comprising a polynucleotide sequence encoding a single chain antibody or a fragment thereof against *Salmonella* surface proteins, comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a food product comprising a recombinant host cell comprising a recombinant DNA vector comprising a recombinant DNA construct comprising a polynucleotide sequence encoding a single chain antibody or a fragment thereof against *Salmonella* surface proteins, comprising of three complementarity determining regions encoded by a polynucleotide sequence selected from the group consisting of: (a) SEQ ID NO:28 for CDR1, SEQ ID NO:29 for CDR2, and SEQ ID NO:30 for CDR3; (b) SEQ ID NO:31 for CDR1, SEQ ID NO:32 for CDR2, and SEQ ID NO:30 for CDR3; (c) SEQ ID NO:33 for CDR1, SEQ ID NO:34 for CDR2, and SEQ ID NO:35 for CDR3; (d) SEQ ID NO:36 for CDR1, SEQ ID NO:37 for CDR2, and SEQ ID NO:38 for CDR3; (e) SEQ ID NO:39 for CDR1, SEQ ID NO:34 for CDR2, and SEQ ID NO:35 for CDR3; (f) SEQ ID NO:40 for CDR1, SEQ ID NO:41 for CDR2, and SEQ ID NO:42 for CDR3; (g) SEQ ID NO:28 for CDR1, SEQ ID NO:43 for CDR2, and SEQ ID NO:30 for CDR3; (h) SEQ ID NO:28 for CDR1, SEQ ID NO:44 for CDR2, and SEQ ID NO:30 for CDR3; (i) SEQ ID NO:28 for CDR1, SEQ ID NO:45 for CDR2, and SEQ ID NO:30 for CDR3; (j) SEQ ID NO:46 for CDR1, SEQ ID NO:47 for CDR2, and SEQ ID NO:48 for CDR3; (k) SEQ ID NO:49 for CDR1, SEQ ID NO:50 for CDR2, and SEQ ID NO:51 for CDR3; and (l) SEQ ID NO:52 for CDR1, SEQ ID NO:53 for CDR2, and SEQ ID NO:54 for CDR3.

In an embodiment of the present disclosure, there is provided a food product comprising a single chain antibody or a fragment thereof having amino acid sequence selected from the group consisting of SEQ ID NO:55, 57, 59, 61, 63, 65, 67, 69, 71, 73, 75, 77, 79, 81, 83, 85, 87, 89, and 91.

In an embodiment of the present disclosure, there is provided a food product comprising a single chain antibody or a fragment thereof encoded by a polynucleotide sequence selected from the group consisting of SEQ ID NO:56, 58, 60, 62, 64, 66, 68, 70, 72, 74, 76, 78, 80, 82, 84, 86, 88, 90, and 92.

In an embodiment of the present disclosure, there is provided a food product comprising a chimeric protein having at least a contiguous amino acid sequence selected from the group consisting of SEQ ID NO:93, 95, 97, 99, 101, 130, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, and 243.

In an embodiment of the present disclosure, there is provided a food product comprising a chimeric protein having at least a contiguous polynucleotide sequence selected from the group consisting of SEQ ID NO: 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, and 244.

In an embodiment of the present disclosure, there is provided a food product comprising of a chimeric protein comprising of a single chain antibody or a fragment thereof against *Salmonella* surface proteins, comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a food product comprising of a chimeric protein comprising of a single chain antibody or a fragment thereof against *Salmonella* surface proteins, comprising of three complementarity determining regions encoded by a polynucleotide sequence selected from the group consisting of: (a) SEQ ID NO:28 for CDR1, SEQ ID NO:29 for CDR2, and SEQ ID NO:30 for CDR3; (b) SEQ ID NO:31 for CDR1, SEQ ID NO:32 for CDR2, and SEQ ID NO:30 for CDR3; (c) SEQ ID NO:33 for CDR1, SEQ ID NO:34 for CDR2, and SEQ ID NO:35 for CDR3; (d) SEQ ID NO:36 for CDR1, SEQ ID NO:37 for CDR2, and SEQ ID NO:38 for CDR3; (e) SEQ ID NO:39 for CDR1, SEQ ID NO:34 for CDR2, and SEQ ID NO:35 for CDR3; (f) SEQ ID NO:40 for CDR1, SEQ ID NO:41 for CDR2, and SEQ ID NO:42 for CDR3; (g) SEQ ID NO:28 for CDR1, SEQ ID NO:43 for CDR2, and SEQ ID NO:30 for CDR3; (h) SEQ ID NO:28 for CDR1, SEQ ID NO:44 for CDR2, and SEQ ID NO:30 for CDR3; (i) SEQ ID NO:28 for CDR1, SEQ ID NO:45 for CDR2, and SEQ ID NO:30 for CDR3; (j) SEQ ID NO:46 for CDR1, SEQ ID NO:47 for CDR2, and SEQ ID NO:48 for CDR3; (k) SEQ ID NO:49 for CDR1, SEQ ID NO:50 for CDR2, and SEQ ID NO:51 for CDR3; and (l) SEQ ID NO:52 for CDR1, SEQ ID NO:53 for CDR2, and SEQ ID NO:54 for CDR3.

In an embodiment of the present disclosure, there is provided a food product comprising a chimeric protein, further comprising a carrier selected from the group consisting of a lubricant, a surfactant, solvent, emulsifier, wetting agent, animal feed, dye or oral solution.

In an embodiment of the present disclosure, there is provided a food product comprising a single chain antibody or a fragment thereof, further comprising a carrier selected from the group consisting of a lubricant, a surfactant, solvent, emulsifier, wetting agent, animal feed, dye or oral solution.

In an embodiment of the present disclosure, there is provided a formulation comprising a single chain antibody or a fragment thereof having amino acid sequence selected from the group consisting of SEQ ID NO: 55, 57, 59, 61, 63, 65, 67, 69, 71, 73, 75, 77, 79, 81, 83, 85, 87, 89, and 91.

In an embodiment of the present disclosure, there is provided a formulation comprising a single chain antibody or a fragment thereof encoded by polynucleotide sequence selected from the group consisting of SEQ ID NO: 56, 58, 60, 62, 64, 66, 68, 70, 72, 74, 76, 78, 80, 82, 84, 86, 88, 90, and 92.

In an embodiment of the present disclosure, there is provided a formulation comprising a single chain antibody or a fragment thereof comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a formulation comprising a single chain antibody or a fragment thereof comprising of three complementarity determining regions encoded by a polynucleotide sequence selected from the group consisting of: (a) SEQ ID NO:28 for CDR1, SEQ ID NO:29 for CDR2, and SEQ ID NO:30 for CDR3; (b) SEQ ID NO:31 for CDR1, SEQ ID NO:32 for CDR2, and SEQ ID NO:30 for CDR3; (c) SEQ ID NO:33 for CDR1, SEQ ID NO:34 for CDR2, and SEQ ID NO:35 for CDR3; (d) SEQ ID NO:36 for CDR1, SEQ ID NO:37 for CDR2, and SEQ ID NO:38 for CDR3; (e) SEQ ID NO:39 for CDR1, SEQ ID NO:34 for CDR2, and SEQ ID NO:35 for CDR3; (f) SEQ ID NO:40 for CDR1, SEQ ID NO:41 for CDR2, and SEQ ID NO:42 for CDR3; (g) SEQ ID NO:28 for CDR1, SEQ ID NO:43 for CDR2, and SEQ ID NO:30 for CDR3; (h) SEQ ID NO:28 for CDR1, SEQ ID NO:44 for CDR2, and SEQ ID NO:30 for CDR3; (i) SEQ ID NO:28 for CDR1, SEQ ID NO:45 for. CDR2, and SEQ ID NO:30 for CDR3; (j) SEQ ID NO:46 for CDR1, SEQ ID NO:47 for CDR2, and SEQ ID NO:48 for CDR3; (k) SEQ ID NO:49 for CDR1, SEQ ID NO:50 for CDR2, and SEQ ID NO:51 for CDR3; and (l) SEQ ID NO:52 for CDR1, SEQ ID NO:53 for CDR2, and SEQ ID NO:54 for CDR3.

In an embodiment of the present disclosure, there is provided a formulation comprising a single chain antibody or a fragment thereof, further consisting of a diluent or an excipient or a carrier.

In an embodiment of the present disclosure, there is provided a method of inhibiting growth of *Salmonella*, said method comprising contacting a sample containing *Salmonella with a food product comprising a single chain antibody or a fragment thereof comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a method of inhibiting growth of *Salmonella*, said method comprising contacting a sample containing *Salmonella* with a food product comprising a chimeric protein with at least a contiguous amino acid sequence selected from the group consisting of SEQ ID NO: 93, 95, 97, 99, 101, 130, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, and 243.

In an embodiment of the present disclosure, there is provided a method of inhibiting activity of *Salmonella*, said method comprising contacting a sample containing *Salmonella* with a food product comprising a single chain antibody or a fragment thereof comprising of three complementarity determining regions having amino acid sequence selected from the group consisting of: (a) SEQ ID NO:1 for CDR1, SEQ ID NO:2 for CDR2, and SEQ ID NO:3 for CDR3; (b) SEQ ID NO:4 for CDR1, SEQ ID NO:5 for CDR2, and SEQ ID NO:3 for CDR3; (c) SEQ ID NO:6 for CDR1, SEQ ID NO:7 for CDR2, and SEQ ID NO:8 for CDR3; (d) SEQ ID NO:9 for CDR1, SEQ ID NO:10 for CDR2, and SEQ ID NO:11 for CDR3; (e) SEQ ID NO:12 for CDR1, SEQ ID NO:7 for CDR2, and SEQ ID NO:8 for CDR3; (f) SEQ ID NO:13 for CDR1, SEQ ID NO:14 for CDR2, and SEQ ID NO:15 for CDR3; (g) SEQ ID NO:1 for CDR1, SEQ ID NO:16 for CDR2, and SEQ ID NO:3 for CDR3; (h) SEQ ID NO:1 for CDR1, SEQ ID NO:17 for CDR2, and SEQ ID NO:3 for CDR3; (i) SEQ ID NO:1 for CDR1, SEQ ID NO:18 for CDR2, and SEQ ID NO:3 for CDR3; (j) SEQ ID NO:19 for CDR1, SEQ ID NO:20 for CDR2, and SEQ ID NO:21 for CDR3; (k) SEQ ID NO:22 for CDR1, SEQ ID NO:23 for CDR2, and SEQ ID NO:24 for CDR3; and (l) SEQ ID NO:25 for CDR1, SEQ ID NO:26 for CDR2, and SEQ ID NO:27 for CDR3.

In an embodiment of the present disclosure, there is provided a method of inhibiting activity of *Salmonella*, said method comprising contacting a sample containing *Salmonella* with a food product comprising a chimeric protein with at least a contiguous amino acid sequence selected from the group consisting of SEQ ID NO: 93, 95, 97, 99, 101, 130, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, and 243.

In an embodiment of the present disclosure, there is provided a method of inhibiting activity of *Salmonella* in-ovo, said method comprising contacting a single chain antibody or a fragment thereof having amino acid sequence selected from the group consisting of SEQ ID NO: 55, 57, 59, 61, 63, 65, 67, 69, 71, 73, 75, 77, 79, 81, 83, 85, 87, 89, and 91 with *Salmonella* present in-ovo.

In an embodiment of the present disclosure, there is provided a method of inhibiting growth of *Salmonella* in-ovo, said method comprising contacting a single chain antibody or a fragment thereof having amino acid sequence selected from the group consisting of SEQ ID NO: 55, 57, 59, 61, 63, 65, 67, 69, 71, 73, 75, 77, 79, 81, 83, 85, 87, 89, and 91 with *Salmonella* present in-ovo.

In an embodiment of the present disclosure, there is provided a single chain antibody A or a fragment thereof comprising of 3 complementarity determining regions having amino acid sequence as set forth in SEQ ID NO: 1 for CDR1, SEQ ID NO: 2 for CDR2, and SEQ ID NO: 3 for CDR3, wherein the nucleotide sequence encoding the CDRs is as set forth in SEQ ID NO: 28 for CDR1, SEQ ID NO: 29 for CDR2, and SEQ ID NO: 30 for CDR3, wherein the amino acid sequence of the single chain antibody A or a fragment thereof is as set forth in SEQ ID NO: 55, and the nucleotide sequence encoding the single chain antibody A or a fragment thereof is as set forth in SEQ ID NO: 56.

In an embodiment of the present disclosure, there is provided a single chain antibody B or a fragment thereof comprising of 3 complementarity determining regions having amino acid sequence as set forth in SEQ ID NO: 4 for CDR1, SEQ ID NO: 5 for CDR2, and SEQ ID NO: 3 for CDR3, wherein the nucleotide sequence encoding the CDRs is as set forth in SEQ ID NO: 31 for CDR1, SEQ ID NO: 32 for CDR2, and SEQ ID NO: 30 for CDR3, wherein the amino acid sequence of the single chain antibody A or a fragment thereof is as set forth in SEQ ID NO: 57, and the nucleotide sequence encoding the single chain antibody A or a fragment thereof is as set forth in SEQ ID NO: 58.

In an embodiment of the present disclosure, there is provided a single chain antibody C or a fragment thereof comprising of 3 complementarity determining regions having amino acid sequence as set forth in SEQ ID NO: 6 for CDR1, SEQ ID NO: 7 for CDR2, and SEQ ID NO: 8 for CDR3, wherein the nucleotide sequence encoding the CDRs is as set forth in SEQ ID NO: 33 for CDR1, SEQ ID NO: 34 for CDR2, and SEQ ID NO: 35 for CDR3, wherein the amino acid sequence of the single chain antibody A or a fragment thereof is as set forth in SEQ ID NO: 59, and the nucleotide sequence encoding the single chain antibody A or a fragment thereof is as set forth in SEQ ID NO: 60.

In an embodiment of the present disclosure, there is provided a single chain antibody D or a fragment thereof comprising of 3 complementarity determining regions having amino acid sequence as set forth in SEQ ID NO: 9 for CDR1, SEQ ID NO: 10 for CDR2, and SEQ ID NO: 11 for CDR3, wherein the nucleotide sequence encoding the CDRs is as set forth in SEQ ID NO: 36 for CDR1, SEQ ID NO: 37 for CDR2, and SEQ ID NO: 38 for CDR3, wherein the amino acid sequence of the single chain antibody A or a fragment thereof is as set forth in SEQ ID NO: 61, and the nucleotide sequence encoding the single chain antibody A or a fragment thereof is as set forth in SEQ ID NO: 62.

In an embodiment of the present disclosure, there is provided a single chain antibody E or a fragment thereof comprising of 3 complementarity determining regions having amino acid sequence as set forth in SEQ ID NO: 12 for CDR1, SEQ ID NO: 7 for CDR2, and SEQ ID NO: 8 for CDR3, wherein the nucleotide sequence encoding the CDRs is as set forth in SEQ ID NO: 39 for CDR1, SEQ ID NO: 34 for CDR2, and SEQ ID NO: 35 for CDR3, wherein the amino acid sequence of the single chain antibody A or a fragment thereof is as set forth in SEQ ID NO: 63, and the nucleotide sequence encoding the single chain antibody A or a fragment thereof is as set forth in SEQ ID NO: 64.

In an embodiment of the present disclosure, there is provided a single chain antibody F or a fragment thereof comprising of 3 complementarity determining regions having amino acid sequence as set forth in SEQ ID NO: 12 for CDR1, SEQ ID NO: 7 for CDR2, and SEQ ID NO: 8 for CDR3, wherein the nucleotide sequence encoding the CDRs is as set forth in SEQ ID NO: 39 for CDR1, SEQ ID NO: 34 for CDR2, and SEQ ID NO: 35 for CDR3, wherein the amino acid sequence of the single chain antibody A or a fragment thereof is as set forth in SEQ ID NO: 65, and the nucleotide sequence encoding the single chain antibody A or a fragment thereof is as set forth in SEQ ID NO: 66.

In an embodiment of the present disclosure, there is provided a single chain antibody G or a fragment thereof comprising of 3 complementarity determining regions having amino acid sequence as set forth in SEQ ID NO: 12 for CDR1, SEQ ID NO: 7 for CDR2, and SEQ ID NO: 8 for CDR3, wherein the nucleotide sequence encoding the CDRs is as set forth in SEQ ID NO: 39 for CDR1, SEQ ID NO: 34 for CDR2, and SEQ ID NO: 35 for CDR3, wherein the amino acid sequence of the single chain antibody A or a fragment thereof is as set forth in SEQ ID NO: 67, and the nucleotide sequence encoding the single chain antibody A or a fragment thereof is as set forth in SEQ ID NO: 68.

In an embodiment of the present disclosure, there is provided a single chain antibody H or a fragment thereof comprising of 3 complementarity determining regions having amino acid sequence as set forth in SEQ ID NO: 13 for CDR1, SEQ ID NO: 14 for CDR2, and SEQ ID NO: 15 for CDR3, wherein the nucleotide sequence encoding the CDRs is as set forth in SEQ ID NO: 40 for CDR1, SEQ ID NO: 41 for CDR2, and SEQ ID NO: 42 for CDR3, wherein the amino acid sequence of the single chain antibody A or a fragment thereof is as set forth in SEQ ID NO: 69, and the nucleotide sequence encoding the single chain antibody A or a fragment thereof is as set forth in SEQ ID NO: 70.

In an embodiment of the present disclosure, there is provided a single chain antibody I or a fragment thereof comprising of 3 complementarity determining regions having amino acid sequence as set forth in SEQ ID NO: 1 for CDR1, SEQ ID NO: 16 for CDR2, and SEQ ID NO: 3 for CDR3, wherein the nucleotide sequence encoding the CDRs is as set forth in SEQ ID NO: 28 for CDR1, SEQ ID NO: 43 for CDR2, and SEQ ID NO: 30 for CDR3, wherein the amino acid sequence of the single chain antibody A or a fragment thereof is as set forth in SEQ ID NO: 71, and the nucleotide sequence encoding the single chain antibody A or a fragment thereof is as set forth in SEQ ID NO: 72.

In an embodiment of the present disclosure, there is provided a single chain antibody J or a fragment thereof comprising of 3 complementarity determining regions having amino acid sequence as set forth in SEQ ID NO: 1 for CDR1, SEQ ID NO: 17 for CDR2, and SEQ ID NO: 3 for CDR3, wherein the nucleotide sequence encoding the CDRs is as set forth in SEQ ID NO: 28 for CDR1, SEQ ID NO: 44 for CDR2, and SEQ ID NO: 30 for CDR3, wherein the amino acid sequence of the single chain antibody A or a fragment thereof is as set forth in SEQ ID NO: 73, and the nucleotide sequence encoding the single chain antibody A or a fragment thereof is as set forth in SEQ ID NO: 74.

In an embodiment of the present disclosure, there is provided a single chain antibody K or a fragment thereof comprising of 3 complementarity determining regions having amino acid sequence as set forth in SEQ ID NO: 1 for CDR1, SEQ ID NO: 18 for CDR2, and SEQ ID NO: 3 for CDR3, wherein the nucleotide sequence encoding the CDRs is as set forth in SEQ ID NO: 28 for CDR1, SEQ ID NO: 45 for CDR2, and SEQ ID NO: 30 for CDR3, wherein the amino acid sequence of the single chain antibody A or a fragment thereof is as set forth in SEQ ID NO: 75, and the nucleotide sequence encoding the single chain antibody A or a fragment thereof is as set forth in SEQ ID NO: 76.

In an embodiment of the present disclosure, there is provided a single chain antibody L or a fragment thereof comprising of 3 complementarity determining regions having amino acid sequence as set forth in SEQ ID NO: 1 for CDR1, SEQ ID NO: 17 for CDR2, and SEQ ID NO: 3 for CDR3, wherein the nucleotide sequence encoding the CDRs is as set forth in SEQ ID NO: 28 for CDR1, SEQ ID NO: 44 for CDR2, and SEQ ID NO: 30 for CDR3, wherein the amino acid sequence of the single chain antibody A or a fragment thereof is as set forth in SEQ ID NO: 77, and the nucleotide sequence encoding the single chain antibody A or a fragment thereof is as set forth in SEQ ID NO: 78.

In an embodiment of the present disclosure, there is provided a single chain antibody M or a fragment thereof comprising of 3 complementarity determining regions having amino acid sequence as set forth in SEQ ID NO: 19 for CDR1, SEQ ID NO: 20 for CDR2, and SEQ ID NO: 21 for CDR3, wherein the nucleotide sequence encoding the CDRs is as set forth in SEQ ID NO: 46 for CDR1, SEQ ID NO: 47 for CDR2, and SEQ ID NO: 48 for CDR3, wherein the amino acid sequence of the single chain antibody A or a fragment thereof is as set forth in SEQ ID NO: 79, and the nucleotide sequence encoding the single chain antibody A or a fragment thereof is as set forth in SEQ ID NO: 80.

In an embodiment of the present disclosure, there is provided a single chain antibody N or a fragment thereof comprising of 3 complementarity determining regions having amino acid sequence as set forth in SEQ ID NO: 13 for CDR1, SEQ ID NO: 14 for CDR2, and SEQ ID NO: 15 for CDR3, wherein the nucleotide sequence encoding the CDRs is as set forth in SEQ ID NO: 40 for CDR1, SEQ ID NO: 41 for CDR2, and SEQ ID NO: 42 for CDR3, wherein the amino acid sequence of the single chain antibody A or a fragment thereof is as set forth in SEQ ID NO: 81, and the nucleotide sequence encoding the single chain antibody A or a fragment thereof is as set forth in SEQ ID NO: 82.

In an embodiment of the present disclosure, there is provided a single chain antibody O or a fragment thereof comprising of 3 complementarity determining regions having amino acid sequence as set forth in SEQ ID NO: 13 for CDR1, SEQ ID NO: 14 for CDR2, and SEQ ID NO: 15 for CDR3, wherein the nucleotide sequence encoding the CDRs is as set forth in SEQ ID NO: 40 for CDR1, SEQ ID NO: 41 for CDR2, and SEQ ID NO: 42 for CDR3, wherein the amino acid sequence of the single chain antibody A or a fragment thereof is as set forth in SEQ ID NO: 83, and the nucleotide sequence encoding the single chain antibody A or a fragment thereof is as set forth in SEQ ID NO: 84.

In an embodiment of the present disclosure, there is provided a single chain antibody P or a fragment thereof comprising of 3 complementarity determining regions having amino acid sequence as set forth in SEQ ID NO: 22 for CDR1, SEQ ID NO: 23 for CDR2, and SEQ ID NO: 24 for CDR3, wherein the nucleotide sequence encoding the CDRs is as set forth in SEQ ID NO: 49 for CDR1, SEQ ID NO: 50 for CDR2, and SEQ ID NO: 51 for CDR3, wherein the amino acid sequence of the single chain antibody A or a fragment thereof is as set forth in SEQ ID NO: 85, and the nucleotide sequence encoding the single chain antibody A or a fragment thereof is as set forth in SEQ ID NO: 86.

In an embodiment of the present disclosure, there is provided a single chain antibody Q or a fragment thereof comprising of 3 complementarity determining regions having amino acid sequence as set forth in SEQ ID NO: 25 for CDR1, SEQ ID NO: 26 for CDR2, and SEQ ID NO: 27 for CDR3, wherein the nucleotide sequence encoding the CDRs is as set forth in SEQ ID NO: 52 for CDR1, SEQ ID NO: 53 for CDR2, and SEQ ID NO: 54 for CDR3, wherein the amino acid sequence of the single chain antibody A or a fragment thereof is as set forth in SEQ ID NO: 87, and the nucleotide sequence encoding the single chain antibody A or a fragment thereof is as set forth in SEQ ID NO: 88.

In an embodiment of the present disclosure, there is provided a single chain antibody R or a fragment thereof comprising of 3 complementarity determining regions having amino acid sequence as set forth in SEQ ID NO: 25 for CDR1, SEQ ID NO: 26 for CDR2, and SEQ ID NO: 27 for CDR3, wherein the nucleotide sequence encoding the CDRs is as set forth in SEQ ID NO: 52 for CDR1, SEQ ID NO: 53 for CDR2, and SEQ ID NO: 54 for CDR3, wherein the amino acid sequence of the single chain antibody A or a fragment thereof is as set forth in SEQ ID NO: 89, and the nucleotide sequence encoding the single chain antibody A or a fragment thereof is as set forth in SEQ ID NO: 90.

In an embodiment of the present disclosure, there is provided a single chain antibody S or a fragment thereof comprising of 3 complementarity determining regions having amino acid sequence as set forth in SEQ ID NO: 25 for CDR1, SEQ ID NO: 26 for CDR2, and SEQ ID NO: 27 for CDR3, wherein the nucleotide sequence encoding the CDRs is as set forth in SEQ ID NO: 52 for CDR1, SEQ ID NO: 53 for CDR2, and SEQ ID NO: 54 for CDR3, wherein the amino acid sequence of the single chain antibody A or a fragment thereof is as set forth in SEQ ID NO: 91, and the nucleotide sequence encoding the single chain antibody A or a fragment thereof is as set forth in SEQ ID NO: 92.

In an embodiment of the present disclosure, there is provided an isolated *Lactobacillus* strain, *Lactobacillus reuteri* 1LB7 deposited with Microbial Type Culture Collection and Gene Bank (MTCC) having accession number (5894) for management of enteric *Salmonella* population in animal husbandry.

In an embodiment of the present disclosure, there is provided a food formulation comprising anti-*Salmonella* VHH antibodies or fragments thereof as described herein that inhibit *Salmonella* growth.

In an embodiment of the present disclosure, there is provided a milk based formulation comprising anti-*Salmonella* VHH antibodies or fragments thereof as described herein that inhibit *Salmonella* growth.

In an embodiment of the present disclosure, there is provided an egg yolk based formulation comprising anti-*Salmonella* VHH antibodies or fragments thereof as described herein that inhibit *Salmonella* growth.

In an embodiment of the present disclosure, there is provided a modified *Lactobacillus reuteri* having anti-*Salmonella* camelid VHH antibody gene insert in the MuB gene as described herein that inhibits *Salmonella* growth upon heat inactivation.

In an embodiment of the present disclosure, there is provided a modified *Lactobacillus reuteri* having anti-*Salmonella* camelid VHH antibody gene insert in the CnBP gene as described herein that inhibits *Salmonella* growth upon heat inactivation.

In an embodiment of the present disclosure, there is provided camelid VHH antibody fragments as described herein that inhibit growth of *Salmonella serovars*.

In an embodiment of the present disclosure, there is provided camelid VHH antibody fragments as described herein that inhibit growth of *Salmonella typhimurium*.

In an embodiment of the present disclosure, there is provided camelid VHH antibody fragments as described herein that inhibit growth of *Salmonella gallinarum*.

In an embodiment of the present disclosure, there is provided camelid VHH antibody fragments as described herein that inhibit growth of *Salmonella newport*.

In an embodiment of the present disclosure, there is provided camelid VHH antibody fragments as described herein that inhibit growth of *Salmonella abony*.

In an embodiment of the present disclosure, there is provided a single chain antibody or a fragment thereof against *Salmonella* surface proteins as described herein, or a recombinant host cell as described herein, or a recombinant DNA construct as described herein, or a recombinant DNA vector as described herein, or a chimeric protein as described herein, or a food product as described herein, or a formulation as described herein, or an isolated *Lactobacillus* strain as described herein, for use in inhibiting *Salmonella* growth or infection.

In an embodiment of the present disclosure, there is provided a single chain antibody or a fragment thereof against *Salmonella* surface proteins as described herein, for use in inhibiting *Salmonella* growth or infection.

In an embodiment of the present disclosure, there is provided a recombinant host cell as described herein, for use in inhibiting *Salmonella* growth or infection.

In an embodiment of the present disclosure, there is provided a recombinant DNA construct as described herein, for use in inhibiting *Salmonella* growth or infection.

In an embodiment of the present disclosure, there is provide a recombinant DNA construct as described herein, for use in inhibiting *Salmonella* growth or infection.

In an embodiment of the present disclosure, there is provided a chimeric protein as described herein, for use in inhibiting *Salmonella* growth or infection.

In an embodiment of the present disclosure, there is provided a food product as described herein, for use in inhibiting *Salmonella* growth or infection.

In an embodiment of the present disclosure, there is provided a formulation as described herein, for use in inhibiting *Salmonella* growth or infection.

In an embodiment of the present disclosure, there is provided an isolated *Lactobacillus* strain as described herein, for use in inhibiting *Salmonella* growth or infection.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs.

Example 1

Isolation and Characterization of *Lactobacillus*

Various organs (trachea, crop, gizzard, small intestine, large intestine, and ceacum) were collected from backyard poultry birds. *Lactobacillus* was isolated by inoculating the field sample in *Lactobacillus* selective broth (LSB) (HiMedia/M1166-500G) and incubated at 37° C. under anaerobic conditions. Selected colonies were enriched on MRS broth (HiMedia/M369-500G). Purity of the selected colonies was checked by Gram staining (gram positive short rods). The genetic identity of *Lactobacillus* was confirmed by carrying out a sequencing reaction of the 900 bp amplicon produced by amplifying the 16S RNA gene using primers as set forth in SEQ ID NO: 245 (forward primer) and SEQ ID NO:246 (reverse primer). The genetic identity of *Lactobacillus reuteri* was confirmed by carrying out a sequencing reaction of the 303 bp amplicon produced by species specific primers as set forth in SEQ ID NO: 247 (forward primer) and SEQ ID NO: 248 (reverse primer). The *Lactobacillus reuteri* 1LB7 strain isolated from poultry bird crop and found in the entire gastrointestinal tract, was selected as the host strain for surface display of a camelid heavy chain antibody or a fragment thereof. The 1LB7 strain is devoid of any plasmids.

Example 2

Isolation of *Lactobacillus reuteri* MuB, and CnBP

Genomic DNA was isolated from the 1LB7 strain by resuspending a bacterial pellet in 5 ml TNE buffer containing lysozyme at a concentration of 10 mg/ml. 500 µl of 10% SDS and 250 µl proteinase K at a concentration of 10 mg/ml was added and incubated at 55° C. for two hours with intermittent shaking. Genomic DNA was isolated using the phenol chloroform extraction method (Raya et al, *Food Microbiology Protocols*, 2001, 14, 135-139).

A partial 1.7 kb region of the MuB gene was PCR amplified using primers as set forth in SEQ ID NO: 249 (forward primer) and SEQ ID NO: 250 (reverse primer). This 1.7 kb region comprises the LPTQG motif. The amplicon was subsequently cloned in to pJet vector as per manufacturer's instructions (catalog number: K1231, Thermo Scientific) and sequenced.

The complete CnBP gene (1.08 kb) was PCR amplified using primers as set forth in SEQ ID NO: 251 (forward primer) and SEQ ID NO: 252 (reverse primer). The amplicon was subsequently cloned in to pJet vector as per manufacturer's instructions and sequenced.

Example 3

Generation of Camelid Antibodies Against Whole Cell *Salmonella*

Immunization of camels with whole cell inactivated *Salmonella enteric*: Briefly, actively growing cultures of *Salmonella enteric* (log phase) was subjected to inactivation for 24 hours at 37° C. by addition of 0.5% of formalin. The culture was kept under constant shaking at 20 rpm. Subsequently the cultures were stored at 4° C. and a representative sample was tested in enriched growth media for innocuity. On confirmation of the inactivation, the bacterial cultures were washed thrice in 1×PBS buffer and re-suspended at a concentration of 200 µg/ml. 5 ml of the suspension was mixed with adjuvant (Montanide ISA 206V) to form an emulsion.

Final bleeding of immunized camels was done at 60 days post immunization. Total RNA was isolated from isolated peripheral blood lymphocytes. PCR reaction was carried out for amplification of heavy chain antibody fragments using primers as set forth in SEQ ID NO: 253 (forward primer) and SEQ ID NO: 254 (reverse primer). {Amplicon size: 900 bps (comprising of the framework and CDR regions & CH1, CH2, CH3 including the hinge region of the camelid conventional heavy chain antibody pairing with the light chain), 690 bp (comprising of the framework and CDR regions & the long hinge, CH2, CH3 regions of the camelid heavy chain VHH antibody), 620 bp (comprising of the framework and CDR regions & the short hinge, CH2, CH3 regions of the camelid heavy chain VHH antibody)}. PCR condition used are given below in Table 1:

TABLE 1

| No. of cycles | Temperature | Time |
| --- | --- | --- |
| 1 | 94° C. | 4 mins |
| 29 | 94° C. | 30 sec |
|  | 50° C. | 1 min |
|  | 72° C. | 90 sec |
| 1 | 72° C. | 5 mins |

Figure 8:
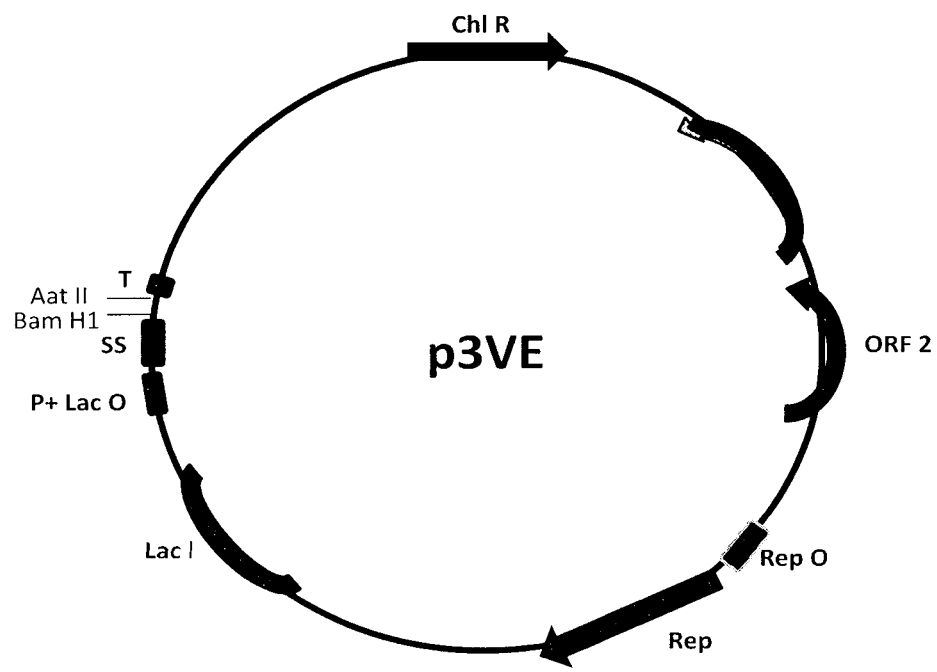
FIG. 8 depicts the vector map used to clone, in accordance with an embodiment of the present disclosure.

The amplicons were subsequently cloned in to a *Bacillus subtilis* secretory vector, 3VE vector (FIG. 8). Single colonies were isolated by limited dilution plating. Single colonies were plated on 2XYT agar plates for growth. Induction of cloned antibodies was carried out by treating 3VE *bacillus* vector cultures with IPTG for secretion of antibodies.

The secreted antibodies were screened for anti-*Salmonella* activity by assaying for anti-*Salmonella* biological activity, and *Salmonella* cell invasion inhibition assay.

Plasmids from clones showing anti-*Salmonella* activity were isolated and the polynucleotide encoding the heavy chain antibody fragment showing anti-*Salmonella* activity was digested with BamHI and AatII restriction enzyme and subsequently cloned in to pJet vector. The heavy chain antibody fragment was further sequenced to identify the complementarity determining regions.

The identified heavy chain antibody fragments showing anti-*Salmonella* activity were further used for site specific insertion in to *Lactobacillus reuteri* MuB and CnBP genes.

Example 4

Generation of Chimeric Proteins

Insertion of Specific Camelid Heavy Chain Antibody (VHH) within MuB Repeat R-VI of the Cloned MuB Gene in pJet Inverse PCR of the MuB gene cloned in pJet was carried out to introduce the flanking enzymes NdeI and BamHI at the VHH antibody insertion sites using primers as set forth in SEQ ID NO: 255 and SEQ ID NO: 256 (amplicon size 4.7 kb). PCR conditions are given below in Table 2:

TABLE 2

| No. of cycles | Temperature | Time |
| --- | --- | --- |
| 1 | 94° C. | 4 mins |
| 29 | 94° C. | 30 sec |

TABLE 2-continued

| No. of cycles | Temperature | Time |
| --- | --- | --- |
|  | 58° C. | 30 sec |
|  | 72° C. | 8 mins |
| 1 | 72° C. | 10 mins |

PCR primers with flanking restriction enzyme sites BamHI and NdeI used to pull out the selected VHH cloned in to the secretory vector 3VE are as set forth in SEQ ID NO: 257 (forward primer) and SEQ ID NO: 258 (reverse primer) (amplicon size 400 bp). The VHH PCR fragment with BamHI and NdeI restriction sites was ligated to the MuB gene inverse PCR product (pJet vector) and transformed in to *E. coli*. Clones harboring the MuB gene with the camelid VHH engineered within the MuB gene were screened and sequenced. PCR conditions are given below in Table 3:

TABLE 3

| No. of cycles | Temperature | Time |
| --- | --- | --- |
| 1 | 94° C. | 4 mins |
| 29 | 94° C. | 30 sec |
|  | 60° C. | 1 min |
|  | 72° C. | 1 mins |
| 1 | 72° C. | 10 mins |

A PCR product of the MuB gene harboring the camelid VHH was obtained using primers as set forth in SEQ ID NO: 259 (forward primer) and SEQ ID NO: 260 (reverse primer) that lack the BamHI or NdeI restriction sites (amplicon size 2.1 kb). PCR conditions are given below in Table 4:

TABLE 4

| No. of cycles | Temperature | Time |
| --- | --- | --- |
| 1 | 94° C. | 4 mins |
| 29 | 94° C. | 30 sec |
|  | 57° C. | 1 min |
|  | 72° C. | 4 mins |
| 1 | 72° C. | 10 mins |

The amplicon obtained was electroporated in to *Lactobacillus reuteri* strain 1LB7 for host genome integration by double-cross over.

Insertion of Specific Camelid Heavy Chain Antibody (VHH) within Cloned CnBP Gene in pJet Inverse PCR of the CnBP gene cloned in pJet was carried out to introduce the flanking enzymes NdeI and BamHI at the VHH antibody insertion sites using primers as set forth in SEQ ID NO: 261 and SEQ ID NO: 262 (amplicon size 4.2 kb). PCR conditions are given below in Table 5:

TABLE 5

| No. of cycles | Temperature | Time |
| --- | --- | --- |
| 1 | 94° C. | 4 mins |
| 29 | 94° C. | 30 sec |
|  | 52° C. | 30 sec |
|  | 72° C. | 7 mins |
| 1 | 72° C. | 10 mins |

PCR primers with flanking restriction enzyme sites BamHI and NdeI used to pull out the selected VHH cloned in to the secretory vector 3VE are as set forth in SEQ ID NO: 263 (forward primer) and SEQ ID NO: 264 (reverse primer) (amplicon size 400 bp). PCR conditions are given below in Table 6:

TABLE 6

| No. of cycles | Temperature | Time |
| --- | --- | --- |
| 1 | 94° C. | 4 mins |
| 29 | 94° C. | 30 sec |
|  | 65° C. | 1 min |
|  | 72° C. | 2 mins |
| 1 | 72° C. | 10 mins |

The VHH PCR fragment with BamHI and NdeI restriction sites was ligated to the CnBP gene inverse PCR product (pJet vector) and transformed in to *E. coli*. Clones harboring the CnBP gene with the camelid VHH engineered within the MuB gene were screened and sequenced.

A PCR product of the CnBP gene harboring the camelid VHH was obtained using primers as set forth in SEQ ID NO: 265 (forward primer) and SEQ ID NO: 266 (reverse primer) (phosphorylated oligos) that lack the BamHI or NdeI restriction sites to form a circular DNA product (amplicon size 1.4 kb). PCR conditions are given below in Table 7:

TABLE 7

| No. of cycles | Temperature | Time |
| --- | --- | --- |
| 1 | 94° C. | 4 mins |
| 29 | 94° C. | 30 sec |
|  | 50° C. | 1 min |
|  | 72° C. | 3 mins |
| 1 | 72° C. | 10 mins |

The circularized DNA product (full length CnBP gene) with the VHH insert was used for electroporation in to the *Lactobacillus reuteri* strain 1LB7 for host genomic integration by single Campbell like cross-over.

Example 5

Identification of Antigenic *Salmonella* Surface Proteins

Primers as set forth in SEQ ID NO: 267 (forward primer) and SEQ ID NO: 268 (reverse primer) for amplification of *Salmonella* FimH protein encoding polynucleotide. The polynucleotide sequence of the amplicon is as set forth in SEQ ID NO: 271.

Primers as set forth in SEQ ID NO: 269 (forward primer) and SEQ ID NO: 270 (reverse primer) for amplification of *Salmonella* OmPD protein encoding polynucleotide. The polynucleotide sequence of the amplicon is as set forth in SEQ ID NO: 272.

Whole Cell (*Lactobacillus reuteri*) ELISA Results

Briefly, *L. reuteri* parental host strain was transformed and modified for surface display of anti-*Salmonella* specific camelid heavy chain antibodies on the MuB and CnBP proteins present at the bacterial cell surface. Selection of the clones/constructs with surface display antibodies specifically against the *Salmonella* FimH and OmPD proteins was done on the basis of binding/attachment/baiting of the clones over the recombinant FimH and OmPD proteins immobilized on nitrocellulose membranes.

Subsequently, the positive binders were subjected to *Lactobacillus* whole cell ELISA, wherein the histidine tagged recombinant *Salmonella* FimH and OmPD was used as the cell surface displayed specific antibody tracers or binders. Subsequently, specific binding of the modified *Lactobacillus reuteri* cell surface displayed antibody molecules to recombinant *Salmonella* FimH and OmPD proteins was traced with mouse monoclonal anti-His antibodies. Table 8 and 9 shows the results of ELISA.

TABLE 8

RECOMBINANT *SALMONELLA* FimH PROTEIN TAGGED WITH HISTIDINE USED IN THE WHOLE CELL ELISA AS A TRACER MOLECULE FOR THE ANTIBODY FRAGMENTS DISPLAYED ON THE SURFACE OF THE MODIFIED *L. reuteri*.

| | | O.D values | | | |
|---|---|---|---|---|---|
| Sr. No | *Lactobacillus reuteri* bacterial sample | Neat | 1:2 dilution | 1:4 dilution | 1:8 dilution | 1:16 dilution |
| 1 | Modified *L. reuteri* with surface displayed camelid antibodies specific against *Salmonella* | 0.925 | 0.411 | 0.249 | 0.165 | 0.106 |
| 2 | *L. reuteri* parental host control | 0.79 | 0.232 | 0.124 | 0.088 | 0.069 |
| 3 | Modified *L. reuteri* with surface displayed camelid antibodies specific against *Salmonella* | 1.29 | 0.552 | 0.341 | 0.264 | 0.18 |
| 4 | *L. reuteri* parental host control | 1.15 | 0.262 | 0.191 | 0.17 | 0.166 |

TABLE 9

RECOMBINANT *SALMONELLA* OmPD PROTEIN TAGGED WITH HISTIDINE USED IN THE WHOLE CELL ELISA AS A TRACER MOLECULE FOR THE ANTIBODY FRAGMENTS DISPLAYED ON THE SURFACE OF THE MODIFIED *L. reuteri*.

| | | O.D values | | | |
|---|---|---|---|---|---|
| Sr. No | *Lactobacillus reuteri* bacterial sample | Neat | 1:2 dilution | 1:4 dilution | 1:8 dilution | 1:16 dilution |
| 1 | Modified *L. reuteri* with surface displayed camelid antibodies specific against *Salmonella* | 0.823 | 0.403 | 0.197 | 0.108 | 0.071 |
| 2 | *L. reuteri* parental host control | 0.832 | 0.139 | 0.073 | 0.053 | 0.047 |
| 3 | Modified *L. reuteri* with surface displayed camelid antibodies specific against *Salmonella* | 1.381 | 0.697 | 0.393 | 0.169 | 0.089 |
| 4 | *L. reuteri* parental host Control | 1.394 | 0.302 | 0.118 | 0.081 | 0.063 |

Based on the results in Table 8, camelid antibodies having amino acid sequence as set forth in SEQ ID NO: 55, 57, 59, 63, 65, 67, 71, 73, 75, 77, and 79 bind to *Salmonella* FimH protein.

Based on the results in Table 9, camelid antibodies having amino acid sequence as set forth in SEQ ID NO: 61, 69, 81, 83, and 85 bind to *Salmonella* OmPD protein.

Camelid antibodies having amino acid sequences as set forth in SEQ ID NO: 87, 89, and 91 bind to whole cell *Salmonella*.

Example 6

Anti-*Salmonella* Biological Activity

Briefly, *Bacillus subtilis* vector clones with the antibody gene fragment (polynucleotide encoding antibody having amino acid sequence as set forth in SEQ ID NO: 61) were induced with IPTG (1 mM, 12 hours at 37° C. on shaker at 180 RPM) and the culture supernatant was collected by centrifugation (5000 RPM for 10 minutes) and filtered through 0.45 um filter. Similar treatment was given to the supernatant of the induced plasmid without any camelid heavy chain antibody gene fragment insert and the 2xYT growth media in which the *Bacillus* cultures was grown and these were used as controls.

Test supernatant and the two controls were subsequently challenged with *Salmonella* bacterium inoculums of 25,000 cells in a total test volume of 2 mL and incubated at 37° C. under shaking at 180 RPM. Representative samples from the test and the two control reactions were drawn at 2, 4, 6, 8 and 24 hours of incubation and were plated on selective XLT agar media to enumerate the *Salmonella* colony forming units. The results are summarized in the Table 10 below.

TABLE 10

| | Colony forming units | | | | |
|---|---|---|---|---|---|
| | Test supernatant from Induced secretory Vector having Camelid Antibody Gene fragment insert | Test Control supernatant from Induced secretory empty vector without Antibody Gene insert | 2xYT growth Media control | % reduction of test supernatant over induced empty vector control | % reduction of test supernatant over 2xYT growth media control |
| 0 hr | 98 | 95 | 97 | | |
| 2 hrs | 60 | 850 | 901 | 92.94 | 93.34 |
| 4 hrs | 66 | TNTC | TNTC | >95 | >95 |
| 6 hrs | 53 | TNTC | TNTC | >95 | >95 |
| 8 hrs | 35 | Mat | Mat | >95 | >95 |
| 24 hrs | 0 | Mat | Mat | 100 | 100 |

TNTC: Colonies too numerous to count.
Mat: Complete Bacterial growth on the plate with merged colonies.

Example 7

Anti-*Salmonella* Biological Activity Titration

*Bacillus subtilis* vector clones with the antibody gene fragments (polynucleotide encoding antibody having amino acid sequence as set forth in SEQ ID NO: 61) were induced with IPTG (1 mM, 12 hours at 37° C. on shaker at 180 RPM) and the culture supernatant was collected by centrifugation (5000 RPM for 10 minutes) and filtered through 0.45 um filter. This was then subjected to two-fold dilution in the 2xYT bacterial growth media and 1:2 and 1:4 along with the neat supernatant were subjected to anti-*Salmonella* biological activity testing. Similar treatment was given to the supernatant of the induced plasmid without any camelid heavy chain antibody gene fragment insert and the 2 xYT growth media in which the *Bacillus* cultures was grown and these were used as controls.

Test supernatant and the two controls were subsequently challenged with *Salmonella* bacterium inoculums of 25,000 cells in a total test volume of 2 ml and incubated at 37° C. under shaking at 180 RPM. Representative samples from the test and the two control reactions were drawn at 2 hours of incubation and were plated on selective XLT agar media to enumerate the *Salmonella* colony forming units. The results are summarized in the Table 11 below.

TABLE 11

| Sample | Colony Forming units | % reduction of test supernatant over supernatant from induced empty vector control |
|---|---|---|
| Test Control supernatant from Induced secretory empty vector (neat) | 991 | — |
| Test Control supernatant from Induced secretory empty vector diluted (1:2) | 889 | — |
| Test Control supernatant from Induced secretory empty vector diluted (1:4) | 868 | — |
| Test supernatant from Induced secretory Vector having Camelid Antibody fragment Gene insert (neat) | 94 | 90.51 |
| Test supernatant from Induced secretory Vector having Camelid Antibody fragment Gene insert diluted (1:2) | 223 | 74.91 |
| Test supernatant from Induced secretory Vector having Camelid Antibody fragment insert in plasmid diluted (1:4) | 402 | 53.68 |
| 2xYT growth Media control | 983 | |

*Salmonella* Cell Invasion Inhibition Assay

The supernatant from the induced plasmid with camelid Heavy chain antibody gene fragment (polynucleotide encoding antibody having amino acid sequence as set forth in SEQ ID NO: 61) insert along with the supernatant from induced plasmid without any antibody gene fragment insert as control as well as 2xYT bacterial growth media as control was tested for the *Salmonella* cell invasion inhibitory properties. Cell substratum used was INT 407 intestinal cell line.

Challenge dose of $2.5 \times 10^8$ *Salmonella bacterium* in 1 ml of MEM (Himedia cat no: AL047S was added in 1 ml of the test and control supernatant. On addition of challenge *bacterium*, supernatant mixtures were incubated at 37° C. for 1 hour under shaking at 180 rpm. Subsequently entire contents of each 2 ml volume of test and control was seeded onto at least 90% confluent INT 407 cell monolayer in each of the six well culture plates and further incubated at 37° C. for 2 hours to allow bacterial invasion to occur.

Upon completion of incubation, INT 407 monolayer cells in each well was washed twice with PBS and the INT 407 cell adhered bacterial cells, including the remaining extracellular bacteria were killed by treating for 2 hours with 2 ml/well of gentamycin at a concentration of 100 micrograms/ml. On completion of gentamycin treatment the cell monolayer in each well was again washed thrice with PBS and the infected INT 407 cells were lysed by treating with 1% of Triton X-100 in PBS at 37° C. for 10 minutes in a total volume of 400 ul/well to release the intracellular *bacterium*. Released *bacterium* was subsequently enumerated by plating on selective XLT agar media. Sample data is given in Table 14.

TABLE 14

| | Test supernatant from Induced secretory Vector having Camelid Antibody fragment insert in plasmid | Test Control supernatant from Induced secretory empty vector | 2xYT growth Media control |
|---|---|---|---|
| No. of INT 407 Internalized *Salmonella* Colonies (CFU) | 4 | TNTC | TNTC |

TNTC: Colonies too numerous to count

Example 9

*Salmonella* Inhibition by Modified *L. reuteri*

Approximately $1.25 \times 10^8$ CFU (Colony forming Units) of modified *L. reuteri* having surface expressed *Salmonella* specific camelid heavy chain antibodies were mixed with approximately $1.25 \times 10^8$ CFU of *Salmonella* challenge dose.

One of the two controls comprised of approximately $1.25 \times 10^8$ CFU of the host parental strain of *L. reuteri* mixed with approximately $1.25 \times 10^8$ CFU of *Salmonella* challenge dose and the second control comprised of only the same *Salmonella* challenge dose mixed with blank cell culture media without any *Lactobacillus bacterium*, all in a total volume of 2 ml each.

The test bacterial mixtures including the two controls were incubated at 37° C. at 110 RPM for two-hours. Subsequently, entire contents of 2 ml of each test mixture including the two controls were seeded onto at least 90% confluent INT 407 cell monolayer in each well of the six well culture plates and further incubated at 37° C. for two-hours to allow bacterial invasion to occur.

Upon completion of incubation, TNT 407 monolayer cells in each well was washed twice with 1xPBS and the INT 407 cell adhered bacterial cells, including the remaining extracellular bacteria were killed by treating for two-hours with 2 ml/well of gentamycin (Abbott Healthcare Pvt. Ltd.) at a concentration of 100 µg/ml. On completion of gentamycin treatment, the cell monolayer in each well was washed thrice with 1xPBS and the infected INT 407 cells were lysed by treating with 1% Triton X-100 in PBS at 37° C. for 10 minutes in a total volume of 400 µl/well to release the intracellular *bacterium*. Released *bacterium* was subsequently enumerated by plating on selective XLT agar media. Results are summarized in the Table 15 (polynucleotide encoding antibody having amino acid sequence as set forth in SEQ ID NO: 55), Table 16 (polynucleotide encoding antibody having amino acid sequence as set forth in SEQ ID NO: 61), and Table 17 (polynucleotide encoding antibody having amino acid sequence as set forth in SEQ ID NO: 63 or 69) below.

TABLE 15

| Sr. No | Sample | No. of INT 407 Internalized *Salmonella* Colonies (CFU) | *Salmonella* INT 407 Cell Invasion Reduction Percent |
|---|---|---|---|
| 1 | Modified *L. reuteri* construct With antibody Expressed in MuB | 186 | 83.91 by the modified construct |
| 2 | Parental *L. reuteri* strain | 1018 | 11.93 by the parental strain |

TABLE 15-continued

| Sr. No | Sample | No. of INT 407 Internalized Salmonella Colonies (CFU) | Salmonella INT 407 Cell Invasion Reduction Percent |
|---|---|---|---|
| 3 | 2xYT growth media Control. | 1156 | — |

TABLE 16

| Sr. No | Sample | No. of INT 407 Internalized Salmonella Colonies (CFU) | Salmonella INT 407 Cell Invasion Reduction Percent |
|---|---|---|---|
| 1 | Modified L. reuteri construct With antibody Expressed in CnBP | 229 | 78.97 by the modified construct |
| 2 | Parental L. reuteri strain | 1089 | 12.94 by the parental strain |
| 3 | 2xYT growth media Control. | 1251 | — |

TABLE 17

| Sr. No | Sample | No. of INT 407 Internalized Salmonella Colonies (CFU) | Salmonella INT 407 Cell Invasion Reduction Percent |
|---|---|---|---|
| 1 | Modified L. reuteri construct With antibody Expressed in CnBP& MuB | 25 | 98.01 by the modified construct |
| 2 | Parental L. reuteri strain | 1093 | 13.32 by the parental strain |
| 3 | 2xYT growth media Control. | 1261 | — |

Example 10

Co-Culture Assay of *Salmonella* and *L. reuteri* Modified Strain with VHH Antibody Insert in MuB The antagonistic, aggregating and growth inhibitory effect of the modified *Lactobacillus reuteri* constructs in comparison with the parental strain 1LB7 *L. reuteri* strain on *Salmonella* was observed on the basis of reduction in *Salmonella* colony forming units (CFU), when grown (co-cultured) with the *Lactobacillus* cultures. Growing cultures of *Salmonella* and *Lactobacillus* were cultured together with a fixed CFU of $1.5 \times 10^4$ *Salmonella* and $5 \times 10^6$ *Lactobacillus*, in equal volumes of PBS. Sampling was performed every 2 hours up to six hours and the samples were plated on *Salmonella* selective XLT agar media, to enumerate the viable *Salmonella* bacterium in the sample of the test mixtures. The growth inhibitory effect is compared with the untransformed parental host *L. reuteri* 1LB7 and media control. Table 18 (polynucleotide encoding antibody having amino acid sequence as set forth in SEQ ID NO: 55) shows the results.

TABLE 18

| Sampling Interval | Modified Test Strain Having Surface Displayed Camelid Antibody. | Untransformed Parental Host 1LB7 Control | Bacterial Growth Media Control | % Reduction Of Salmonella in Co-Culture With Parental Host Strain | % Reduction Of Salmonella in Co-Culture With Modified Strain. |
|---|---|---|---|---|---|
| 0 hr | 42 | 64 | 74 | — | — |
| 2 hrs | 45 | 83 | 92 | 9.78 | 51.08 |
| 4 hrs | 115 | 204 | 299 | 31.77 | 61.53 |
| 6 hrs | 256 | 600 | 700 | 14.28 | 63.42 |

Example 11

Co-Culture Assay of *Salmonella* and *L. reuteri* Modified Strain with VHH Antibody Insert in MuB and CnBP.

Table 19 depicts the results of the effect of a modified *L. reuteri* strain having surface displayed camelid antibody in MuB and CnBP (polynucleotide encoding antibody having amino acid sequence as set forth in SEQ ID NO: 63 or 69).

TABLE 19

| Sampling Interval | Modified Test Strain Having Surface Displayed Camelid Antibody. | Untransformed Parental Host 1LB7 Control | Media Control | % Reduction Of Salmonella in Co-Culture With Parental Host Strain | % Reduction Of Salmonella in Co-Culture With Modified Strain. |
|---|---|---|---|---|---|
| 0 hr | 31 | 33 | 30 | — | — |
| 2 hrs | 30 | 42 | 64 | 34.37 | 53.12 |

TABLE 19-continued

| Sampling Interval | Modified Test Strain Having Surface Displayed Camelid Antibody. | Untransformed Parental Host 1LB7 Control | Media Control | % Reduction Of Salmonella in Co-Culture With Parental Host Strain | % Reduction Of Salmonella in Co-Culture With Modified Strain. |
|---|---|---|---|---|---|
| 4 hrs | 40 | 93 | 132 | 29.54 | 69.69 |
| 6 hrs | 130 | 291 | 365 | 20.27 | 64.38 |

24 hrs observation:

Example 12

Co-Culture Assay of *Salmonella* and *L. reuteri* Modified Strain with VHH Antibody Insert in CnBP.

Table 20 depicts the results of the effect of a modified *L. reuteri* strain having surface displayed camelid antibody in CnBP (polynucleotide encoding antibody having amino acid sequence as set forth in SEQ ID NO: 61).

TABLE 20

| Sampling Interval | Modified Test Strain Having Surface Displayed Camelid Antibody. | Untransformed Parental Host 1LB7 Control | Media Control | % Reduction Of Salmonella in Co-Culture With Parental Host Strain | % Reduction Of Salmonella in Co-Culture With Modified Strain. |
|---|---|---|---|---|---|
| 0 hr | 41 | 35 | 32 | | |
| 2 hrs | 31 | 51 | 61 | 16.31 | 49.18 |
| 4 hrs | 53 | 108 | 128 | 15.62 | 58.59 |
| 6 hrs | 129 | 242 | 322 | 24.84 | 59.93 |

Example 13

Usage of Anti-*Salmonella* VHH Antibodies and Fragments Thereof in Milk Based Food Preparation To test the usage of anti-*Salmonella* VHH antibodies and fragments thereof as described in the present disclosure in various food preparation formulations, a formulation was made by blending the VHH antibody fragments, obtained from the culture supernatant of the induced secretory *bacillus* vector into 70% of skimmed milk powder dissolved in ultrapure water. Induced secretory *bacillus* vector culture supernatant solution was used as neat and as 1:2 dilution in PBS. The antibody solution was added at the rate of 10% in a volume of 1.5 ml of the 70% skimmed milk solution. After addition of the antibody solution, the skimmed milk solution was vortexed at 500 rpm for 30 seconds five times. Negative control comprised of 10% induced culture supernatant of secretory *bacillus* vector without the antibody gene fragment insert.

Subsequently, *Salmonella* bacterium at a challenge dose of 10,000 organisms in 10 μl was added to the skimmed milk solution having the antibodies, as well as the control without antibodies. Representative samples from the skimmed milk test solutions with added antibodies in two concentrations, i.e. the neat solution and the 1:2 diluted solutions, as well as the control were drawn and plated on XLT4 agar media to enumerate the *Salmonella* colony forming units. Table 21 shows the results of the assay in tabulated format.

TABLE 21

| Sampling Interval | Test- Culture supernatant from Induced secretory Vector having Camelid Antibody fragment insert in plasmid. | Test- Culture supernatant from Induced secretory Vector having Camelid Antibody fragment insert in plasmid, diluted 1:2 in PBS | Control- Culture supernatant from Induced secretory without antibody gene insert | Control- 2xYT growth media |
|---|---|---|---|---|
| 0 hr. | 68 | 68 | 58 | 49 |
| 2 hr. | 118 | 350 | 945 | 1103 |
| 4 hr. | 445 | 850 | TNTC | TNTC |

TNTC: colonies too numerous to count

FIG. 1 depicts the graphical representation of *Salmonella* colony forming units at various time points. It can be inferred from FIG. 1 that the number of *Salmonella* colony forming units is significantly less in samples that have the supernatant from the induced secretory vector Having camelid antibody than samples with no antibody. The number of colonies in cultures without antibody were too numerous to count (TNTC). As FIG. 1 suggests, by 4 hours, the fold inhibition of *Salmonella* colony forming units in culture that has supernatant from the induced secretory vector is at least more than four-fold. This data suggests that the antibody fragments are stable and retain their function when incorporated into a food preparation, and is able to substantially reduce the *Salmonella* colony forming units.

Example 14

Usage of Anti-*Salmonella* VHH Antibodies and Fragments Thereof in an Egg Based Food Preparation A formulation of egg yolk was developed with the culture supernatants of induced secretory *bacillus* vector having camelid VHH genes. Egg yolk was diluted 1:2 in PBS solution comprising of 2% Tween 80. To this egg yolk solution, VHH antibody test solution was added at a rate of 20% and the mixture was vortexed at 1000 rpm for 30 seconds five times. The culture supernatant from the induced empty secretory *bacillus* vector was used as control. Representative samples were drawn from the test egg yolk formulation and the control at two hour intervals from the start till four hours and were immediately plated in XLT4 agar media to enumerate the *Salmonella* colony forming units. Table 22 shows the results in tabulated format.

TABLE 22

| Sampling Interval | Test- Culture supernatant from Induced secretory *bacillus* vector having Camelid aAntibody fragment gene insert in plasmid | Control - Culture supernatant from Induced secretory *bacillus* vector without Camelid antibody gene insert in plasmid | Control-2xYT growth Media control |
|---|---|---|---|
| 0 hr. | 363 | 373 | 362 |
| 2 hr. | 620 | 1133 | 1456 |
| 4 hr. | 924 | 1960 | 2376 |

Figure 2:
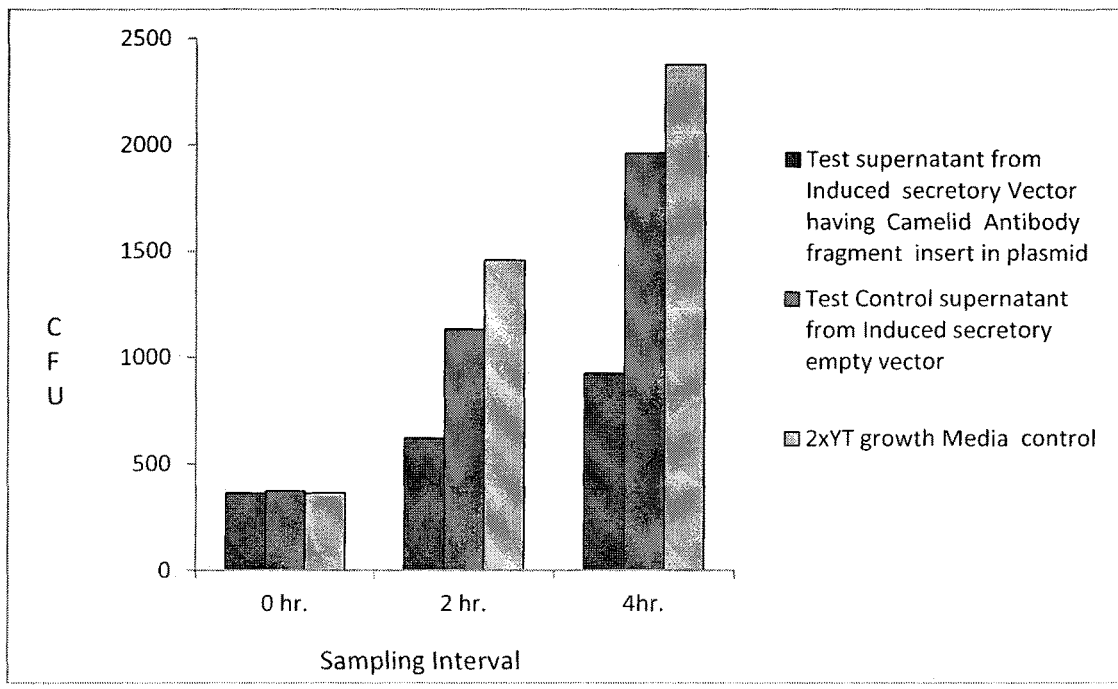
FIG. 2 depicts the effect of secreted anti-*Salmonella* camelid VHH antibody fragments in an egg based formulation on growth of *Salmonella*, in accordance with an embodiment of the present disclosure.

FIG. 2 depicts the graphical representation of *Salmonella* colony forming units at various time points. It can be inferred from FIG. 2 that by four hours, the *Salmonella* colony forming units is decreased by more than two-fold in case of the culture comprising supernatant from induced secretory vector having camelid antibody fragment insert in plasmid. This data suggests that the antibody fragments are stable and retain their function when incorporated into a food preparation, and is able to substantially reduce the *Salmonella* colony forming units.

Example 15

Efficacy of Heat-Inactivated Modified *Lactobacillus reuteri* on Inhibition of *Salmonella* Growth The antagonistic, aggregating and growth inhibitory effect of both the heat inactivated modified *Lactobacillus* construct and the parental *Lactobacillus reuteri* strain 1LB7 on *Salmonella* was observed on the basis of reduction in *Salmonella* colony forming units (CFU) during co-culture.

Growing cultures of *Lactobacillus* were inactivated by heating for 30 minutes at 85° C. Complete inactivation was checked by carrying out three blind passages of the inactivated cultures in MRS growth media. Growing cultures of *Salmonella* and the inactivated modified *Lactobacillus*, including the control host parental strain 1LB7 were mixed together at a rate of 1×10$^4$ CFU of *Salmonella* bacterium with 1.5×10$^6$ CFU of *Lactobacillus* bacterium. Representative culture samples starting from the 0 hour, were taken every 2 hours up to 6 hours, and then at 24 hours. The samples were plated on XLT4 agar media to enumerate the *Salmonella* bacterium present in the samples. The antagonistic, aggregating and growth inhibitory effect against *Salmonella* by the inactivated modified and transformed *Lactobacillus reuteri* strain was compared with the inactivated untransformed parental host strain 1LB7.

Table 23 shows the results in tabulated format

TABLE 23

| Sampling Interval | Test- Inactivated Modified *L. reuteri* Strain having VHH antibody gene insert in MuB | Control-Inactivated Untransformed *L. reuteri* Parental Host strain 1LB7 |
|---|---|---|
| 0 hr | 54 | 62 |
| 2 hrs | 35 | 120 |
| 4 hrs | 68 | 475 |
| 6 hrs | 78 | 752 |
| 24 hrs | 121 | Mat |

Mat: complete bacterial growth on the plate with merged colonies

Figure 3:
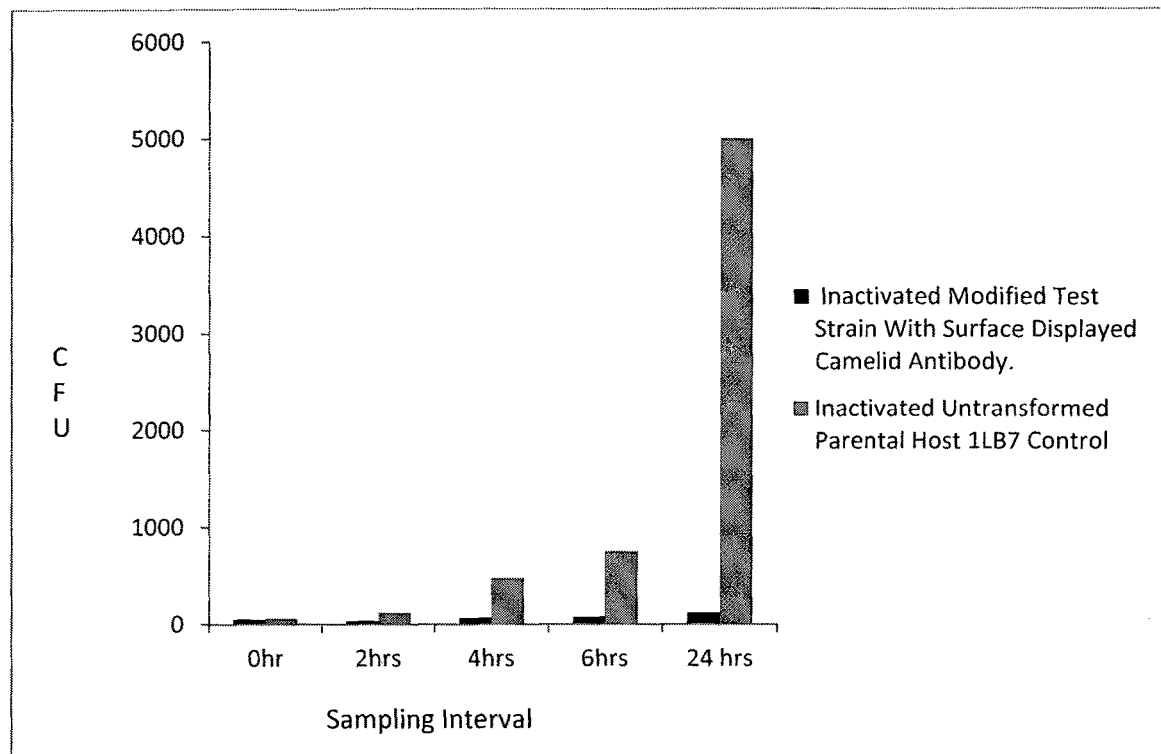
FIG. 3 depicts the effect of heat inactivated modified *Lactobacillus reuteri* expressing on its surface anti-*Salmonella* camelid VHH antibody fragment on growth of *Salmonella*, in accordance with an embodiment of the present disclosure.

FIG. 3 depicts the graphical representation of *Salmonella* colony forming units when co-cultured with heat-inactivated modified *Lactobacillus*. It can be inferred from FIG. 3 that even up to 24 hours, the inactivated modified *Lactobacillus* strain that displays on its surface the camelid VHH antibody is able to effectively inhibit the growth of *Salmonella*. This data suggests that the modified *Lactobacillus* is effective even when it is heat-inactivated and incapable of growth and self-replication.

Example 16

Anti-*Salmonella* Activity of Camelid VHH Antibodies Against *Salmonella* Serovars

*Bacillus subtilis* secretory vector with cloned camelid antibody gene fragments were induced with IPTG (1 mM, 12 hours at 37° C. on shaker at 180 RPM) and the culture supernatant was collected by centrifugation and filtered through 0.45 um filter. Similar treatment was given to the supernatant of the induced plasmid, devoid of camelid heavy chain antibody gene fragment insert and the 2xYT growth media in which the *Bacillus* cultures was grown and these were used as controls.

Test supernatant and the two controls were subsequently challenged with *Salmonella* serovars, having bacterium inoculums of approximately 10,000 cells in a total test volume of 2 ml and incubated at 37° C. under 180 r.p.m shaking. Representative samples from the test and the two control reactions were drawn at 0, 2, 4, 6 and 24 hours of incubation and were plated on selective XLT4 agar media to enumerate the *Salmonella* colony forming units. Table 24-27 denote the results using different *Salmonella* serovars.

TABLE 24

**Anti *Salmonella* Biological activity on *Salmonella typhimurium***

| Sampling Interval | Test- Culture supernatant from Induced secretory *bacillus* vector having Camelid antibody gene fragment insert in plasmid | Control- Culture supernatant from Induced secretory *bacillus* vector without Camelid antibody gene insert in plasmid | Control- 2xYT growth Media |
|---|---|---|---|
| 0 | 98 | 109 | 114 |
| 2 | 91 | 295 | 398 |
| 4 | 63 | TNTC | TNTC |
| 6 | 48 | TNTC | TNTC |
| 24 | 1 | Mat | Mat |

TNTC: Colonies too numerous to count.
Mat: Complete Bacterial growth on the plate with merged colonies.

TABLE 25

**Anti *Salmonella* Biological activity on *Salmonella gallinarum***

| Sampling Interval | Test- Culture supernatant from Induced secretory *bacillus* vector having Camelid antibody gene fragment insert in plasmid | Control- Culture supernatant from Induced secretory *bacillus* vector without Camelid antibody gene insert in plasmid | Control- 2xYT growth Media |
|---|---|---|---|
| 0 hrs | 85 | 89 | 93 |
| 2 hrs | 63 | 119 | 166 |
| 4 hrs | 48 | 146 | 190 |
| 6 hrs | 49 | TNTC | TNTC |
| 24 hrs | 2 | Mat | Mat |

TNTC: Colonies too numerous to count.
Mat: Complete Bacterial growth on the plate with merged colonies.

TABLE 26

**Anti *Salmonella* Biological activity on *Salmonella newport***

| Sampling Interval | Test- Culture supernatant from Induced secretory *bacillus* vector having Camelid antibody gene fragment insert in plasmid | Control- Culture supernatant from Induced secretory *bacillus* vector without Camelid antibody gene insert in plasmid | Control- 2xYT growth Media |
|---|---|---|---|
| 0 hrs | 42 | 52 | 57 |
| 2 hrs | 20 | 100 | 149 |
| 4 hrs | 4 | TNTC | TNTC |
| 6 hrs | 3 | Mat | Mat |
| 24 hrs | 0 | Mat | Mat |

TNTC: Colonies too numerous to count.
Mat: Complete Bacterial growth on the plate with merged colonies.

TABLE 27

**Anti *Salmonella* Biological activity on *Salmonella abony***

| Sampling Interval | Test- Culture supernatant from Induced secretory *bacillus* vector having Camelid antibody gene fragment insert in plasmid | Control- Culture supernatant from Induced secretory *bacillus* vector without Camelid antibody gene insert in plasmid | Control- 2xYT growth Media |
|---|---|---|---|
| 0 hrs | 76 | 74 | 83 |
| 2 hrs | 43 | 100 | 324 |
| 4 hrs | 5 | TNTC | TNTC |
| 6 hrs | 2 | Mat | Mat |
| 24 hrs | 0 | Mat | Mat |

TNTC: Colonies too numerous to count.
Mat: Complete Bacterial growth on the plate with merged colonies.

Figure 4:
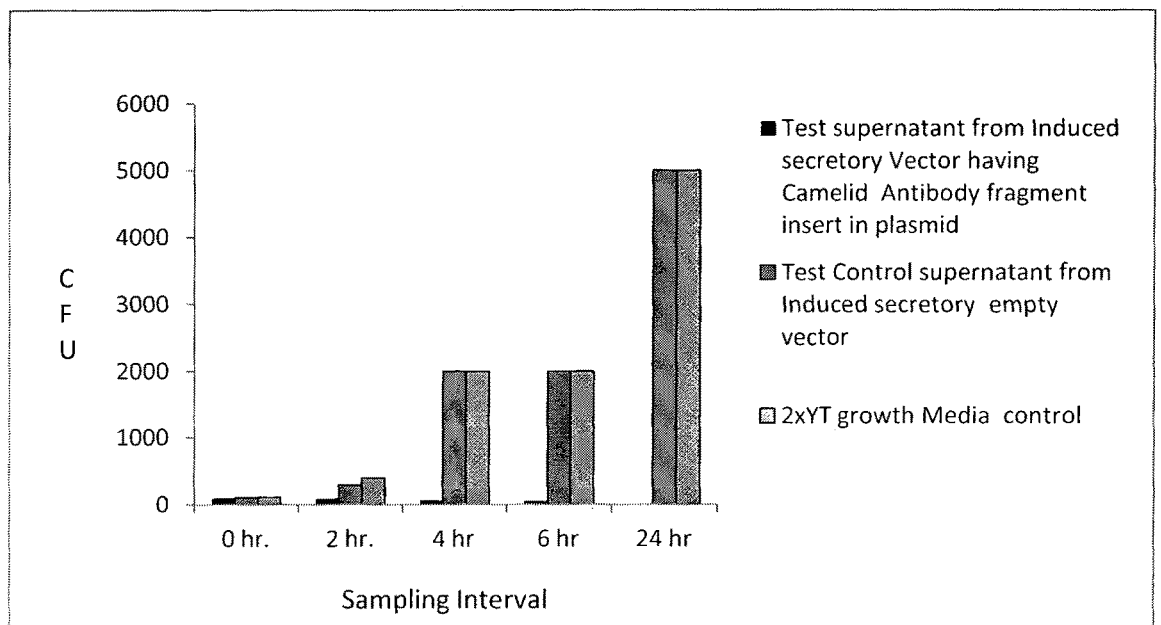
FIG. 4 depicts the effect of secreted anti-*Salmonella* camelid VHH antibody fragments on growth of *Salmonella typhimurium*, in accordance with an embodiment of the present disclosure.

FIG. 4 show that the supernatant containing the secreted camelid VHH antibodies effectively inhibits *Salmonella typhimurium* growth up to 24 hours.

Figure 5:
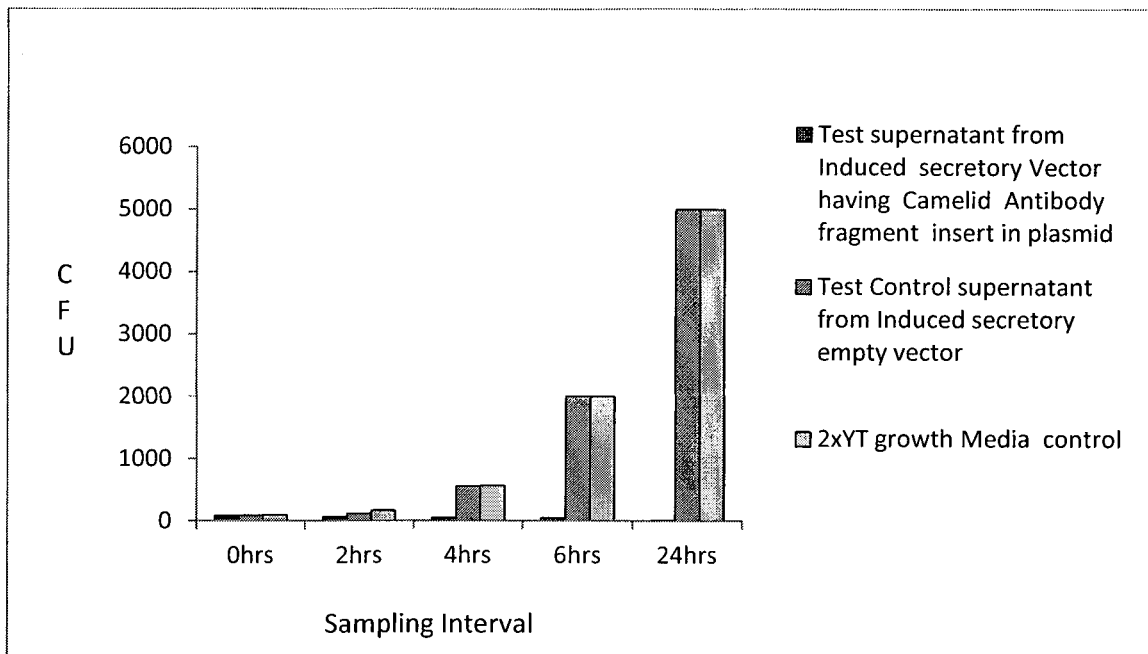
FIG. 5 depicts the effect of secreted anti-*Salmonella* camelid VHH antibody fragments on growth of *Salmonella gallinarium*, in accordance with an embodiment of the present disclosure.

FIG. 5 show that the supernatant containing the secreted camelid. VHH antibodies effectively inhibits *Salmonella gallinarium* growth up to 24 hours.

Figure 6:
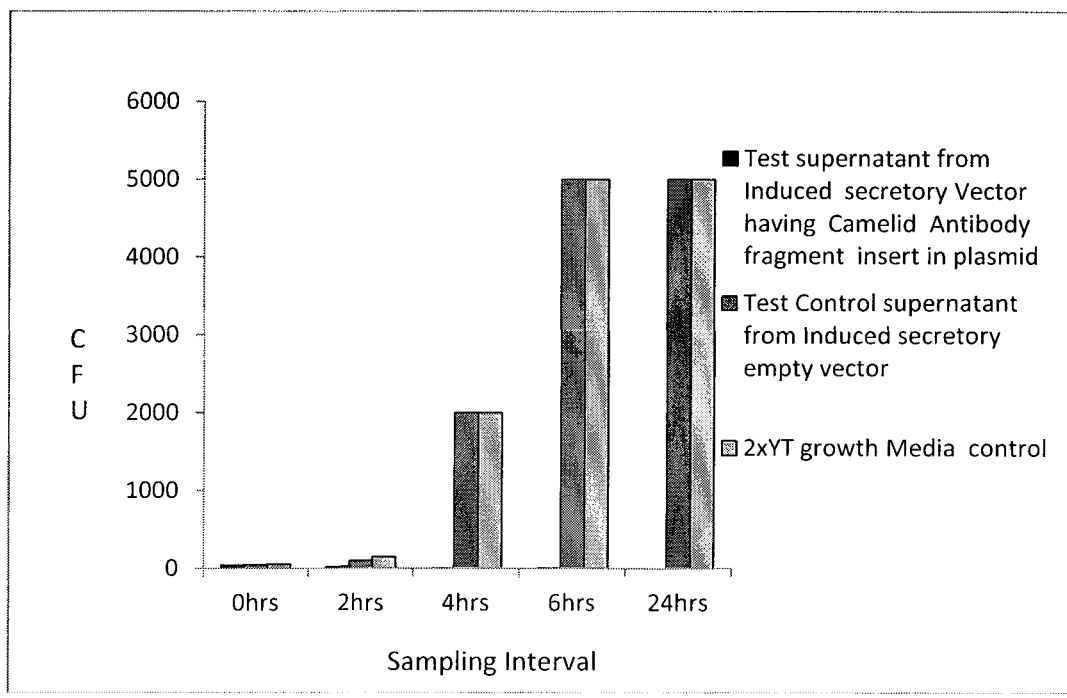
FIG. 6 depicts the effect of secreted anti-*Salmonella* camelid VHH antibody fragments on growth of *Salmonella newport*, in accordance with an embodiment of the present disclosure.

FIG. 6 show that the supernatant containing the secreted camelid VHH antibodies effectively inhibits *Salmonella newport* growth up to 24 hours.

Figure 7:
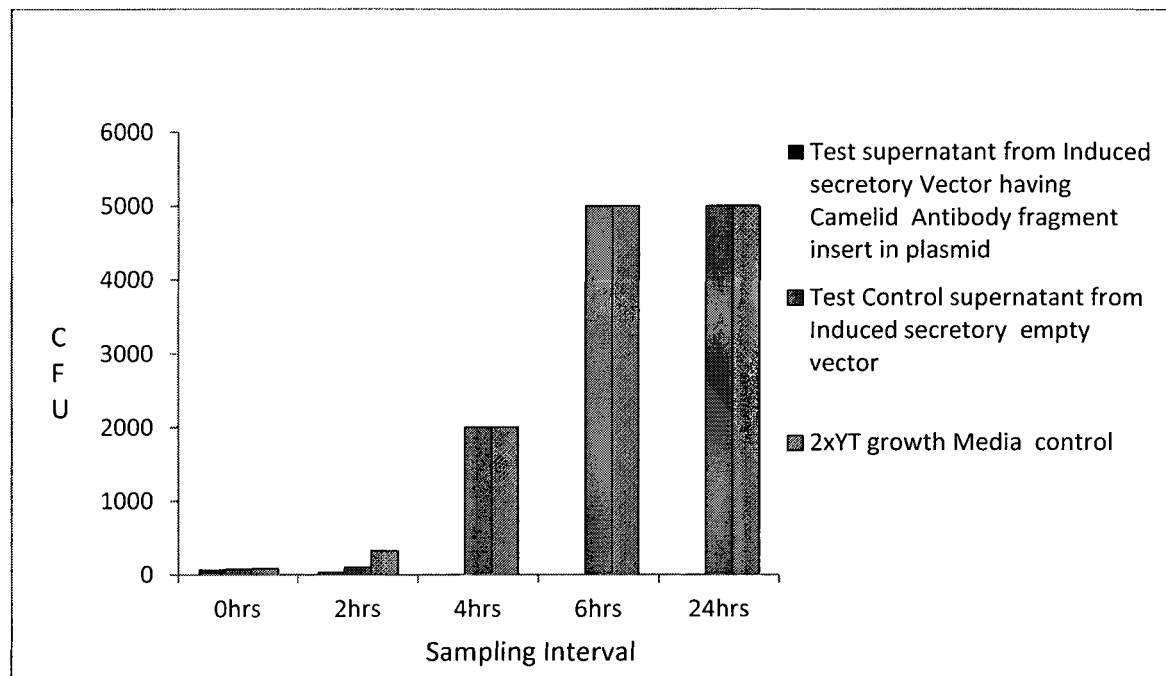
FIG. 7 depicts the effect of secreted anti-*Salmonella* camelid VHH antibody fragments on growth of *Salmonella abony*, in accordance with an embodiment of the present disclosure.

FIG. 7 show that the supernatant containing the secreted camelid VHH antibodies effectively inhibits *Salmonella abony* growth up to 24 hours.

Overall, FIGS. 4-7 collectively show that the camelid VHH antibody is effective against a wide range of *Salmonella* species members, and can be used as a pan inhibitor of *Salmonella* growth and infection.

We claim:

1. A single chain antibody or a fragment thereof raised against *Salmonella* surface protein, OmpD, the antibody consisting of the amino acid sequence of SEQ ID NO:61.

2. A formulation comprising the single chain antibody or a fragment thereof of claim 1, and at least one of a diluent, excipient or a carrier.

3. A method of inhibiting the in vitro growth of *Salmonella*, the method comprising contacting the formulation of claim 2 with a sample containing *Salmonella*, wherein *Salmonella* is selected from the group consisting of *Salmonella typhimurium, Salmonella gallinarium, Salmonella newport*, and *Salmonella abony*.

4. A single chain antibody or a fragment thereof raised against *Salmonella* surface protein, OmpD, the antibody consisting of the amino acid sequence of SEQ ID NO:61, wherein the single chain antibody is encoded by a polynucleotide consisting of the nucleic acid sequence of SEQ ID NO:62.

5. A food product comprising the single chain antibody or a fragment thereof of claim 4.

* * * * *

SEQUENCE LISTING

```
<160> NUMBER OF SEQ ID NOS: 272

<210> SEQ ID NO 1
<211> LENGTH: 7
<212> TYPE: PRT
<213> ORGANISM: artificial sequence
<220> FEATURE:
<223> OTHER INFORMATION: antibody A CDR1

<400> SEQUENCE: 1

Gly His Thr Tyr Tyr Gly Pro
1               5

<210> SEQ ID NO 2
<211> LENGTH: 7
<212> TYPE: PRT
<213> ORGANISM: artificial sequence
<220> FEATURE:
<223> OTHER INFORMATION: antibody A CDR2

<400> SEQUENCE: 2

Ile Ser Pro Ser Gly Gly Ser
1               5

<210> SEQ ID NO 3
<211> LENGTH: 15
<212> TYPE: PRT
<213> ORGANISM: artificial sequence
<220> FEATURE:
<223> OTHER INFORMATION: antibody A CDR3

<400> SEQUENCE: 3

Asp Ser Gly Gly Leu Cys Ser His Arg Glu Arg Asp Tyr Asp Ile
1               5                   10                  15

<210> SEQ ID NO 4
<211> LENGTH: 8
<212> TYPE: PRT
<213> ORGANISM: artificial sequence
<220> FEATURE:
<223> OTHER INFORMATION: antibody B CDR1

<400> SEQUENCE: 4

Gly Ser Glu Tyr Tyr Gly Ser Pro
1               5

<210> SEQ ID NO 5
<211> LENGTH: 8
<212> TYPE: PRT
<213> ORGANISM: artificial sequence
<220> FEATURE:
<223> OTHER INFORMATION: antibody B CDR2

<400> SEQUENCE: 5

Ile Val Pro Ile Gly Gly Ser Val
1               5
```

```
<210> SEQ ID NO 6
<211> LENGTH: 8
<212> TYPE: PRT
<213> ORGANISM: artificial sequence
<220> FEATURE:
<223> OTHER INFORMATION: antibody C CDR1

<400> SEQUENCE: 6

Gly Phe Gly Ile Gly Ser Phe Pro
1               5

<210> SEQ ID NO 7
<211> LENGTH: 8
<212> TYPE: PRT
<213> ORGANISM: artificial sequence
<220> FEATURE:
<223> OTHER INFORMATION: antibody C CDR2

<400> SEQUENCE: 7

Ile Gly Ser Asp Tyr Thr Thr His
1               5

<210> SEQ ID NO 8
<211> LENGTH: 9
<212> TYPE: PRT
<213> ORGANISM: artificial sequence
<220> FEATURE:
<223> OTHER INFORMATION: antibody CDR3

<400> SEQUENCE: 8

Asp Val Leu Asp Tyr His Pro Asp Leu
1               5

<210> SEQ ID NO 9
<211> LENGTH: 8
<212> TYPE: PRT
<213> ORGANISM: artificial sequence
<220> FEATURE:
<223> OTHER INFORMATION: antibody D CDR1

<400> SEQUENCE: 9

Lys Trp Ser Tyr Thr Tyr Tyr Cys
1               5

<210> SEQ ID NO 10
<211> LENGTH: 6
<212> TYPE: PRT
<213> ORGANISM: artificial sequence
<220> FEATURE:
<223> OTHER INFORMATION: antibody D CDR2

<400> SEQUENCE: 10

Ile Asp Ser Glu Gly Thr
1               5

<210> SEQ ID NO 11
<211> LENGTH: 16
<212> TYPE: PRT
<213> ORGANISM: artificial sequence
<220> FEATURE:
<223> OTHER INFORMATION: antibody D CDR3

<400> SEQUENCE: 11

Gly Gly Tyr Cys Leu Arg Pro Arg Gln Leu Ala Ala Asp Tyr Glu Tyr
1               5                   10                  15
```

```
<210> SEQ ID NO 12
<211> LENGTH: 8
<212> TYPE: PRT
<213> ORGANISM: artificial sequence
<220> FEATURE:
<223> OTHER INFORMATION: antibody E CDR1

<400> SEQUENCE: 12

Gly Phe Gly Ile Gly Ser Phe Ala
1               5

<210> SEQ ID NO 13
<211> LENGTH: 8
<212> TYPE: PRT
<213> ORGANISM: artificial sequence
<220> FEATURE:
<223> OTHER INFORMATION: antibody H CDR1

<400> SEQUENCE: 13

Gly Asp Ser Ile Thr Thr Tyr His
1               5

<210> SEQ ID NO 14
<211> LENGTH: 8
<212> TYPE: PRT
<213> ORGANISM: artificial sequence
<220> FEATURE:
<223> OTHER INFORMATION: antibody H CDR2

<400> SEQUENCE: 14

Ile Asn Asp Asp Ala Asn Ser Arg
1               5

<210> SEQ ID NO 15
<211> LENGTH: 18
<212> TYPE: PRT
<213> ORGANISM: artificial sequence
<220> FEATURE:
<223> OTHER INFORMATION: antibody H CDR3

<400> SEQUENCE: 15

Asp Leu Arg Cys Val Pro Gly Thr Asp Ser Gly His Pro Tyr Ser Tyr
1               5                   10                  15

Asn Tyr

<210> SEQ ID NO 16
<211> LENGTH: 7
<212> TYPE: PRT
<213> ORGANISM: artificial sequence
<220> FEATURE:
<223> OTHER INFORMATION: antibody I CDR2

<400> SEQUENCE: 16

Ile Ser Pro Ile Gly Gly Ser
1               5

<210> SEQ ID NO 17
<211> LENGTH: 6
<212> TYPE: PRT
<213> ORGANISM: artificial sequence
<220> FEATURE:
<223> OTHER INFORMATION: antibody J CDR2

<400> SEQUENCE: 17

Ile Pro Ile Gly Gly Ser
1               5
```

<210> SEQ ID NO 18
<211> LENGTH: 6
<212> TYPE: PRT
<213> ORGANISM: artificial sequence
<220> FEATURE:
<223> OTHER INFORMATION: antibody K CDR2

<400> SEQUENCE: 18

Ile Pro Ile Gly Gly Ser
1               5

<210> SEQ ID NO 19
<211> LENGTH: 9
<212> TYPE: PRT
<213> ORGANISM: artificial sequence
<220> FEATURE:
<223> OTHER INFORMATION: antibody M CDR1

<400> SEQUENCE: 19

Ser Glu Tyr Thr Ala Ile Thr Tyr Cys
1               5

<210> SEQ ID NO 20
<211> LENGTH: 9
<212> TYPE: PRT
<213> ORGANISM: artificial sequence
<220> FEATURE:
<223> OTHER INFORMATION: antibody M CDR2

<400> SEQUENCE: 20

Ile Asn Arg Gly Gly Gly Ser Thr Tyr
1               5

<210> SEQ ID NO 21
<211> LENGTH: 14
<212> TYPE: PRT
<213> ORGANISM: artificial sequence
<220> FEATURE:
<223> OTHER INFORMATION: antibody M CDR3

<400> SEQUENCE: 21

Lys Gln Thr Gly Asp Cys Gly Ile Phe Gln Phe Phe Gly Asn
1               5                   10

<210> SEQ ID NO 22
<211> LENGTH: 8
<212> TYPE: PRT
<213> ORGANISM: artificial sequence
<220> FEATURE:
<223> OTHER INFORMATION: antibody P CDR1

<400> SEQUENCE: 22

Gly Ser Thr Ala Ser Met Tyr Cys
1               5

<210> SEQ ID NO 23
<211> LENGTH: 7
<212> TYPE: PRT
<213> ORGANISM: artificial sequence
<220> FEATURE:
<223> OTHER INFORMATION: antibody M CDR2

<400> SEQUENCE: 23

Ile Ser Gly Asp Asp Lys Gly
1               5

<210> SEQ ID NO 24
<211> LENGTH: 18
<212> TYPE: PRT
<213> ORGANISM: artificial sequence
<220> FEATURE:
<223> OTHER INFORMATION: antibody P CDR3

<400> SEQUENCE: 24

Asp Ala Arg Ala Thr Thr Thr Gly Glu Arg Leu His Ala Arg Thr Tyr
1               5                   10                  15

Glu Phe

<210> SEQ ID NO 25
<211> LENGTH: 8
<212> TYPE: PRT
<213> ORGANISM: artificial sequence
<220> FEATURE:
<223> OTHER INFORMATION: antibody Q CDR1

<400> SEQUENCE: 25

Gly Asp Thr Leu Ser Thr Tyr Cys
1               5

<210> SEQ ID NO 26
<211> LENGTH: 8
<212> TYPE: PRT
<213> ORGANISM: artificial sequence
<220> FEATURE:
<223> OTHER INFORMATION: antibody Q CDR2

<400> SEQUENCE: 26

Ile Tyr Arg Leu Arg Asp Met Thr
1               5

<210> SEQ ID NO 27
<211> LENGTH: 17
<212> TYPE: PRT
<213> ORGANISM: artificial sequence
<220> FEATURE:
<223> OTHER INFORMATION: antibody Q CDR3

<400> SEQUENCE: 27

Arg Cys Val Arg Leu Phe Gly Thr Cys Gln Leu Val Glu Asp Phe Glu
1               5                   10                  15

Leu

<210> SEQ ID NO 28
<211> LENGTH: 24
<212> TYPE: DNA
<213> ORGANISM: artificial sequence
<220> FEATURE:
<223> OTHER INFORMATION: antibody A CDR1

<400> SEQUENCE: 28
ggtcatacgt attatggacc ttgt                                      24

<210> SEQ ID NO 29
<211> LENGTH: 20
<212> TYPE: DNA
<213> ORGANISM: artificial sequence
<220> FEATURE:
<223> OTHER INFORMATION: antibody A CDR2

<400> SEQUENCE: 29
attagtccta gtggtgggag                                           20

```
<210> SEQ ID NO 30
<211> LENGTH: 45
<212> TYPE: DNA
<213> ORGANISM: artificial sequence
<220> FEATURE:
<223> OTHER INFORMATION: antibody A CDR3

<400> SEQUENCE: 30
gattcagggg gactctgcag ccatcgtgag cgcgactatg acatt            45

<210> SEQ ID NO 31
<211> LENGTH: 23
<212> TYPE: DNA
<213> ORGANISM: artificial sequence
<220> FEATURE:
<223> OTHER INFORMATION: antibody B CDR1

<400> SEQUENCE: 31
gggttccgaa tattatggtt ccc                                    23

<210> SEQ ID NO 32
<211> LENGTH: 21
<212> TYPE: DNA
<213> ORGANISM: artificial sequence
<220> FEATURE:
<223> OTHER INFORMATION: antibody B CDR2

<400> SEQUENCE: 32
attgttccta ttggtgggag t                                      21

<210> SEQ ID NO 33
<211> LENGTH: 24
<212> TYPE: DNA
<213> ORGANISM: artificial sequence
<220> FEATURE:
<223> OTHER INFORMATION: antibody C CDR1

<400> SEQUENCE: 33
ggattcggaa tcggtagttt cccc                                   24

<210> SEQ ID NO 34
<211> LENGTH: 18
<212> TYPE: DNA
<213> ORGANISM: artificial sequence
<220> FEATURE:
<223> OTHER INFORMATION: antibody C CDR2

<400> SEQUENCE: 34
attggtagtg attatacg                                          18

<210> SEQ ID NO 35
<211> LENGTH: 26
<212> TYPE: DNA
<213> ORGANISM: artificial sequence
<220> FEATURE:
<223> OTHER INFORMATION: antibody C CDR3

<400> SEQUENCE: 35
gacgtacttg actaccaccc agattt                                 26

<210> SEQ ID NO 36
<211> LENGTH: 24
<212> TYPE: DNA
<213> ORGANISM: artificial sequence
<220> FEATURE:
<223> OTHER INFORMATION: antibody D CDR1
```

```
<400> SEQUENCE: 36
aaatggagct acacgtacta ttgt                                    24

<210> SEQ ID NO 37
<211> LENGTH: 17
<212> TYPE: DNA
<213> ORGANISM: artificial sequence
<220> FEATURE:
<223> OTHER INFORMATION: antibody D CDR2

<400> SEQUENCE: 37
attgatagtg aaggcac                                            17

<210> SEQ ID NO 38
<211> LENGTH: 52
<212> TYPE: DNA
<213> ORGANISM: artificial sequence
<220> FEATURE:
<223> OTHER INFORMATION: antibody D CDR3

<400> SEQUENCE: 38
caatggtggt tattgcctca gaccccgtca actcgccgcg gattatgagt at     52

<210> SEQ ID NO 39
<211> LENGTH: 24
<212> TYPE: DNA
<213> ORGANISM: artificial sequence
<220> FEATURE:
<223> OTHER INFORMATION: antibody E CDR1

<400> SEQUENCE: 39
ggattcggaa tcggtagttt cgcc                                    24

<210> SEQ ID NO 40
<211> LENGTH: 24
<212> TYPE: DNA
<213> ORGANISM: artificial sequence
<220> FEATURE:
<223> OTHER INFORMATION: antibody H CDR1

<400> SEQUENCE: 40
ggagattcca tcactaccta ccac                                    24

<210> SEQ ID NO 41
<211> LENGTH: 20
<212> TYPE: DNA
<213> ORGANISM: artificial sequence
<220> FEATURE:
<223> OTHER INFORMATION: antibody H CDR2

<400> SEQUENCE: 41
ataaatgatg atgctaattc                                         20

<210> SEQ ID NO 42
<211> LENGTH: 52
<212> TYPE: DNA
<213> ORGANISM: artificial sequence
<220> FEATURE:
<223> OTHER INFORMATION: antibody H CDR3

<400> SEQUENCE: 42
tttgaggtgc gtccctggga ccgactctgg tcatccttat tcgtataact ac     52

<210> SEQ ID NO 43
```

```
<211> LENGTH: 21
<212> TYPE: DNA
<213> ORGANISM: artificial sequence
<220> FEATURE:
<223> OTHER INFORMATION: antibody I CDR2

<400> SEQUENCE: 43
attagtccta ttggtgggag t                                              21

<210> SEQ ID NO 44
<211> LENGTH: 21
<212> TYPE: DNA
<213> ORGANISM: artificial sequence
<220> FEATURE:
<223> OTHER INFORMATION: antibody J CDR2

<400> SEQUENCE: 44
atgattccta ttggtgggag t                                              21

<210> SEQ ID NO 45
<211> LENGTH: 21
<212> TYPE: DNA
<213> ORGANISM: artificial sequence
<220> FEATURE:
<223> OTHER INFORMATION: antibody K CDR2

<400> SEQUENCE: 45
attattccta ttggtgggag t                                              21

<210> SEQ ID NO 46
<211> LENGTH: 24
<212> TYPE: DNA
<213> ORGANISM: artificial sequence
<220> FEATURE:
<223> OTHER INFORMATION: antibody M CDR1

<400> SEQUENCE: 46
gaatacaccg ctattaccta ctgt                                           24

<210> SEQ ID NO 47
<211> LENGTH: 18
<212> TYPE: DNA
<213> ORGANISM: artificial sequence
<220> FEATURE:
<223> OTHER INFORMATION: antibody M CDR2

<400> SEQUENCE: 47
atcaatcgcg gtggtggt                                                  18

<210> SEQ ID NO 48
<211> LENGTH: 46
<212> TYPE: DNA
<213> ORGANISM: artificial sequence
<220> FEATURE:
<223> OTHER INFORMATION: antibody M CDR3

<400> SEQUENCE: 48
gtacaaacag accggtgatt gtgggatctt ccaattcttt ggaaac                   46

<210> SEQ ID NO 49
<211> LENGTH: 24
<212> TYPE: DNA
<213> ORGANISM: artificial sequence
<220> FEATURE:
<223> OTHER INFORMATION: antibody P CDR1

<400> SEQUENCE: 49
```

```
ggatcgaccg ccagtatgta ctgc                                          24

<210> SEQ ID NO 50
<211> LENGTH: 21
<212> TYPE: DNA
<213> ORGANISM: artificial sequence
<220> FEATURE:
<223> OTHER INFORMATION: antibody P CDR2

<400> SEQUENCE: 50
attagtggag atgataaagg g                                             21

<210> SEQ ID NO 51
<211> LENGTH: 49
<212> TYPE: DNA
<213> ORGANISM: artificial sequence
<220> FEATURE:
<223> OTHER INFORMATION: antibody P CDR3

<400> SEQUENCE: 51
cgcgagcgac aacaactggt gaacgtctac acgcccggac gtacgaatt               49

<210> SEQ ID NO 52
<211> LENGTH: 24
<212> TYPE: DNA
<213> ORGANISM: artificial sequence
<220> FEATURE:
<223> OTHER INFORMATION: antibody Q CDR1

<400> SEQUENCE: 52
ggagataccc tcagtaccta ctgc                                          24

<210> SEQ ID NO 53
<211> LENGTH: 21
<212> TYPE: DNA
<213> ORGANISM: artificial sequence
<220> FEATURE:
<223> OTHER INFORMATION: antibody Q CDR2

<400> SEQUENCE: 53
atttatcgtc ttagggatat g                                             21

<210> SEQ ID NO 54
<211> LENGTH: 48
<212> TYPE: DNA
<213> ORGANISM: artificial sequence
<220> FEATURE:
<223> OTHER INFORMATION: antibody Q CDR3

<400> SEQUENCE: 54
tgtgtgcgac tattcggtac ttgtcagcta gtcgaagatt ttgaacta                48

<210> SEQ ID NO 55
<211> LENGTH: 126
<212> TYPE: PRT
<213> ORGANISM: artificial sequence
<220> FEATURE:
<223> OTHER INFORMATION: antibody A

<400> SEQUENCE: 55

Asp Val Gln Leu Gln Glu Ser Gly Gly Gly Ser Val Gln Ala Gly Gly
1               5                   10                  15

Ser Leu Thr Leu Ser Cys Leu Met Ser Gly His Thr Tyr Tyr Gly Pro
            20                  25                  30
```

Cys Val Gly Trp Phe Arg Gln Arg Pro Gly Lys Ala Arg Glu Gly Ile
         35                  40                  45

Ala Gln Ile Ser Pro Ser Gly Gly Ser Val Ser Tyr Ser Gly Gly Val
 50                  55                  60

Lys Gly Arg Phe Thr Ile Ser Arg Asp Asn Ser Lys Asn Thr Ile Ala
65                   70                  75                  80

Leu Ile Met Asn Asp Leu Val Pro Glu Asp Thr Ala Thr Tyr Tyr Cys
                 85                  90                  95

Ala Ala Asp Ser Gly Gly Leu Cys Ser His Arg Glu Arg Asp Tyr Asp
             100                 105                 110

Ile Trp Gly Gln Gly Thr Gln Val Thr Val Cys Ser Gly Arg
         115                 120                 125

<210> SEQ ID NO 56
<211> LENGTH: 379
<212> TYPE: DNA
<213> ORGANISM: artificial sequence
<220> FEATURE:
<223> OTHER INFORMATION: antibody A

<400> SEQUENCE: 56

```
atgtgcagct gcaggagtct gggggaggct cggtgcaggc tggaggctcc ctgacgctct    60
cttgtttaat gtctggtcat acgtattatg daccttgtgt gggttggttc cgccagcgtc   120
cagggaaagc gcgtgaggga atcgcacaga ttagtcctag tggtgggagt gttagttaca   180
gtggtggcgt gaagggccga ttcaccattt cccgagacaa ctccaagaat actattgctc   240
tcataatgaa cgacctcgtg cctgaagaca cggccactta ttattgcgca gcagattcag   300
ggggactctg cagccatcgt gagcgcgact atgacatttg gggccagggg acccaggtca   360
ccgtctgcag cggccgcac                                                 379
```

<210> SEQ ID NO 57
<211> LENGTH: 125
<212> TYPE: PRT
<213> ORGANISM: artificial sequence
<220> FEATURE:
<223> OTHER INFORMATION: antibody B

<400> SEQUENCE: 57

Asp Pro Asp Val His Leu Gln Asp Ser Gly Gly Gly Trp Val His Pro
 1               5                  10                  15

Gly Gly Ser Leu Thr Leu Ser Cys Leu Met Ser Gly Ser Glu Tyr Tyr
             20                  25                  30

Gly Ser Pro Val Gly Trp Phe Pro Gln Pro Pro Gly Lys Gly Arg Glu
         35                  40                  45

Glu Ile Ala Glu Ile Val Pro Ile Gly Gly Ser Val Ile Tyr Ile Gly
 50                  55                  60

Gly Val Glu Gly Arg Phe Thr Ile Ser Arg Asp Asn Ser Lys Asn Thr
65                   70                  75                  80

Ile Ala Leu Ile Met Asn Asp Leu Leu Pro Glu Asp Thr Ala Thr Tyr
                 85                  90                  95

Tyr Cys Ala Ala Asp Ser Gly Gly Leu Cys Ser His Arg Glu Arg Asp
             100                 105                 110

Tyr Asp Ile Trp Gly Gln Gly Thr Gln Val Thr Val Cys
         115                 120                 125

<210> SEQ ID NO 58
<211> LENGTH: 375

<212> TYPE: DNA
<213> ORGANISM: artificial sequence
<220> FEATURE:
<223> OTHER INFORMATION: antibody B

<400> SEQUENCE: 58

```
gatccagatg tgcacctgca ggattcggga ggaggctggg tgcacccggg gggctccctg      60
accctctctt gtttaatgtc gggttccgaa tattatggtt ccctgtggg ttggttcccc     120
cagcccccag gaaaggggcg tgaggaaatc gcggaaattg ttcctattgg tgggagtgtt    180
atttacattg gtggcgtgga gggccgattc accatttccc gagacaactc caagaatact    240
attgctctca taatgaacga cctcctgcct gaagacacgg ccacttatta ttgcgcagca    300
gattcagggg gactctgcag ccatcgtgag cgcgactatg acatttgggg ccaggggacc    360
caggtcaccg tctgc                                                     375
```

<210> SEQ ID NO 59
<211> LENGTH: 119
<212> TYPE: PRT
<213> ORGANISM: artificial sequence
<220> FEATURE:
<223> OTHER INFORMATION: antibody C

<400> SEQUENCE: 59

```
Asp Val Gln Leu Pro Glu Ser Gly Arg Thr Leu Val Pro Pro Gly Gly
1               5                   10                  15

Ser Leu Lys Leu Ser Trp Ala Thr His Gly Phe Gly Ile Gly Ser Phe
            20                  25                  30

Pro Met Leu Trp Val Pro Pro Ala Pro Gly Lys Gly Leu Glu Tyr Ile
        35                  40                  45

Ala Gly Ile Gly Ser Asp Tyr Thr Thr His Tyr Ser Asn Ser Leu Ser
    50                  55                  60

Gly Arg Phe Thr Ile Ser Lys Asp Ile Ala Lys Asn Thr Leu Asp Leu
65                  70                  75                  80

Arg Met Asp Asp Leu Leu Pro Glu Asp Thr Ala Asn Tyr Tyr Cys Ala
                85                  90                  95

Lys Asp Val Leu Asp Tyr His Pro Asp Leu Trp Gly Arg Gly Thr Gln
            100                 105                 110

Val Thr Val Cys Arg Gly Arg
        115
```

<210> SEQ ID NO 60
<211> LENGTH: 359
<212> TYPE: DNA
<213> ORGANISM: artificial sequence
<220> FEATURE:
<223> OTHER INFORMATION: antibody C

<400> SEQUENCE: 60

```
agatgtgcag ctgccagaat ccggaagaac gttggtgcca cccgggggt ccctgaagct      60
ctcctgggca acgcacggat tcggaatcgg tagtttcccc atgctgtggg tccccccggc    120
ccccggaaaa gggctcgaat atattgcggg cattggtagt gattatacga cacactattc    180
aaattccctc tcgggccgct tcaccatctc taaagacatt gccaagaata cactagatct    240
gcgcatggac gacctactgc ctgaagacac ggccaattat tattgtgcga agacgtact    300
tgactaccac ccagatttgt ggggccgggg aacccaggtc accgtctgca ggggccgca    359
```

<210> SEQ ID NO 61

```
<211> LENGTH: 125
<212> TYPE: PRT
<213> ORGANISM: artificial sequence
<220> FEATURE:
<223> OTHER INFORMATION: antibody D

<400> SEQUENCE: 61

Val Gln Leu Gln Glu Ser Gly Gly Gly Ser Val Gln Asp Gly Gly Thr
1               5                   10                  15

Leu Gln Leu Ser Cys Glu Asp Ser Lys Trp Ser Tyr Thr Tyr Tyr Cys
            20                  25                  30

Met Gly Trp Phe Arg Gln Ala Pro Gly Lys Glu Arg Glu Pro Val Ala
        35                  40                  45

His Ile Asp Ser Glu Gly Thr Val Ala Tyr Ala Asp Thr Val Lys Gly
    50                  55                  60

Arg Phe Thr Ile Ser Arg Gly Asp Ala Lys His Arg Val Tyr Leu Gln
65                  70                  75                  80

Met Asn Asn Leu Lys Ala Asp Asp Thr Ala Ile Tyr Tyr Cys Ala Ala
                85                  90                  95

Asn Gly Gly Tyr Cys Leu Arg Pro Arg Gln Leu Ala Ala Asp Tyr Glu
            100                 105                 110

Tyr Trp Gly Gln Gly Ala Gln Val Thr Val Ser Ser Gly
        115                 120                 125

<210> SEQ ID NO 62
<211> LENGTH: 381
<212> TYPE: DNA
<213> ORGANISM: artificial sequence
<220> FEATURE:
<223> OTHER INFORMATION: antibody D

<400> SEQUENCE: 62
aagtgcagct gcaggagtct gggggaggct cggtgcagga tggagggact tacaactct       60 cttgtgaaga ctctaaatgg agctacacgt actattgtat ggggtggttc cgccaggctc     120
cagggaagga gcgagagccg gtcgcgcaca ttgatagtga aggcactgtc gcttacgccg     180
acaccgtgaa gggccgattc accatctccc gggggacgc caagcatagg gtttacctgc      240
aaatgaataa cttgaaggct gatgacacgg ccatctatta ttgtgcggcc aatggtggtt     300
attgcctcag accccgtcaa ctcgccgcgg attatgagta ttgggccag ggggcccagg      360 tcaccgtctc cagcggccgc a                                                381

<210> SEQ ID NO 63
<211> LENGTH: 119
<212> TYPE: PRT
<213> ORGANISM: artificial sequence
<220> FEATURE:
<223> OTHER INFORMATION: antibody E

<400> SEQUENCE: 63

Asp Val Gln Leu Gln Glu Ser Gly Gly Thr Leu Val Gln Pro Gly Gly
1               5                   10                  15

Ser Leu Thr Leu Ser Cys Ala Ala His Gly Phe Gly Ile Gly Ser Phe
            20                  25                  30

Ala Met Leu Trp Val Arg Gln Ala Pro Gly Lys Gly Leu Glu Tyr Ile
        35                  40                  45

Ala Gly Ile Gly Ser Asp Tyr Thr Thr His Tyr Ser Asn Ser Leu Ser
    50                  55                  60

Gly Arg Phe Thr Ile Ser Lys Asp Ile Ala Lys Asn Thr Leu Asp Leu
```

```
                65                  70                  75                  80
Arg Met Asp Asp Leu Val Pro Glu Asp Thr Ala Asn Tyr Tyr Cys Ala
                    85                  90                  95

Lys Asp Val Leu Asp Tyr His Pro Asp Leu Trp Gly Gln Gly Thr Gln
                100                 105                 110

Val Thr Val Cys Ser Gly Arg
        115
```

```
<210> SEQ ID NO 64
<211> LENGTH: 361
<212> TYPE: DNA
<213> ORGANISM: artificial sequence
<220> FEATURE:
<223> OTHER INFORMATION: antibody E

<400> SEQUENCE: 64
agatgtgcag ctgcaggagt ctggaggaac attggtgcag cccgggggt ctctgacgct      60 ctcctgtgca gcgcatggat tcggaatcgg tagtttcgcc atgctgtggg tccgccaggc    120
cccaggaaag gggctcgagt atattgcggg cattggtagt gattatacga cacactattc    180
aaattccctc tcgggccgct tcaccatctc taaagacatt gccaagaata cactagatct    240
gcgcatggac gacctagtgc ctgaagacac ggccaattat tattgtgcga agacgtact     300 tgactaccac ccagatttgt ggggccaggg aacccaggtc accgtctgca gcggccgcac    360
t                                                                    361
```

```
<210> SEQ ID NO 65
<211> LENGTH: 119
<212> TYPE: PRT
<213> ORGANISM: artificial sequence
<220> FEATURE:
<223> OTHER INFORMATION: antibody F

<400> SEQUENCE: 65

Asp Val Gln Leu Gln Glu Ser Gly Gly Thr Leu Val Gln Pro Gly Gly
1               5                   10                  15

Ser Leu Thr Leu Ser Cys Ala Ala His Gly Phe Gly Ile Gly Ser Phe
            20                  25                  30

Ala Met Leu Trp Val Arg Gln Ala Pro Gly Lys Gly Leu Glu Tyr Ile
        35                  40                  45

Ala Gly Ile Gly Ser Asp Tyr Thr Thr His Tyr Ser Asn Ser Leu Ser
    50                  55                  60

Gly Arg Phe Thr Ile Ser Lys Asp Ile Ala Lys Asn Thr Leu Asp Leu
65                  70                  75                  80

Arg Met Asp Asp Leu Val Pro Glu Asp Thr Ala Asn Tyr Tyr Cys Ala
                    85                  90                  95

Lys Asp Val Leu Asp Tyr His Pro Asp Leu Trp Gly Gln Gly Thr Gln
                100                 105                 110

Val Thr Val Cys Ser Gly Arg
        115
```

```
<210> SEQ ID NO 66
<211> LENGTH: 358
<212> TYPE: DNA
<213> ORGANISM: artificial sequence
<220> FEATURE:
<223> OTHER INFORMATION: antibody F

<400> SEQUENCE: 66
```

```
agatgtgcag ctgcaggagt ctggaggaac attggtgcag cccgggggt ctctgacgct    60 ctcctgtgca gcgcatggat tcggaatcgg tagtttcgcc atgctgtggg tccgccaggc   120
cccaggaaag gggctcgagt atattgcggg cattggtagt gattatacga cacactattc   180
aaattccctc tcgggccgct tcaccatctc taaagacatt gccaagaata cactagatct   240
gcgcatggac gacctagtgc ctgaagacac ggccaattat tattgtgcga aagacgtact   300
tgactaccac ccagatttgt ggggccaggg aacccaggtc accgtctgca gcggccgc    358
```

```
<210> SEQ ID NO 67
<211> LENGTH: 119
<212> TYPE: PRT
<213> ORGANISM: artificial sequence
<220> FEATURE:
<223> OTHER INFORMATION: antibody G

<400> SEQUENCE: 67
```

Asp Val Gln Leu Gln Glu Ser Gly Gly Thr Leu Val Gln Pro Gly Gly
1               5                   10                  15

Ser Leu Thr Leu Ser Cys Ala Ala His Gly Phe Gly Ile Gly Ser Phe
            20                  25                  30

Ala Met Leu Trp Val Arg Gln Ala Pro Gly Lys Gly Leu Glu Tyr Ile
        35                  40                  45

Ala Gly Ile Gly Ser Asp Tyr Thr Thr His Tyr Ser Asn Ser Leu Ser
    50                  55                  60

Gly Arg Phe Thr Ile Ser Lys Asp Ile Ala Lys Asn Thr Leu Asp Leu
65                  70                  75                  80

Arg Met Asp Asp Leu Val Pro Glu Asp Thr Ala Asn Tyr Tyr Cys Ala
                85                  90                  95

Lys Asp Val Leu Asp Tyr His Pro Asp Leu Trp Gly Gln Gly Thr Gln
            100                 105                 110

Val Thr Val Cys Ser Gly Arg
        115

```
<210> SEQ ID NO 68
<211> LENGTH: 361
<212> TYPE: DNA
<213> ORGANISM: artificial sequence
<220> FEATURE:
<223> OTHER INFORMATION: antibody G

<400> SEQUENCE: 68
agatgtgcag ctgcaggagt ctggaggaac attggtgcag cccgggggt ctctgacgct    60 ctcctgtgca gcgcatggat tcggaatcgg tagtttcgcc atgctgtggg tccgccaggc   120
cccaggaaag gggctcgagt atattgcggg cattggtagt gattatacga cacactattc   180
aaattccctc tcgggccgct tcaccatctc taaagacatt gccaagaata cactagatct   240
gcgcatggac gacctagtgc ctgaagacac ggccaattat tattgtgcga aagacgtact   300
tgactaccac ccagatttgt ggggccaggg aacccaggtc accgtctgca gcggccgcac  360
t                                                                  361
```

```
<210> SEQ ID NO 69
<211> LENGTH: 128
<212> TYPE: PRT
<213> ORGANISM: artificial sequence
<220> FEATURE:
<223> OTHER INFORMATION: antibody H

<400> SEQUENCE: 69
```

Asp Val Gln Leu Gln Glu Ser Gly Gly Gly Ser Val Gln Thr Gly
1               5                   10                  15

Ser Leu Arg Leu Ser Cys Ala Ala Ser Gly Asp Ser Ile Thr Thr Tyr
            20                  25                  30

His Met Ala Trp Phe Arg Gln Thr Pro Gly Lys Glu Arg Glu Val
        35                  40                  45

Ala Val Ile Asn Asp Asp Ala Asn Ser Arg Ile Tyr Val Asp Ser Val
    50                  55                  60

Lys Gly Arg Phe Thr Ile Ser Gln Asp Lys Ala Lys Asn Thr Val Tyr
65                  70                  75                  80

Leu Gln Met Asn Tyr Leu Thr Pro Glu Asp Thr Ala Ile Tyr Tyr Cys
                85                  90                  95

Ala Ala Asp Leu Arg Cys Val Pro Gly Thr Asp Ser Gly His Pro Tyr
            100                 105                 110

Ser Tyr Asn Tyr Trp Gly Gln Gly Thr Gln Val Thr Val Cys Ser Gly
        115                 120                 125

<210> SEQ ID NO 70
<211> LENGTH: 386
<212> TYPE: DNA
<213> ORGANISM: artificial sequence
<220> FEATURE:
<223> OTHER INFORMATION: antibody H

<400> SEQUENCE: 70
agatgtgcag ctgcaggagt ctggaggagg ttcggtgcag actggaggat ctctgagact    60
ctcctgtgca gcctctggag attccatcac tacctaccac atggcctggt tccgccagac   120
tccagggaag gagcgtgagg aggtcgcagt tataaatgat gatgctaatt cgagaatcta   180
tgtcgactcc gtgaagggcc gattcaccat ctcccaagac aaggccaaga acacggtgta   240
tctgcaaatg aactacctga cgcctgagga cacggccatc tactactgtg cggcagattt   300
gaggtgcgtc cctgggaccg actctggtca tccttattcg tataactact ggggccaggg   360
gacccaggtc accgtctgca gcggcc                                        386

<210> SEQ ID NO 71
<211> LENGTH: 125
<212> TYPE: PRT
<213> ORGANISM: artificial sequence
<220> FEATURE:
<223> OTHER INFORMATION: antibody I

<400> SEQUENCE: 71

Asp Val His Leu Gln Asp Ser Gly Gly Gly Ser Val Gln Ala Gly Gly
1               5                   10                  15

Ser Leu Thr Leu Ser Trp Leu Met Ser Gly His Thr Tyr Tyr Gly Pro
            20                  25                  30

Cys Val Gly Trp Phe Arg Gln Pro Pro Gly Lys Ala Arg Glu Gly Ile
        35                  40                  45

Pro Gln Ile Ser Pro Ile Gly Gly Ser Val Ile Tyr Ile Gly Gly Val
    50                  55                  60

Lys Gly Arg Phe Thr Ile Ser Arg Asp Asn Ser Lys Asn Thr Ile Ala
65                  70                  75                  80

Leu Ile Met Asn Asp Leu Leu Pro Glu Asp Thr Ala Thr Tyr Tyr Cys
                85                  90                  95

Ala Ala Asp Ser Gly Gly Leu Cys Ser His Arg Glu Arg Asp Tyr Asp
            100                 105                 110

Ile Trp Gly Gln Gly Thr Gln Val Thr Val Cys Ser Gly
    115                 120                 125

<210> SEQ ID NO 72
<211> LENGTH: 374
<212> TYPE: DNA
<213> ORGANISM: artificial sequence
<220> FEATURE:
<223> OTHER INFORMATION: antibody I

<400> SEQUENCE: 72
agatgtgcac ctgcaggatt ctggaggagg ctcggtgcag gctggaggct ccctgacgct    60
ctcttggtta atgtcgggtc atacgtatta tggaccttgt gtgggttggt tccgccagcc   120
cccagggaaa gcgcgtgagg gaatcccaca gattagtcct attggtggga gtgttattta   180
cattggtggc gtgaagggcc gattcaccat ttcccgagac aactccaaga atactattgc   240
tctcataatg aacgacctcc tgcctgaaga cacggccact tattattgcg cagcagattc   300 aggggggactc tgcagccatc gtgagcgcga ctatgacatt tggggccagg ggacccagt   360 caccgtctgc ggcc                                                     374

<210> SEQ ID NO 73
<211> LENGTH: 125
<212> TYPE: PRT
<213> ORGANISM: artificial sequence
<220> FEATURE:
<223> OTHER INFORMATION: antibody J

<400> SEQUENCE: 73

Asp Val His Leu Gln Asp Ser Gly Glu Gly Trp Gly His Ala Gly Gly
1               5                   10                  15

Ser Leu Thr Leu Ser Cys Leu Met Ser Gly His Thr Tyr Tyr Gly Pro
            20                  25                  30

Cys Gly Gly Gly Phe Pro Gln Pro Pro Gly Lys Ala Arg Glu Gly Ile
        35                  40                  45

Pro Gln Met Ile Pro Ile Gly Gly Ser Val Ile Tyr Ile Gly Gly Val
    50                  55                  60

Lys Gly Arg Phe Thr Ile Ser Arg Asp Asn Ser Lys Asn Thr Ile Ala
65                  70                  75                  80

Leu Ile Met Asn Asp Leu Val Pro Glu Asp Thr Ala Thr Tyr Tyr Cys
                85                  90                  95

Ala Thr Asp Ser Gly Gly Leu Cys Ser His Arg Glu Arg Asp Tyr Asp
            100                 105                 110

Ile Trp Gly Gln Gly Thr Gln Val Thr Val Cys Ser Gly
    115                 120                 125

<210> SEQ ID NO 74
<211> LENGTH: 374
<212> TYPE: DNA
<213> ORGANISM: artificial sequence
<220> FEATURE:
<223> OTHER INFORMATION: antibody J

<400> SEQUENCE: 74
agatgtgcac ctgcaggatt cgggagaagg ctggggcac gctggaggct ccctgaccct    60
ctcttgttta atgtcgggtc atacgtatta tggaccttgt ggggtgggt tccccagcc   120 cccagggaaa gcccgtgagg gaatcccaca aatgattcct attggtggga gtgttattta   180
cattggtggc gtgaagggcc gattcaccat ttcccgagac aactccaaga atactattgc   240

```
tctcataatg aacgacctcg tgcctgaaga cacggccact tattattgcg caacagattc    300
agggggactc tgcagccatc gtgagcgcga ctatgacatt tggggccagg ggacccaggt    360
caccgtctgc ggcc                                                      374
```

<210> SEQ ID NO 75
<211> LENGTH: 124
<212> TYPE: PRT
<213> ORGANISM: artificial sequence
<220> FEATURE:
<223> OTHER INFORMATION: antibody K

<400> SEQUENCE: 75

Asp Val His Leu Gln Asp Ser Gly Gly Gly Ser Val His Ala Gly Gly
1               5                   10                  15

Ser Leu Thr Leu Ser Cys Leu Met Ser Gly His Thr Tyr Tyr Gly Pro
            20                  25                  30

Cys Gly Gly Gly Phe Pro Arg Pro Gly Lys Gly Arg Glu Gly Ile
        35                  40                  45

Ala Gln Ile Ile Pro Ile Gly Gly Ser Val Ile Tyr Ile Gly Gly Val
    50                  55                  60

Lys Gly Arg Phe Thr Ile Ser Arg Tyr Asn Ser Lys Asn Thr Ile Ala
65                  70                  75                  80

Leu Ile Met Asn Asp Leu Val Pro Glu Asp Thr Ala Thr Tyr Cys Ala
                85                  90                  95

Thr Asp Ser Gly Gly Leu Cys Ser His Arg Glu Arg Asp Tyr Asp Ile
            100                 105                 110

Trp Gly Gln Gly Thr Gln Val Thr Val Cys Ser Gly
        115                 120

<210> SEQ ID NO 76
<211> LENGTH: 377
<212> TYPE: DNA
<213> ORGANISM: artificial sequence
<220> FEATURE:
<223> OTHER INFORMATION: antibody K

<400> SEQUENCE: 76

```
agatgtgcac ctgcaggatt ctggaggagg ctcggtgcac gctgggggct ccctgacgct    60
ctcttgttta atgtcgggtc atacgtatta tggaccttgt gggggtgggt tcccccggcc    120
cccaggaaaa gggcgtgagg gaatcgcaca aattattcct attggtggga gtgttattta    180
cattggtggc gtgaagggcc gattcaccat ttcccgatac aactccaaga atactattgc    240
tctcataatg aacgacctcg tgcctgaaga cacggccact tattattgcg caacagattc    300
agggggactc tgcagccatc gtgagcgcga ctatgacatt tggggccagg ggacccaggt    360
caccgtctgc agcggcc                                                   377
```

<210> SEQ ID NO 77
<211> LENGTH: 124
<212> TYPE: PRT
<213> ORGANISM: artificial sequence
<220> FEATURE:
<223> OTHER INFORMATION: antibody L

<400> SEQUENCE: 77

Asp Val His Leu Gln Asp Ser Gly Gly Gly Ser Val Gln Ala Gly Gly
1               5                   10                  15

Ser Leu Thr Leu Ser Cys Leu Met Ser Gly His Thr Tyr Tyr Gly Pro

```
                20                  25                  30
Cys Val Gly Trp Phe Pro Gln Arg Pro Gly Lys Ala Arg Glu Gly Ile
            35                  40                  45

Ala Gln Met Ile Pro Ile Gly Gly Ser Val Ser Tyr Ser Gly Gly Val
        50                  55                  60

Lys Gly Arg Phe Thr Ile Ser Arg Asp Asn Ser Lys Asn Thr Ile Ala
65                  70                  75                  80

Leu Ile Met Asn Asp Leu Val Pro Glu Asp Thr Ala Thr Tyr Tyr Cys
                85                  90                  95

Ala Thr Asp Ser Gly Gly Leu Cys Ser His Arg Glu Arg Asp Tyr Asp
            100                 105                 110

Ile Trp Gly Gln Gly Thr Gln Val Thr Val Cys Ser
            115                 120
```

<210> SEQ ID NO 78
<211> LENGTH: 373
<212> TYPE: DNA
<213> ORGANISM: artificial sequence
<220> FEATURE:
<223> OTHER INFORMATION: antibody L

<400> SEQUENCE: 78

```
agatgtgcac ctgcaggatt ctggaggagg ctcggtgcag gctggaggct ccctgaccct    60
ctcttgttta atgtcgggtc atacgtatta tggaccttgt gtgggttggt tcccccagcg   120
tccagggaaa gcgcgtgagg gaatcgcaca aatgattcct attggtggga gtgttagtta   180
cagtggtggc gtgaagggcc gattcaccat ttcccgagac aactccaaga atactattgc   240
tctcataatg aacgacctcg tgcctgaaga cacggccact tattattgcg caacagattc   300
aggggggactc tgcagccatc gtgagcgcga ctatgacatt tggggccagg ggacccaggt   360
caccgtctgc agc                                                      373
```

<210> SEQ ID NO 79
<211> LENGTH: 127
<212> TYPE: PRT
<213> ORGANISM: artificial sequence
<220> FEATURE:
<223> OTHER INFORMATION: antibody M

<400> SEQUENCE: 79

```
Asp Val Gln Leu Gln Glu Ser Gly Gly Gly Ser Val Gln Glu Gly Gly
1               5                  10                  15

Ser Leu Arg Leu Ser Cys Ala Ala Ser Glu Tyr Thr Ala Ile Thr Tyr
            20                  25                  30

Cys Met Ala Trp Phe Arg Gln Ala Pro Gly Lys Glu Arg Glu Gly Val
            35                  40                  45

Ala Ala Ile Asn Arg Gly Gly Ser Thr Tyr Tyr Ala Asp Ser Val
        50                  55                  60

Lys Gly Arg Phe Thr Ile Ser Gln Asp Asn Ala Lys Asn Thr Val Tyr
65                  70                  75                  80

Leu Leu Met Asn Ser Leu Lys Pro Glu Asp Thr Gly Met Tyr Tyr Cys
                85                  90                  95

Ala Tyr Lys Gln Thr Gly Asp Cys Gly Ile Phe Gln Phe Phe Gly Asn
            100                 105                 110

Tyr Gly Gln Gly Thr Gln Val Thr Val Ser Ser Gly Arg Thr His
            115                 120                 125
```

```
<210> SEQ ID NO 80
<211> LENGTH: 379
<212> TYPE: DNA
<213> ORGANISM: artificial sequence
<220> FEATURE:
<223> OTHER INFORMATION: antibody M

<400> SEQUENCE: 80
gatccagatg tgcagctgca ggagtctggg ggaggctcgg tgcaggaggg agggtctctg    60
agactctcct gtgcagcctc tgaatacacc gctattacct actgtatggc ctggttccgc   120
caggctccag ggaaggagcg tgaggggtc gcggctatca atcgcggtgg tggtagtaca   180
tattacgccg actccgtgaa gggccgattc accatctccc aggacaacgc caagaacacg   240
gtgtatctcc taatgaacag cctgaaacct gaggacactg gcatgtacta ctgtgcgtac   300
aaacagaccg tgattgtggg gatcttccaa ttctttggaa actatggcca ggggacccag   360
gtcaccgtct ccagcggcc                                                379

<210> SEQ ID NO 81
<211> LENGTH: 128
<212> TYPE: PRT
<213> ORGANISM: artificial sequence
<220> FEATURE:
<223> OTHER INFORMATION: antibody N

<400> SEQUENCE: 81

Asp Val Gln Leu Gln Glu Ser Gly Gly Gly Ser Val Gln Thr Gly Gly
1               5                   10                  15

Ser Leu Arg Leu Ser Cys Ala Ala Ser Gly Asp Ser Ile Thr Thr Tyr
            20                  25                  30

His Met Ala Trp Phe Arg Gln Thr Pro Gly Lys Glu Arg Glu Glu Val
        35                  40                  45

Ala Val Ile Asn Asp Asp Ala Asn Ser Arg Ile Tyr Val Asp Ser Val
    50                  55                  60

Lys Gly Arg Phe Thr Ile Ser Gln Asp Lys Ala Lys Asn Thr Val Tyr
65                  70                  75                  80

Leu Gln Met Asn Tyr Leu Thr Pro Glu Asp Thr Ala Ile Tyr Tyr Cys
                85                  90                  95

Ala Ala Asp Leu Arg Cys Val Pro Gly Thr Asp Ser Gly His Pro Tyr
            100                 105                 110

Ser Tyr Asn Tyr Trp Gly Gln Gly Thr Gln Val Thr Ala Ser Ser Gly
        115                 120                 125

<210> SEQ ID NO 82
<211> LENGTH: 386
<212> TYPE: DNA
<213> ORGANISM: artificial sequence
<220> FEATURE:
<223> OTHER INFORMATION: antibody N

<400> SEQUENCE: 82
agatgtgcag ctgcaggagt ctggaggagg ttcggtgcag actggaggat ctctgagact    60
ctcctgtgca gcctctggag attccatcac tacctaccac atggcctggt tccgccagac   120
tccagggaag gagcgtgagg aggtcgcagt tataaatgat gatgctaatt cgagaatcta   180
tgtcgactcc gtgaagggcc gattcaccat ctcccaagac aaggccaaga acacggtgta   240
tctgcaaatg aactacctga cgcctgagga cacggccatc tactactgtg cggcagattt   300
gaggtgcgtc cctgggaccg actctggtca tcttattcg tataactact ggggccaggg   360
```
gacccaggtc accgcctcca gcggcc         386

<210> SEQ ID NO 83
<211> LENGTH: 129
<212> TYPE: PRT
<213> ORGANISM: artificial sequence
<220> FEATURE:
<223> OTHER INFORMATION: antibody O

<400> SEQUENCE: 83

Asp Val Gln Leu Gln Glu Ser Gly Gly Gly Ser Val Gln Thr Gly Gly
1               5                   10                  15

Ser Leu Arg Leu Ser Cys Ala Ala Ser Gly Asp Ser Ile Thr Thr Tyr
            20                  25                  30

His Met Ala Trp Phe Arg Gln Thr Pro Gly Lys Glu Arg Glu Glu Val
        35                  40                  45

Ala Val Ile Asn Asp Asp Ala Asn Ser Arg Ile Tyr Val Asp Ser Val
    50                  55                  60

Lys Gly Arg Phe Thr Ile Ser Gln Asp Lys Ala Lys Asn Thr Val Tyr
65                  70                  75                  80

Leu Gln Met Asn Tyr Leu Thr Pro Glu Asp Thr Ala Ile Tyr Tyr Cys
                85                  90                  95

Ala Ala Asp Leu Arg Cys Val Pro Gly Thr Asp Ser Gly His Pro Tyr
            100                 105                 110

Ser Tyr Asn Tyr Trp Gly Gln Gly Thr Gln Val Thr Ala Ser Ser Gly
        115                 120                 125

Arg

<210> SEQ ID NO 84
<211> LENGTH: 386
<212> TYPE: DNA
<213> ORGANISM: artificial sequence
<220> FEATURE:
<223> OTHER INFORMATION: antibody O

<400> SEQUENCE: 84
agatgtgcag ctgcaggagt ctggaggagg ttcggtgcag actggaggat ctctgagact      60
ctcctgtgca gcctctggag attccatcac tacctaccac atggcctggt tccgccagac     120
tccagggaag gagcgtgagg aggtcgcagt tataaatgat gatgctaatt cgagaatcta     180
tgtcgactcc gtgaagggcc gattcaccat ctcccaagac aaggccaaga acacggtgta     240
tctgcaaatg aactacctga cgcctgagga cacggccatc tactactgtg cggcagattt     300
gaggtgcgtc cctgggaccg actctggtca tccttattcg tataactact ggggccaggg     360
gacccaggtc accgcctcca gcggcc                                          386

<210> SEQ ID NO 85
<211> LENGTH: 130
<212> TYPE: PRT
<213> ORGANISM: artificial sequence
<220> FEATURE:
<223> OTHER INFORMATION: antibody P

<400> SEQUENCE: 85

Asp Val Gln Leu Gln Glu Ser Gly Gly Gly Ser Ala Gln Pro Gly Gly
1               5                   10                  15

Ser Leu Arg Leu Ser Cys Ala Val Ser Gly Ser Thr Ala Ser Met Tyr
            20                  25                  30

Cys Leu Ala Trp Phe Arg Gln Ala Pro Gly Lys Glu Pro Glu Gly Val

```
                35                  40                  45
Ala Ala Ile Ser Gly Asp Asp Lys Gly Phe Thr Asn Tyr Ala Asp Ser
    50                  55                  60
Val Lys Gly Arg Phe Thr Ile Ser Gln Asn Lys Ala Asn Lys Thr Val
65                  70                  75                  80
Asn Leu Gln Met Asn Ser Leu Lys Pro Glu Asp Thr Ala Ile Tyr Tyr
                85                  90                  95
Cys Ala Val Asp Ala Arg Ala Thr Thr Thr Gly Glu Arg Leu His Ala
            100                 105                 110
Arg Thr Tyr Glu Phe Trp Gly Gln Gly Thr Gln Val Thr Val Cys Ser
            115                 120                 125
Gly Arg
    130

<210> SEQ ID NO 86
<211> LENGTH: 390
<212> TYPE: DNA
<213> ORGANISM: artificial sequence
<220> FEATURE:
<223> OTHER INFORMATION: antibody P

<400> SEQUENCE: 86
gatgtgcagc tgcaggagtc tgggggaggc tcggcgcagc ctggagggtc tctgagactc    60
tcctgtgcag tctctggatc gaccgccagt atgtactgct ggcctggtt ccgccaggct    120 ccagggaagg agcctgaggg ggttgctgct attagtggag atgataaagg gtttacgaat    180
tacgccgact ccgtgaaggg ccggttcacc atctcccaaa acaaggccaa taaaacggtg    240
aatctgcaaa tgaacagcct gaaacctgaa gacacggcca tttattactg tgccgttgat    300
gcgcgagcga caacaactgg tgaacgtcta cacgcccgga cgtacgaatt ctggggccag    360
gggacccagg tcaccgtctg cagcggccgc                                     390

<210> SEQ ID NO 87
<211> LENGTH: 128
<212> TYPE: PRT
<213> ORGANISM: artificial sequence
<220> FEATURE:
<223> OTHER INFORMATION: antibody Q

<400> SEQUENCE: 87

Asp Val Gln Met Gln Glu Ser Gly Gly Gly Ser Val Gln Ala Gly Gly
1               5                  10                  15
Ser Leu Arg Leu Ser Cys Ala Ala Ser Gly Asp Thr Leu Ser Thr Tyr
            20                  25                  30
Cys Met Gly Trp Phe Arg Gln Val Pro Gly Lys Asp Arg Glu Gly Val
            35                  40                  45
Ala Ala Ile Tyr Arg Leu Arg Asp Met Thr Phe Tyr Ala Asp Ser Val
    50                  55                  60
Lys Gly Arg Phe Thr Ile Ser Arg Asp Asn Ala Asn Asp Thr Val Asp
65                  70                  75                  80
Leu Gln Met Asn Ser Leu Lys Pro Glu Asp Thr Ala Val Tyr Tyr Cys
                85                  90                  95
Ala Ala Arg Cys Val Arg Leu Phe Gly Thr Cys Gln Leu Val Glu Asp
            100                 105                 110
Phe Glu Leu Trp Gly Gln Gly Thr Gln Val Thr Val Ser Ser Gly Leu
            115                 120                 125
```

<210> SEQ ID NO 88
<211> LENGTH: 382
<212> TYPE: DNA
<213> ORGANISM: artificial sequence
<220> FEATURE:
<223> OTHER INFORMATION: antibody Q

<400> SEQUENCE: 88

```
agatgtgcag atgcaggagt ctgggggagg gtcggtgcag gctggagggt ctctgagact      60
ctcctgtgca gcctctggag ataccctcag tacctactgc atgggctggt tccgccaagt     120
tccagggaag gaccgtgagg gggtcgcagc gatttatcgt cttagggata tgacgttcta     180
tgccgactcc gtgaagggcc gattcaccat ttcccgtgac aacgccaacg acacggtaga     240
tctgcaaatg aacagcctga aacctgagga cacagccgtg tactactgtg cagcaagatg     300
tgtgcgacta ttcggtactt gtcagctagt cgaagatttt gaactatggg gccaggggac     360
ccaggtcacc gtctccagcg gc                                             382
```

<210> SEQ ID NO 89
<211> LENGTH: 129
<212> TYPE: PRT
<213> ORGANISM: artificial sequence
<220> FEATURE:
<223> OTHER INFORMATION: antibody R

<400> SEQUENCE: 89

```
Asp Val Gln Met Gln Glu Ser Gly Gly Gly Ser Val Gln Ala Gly Gly
1               5                   10                  15
Ser Leu Arg Leu Ser Cys Ala Ala Ser Gly Asp Thr Leu Ser Thr Tyr
            20                  25                  30
Cys Met Gly Trp Phe Arg Gln Ala Pro Gly Lys Asp Arg Glu Gly Val
        35                  40                  45
Ala Ala Ile Tyr Arg Leu Arg Asp Met Thr Phe Tyr Ala Asp Ser Val
    50                  55                  60
Lys Gly Arg Phe Thr Ile Ser Arg Asp Asn Ala Asn Asp Thr Val Asp
65                  70                  75                  80
Leu Gln Met Asn Ser Leu Lys Pro Glu Asp Thr Ala Val Tyr Tyr Cys
                85                  90                  95
Ala Ala Arg Cys Val Arg Leu Phe Gly Thr Cys Gln Leu Val Glu Asp
            100                 105                 110
Phe Glu Leu Trp Gly Gln Gly Thr Gln Val Thr Val Ser Ser Gly Leu
        115                 120                 125
Thr
```

<210> SEQ ID NO 90
<211> LENGTH: 382
<212> TYPE: DNA
<213> ORGANISM: artificial sequence
<220> FEATURE:
<223> OTHER INFORMATION: antibody R

<400> SEQUENCE: 90

```
agatgtgcag atgcaggagt ctgggggagg gtcggtgcag gctggagggt ctctgagact      60
ctcctgtgca gcctctggag ataccctcag tacctactgc atgggctggt tccgccaagt     120
tccagggaag gaccgtgagg gggtcgcagc gatttatcgt cttagggata tgacgttcta     180
tgccgactcc gtgaagggcc gattcaccat ttcccgtgac aacgccaacg acacggtaga     240
tctgcaaatg aacagcctga aacctgagga cacagccgtg tactactgtg cagcaagatg     300
```

```
tgtgcgacta ttcggtactt gtcagctagt cgaagatttt gaactatggg gccaggggac    360
ccaggtcacc gtctccagcg gc                                             382
```

<210> SEQ ID NO 91
<211> LENGTH: 129
<212> TYPE: PRT
<213> ORGANISM: artificial sequence
<220> FEATURE:
<223> OTHER INFORMATION: antibody S

<400> SEQUENCE: 91

```
Asp Val Gln Met Gln Glu Ser Gly Gly Gly Ser Val Gln Ala Gly Gly
1               5                   10                  15

Ser Leu Arg Leu Ser Cys Ala Ala Ser Gly Asp Thr Leu Ser Thr Tyr
            20                  25                  30

Cys Met Gly Trp Phe Arg Gln Val Pro Gly Lys Asp Arg Glu Gly Val
        35                  40                  45

Ala Ala Ile Tyr Arg Leu Arg Asp Met Thr Phe Tyr Ala Asp Ser Val
    50                  55                  60

Lys Gly Arg Phe Thr Ile Ser Arg Asp Asn Ala Asn Asp Thr Val Asp
65                  70                  75                  80

Leu Gln Met Asn Ser Leu Lys Pro Glu Asp Thr Ala Val Tyr Tyr Cys
                85                  90                  95

Ala Ala Arg Cys Val Arg Leu Phe Gly Thr Cys Gln Leu Val Glu Asp
            100                 105                 110

Phe Glu Leu Trp Gly Gln Gly Thr Gln Val Thr Val Ser Ser Gly Leu
        115                 120                 125

Thr
```

<210> SEQ ID NO 92
<211> LENGTH: 383
<212> TYPE: DNA
<213> ORGANISM: artificial sequence
<220> FEATURE:
<223> OTHER INFORMATION: antibody S

<400> SEQUENCE: 92

```
agatgtgcag atgcaggagt ctgggggagg gtcggtgcag gctggagggt ctctgagact     60
ctcctgtgca gcctctggag ataccctcag tacctactgc atgggctggt tccgccaagt    120
tccagggaag gaccgtgagg gggtcgcagc gatttatcgt cttagggata tgacgttcta    180
tgccgactcc gtgaagggcc gattcaccat ttcccgtgac aacgccaacg acacggtaga    240
tctgcaaatg aacagcctga aacctgagga cacagccgtg tactactgtg cagcaagatg    300
tgtgcgacta ttcggtactt gtcagctagt cgaagatttt gaactatggg gccaggggac    360
ccaggtcacc gtctccagcg gcc                                            383
```

<210> SEQ ID NO 93
<211> LENGTH: 148
<212> TYPE: PRT
<213> ORGANISM: artificial sequence
<220> FEATURE:
<223> OTHER INFORMATION: mub insertion site 1 antibody A

<400> SEQUENCE: 93

```
Ala Glu Gly Ile Lys Lys Phe Glu Gly Asp Asp Val Gln Leu Gln Glu
1               5                   10                  15

Ser Gly Gly Gly Ser Val Gln Ala Gly Gly Ser Leu Thr Leu Ser Cys
            20                  25                  30
```

Leu Met Ser Gly His Thr Tyr Tyr Gly Pro Cys Val Gly Trp Phe Arg
            35                  40                  45

Gln Arg Pro Gly Lys Ala Arg Glu Gly Ile Ala Gln Ile Ser Pro Ser
 50                  55                  60

Gly Gly Ser Val Ser Tyr Ser Gly Gly Val Lys Gly Arg Phe Thr Ile
 65                  70                  75                  80

Ser Arg Asp Asn Ser Lys Asn Thr Ile Ala Leu Ile Met Glu Thr Asn
                 85                  90                  95

Asp Leu Val Pro Glu Asp Thr Ala Thr Tyr Tyr Cys Ala Ala Asp Ser
            100                 105                 110

Gly Gly Leu Cys Ser His Arg Glu Arg Asp Tyr Asp Ile Trp Gly Gln
            115                 120                 125

Gly Thr Gln Val Thr Val Cys Ser Gly Arg Gly Tyr Val Leu Val Ser
130                 135                 140

Asp Gly Phe Lys
145

<210> SEQ ID NO 94
<211> LENGTH: 439
<212> TYPE: DNA
<213> ORGANISM: artificial sequence
<220> FEATURE:
<223> OTHER INFORMATION: mub insertion site 1 antibody A

<400> SEQUENCE: 94
gctgaaggca tcaagaagtt cgaaggcgac atgtgcagct gcaggagtct gggggaggct      60
cggtgcaggc tggaggctcc ctgacgctct cttgtttaat gtctggtcat acgtattatg     120
gaccttgtgt gggttggttc cgccagcgtc cagggaaagc gcgtgaggga atcgcacaga     180
ttagtcctag tggtgggagt gttagttaca gtggtggcgt gaagggccga ttcaccattt     240
cccgagacaa ctccaagaat actattgctc tcataatgaa cgacctcgtg cctgaagaca     300
cggccactta ttattgcgca gcagattcag ggggactctg cagccatcgt gagcgcgact     360
atgacatttg gggccagggg acccaggtca ccgtctgcag cggccgcacg ctacgttctg     420
gtatcggacg gcttcaagc                                                  439

<210> SEQ ID NO 95
<211> LENGTH: 145
<212> TYPE: PRT
<213> ORGANISM: artificial sequence
<220> FEATURE:
<223> OTHER INFORMATION: mub insertion site 1 antibody B

<400> SEQUENCE: 95

Ala Glu Gly Ile Lys Lys Phe Glu Gly Asp Asp Pro Asp Val His Leu
  1               5                  10                  15

Gln Asp Ser Gly Gly Gly Trp Val His Pro Gly Gly Ser Leu Thr Leu
             20                  25                  30

Ser Cys Leu Met Ser Gly Ser Glu Tyr Tyr Gly Ser Pro Val Gly Trp
             35                  40                  45

Phe Pro Gln Pro Pro Gly Lys Gly Arg Glu Glu Ile Ala Glu Ile Val
 50                  55                  60

Pro Ile Gly Gly Ser Val Ile Tyr Ile Gly Gly Val Glu Gly Arg Phe
 65                  70                  75                  80

Thr Ile Ser Arg Asp Asn Ser Lys Asn Thr Ile Ala Leu Ile Met Asn
                 85                  90                  95

Asp Leu Leu Pro Glu Asp Thr Ala Thr Tyr Tyr Cys Ala Ala Asp Ser
                100                 105                 110

Gly Gly Leu Cys Ser His Arg Glu Arg Asp Tyr Asp Ile Trp Gly Gln
        115                 120                 125

Gly Thr Gln Val Thr Val Cys Gly Tyr Val Leu Val Ser Asp Gly Phe
    130                 135                 140

Lys
145

<210> SEQ ID NO 96
<211> LENGTH: 435
<212> TYPE: DNA
<213> ORGANISM: artificial sequence
<220> FEATURE:
<223> OTHER INFORMATION: mub insertion site 1 antibody B

<400> SEQUENCE: 96
gctgaaggca tcaagaagtt cgaaggcgac gatccagatg tgcacctgca ggattcggga      60
ggaggctggg tgcacccggg gggctccctg accctctctt gtttaatgtc gggttccgaa     120
tattatggtt ccctgtgggg ttggttcccc cagcccccag gaaagggggcg tgaggaaatc    180 gcggaaattg ttcctattgg tgggagtgtt atttacattg gtggcgtgga gggccgattc     240
accatttccc gagacaactc caagaatact attgctctca taatgaacga cctcctgcct     300
gaagacacgg ccacttatta ttgcgcagca gattcagggg gactctgcag ccatcgtgag     360
cgcgactatg acatttgggg ccaggggacc caggtcaccg tctgcgctac gttctggtat     420
cggacggctt caagc                                                      435

<210> SEQ ID NO 97
<211> LENGTH: 139
<212> TYPE: PRT
<213> ORGANISM: artificial sequence
<220> FEATURE:
<223> OTHER INFORMATION: mub insertion site 1 antibody C

<400> SEQUENCE: 97

Ala Glu Gly Ile Lys Lys Phe Glu Gly Asp Asp Val Gln Leu Pro Glu
1               5                   10                  15

Ser Gly Arg Thr Leu Val Pro Pro Gly Gly Ser Leu Lys Leu Ser Trp
            20                  25                  30

Ala Thr His Gly Phe Gly Ile Gly Ser Phe Pro Met Leu Trp Val Pro
        35                  40                  45

Pro Ala Pro Gly Lys Gly Leu Glu Tyr Ile Ala Gly Ile Gly Ser Asp
    50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Leu
                85                  90                  95

Pro Glu Asp Thr Ala Asn Tyr Tyr Cys Ala Lys Asp Val Leu Asp Tyr
                100                 105                 110

His Pro Asp Leu Trp Gly Arg Gly Thr Gln Val Thr Val Cys Arg Gly
        115                 120                 125

Arg Gly Tyr Val Leu Val Ser Asp Gly Phe Lys
    130                 135

<210> SEQ ID NO 98
<211> LENGTH: 419
<212> TYPE: DNA

<210> SEQ ID NO 99
<211> LENGTH: 147
<212> TYPE: PRT
<213> ORGANISM: artificial sequence
<220> FEATURE:
<223> OTHER INFORMATION: mub insertion site 1 antibody C

<400> SEQUENCE: 98

```
gctgaaggca tcaagaagtt cgaaggcgac agatgtgcag ctgccagaat ccggaagaac    60
gttggtgcca cccgggggggt ccctgaagct ctcctgggca acgcacggat tcggaatcgg   120
tagtttcccc atgctgtggg tccccccggc ccccggaaaa gggctcgaat atattgcggg   180
cattggtagt gattatacga cacactattc aaattccctc tcgggccgct tcaccatctc   240
taaagacatt gccaagaata cactagatct gcgcatggac gacctactgc ctgaagacac   300
ggccaattat tattgtgcga agacgtact tgactaccac ccagatttgt ggggccgggg   360
aacccaggtc accgtctgca ggggccgcag ctacgttctg gtatcggacg gcttcaagc    419
```

<210> SEQ ID NO 99
<211> LENGTH: 147
<212> TYPE: PRT
<213> ORGANISM: artificial sequence
<220> FEATURE:
<223> OTHER INFORMATION: mub insertion site 1 antibody D

<400> SEQUENCE: 99

Ala Glu Gly Ile Lys Lys Phe Glu Gly Asp Val Gln Leu Gln Glu Ser
1               5                   10                  15

Gly Gly Gly Ser Val Gln Asp Gly Gly Thr Leu Gln Leu Ser Cys Glu
            20                  25                  30

Asp Ser Lys Trp Ser Tyr Thr Tyr Tyr Cys Met Gly Trp Phe Arg Gln
        35                  40                  45

Ala Pro Gly Lys Glu Arg Glu Pro Val Ala His Ile Asp Ser Glu Gly
    50                  55                  60

Thr Val Ala Tyr Ala Asp Thr Val Lys Gly Arg Phe Thr Ile Ser Arg
65                  70                  75                  80

Gly Asp Ala Lys His Arg Val Tyr Leu Gln Met Glu Thr Asn Asn Leu
                85                  90                  95

Lys Ala Asp Asp Thr Ala Ile Tyr Tyr Cys Ala Ala Asn Gly Gly Tyr
            100                 105                 110

Cys Leu Arg Pro Arg Gln Leu Ala Ala Asp Tyr Glu Tyr Trp Gly Gln
        115                 120                 125

Gly Ala Gln Val Thr Val Ser Ser Gly Gly Tyr Val Leu Val Ser Asp
    130                 135                 140

Gly Phe Lys
145

<210> SEQ ID NO 100
<211> LENGTH: 441
<212> TYPE: DNA
<213> ORGANISM: artificial sequence
<220> FEATURE:
<223> OTHER INFORMATION: mub insertion site 1 antibody D

<400> SEQUENCE: 100

```
gctgaaggca tcaagaagtt cgaaggcgac aagtgcagct gcaggagtct gggggaggct    60
cggtgcagga tggagggact ttacaactct cttgtgaaga ctctaaatgg agctacacgt   120
actattgtat gggtggttc cgccaggctc cagggaagga gcgagagccg gtcgcgcaca   180
ttgatagtga aggcactgtc gcttacgccg acaccgtgaa gggccgattc accatctccc   240
ggggggacgc caagcatagg gtttacctgc aaatgaataa cttgaaggct gatgacacgg   300
```

```
ccatctatta ttgtgcggcc aatggtggtt attgcctcag accccgtcaa ctcgccgcgg    360
attatgagta ttggggccag ggggcccagg tcaccgtctc cagcggccgc agctacgttc    420
tggtatcgga cggcttcaag c                                              441
```

<210> SEQ ID NO 101
<211> LENGTH: 139
<212> TYPE: PRT
<213> ORGANISM: artificial sequence
<220> FEATURE:
<223> OTHER INFORMATION: mub insertion site 1 antibody E

<400> SEQUENCE: 101

```
Ala Glu Gly Ile Lys Lys Phe Glu Gly Asp Asp Val Gln Leu Gln Glu
1               5                   10                  15

Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
        35                  40                  45

Gln Ala Pro Gly Lys Gly Leu Glu Tyr Ile Ala Gly Ile Gly Ser Asp
    50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Val
                85                  90                  95

Pro Glu Asp Thr Ala Asn Tyr Tyr Cys Ala Lys Asp Val Leu Asp Tyr
            100                 105                 110

His Pro Asp Leu Trp Gly Gln Gly Thr Gln Val Thr Val Cys Ser Gly
        115                 120                 125

Arg Gly Tyr Val Leu Val Ser Asp Gly Phe Lys
    130                 135
```

<210> SEQ ID NO 102
<211> LENGTH: 421
<212> TYPE: DNA
<213> ORGANISM: artificial sequence
<220> FEATURE:
<223> OTHER INFORMATION: mub insertion site antibody E

<400> SEQUENCE: 102

```
gctgaaggca tcaagaagtt cgaaggcgac agatgtgcag ctgcaggagt ctggaggaac    60
attggtgcag cccggggggt ctctgacgct tcctgtgca gcgcatggat cggaatcgg     120 tagtttcgcc atgctgtggg tccgccaggc cccaggaaag gggctcgagt atattgcggg   180
cattggtagt gattatacga cacactattc aaattccctc tcgggccgct tcaccatctc   240
taaagacatt gccaagaata cactagatct gcgcatggac gacctagtgc ctgaagacac   300
ggccaattat tattgtgcga aagacgtact tgactaccac ccagatttgt ggggccaggg   360
aacccaggtc accgtctgca gcggccgcac tgctacgttc tggtatcgga cggcttcaag   420
c                                                                    421
```

<210> SEQ ID NO 103
<211> LENGTH: 139
<212> TYPE: PRT
<213> ORGANISM: artificial sequence
<220> FEATURE:
<223> OTHER INFORMATION: mub insertion site 1 antibody F

<400> SEQUENCE: 103

```
Ala Glu Gly Ile Lys Lys Phe Glu Gly Asp Asp Val Gln Leu Gln Glu
1               5                   10                  15

Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
            35                  40                  45

Gln Ala Pro Gly Lys Gly Leu Glu Tyr Ile Ala Gly Ile Gly Ser Asp
        50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Val
                85                  90                  95

Pro Glu Asp Thr Ala Asn Tyr Tyr Cys Ala Lys Asp Val Leu Asp Tyr
            100                 105                 110

His Pro Asp Leu Trp Gly Gln Gly Thr Gln Val Thr Val Cys Ser Gly
        115                 120                 125

Arg Gly Tyr Val Leu Val Ser Asp Gly Phe Lys
        130                 135

<210> SEQ ID NO 104
<211> LENGTH: 418
<212> TYPE: DNA
<213> ORGANISM: artificial sequence
<220> FEATURE:
<223> OTHER INFORMATION: mub insertion site 1 antibody F

<400> SEQUENCE: 104
gctgaaggca tcaagaagtt cgaaggcgac agatgtgcag ctgcaggagt ctggaggaac      60
attggtgcag cccggggggt ctctgacgct ctcctgtgca gcgcatggat tcggaatcgg     120
tagtttcgcc atgctgtggg tccgccaggc cccaggaaag gggctcgagt atattgcggg     180
cattggtagt gattatacga cacactattc aaattccctc tcgggccgct tcaccatctc     240
taaagacatt gccaagaata cactagatct gcgcatggac gacctagtgc ctgaagacac     300
ggccaattat tattgtgcga agacgtact tgactaccac ccagatttgt ggggccaggg     360
aacccaggtc accgtctgca gcggccgcgc tacgttctgg tatcggacgg cttcaagc      418

<210> SEQ ID NO 105
<211> LENGTH: 139
<212> TYPE: PRT
<213> ORGANISM: artificial sequence
<220> FEATURE:
<223> OTHER INFORMATION: mub insertion site 1 antibody G

<400> SEQUENCE: 105

Ala Glu Gly Ile Lys Lys Phe Glu Gly Asp Asp Val Gln Leu Gln Glu
1               5                   10                  15

Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
            35                  40                  45

Gln Ala Pro Gly Lys Gly Leu Glu Tyr Ile Ala Gly Ile Gly Ser Asp
        50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Val
                85                  90                  95
```

```
Pro Glu Asp Thr Ala Asn Tyr Tyr Cys Ala Lys Asp Val Leu Asp Tyr
            100                 105                 110

His Pro Asp Leu Trp Gly Gln Gly Thr Gln Val Thr Val Cys Ser Gly
            115                 120                 125

Arg Gly Tyr Val Leu Val Ser Asp Gly Phe Lys
        130                 135
```

<210> SEQ ID NO 106
<211> LENGTH: 421
<212> TYPE: DNA
<213> ORGANISM: artificial sequence
<220> FEATURE:
<223> OTHER INFORMATION: mub insertion site 1 antibody G

<400> SEQUENCE: 106

```
gctgaaggca tcaagaagtt cgaaggcgac agatgtgcag ctgcaggagt ctggaggaac    60
attggtgcag cccgggggt ctctgacgct ctcctgtgca gcgcatggat tcggaatcgg    120
tagtttcgcc atgctgtggg tccgccaggc cccaggaaag gggctcgagt atattgcggg    180
cattggtagt gattatacga cacactattc aaattccctc tcgggccgct tcaccatctc    240
taaagacatt gccaagaata cactagatct gcgcatggac gacctagtgc tgaagacac    300
ggccaattat tattgtgcga aagacgtact tgactaccac ccagatttgt ggggccaggg    360
aacccaggtc accgtctgca gcggccgcac tgctacgttc tggtatcgga cggcttcaag    420
c                                                                    421
```

<210> SEQ ID NO 107
<211> LENGTH: 148
<212> TYPE: PRT
<213> ORGANISM: artificial sequence
<220> FEATURE:
<223> OTHER INFORMATION: mub insertion site 1 antibody H

<400> SEQUENCE: 107

```
Ala Glu Gly Ile Lys Lys Phe Glu Gly Asp Asp Val Gln Leu Gln Glu
1               5                   10                  15

Ser Gly Gly Gly Ser Val Gln Thr Gly Gly Ser Leu Arg Leu Ser Cys
            20                  25                  30

Ala Ala Ser Gly Asp Ser Ile Thr Thr Tyr His Met Ala Trp Phe Arg
        35                  40                  45

Gln Thr Pro Gly Lys Glu Arg Glu Glu Val Ala Val Ile Asn Asp Asp
    50                  55                  60

Ala Asn Ser Arg Ile Tyr Val Asp Ser Val Lys Gly Arg Phe Thr Ile
65                  70                  75                  80

Ser Gln Asp Lys Ala Lys Asn Thr Val Tyr Leu Gln Met Asn Tyr Leu
                85                  90                  95

Thr Pro Glu Asp Thr Ala Ile Tyr Tyr Cys Ala Ala Asp Leu Arg Cys
            100                 105                 110

Val Pro Gly Thr Asp Ser Gly His Pro Tyr Ser Tyr Asn Tyr Trp Gly
        115                 120                 125

Gln Gly Thr Gln Val Thr Val Cys Ser Gly Tyr Val Leu Val Ser
    130                 135                 140

Asp Gly Phe Lys
145
```

<210> SEQ ID NO 108
<211> LENGTH: 446

```
<212> TYPE: DNA
<213> ORGANISM: artificial sequence
<220> FEATURE:
<223> OTHER INFORMATION: mub insertion site 1 antibody H

<400> SEQUENCE: 108
gctgaaggca tcaagaagtt cgaaggcgac agatgtgcag ctgcaggagt ctggaggagg      60
ttcggtgcag actggaggat ctctgagact ctcctgtgca gcctctggag attccatcac     120
tacctaccac atggcctggt tccgccagac tccaggaaag gagcgtgagg aggtcgcagt     180
tataaatgat gatgctaatt cgagaatcta tgtcgactcc gtgaagggcc gattcaccat     240
ctcccaagac aaggccaaga acacggtgta tctgcaaatg aactacctga cgcctgagga     300
cacggccatc tactactgtg cggcagattt gaggtgcgtc cctgggaccg actctggtca     360
tccttattcg tataactact ggggccaggg gacccaggtc accgtctgca gcggccgcta     420
cgttctggta tcggacggct tcaagc                                          446

<210> SEQ ID NO 109
<211> LENGTH: 145
<212> TYPE: PRT
<213> ORGANISM: artificial sequence
<220> FEATURE:
<223> OTHER INFORMATION: mub insertion site 1 antibody I

<400> SEQUENCE: 109

Ala Glu Gly Ile Lys Lys Phe Glu Gly Asp Asp Val His Leu Gln Asp
  1               5                  10                  15

Ser Gly Gly Gly Ser Val Gln Ala Gly Gly Ser Leu Thr Leu Ser Trp
             20                  25                  30

Leu Met Ser Gly His Thr Tyr Tyr Gly Pro Cys Val Gly Trp Phe Arg
         35                  40                  45

Gln Pro Pro Gly Lys Ala Arg Glu Gly Ile Pro Gln Ile Ser Pro Ile
     50                  55                  60

Gly Gly Ser Val Ile Tyr Ile Gly Gly Val Lys Gly Arg Phe Thr Ile
 65                  70                  75                  80

Ser Arg Asp Asn Ser Lys Asn Thr Ile Ala Leu Ile Met Asn Asp Leu
                 85                  90                  95

Leu Pro Glu Asp Thr Ala Thr Tyr Tyr Cys Ala Ala Asp Ser Gly Gly
            100                 105                 110

Leu Cys Ser His Arg Glu Arg Asp Tyr Asp Ile Trp Gly Gln Gly Thr
        115                 120                 125

Gln Val Thr Val Cys Ser Gly Gly Tyr Val Leu Val Ser Asp Gly Phe
    130                 135                 140

Lys
145

<210> SEQ ID NO 110
<211> LENGTH: 434
<212> TYPE: DNA
<213> ORGANISM: artificial sequence
<220> FEATURE:
<223> OTHER INFORMATION: mub insertion site 1 antibody I

<400> SEQUENCE: 110
gctgaaggca tcaagaagtt cgaaggcgac agatgtgcac ctgcaggatt ctggaggagg      60
ctcggtgcag gctggaggct ccctgacgct ctcttggtta atgtcgggtc atacgtatta    120
tggaccttgt gtgggttggt tccgccagcc cccagggaaa gcgcgtgagg gaatcccaca    180
```

```
gattagtcct attggtggga gtgttattta cattggtggc gtgaagggcc gattcaccat    240
ttcccgagac aactccaaga atactattgc tctcataatg aacgacctcc tgcctgaaga    300
cacggccact tattattgcg cagcagattc aggggg actc tgcagccatc gtgagcgcga    360
ctatgacatt tggggccagg ggacccaggt caccgtctgc ggccgctacg ttctggtatc    420
ggacggcttc aagc                                                       434
```

<210> SEQ ID NO 111
<211> LENGTH: 145
<212> TYPE: PRT
<213> ORGANISM: artificial sequence
<220> FEATURE:
<223> OTHER INFORMATION: mub insertion site 1 antibody J

<400> SEQUENCE: 111

```
Ala Glu Gly Ile Lys Lys Phe Glu Gly Asp Val His Leu Gln Asp
 1               5                  10                  15

Ser Gly Glu Gly Trp Gly His Ala Gly Gly Ser Leu Thr Leu Ser Cys
            20                  25                  30

Leu Met Ser Gly His Thr Tyr Tyr Gly Pro Cys Gly Gly Gly Phe Pro
        35                  40                  45

Gln Pro Pro Gly Lys Ala Arg Glu Gly Ile Pro Gln Met Ile Pro Ile
    50                  55                  60

Gly Gly Ser Val Ile Tyr Ile Gly Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Val Pro Glu Asp Thr Ala Thr Tyr Tyr Cys Ala Thr Asp Ser Gly Gly
            100                 105                 110

Leu Cys Ser His Arg Glu Arg Asp Tyr Asp Ile Trp Gly Gln Gly Thr
        115                 120                 125

Gln Val Thr Val Cys Ser Gly Gly Tyr Val Leu Val Ser Asp Gly Phe
    130                 135                 140

Lys
145
```

<210> SEQ ID NO 112
<211> LENGTH: 434
<212> TYPE: DNA
<213> ORGANISM: artificial sequence
<220> FEATURE:
<223> OTHER INFORMATION: mub insertion site 1 antibody J

<400> SEQUENCE: 112

```
gctgaaggca tcaagaagtt cgaaggcgac agatgtgcac ctgcaggatt cgggagaagg     60
ctgggggcac gctggaggct ccctgaccct ctcttgttta atgtcgggtc atacgtatta    120
tggaccttgt gggggtgggt tcccccagcc cccaggaaaa gcccgtgagg aatcccaca    180 aatgattcct attggtggga gtgttattta cattggtggc gtgaagggcc gattcaccat    240
ttcccgagac aactccaaga atactattgc tctcataatg aacgacctcg tgcctgaaga    300
cacggccact tattattgcg caacagattc aggggg actc tgcagccatc gtgagcgcga    360
ctatgacatt tggggccagg ggacccaggt caccgtctgc ggccgctacg ttctggtatc    420
ggacggcttc aagc                                                      434
```

<210> SEQ ID NO 113
<211> LENGTH: 144

```
<212> TYPE: PRT
<213> ORGANISM: artificial sequence
<220> FEATURE:
<223> OTHER INFORMATION: mub insertion site 1 antibody K

<400> SEQUENCE: 113

Ala Glu Gly Ile Lys Lys Phe Glu Gly Asp Asp Val His Leu Gln Asp
1               5                   10                  15

Ser Gly Gly Gly Ser Val His Ala Gly Gly Ser Leu Thr Leu Ser Cys
            20                  25                  30

Leu Met Ser Gly His Thr Tyr Tyr Gly Pro Cys Gly Gly Gly Phe Pro
        35                  40                  45

Arg Pro Pro Gly Lys Gly Arg Glu Gly Ile Ala Gln Ile Ile Pro Ile
    50                  55                  60

Gly Gly Ser Val Ile Tyr Ile Gly Gly Val Lys Gly Arg Phe Thr Ile
65                  70                  75                  80

Ser Arg Tyr Asn Ser Lys Asn Thr Ile Ala Leu Ile Met Asn Asp Leu
                85                  90                  95

Val Pro Glu Asp Thr Ala Thr Tyr Cys Ala Thr Asp Ser Gly Gly Leu
            100                 105                 110

Cys Ser His Arg Glu Arg Asp Tyr Asp Ile Trp Gly Gln Gly Thr Gln
        115                 120                 125

Val Thr Val Cys Ser Gly Gly Tyr Val Leu Val Ser Asp Gly Phe Lys
    130                 135                 140

<210> SEQ ID NO 114
<211> LENGTH: 437
<212> TYPE: DNA
<213> ORGANISM: artificial sequence
<220> FEATURE:
<223> OTHER INFORMATION: mub insertion site 1 antibody K

<400> SEQUENCE: 114
gctgaaggca tcaagaagtt cgaaggcgac agatgtgcac ctgcaggatt ctggaggagg    60
ctcggtgcac gctgggggct ccctgacgct ctcttgttta atgtcgggtc atacgtatta   120
tggaccttgt gggggtgggt tcccccggcc cccaggaaaa gggcgtgagg gaatcgcaca   180
aattattcct attggtggga gtgttattta cattggtggc gtgaagggcc gattcaccat   240
ttcccgatac aactccaaga atactattgc tctcataatg aacgacctcg tgcctgaaga   300
cacggccact tattattgcg caacagattc aggggggactc tgcagccatc gtgagcgcga   360
ctatgacatt tggggccagg ggacccaggt caccgtctgc agcggccgct acgttctggt   420
atcggacggc ttcaagc                                                 437

<210> SEQ ID NO 115
<211> LENGTH: 144
<212> TYPE: PRT
<213> ORGANISM: artificial sequence
<220> FEATURE:
<223> OTHER INFORMATION: mub insertion site antibody L

<400> SEQUENCE: 115

Ala Glu Gly Ile Lys Lys Phe Glu Gly Asp Asp Val His Leu Gln Asp
1               5                   10                  15

Ser Gly Gly Gly Ser Val Gln Ala Gly Gly Ser Leu Thr Leu Ser Cys
            20                  25                  30

Leu Met Ser Gly His Thr Tyr Tyr Gly Pro Cys Val Gly Trp Phe Pro
        35                  40                  45
```

Gln Arg Pro Gly Lys Ala Arg Glu Gly Ile Ala Gln Met Ile Pro Ile
            50                  55                  60

Gly Gly Ser Val Ser Tyr Ser Gly Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Val Pro Glu Asp Thr Ala Thr Tyr Tyr Cys Ala Thr Asp Ser Gly Gly
            100                 105                 110

Leu Cys Ser His Arg Glu Arg Asp Tyr Asp Ile Trp Gly Gln Gly Thr
                115                 120                 125

Gln Val Thr Val Cys Ser Gly Tyr Val Leu Val Ser Asp Gly Phe Lys
            130                 135                 140

<210> SEQ ID NO 116
<211> LENGTH: 433
<212> TYPE: DNA
<213> ORGANISM: artificial sequence
<220> FEATURE:
<223> OTHER INFORMATION: mub insertion site 1 antibody L

<400> SEQUENCE: 116
gctgaaggca tcaagaagtt cgaaggcgac agatgtgcac ctgcaggatt ctggaggagg     60
ctcggtgcag gctggaggct ccctgaccct ctcttgttta atgtcgggtc atacgtatta    120
tggaccttgt gtgggttggt tcccccagcg tccaggaaaa gcgcgtgagg gaatcgcaca    180
aatgattcct attggtggga gtgttagtta cagtggtggc gtgaagggcc gattcaccat    240
ttcccgagac aactccaaga atactattgc tctcataatg aacgaccgcg tgcctgaaga    300
cacggccact tattattgcg caacagattc aggggggactc tgcagccatc gtgagcgcga    360
ctatgacatt tggggccagg ggacccaggt caccgtctgc agcgctacgt tctggtatcg    420
gacggcttca agc                                                      433

<210> SEQ ID NO 117
<211> LENGTH: 147
<212> TYPE: PRT
<213> ORGANISM: artificial sequence
<220> FEATURE:
<223> OTHER INFORMATION: mub insertion site 1 antibody M

<400> SEQUENCE: 117

Ala Glu Gly Ile Lys Lys Phe Glu Gly Asp Asp Val Gln Leu Gln Glu
1               5                   10                  15

Ser Gly Gly Gly Ser Val Gln Glu Gly Gly Ser Leu Arg Leu Ser Cys
            20                  25                  30

Ala Ala Ser Glu Tyr Thr Ala Ile Thr Tyr Cys Met Ala Trp Phe Arg
            35                  40                  45

Gln Ala Pro Gly Lys Glu Arg Glu Gly Val Ala Ala Ile Asn Arg Gly
        50                  55                  60

Gly Gly Ser Thr Tyr Tyr Ala Asp Ser Val Lys Gly Arg Phe Thr Ile
65                  70                  75                  80

Ser Gln Asp Asn Ala Lys Asn Thr Val Tyr Leu Leu Met Asn Ser Leu
                85                  90                  95

Lys Pro Glu Asp Thr Gly Met Tyr Tyr Cys Ala Tyr Lys Gln Thr Gly
            100                 105                 110

Asp Cys Gly Ile Phe Gln Phe Phe Gly Asn Tyr Gly Gln Gly Thr Gln
            115                 120                 125

Val Thr Val Ser Ser Gly Arg Thr His Gly Tyr Val Leu Val Ser Asp

Gly Phe Lys
145

<210> SEQ ID NO 118
<211> LENGTH: 439
<212> TYPE: DNA
<213> ORGANISM: artificial sequence
<220> FEATURE:
<223> OTHER INFORMATION: mub insertion site 1 antibody M

<400> SEQUENCE: 118

```
gctgaaggca tcaagaagtt cgaaggcgac gatccagatg tgcagctgca ggagtctggg      60
ggaggctcgg tgcaggaggg agggtctctg agactctcct gtgcagcctc tgaatacacc     120
gctattacct actgtatggc ctggttccgc caggctccag ggaaggagcg tgaggggtc      180
gcggctatca atcgcggtgg tggtagtaca tattacgccg actccgtgaa gggccgattc     240
accatctccc aggacaacgc caagaacacg gtgtatctcc taatgaacag cctgaaacct     300
gaggacactg gcatgtacta ctgtgcgtac aaacagaccg tgattgtgg gatcttccaa      360
ttctttggaa actatggcca ggggacccag gtcaccgtct ccagcggccg ctacgttctg     420
gtatcggacg gcttcaagc                                                  439
```

<210> SEQ ID NO 119
<211> LENGTH: 148
<212> TYPE: PRT
<213> ORGANISM: artificial sequence
<220> FEATURE:
<223> OTHER INFORMATION: mub insertion site 1 antibody N

<400> SEQUENCE: 119

Ala Glu Gly Ile Lys Lys Phe Glu Gly Asp Asp Val Gln Leu Gln Glu
1               5                   10                  15

Ser Gly Gly Gly Ser Val Gln Thr Gly Gly Ser Leu Arg Leu Ser Cys
            20                  25                  30

Ala Ala Ser Gly Asp Ser Ile Thr Thr Tyr His Met Ala Trp Phe Arg
        35                  40                  45

Gln Thr Pro Gly Lys Glu Arg Glu Glu Val Ala Val Ile Asn Asp Asp
    50                  55                  60

Ala Asn Ser Arg Ile Tyr Val Asp Ser Val Lys Gly Arg Phe Thr Ile
65                  70                  75                  80

Ser Gln Asp Lys Ala Lys Asn Thr Val Tyr Leu Gln Met Asn Tyr Leu
                85                  90                  95

Thr Pro Glu Asp Thr Ala Ile Tyr Tyr Cys Ala Ala Asp Leu Arg Cys
            100                 105                 110

Val Pro Gly Thr Asp Ser Gly His Pro Tyr Ser Tyr Asn Tyr Trp Gly
        115                 120                 125

Gln Gly Thr Gln Val Thr Ala Ser Ser Gly Tyr Val Leu Val Ser
    130                 135                 140

Asp Gly Phe Lys
145

<210> SEQ ID NO 120
<211> LENGTH: 446
<212> TYPE: DNA
<213> ORGANISM: artificial sequence
<220> FEATURE:
<223> OTHER INFORMATION: mub insertion site 1 antibody N

<400> SEQUENCE: 120

| | |
|---|---|
| gctgaaggca tcaagaagtt cgaaggcgac agatgtgcag ctgcaggagt ctggaggagg | 60 |
| ttcggtgcag actggaggat ctctgagact ctcctgtgca gcctctggag attccatcac | 120 |
| tacctaccac atggcctggt tccgccagac tccagggaag gagcgtgagg aggtcgcagt | 180 |
| tataaatgat gatgctaatt cgagaatcta tgtcgactcc gtgaagggcc gattcaccat | 240 |
| ctcccaagac aaggccaaga acacggtgta tctgcaaatg aactacctga cgcctgagga | 300 |
| cacggccatc tactactgtg cggcagattt gaggtgcgtc cctgggaccg actctggtca | 360 |
| tccttattcg tataactact ggggccaggg gacccaggtc accgcctcca gcggccgcta | 420 |
| cgttctggta tcggacggct tcaagc | 446 |

<210> SEQ ID NO 121
<211> LENGTH: 149
<212> TYPE: PRT
<213> ORGANISM: artificial sequence
<220> FEATURE:
<223> OTHER INFORMATION: mub insertion site 1 antibody O

<400> SEQUENCE: 121

Ala Glu Gly Ile Lys Lys Phe Glu Gly Asp Asp Val Gln Leu Gln Glu
1               5                   10                  15

Ser Gly Gly Gly Ser Val Gln Thr Gly Gly Ser Leu Arg Leu Ser Cys
            20                  25                  30

Ala Ala Ser Gly Asp Ser Ile Thr Thr Tyr His Met Ala Trp Phe Arg
        35                  40                  45

Gln Thr Pro Gly Lys Glu Arg Glu Glu Val Ala Val Ile Asn Asp Asp
    50                  55                  60

Ala Asn Ser Arg Ile Tyr Val Asp Ser Val Lys Gly Arg Phe Thr Ile
65                  70                  75                  80

Ser Gln Asp Lys Ala Lys Asn Thr Val Tyr Leu Gln Met Asn Tyr Leu
                85                  90                  95

Thr Pro Glu Asp Thr Ala Ile Tyr Tyr Cys Ala Ala Asp Leu Arg Cys
            100                 105                 110

Val Pro Gly Thr Asp Ser Gly His Pro Tyr Ser Tyr Asn Tyr Trp Gly
        115                 120                 125

Gln Gly Thr Gln Val Thr Ala Ser Ser Gly Arg Gly Tyr Val Leu Val
    130                 135                 140

Ser Asp Gly Phe Lys
145

<210> SEQ ID NO 122
<211> LENGTH: 446
<212> TYPE: DNA
<213> ORGANISM: artificial sequence
<220> FEATURE:
<223> OTHER INFORMATION: mub insertion site 1 antibody O

<400> SEQUENCE: 122

| | |
|---|---|
| gctgaaggca tcaagaagtt cgaaggcgac agatgtgcag ctgcaggagt ctggaggagg | 60 |
| ttcggtgcag actggaggat ctctgagact ctcctgtgca gcctctggag attccatcac | 120 |
| tacctaccac atggcctggt tccgccagac tccagggaag gagcgtgagg aggtcgcagt | 180 |
| tataaatgat gatgctaatt cgagaatcta tgtcgactcc gtgaagggcc gattcaccat | 240 |
| ctcccaagac aaggccaaga acacggtgta tctgcaaatg aactacctga cgcctgagga | 300 |
| cacggccatc tactactgtg cggcagattt gaggtgcgtc cctgggaccg actctggtca | 360 | tccttattcg tataactact ggggccaggg gacccaggtc accgcctcca gcggccgcta    420 cgttctggta tcggacggct tcaagc    446

<210> SEQ ID NO 123
<211> LENGTH: 150
<212> TYPE: PRT
<213> ORGANISM: artificial sequence
<220> FEATURE:
<223> OTHER INFORMATION: mub insertion site 1 antibody P

<400> SEQUENCE: 123

Ala Glu Gly Ile Lys Lys Phe Glu Gly Asp Val Gln Leu Gln Glu
1               5                   10                  15

Ser Gly Gly Gly Ser Ala Gln Pro Gly Gly Ser Leu Arg Leu Ser Cys
            20                  25                  30

Ala Val Ser Gly Ser Thr Ala Ser Met Tyr Cys Leu Ala Trp Phe Arg
        35                  40                  45

Gln Ala Pro Gly Lys Glu Pro Glu Gly Val Ala Ala Ile Ser Gly Asp
    50                  55                  60

Asp Lys Gly Phe Thr Asn Tyr Ala Asp Ser Val Lys Gly Arg Phe Thr
65                  70                  75                  80

Ile Ser Gln Asn Lys Ala Asn Lys Thr Val Asn Leu Gln Met Asn Ser
                85                  90                  95

Leu Lys Pro Glu Asp Thr Ala Ile Tyr Tyr Cys Ala Val Asp Ala Arg
            100                 105                 110

Ala Thr Thr Thr Gly Glu Arg Leu His Ala Arg Thr Tyr Glu Phe Trp
        115                 120                 125

Gly Gln Gly Thr Gln Val Thr Val Cys Ser Gly Arg Gly Tyr Val Leu
    130                 135                 140

Val Ser Asp Gly Phe Lys
145                 150

<210> SEQ ID NO 124
<211> LENGTH: 450
<212> TYPE: DNA
<213> ORGANISM: artificial sequence
<220> FEATURE:
<223> OTHER INFORMATION: mub insertion site 1 antibody P

<400> SEQUENCE: 124
gctgaaggca tcaagaagtt cgaaggcgac gatgtgcagc tgcaggagtc tgggggaggc    60
tcggcgcagc ctggagggtc tctgagactc tcctgtgcag tctctggatc gaccgccagt    120
atgtactgct tggcctggtt ccgccaggct ccagggaagg agcctgaggg ggttgctgct    180
attagtggag atgataaagg gtttacgaat tacgccgact ccgtgaaggg ccggttcacc    240
atctcccaaa acaaggccaa taaaacggtg aatctgcaaa tgaacagcct gaaacctgaa    300
gacacggcca tttattactg tgccgttgat gcgcgagcga caacaactgg tgaacgtcta    360
cacgcccgga cgtacgaatt ctggggccag gggacccagg tcaccgtctg cagcggccgc    420
gctacgttct ggtatcggac ggcttcaagc    450

<210> SEQ ID NO 125
<211> LENGTH: 150
<212> TYPE: PRT
<213> ORGANISM: artificial sequence
<220> FEATURE:
<223> OTHER INFORMATION: mub insertion site 1 antibody Q

<400> SEQUENCE: 125

Ala Glu Gly Ile Lys Lys Phe Glu Gly Asp Asp Val Gln Met Gln Glu
1               5                   10                  15

Ser Gly Gly Gly Ser Val Gln Ala Gly Gly Ser Leu Arg Leu Ser Cys
            20                  25                  30

Ala Ala Ser Gly Asp Thr Leu Ser Thr Tyr Cys Met Gly Trp Phe Arg
        35                  40                  45

Gln Val Pro Gly Lys Asp Arg Glu Gly Val Ala Ala Ile Tyr Arg Leu
    50                  55                  60

Arg Asp Met Thr Phe Tyr Ala Asp Ser Val Lys Gly Arg Phe Thr Ile
65                  70                  75                  80

Ser Arg Asp Asn Ala Asn Asp Thr Val Asp Leu Gln Met Glu Thr Asn
                85                  90                  95

Ser Leu Lys Pro Glu Asp Thr Ala Val Tyr Tyr Cys Ala Ala Arg Cys
            100                 105                 110

Val Arg Leu Phe Gly Thr Cys Gln Leu Val Glu Asp Phe Glu Leu Trp
        115                 120                 125

Gly Gln Gly Thr Gln Val Thr Val Ser Ser Gly Leu Gly Tyr Val Leu
    130                 135                 140

Val Ser Asp Gly Phe Lys
145                 150

<210> SEQ ID NO 126
<211> LENGTH: 442
<212> TYPE: DNA
<213> ORGANISM: artificial sequence
<220> FEATURE:
<223> OTHER INFORMATION: mub insertion site 1 antibody Q

<400> SEQUENCE: 126
gctgaaggca tcaagaagtt cgaaggcgac agatgtgcag atgcaggagt ctgggggagg      60
gtcggtgcag gctggagggt ctctgagact ctcctgtgca gcctctggag ataccctcag     120
tacctactgc atgggctggt tccgccaagt tccagggaag gaccgtgagg gggtcgcagc     180
gatttatcgt cttagggata tgacgttcta tgccgactcc gtgaagggcc gattcaccat     240
ttcccgtgac aacgccaacg acacggtaga tctgcaaatg aacagcctga aacctgagga     300
cacagccgtg tactactgtg cagcaagatg tgtgcgacta ttcggtactt gtcagctagt     360
cgaagatttt gaactatggg gccaggggac ccaggtcacc gtctccagcg gcgctacgtt     420
ctggtatcgg acggcttcaa gc                                              442

<210> SEQ ID NO 127
<211> LENGTH: 149
<212> TYPE: PRT
<213> ORGANISM: artificial sequence
<220> FEATURE:
<223> OTHER INFORMATION: mub insertion site 1 antibody R

<400> SEQUENCE: 127

Ala Glu Gly Ile Lys Lys Phe Glu Gly Asp Asp Val Gln Met Gln Glu
1               5                   10                  15

Ser Gly Gly Gly Ser Val Gln Ala Gly Gly Ser Leu Arg Leu Ser Cys
            20                  25                  30

Ala Ala Ser Gly Asp Thr Leu Ser Thr Tyr Cys Met Gly Trp Phe Arg
        35                  40                  45

Gln Ala Pro Gly Lys Asp Arg Glu Gly Val Ala Ala Ile Tyr Arg Leu
    50                  55                  60

Arg Asp Met Thr Phe Tyr Ala Asp Ser Val Lys Gly Arg Phe Thr Ile
65                  70                  75                  80

Ser Arg Asp Asn Ala Asn Asp Thr Val Asp Leu Gln Met Asn Ser Leu
                85                  90                  95

Lys Pro Glu Asp Thr Ala Val Tyr Tyr Cys Ala Ala Arg Cys Val Arg
            100                 105                 110

Leu Phe Gly Thr Cys Gln Leu Val Glu Asp Phe Glu Leu Trp Gly Gln
        115                 120                 125

Gly Thr Gln Val Thr Val Ser Ser Gly Leu Thr Gly Tyr Val Leu Val
    130                 135                 140

Ser Asp Gly Phe Lys
145

<210> SEQ ID NO 128
<211> LENGTH: 442
<212> TYPE: DNA
<213> ORGANISM: artificial sequence
<220> FEATURE:
<223> OTHER INFORMATION: mub insertion site 1 antibody R

<400> SEQUENCE: 128
gctgaaggca tcaagaagtt cgaaggcgac agatgtgcag atgcaggagt ctggggagg      60 gtcggtgcag ctggagggt ctctgagact ctcctgtgca gcctctggag ataccctcag     120
tacctactgc atgggctggt tccgccaagt tccagggaag gaccgtgagg gggtcgcagc    180
gatttatcgt cttagggata tgacgttcta tgccgactcc gtgaagggcc gattcaccat    240
tccccgtgac aacgccaacg acacggtaga tctgcaaatg aacagcctga acctgagga    300 cacagccgtg tactactgtg cagcaagatg tgtgcgacta ttcggtactt gtcagctagt   360
cgaagatttt gaactatggg gccaggggac ccaggtcacc gtctccagcg gcgctacgtt   420
ctggtatcgg acggcttcaa gc                                             442

<210> SEQ ID NO 129
<211> LENGTH: 149
<212> TYPE: PRT
<213> ORGANISM: artificial sequence
<220> FEATURE:
<223> OTHER INFORMATION: mub insertion site 1 antibody S

<400> SEQUENCE: 129

Ala Glu Gly Ile Lys Lys Phe Glu Gly Asp Asp Val Gln Met Gln Glu
1               5                   10                  15

Ser Gly Gly Gly Ser Val Gln Ala Gly Gly Ser Leu Arg Leu Ser Cys
            20                  25                  30

Ala

Gly Thr Gln Val Thr Val Ser Ser Gly Leu Thr Gly Tyr Val Leu Val
        130                 135                 140

Ser Asp Gly Phe Lys
145

<210> SEQ ID NO 130
<211> LENGTH: 443
<212> TYPE: DNA
<213> ORGANISM: artificial sequence
<220> FEATURE:
<223> OTHER INFORMATION: mub insertion site 1 antibody S

<400> SEQUENCE: 130
gctgaaggca tcaagaagtt cgaaggcgac agatgtgcag atgcaggagt ctgggggagg     60
gtcggtgcag gctggagggt ctctgagact ctcctgtgca gcctctggag atacactcag    120
tacctactgc atgggctggt tccgccaagt tccagggaag gaccgtgagg gggtcgcagc    180
gatttatcgt cttagggata tgacgttcta tgccgactcc gtgaagggcc gattcaccat    240
ttcccgtgac aacgccaacg acacggtaga tctgcaaatg aacagcctga aacctgagga    300
cacagccgtg tactactgtg cagcaagatg tgtgcgacta ttcggtactt gtcagctagt    360
cgaagatttt gaactatggg gccaggggac ccaggtcacc gtctccagcg gccgaagtcg    420
tcaaggaact cgaaaagcag ggt                                            443

<210> SEQ ID NO 131
<211> LENGTH: 146
<212> TYPE: PRT
<213> ORGANISM: artificial sequence
<220> FEATURE:
<223> OTHER INFORMATION: mub insertion site 2 antibody A

<400> SEQUENCE: 131

Thr Pro Asp Ser Lys Asp Ile Val Lys Thr Asp Val Gln Leu Gln Glu
1               5                   10                  15

Ser Gly Gly Gly Ser Val Gln Ala Gly Gly Ser Leu Thr Leu Ser Cys
            20                  25                  30

Leu Met Ser Gly His Thr Tyr Tyr Gly Pro Cys Val Gly Trp Phe Arg
        35                  40                  45

Gln Arg Pro Gly Lys Ala Arg Glu Gly Ile Ala Gln Ile Ser Pro Ser
    50                  55                  60

Gly Gly Ser Val Ser Tyr Ser Gly Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Val Pro Glu Asp Thr Ala Thr Tyr Tyr Cys Ala Ala Asp Ser Gly Gly
            100                 105                 110

Leu Cys Ser His Arg Glu Arg Asp Tyr Asp Ile Trp Gly Gln Gly Thr
        115                 120                 125

Gln Val Thr Val Cys Ser Gly Arg Val Val Tyr Val Gly Asn Pro Gln
    130                 135                 140

Glu Ala
145

<210> SEQ ID NO 132
<211> LENGTH: 439
<212> TYPE: DNA
<213> ORGANISM: artificial sequence
<220> FEATURE:
<223> OTHER INFORMATION: mub insertion site 2 antibody A

<400> SEQUENCE: 132

```
acgccagatt caaaagacat tgtcaagacg atgtgcagct gcaggagtct gggggaggct    60
cggtgcaggc tggaggctcc ctgacgctct cttgtttaat gtctggtcat acgtattatg   120
gaccttgtgt gggttggttc cgccagcgtc cagggaaagc gcgtgaggga atcgcacaga   180
ttagtcctag tggtgggagt gttagttaca gtggtggcgt gaagggccga ttcaccattt   240
cccgagacaa ctccaagaat actattgctc tcataatgaa cgacctcgtg cctgaagaca   300
cggccactta ttattgcgca gcagattcag ggggactctg cagccatcgt gagcgcgact   360
atgacatttg gggccagggg acccaggtca ccgtctgcag cggccgcacg tcgtttatgt   420
tgggaatcct caagaagct                                                439
```

<210> SEQ ID NO 133
<211> LENGTH: 145
<212> TYPE: PRT
<213> ORGANISM: artificial sequence
<220> FEATURE:
<223> OTHER INFORMATION: mub insertion site 2 antibody B

<400> SEQUENCE: 133

```
Thr Pro Asp Ser Lys Asp Ile Val Lys Thr Asp Pro Asp Val His Leu
  1               5                  10                  15
Gln Asp Ser Gly Gly Gly Trp Val His Pro Gly Gly Ser Leu Thr Leu
                 20                  25                  30
Ser Cys Leu Met Ser Gly Ser Glu Tyr Tyr Gly Ser Pro Val Gly Trp
             35                  40                  45
Phe Pro Gln Pro Pro Gly Lys Gly Arg Glu Glu Ile Ala Glu Ile Val
         50                  55                  60
Pro Ile Gly Gly Ser Val Ile Tyr Ile Gly Gly Val Glu Gly Arg Phe
 65                  70                  75                  80
Thr Ile Ser Arg Asp Asn Ser Lys Asn Thr Ile Ala Leu Ile Met Asn
                 85                  90                  95
Asp Leu Leu Pro Glu Asp Thr Ala Thr Tyr Tyr Cys Ala Ala Asp Ser
                100                 105                 110
Gly Gly Leu Cys Ser His Arg Glu Arg Asp Tyr Asp Ile Trp Gly Gln
            115                 120                 125
Gly Thr Gln Val Thr Val Cys Val Val Tyr Val Gly Asn Pro Gln Glu
        130                 135                 140
Ala
145
```

<210> SEQ ID NO 134
<211> LENGTH: 435
<212> TYPE: DNA
<213> ORGANISM: artificial sequence
<220> FEATURE:
<223> OTHER INFORMATION: mub insertion site 2 antibody B

<400> SEQUENCE: 134

```
acgccagatt caaaagacat tgtcaagacg gatccagatg tgcacctgca ggattcggga    60
ggaggctggg tgcacccggg gggctccctg accctctctt gtttaatgtc gggttccgaa   120
tattatggtt cccctgtggg ttggttcccc cagcccccag gaaaggggcg tgaggaaatc   180
gcggaaattg ttcctattgg tgggagtgtt atttacattg gtggcgtgga gggccgattc   240
accatttccc gagacaactc caagaatact attgctctca taatgaacga cctcctgcct   300
```

```
gaagacacgg ccacttatta ttgcgcagca gattcagggg gactctgcag ccatcgtgag      360
cgcgactatg acatttgggg ccaggggacc caggtcaccg tctgcgtcgt ttatgttggg      420
aatcctcaag aagct                                                       435
```

<210> SEQ ID NO 135
<211> LENGTH: 139
<212> TYPE: PRT
<213> ORGANISM: artificial sequence
<220> FEATURE:
<223> OTHER INFORMATION: mub insertion site 2 antibody C

<400> SEQUENCE: 135

```
Thr Pro Asp Ser Lys Asp Ile Val Lys Thr Asp Val Gln Leu Pro Glu
1               5                   10                  15

Ser Gly Arg Thr Leu Val Pro Pro Gly Gly Ser Leu Lys Leu Ser Trp
            20                  25                  30

Ala Thr His Gly Phe Gly Ile Gly Ser Phe Pro Met Leu Trp Val Pro
        35                  40                  45

Pro Ala Pro Gly Lys Gly Leu Glu Tyr Ile Ala Gly Ile Gly Ser Asp
    50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Leu
                85                  90                  95

Pro Glu Asp Thr Ala Asn Tyr Tyr Cys Ala Lys Asp Val Leu Asp Tyr
            100                 105                 110

His Pro Asp Leu Trp Gly Arg Gly Thr Gln Val Thr Val Cys Arg Gly
        115                 120                 125

Arg Val Val Tyr Val Gly Asn Pro Gln Glu Ala
    130                 135
```

<210> SEQ ID NO 136
<211> LENGTH: 419
<212> TYPE: DNA
<213> ORGANISM: artificial sequence
<220> FEATURE:
<223> OTHER INFORMATION: mub insertion site 2 antibody C

<400> SEQUENCE: 136

```
acgccagatt caaaagacat tgtcaagacg agatgtgcag ctgccagaat ccggaagaac       60
gttggtgcca cccggggggt ccctgaagct ctcctgggca acgcacggat tcggaatcgg      120
tagtttcccc atgctgtggg tccccccggc cccggaaaa gggctcgaat atattgcggg       180
cattggtagt gattatacga cacactattc aaattccctc tcgggccgct tcaccatctc      240
taaagacatt gccaagaata cactagatct gcgcatggac gacctactgc ctgaagacac      300
ggccaattat tattgtgcga aagacgtact tgactaccac ccagatttgt ggggccgggg      360
aacccaggtc accgtctgca ggggccgcag tcgtttatgt tgggaatcct caagaagct      419
```

<210> SEQ ID NO 137
<211> LENGTH: 145
<212> TYPE: PRT
<213> ORGANISM: artificial sequence
<220> FEATURE:
<223> OTHER INFORMATION: mub insertion site 2 antibody D

<400> SEQUENCE: 137

```
Thr Pro Asp Ser Lys Asp Ile Val Lys Thr Val Gln Leu Gln Glu Ser
1               5                   10                  15
```

Gly Gly Gly Ser Val Gln Asp Gly Gly Thr Leu Gln Leu Ser Cys Glu
            20                  25                  30

Asp Ser Lys Trp Ser Tyr Thr Tyr Tyr Cys Met Gly Trp Phe Arg Gln
        35                  40                  45

Ala Pro Gly Lys Glu Arg Glu Pro Val Ala His Ile Asp Ser Glu Gly
    50                  55                  60

Thr Val Ala Tyr Ala Asp Thr Val Lys Gly Arg Phe Thr Ile Ser Arg
65                  70                  75                  80

Gly Asp Ala Lys His Arg Val Tyr Leu Gln Met Asn Asn Leu Lys Ala
                85                  90                  95

Asp Asp Thr Ala Ile Tyr Tyr Cys Ala Ala Asn Gly Tyr Cys Leu
            100                 105                 110

Arg Pro Arg Gln Leu Ala Ala Asp Tyr Glu Tyr Trp Gly Gln Gly Ala
        115                 120                 125

Gln Val Thr Val Ser Ser Gly Val Val Tyr Val Gly Asn Pro Gln Glu
    130                 135                 140

Ala
145

<210> SEQ ID NO 138
<211> LENGTH: 441
<212> TYPE: DNA
<213> ORGANISM: artificial sequence
<220> FEATURE:
<223> OTHER INFORMATION: mub insertion site 2 antibody D

<400> SEQUENCE: 138
acgccagatt caaaagacat tgtcaagacg aagtgcagct gcaggagtct gggggaggct      60
cggtgcagga tggagggact ttacaactct cttgtgaaga ctctaaatgg agctacacgt     120
actattgtat ggggtggttc cgccaggctc cagggaagga gcgagagccg gtcgcgcaca     180
ttgatagtga aggcactgtc gcttacgccg acaccgtgaa gggccgattc accatctccc     240 gggggggacgc caagcatagg gtttacctgc aaatgaataa cttgaaggct gatgacacgg     300
ccatctatta ttgtgcggcc aatggtggtt attgcctcag accccgtcaa ctcgccgcgg     360
attatgagta ttggggccag ggggcccagg tcaccgtctc cagcggccgc agtcgtttat     420
gttgggaatc ctcaagaagc t                                              441

<210> SEQ ID NO 139
<211> LENGTH: 139
<212> TYPE: PRT
<213> ORGANISM: artificial sequence
<220> FEATURE:
<223> OTHER INFORMATION: mub insertion site 2 antibody E

<400> SEQUENCE: 139

Thr Pro Asp Ser Lys Asp Ile Val Lys Thr Asp Val Gln Leu Gln Glu
1               5                   10                  15

Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
        35                  40                  45

Gln Ala Pro Gly Lys Gly Leu Glu Tyr Ile Ala Gly Ile Gly Ser Asp
    50                  55                  60

Tyr Thr Thr His Tyr Ser Asn Ser Leu Ser Gly Arg Phe Thr Ile Ser
65                  70                  75                  80

```
Lys Asp Ile Ala Lys Asn Thr Leu Asp Leu Arg Met Asp Asp Leu Val
                85                  90                  95

Pro Glu Asp Thr Ala Asn Tyr Tyr Cys Ala Lys Asp Val Leu Asp Tyr
            100                 105                 110

His Pro Asp Leu Trp Gly Gln Gly Thr Gln Val Thr Val Cys Ser Gly
        115                 120                 125

Arg Val Val Tyr Val Gly Asn Pro Gln Glu Ala
        130                 135
```

<210> SEQ ID NO 140
<211> LENGTH: 421
<212> TYPE: DNA
<213> ORGANISM: artificial sequence
<220> FEATURE:
<223> OTHER INFORMATION: mub insertion site 2 antibody E

<400> SEQUENCE: 140

```
acgccagatt caaaagacat tgtcaagacg agatgtgcag ctgcaggagt ctggaggaac    60
attggtgcag cccgggggt  ctctgacgct ctcctgtgca gcgcatggat tcggaatcgg   120
tagtttcgcc atgctgtggg tccgccaggc cccaggaaag gggctcgagt atattgcggg   180
cattggtagt gattatacga cacactattc aaattccctc tcgggccgct tcaccatctc   240
taaagacatt gccaagaata cactagatct gcgcatggac gacctagtgc ctgaagacac   300
ggccaattat tattgtgcga agacgtact  tgactaccac ccagatttgt ggggccaggg   360
aacccaggtc accgtctgca gcggccgcac tgtcgtttat gttgggaatc ctcaagaagc   420
t                                                                  421
```

<210> SEQ ID NO 141
<211> LENGTH: 139
<212> TYPE: PRT
<213> ORGANISM: artificial sequence
<220> FEATURE:
<223> OTHER INFORMATION: mub insertion site 2 antibody F

<400> SEQUENCE: 141

```
Thr Pro Asp Ser Lys Asp Ile Val Lys Thr Asp Val Gln Leu Gln Glu
1               5                   10                  15

Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
        35                  40                  45

Gln Ala Pro Gly Lys Gly Leu Glu Tyr Ile Ala Gly Ile Gly Ser Asp
    50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Val
                85                  90                  95

Pro Glu Asp Thr Ala Asn Tyr Tyr Cys Ala Lys Asp Val Leu Asp Tyr
            100                 105                 110

His Pro Asp Leu Trp Gly Gln Gly Thr Gln Val Thr Val Cys Ser Gly
        115                 120                 125

Arg Val Val Tyr Val Gly Asn Pro Gln Glu Ala
        130                 135
```

<210> SEQ ID NO 142
<211> LENGTH: 418
<212> TYPE: DNA

<213> ORGANISM: artificial sequence
<220> FEATURE:
<223> OTHER INFORMATION: mub insertion site 2 antibody F

<400> SEQUENCE: 142

```
acgccagatt caaaagacat tgtcaagacg agatgtgcag ctgcaggagt ctggaggaac    60
attggtgcag cccggggggt ctctgacgct ctcctgtgca gcgcatggat tcggaatcgg   120
tagtttcgcc atgctgtggg tccgccaggc cccaggaaag gggctcgagt atattgcggg   180
cattggtagt gattatacga cacactattc aaattccctc tcgggccgct tcaccatctc   240
taaagacatt gccaagaata cactagatct gcgcatggac gacctagtgc ctgaagacac   300
ggccaattat tattgtgcga agacgtact tgactaccac ccagatttgt ggggccaggg   360
aacccaggtc accgtctgca gcggccgcgt cgtttatgtt gggaatcctc aagaagct    418
```

<210> SEQ ID NO 143
<211> LENGTH: 139
<212> TYPE: PRT
<213> ORGANISM: artificial sequence
<220> FEATURE:
<223> OTHER INFORMATION: mub insertion site 2 antibody G

<400> SEQUENCE: 143

```
Thr Pro Asp Ser Lys Asp Ile Val Lys Thr Asp Val Gln Leu Gln Glu
1               5                   10                  15
Ser Gly Gly Thr Leu Val Gln Pro Gly Ser Leu Thr Leu Ser Cys
            20                  25                  30
Ala Ala His Gly Phe Gly Ile Gly Ser Phe Ala Met Leu Trp Val Arg
        35                  40                  45
Gln Ala Pro Gly Lys Gly Leu Glu Tyr Ile Ala Gly Ile Gly Ser Asp
    50                  55                  60
Tyr Thr Thr His Tyr Ser Asn Ser Leu Ser Gly Arg Phe Thr Ile Ser
65                  70                  75                  80
Lys Asp Ile Ala Lys Asn Thr Leu Asp Leu Arg Met Asp Asp Leu Val
                85                  90                  95
Pro Glu Asp Thr Ala Asn Tyr Tyr Cys Ala Lys Asp Val Leu Asp Tyr
            100                 105                 110
His Pro Asp Leu Trp Gly Gln Gly Thr Gln Val Thr Val Cys Ser Gly
        115                 120                 125
Arg Val Val Tyr Val Gly Asn Pro Gln Glu Ala
    130                 135
```

<210> SEQ ID NO 144
<211> LENGTH: 421
<212> TYPE: DNA
<213> ORGANISM: artificial sequence
<220> FEATURE:
<223> OTHER INFORMATION: mub insertion site 2 antibody G

<400> SEQUENCE: 144

```
acgccagatt caaaagacat tgtcaagacg agatgtgcag ctgcaggagt ctggaggaac    60
attggtgcag cccggggggt ctctgacgct ctcctgtgca gcgcatggat tcggaatcgg   120
tagtttcgcc atgctgtggg tccgccaggc cccaggaaag gggctcgagt atattgcggg   180
cattggtagt gattatacga cacactattc aaattccctc tcgggccgct tcaccatctc   240
taaagacatt gccaagaata cactagatct gcgcatggac gacctagtgc ctgaagacac   300
ggccaattat tattgtgcga agacgtact tgactaccac ccagatttgt ggggccaggg   360
```

```
aacccaggtc accgtctgca gcggccgcac tgtcgtttat gttgggaatc ctcaagaagc    420
t                                                                   421
```

<210> SEQ ID NO 145
<211> LENGTH: 148
<212> TYPE: PRT
<213> ORGANISM: artificial sequence
<220> FEATURE:
<223> OTHER INFORMATION: mub insertion site 2 antibody H

<400> SEQUENCE: 145

```
Thr Pro Asp Ser Lys Asp Ile Val Lys Thr Asp Val Gln Leu Gln Glu
1               5                   10                  15

Ser Gly Gly Gly Ser Val Gln Thr Gly Gly Ser Leu Arg Leu Ser Cys
            20                  25                  30

Ala Ala Ser Gly Asp Ser Ile Thr Thr Tyr His Met Ala Trp Phe Arg
        35                  40                  45

Gln Thr Pro Gly Lys Glu Arg Glu Glu Val Ala Val Ile Asn Asp Asp
    50                  55                  60

Ala Asn Ser Arg Ile Tyr Val Asp Ser Val Lys Gly Arg Phe Thr Ile
65                  70                  75                  80

Ser Gln Asp Lys Ala Lys Asn Thr Val Tyr Leu Gln Met Asn Tyr Leu
                85                  90                  95

Thr Pro Glu Asp Thr Ala Ile Tyr Tyr Cys Ala Ala Asp Leu Arg Cys
            100                 105                 110

Val Pro Gly Thr Asp Ser Gly His Pro Tyr Ser Tyr Asn Tyr Trp Gly
        115                 120                 125

Gln Gly Thr Gln Val Thr Val Cys Ser Gly Val Val Tyr Val Gly Asn
    130                 135                 140

Pro Gln Glu Ala
145
```

<210> SEQ ID NO 146
<211> LENGTH: 446
<212> TYPE: DNA
<213> ORGANISM: artificial sequence
<220> FEATURE:
<223> OTHER INFORMATION: mub insertion site 2 antibody H

<400> SEQUENCE: 146

```
acgccagatt caaaagacat tgtcaagacg agatgtgcag ctgcaggagt ctggaggagg    60
ttcggtgcag actggaggat ctctgagact tcctgtgca gcctctggag attccatcac    120
tacctaccac atggcctggt tccgccagac tccagggaag gagcgtgagg aggtcgcagt    180
tataaatgat gatgctaatt cgagaatcta tgtcgactcc gtgaagggcc gattcaccat    240
ctcccaagac aaggccaaga acacggtgta tctgcaaatg aactacctga cgcctgagga    300
cacggccatc tactactgtg cggcagattt gaggtgcgtc cctgggaccg actctggtca    360
tccttattcg tataactact ggggccaggg gacccaggtc accgtctgca gcggccgtcg    420
tttatgttgg gaatcctcaa gaagct                                        446
```

<210> SEQ ID NO 147
<211> LENGTH: 145
<212> TYPE: PRT
<213> ORGANISM: artificial sequence
<220> FEATURE:
<223> OTHER INFORMATION: mub insertion site 2 antibody I

<400> SEQUENCE: 147

Thr Pro Asp Ser Lys Asp Ile Val Lys Thr Asp Val His Leu Gln Asp
1               5                   10                  15

Ser Gly Gly Gly Ser Val Gln Ala Gly Gly Ser Leu Thr Leu Ser Trp
            20                  25                  30

Leu Met Ser Gly His Thr Tyr Tyr Gly Pro Cys Val Gly Trp Phe Arg
            35                  40                  45

Gln Pro Pro Gly Lys Ala Arg Glu Gly Ile Pro Gln Ile Ser Pro Ile
    50                  55                  60

Gly Gly Ser Val Ile Tyr Ile Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Leu Pro Glu Asp Thr Ala Thr Tyr Tyr Cys Ala Ala Asp Ser Gly Gly
            100                 105                 110

Leu Cys Ser His Arg Glu Arg Asp Tyr Asp Ile Trp Gly Gln Gly Thr
            115                 120                 125

Gln Val Thr Val Cys Ser Gly Val Val Tyr Val Gly Asn Pro Gln Glu
    130                 135                 140

Ala
145

<210> SEQ ID NO 148
<211> LENGTH: 434
<212> TYPE: DNA
<213> ORGANISM: artificial sequence
<220> FEATURE:
<223> OTHER INFORMATION: mub insertion site 2 antibody I

<400> SEQUENCE: 148
acgccagatt caaaagacat tgtcaagacg agatgtgcac ctgcaggatt ctggaggagg    60
ctcggtgcag gctggaggct ccctgacgct ctcttggtta atgtcgggtc atacgtatta   120
tggaccttgt gtgggttggt tccgccagcc cccagggaaa gcgcgtgagg gaatcccaca   180
gattagtcct attggtggga gtgttattta cattggtggc gtgaagggcc gattcaccat   240
ttcccgagac aactccaaga atactattgc tctcataatg aacgacctcc tgcctgaaga   300
cacggccact tattattgcg cagcagattc agggggactc tgcagccatc gtgagcgcga   360
ctatgacatt tggggccagg ggacccaggt caccgtctgc ggccgtcgtt tatgttggga   420
atcctcaaga agct                                                    434

<210> SEQ ID NO 149
<211> LENGTH: 145
<212> TYPE: PRT
<213> ORGANISM: artificial sequence
<220> FEATURE:
<223> OTHER INFORMATION: mub insertion site 2 antibody J

<400> SEQUENCE: 149

Thr Pro Asp Ser Lys Asp Ile Val Lys Thr Asp Val His Leu Gln Asp
1               5                   10                  15

Ser Gly Glu Gly Trp Gly His Ala Gly Gly Ser Leu Thr Leu Ser Cys
            20                  25                  30

Leu Met Ser Gly His Thr Tyr Tyr Gly Pro Cys Gly Gly Gly Phe Pro
            35                  40                  45

Gln Pro Pro Gly Lys Ala Arg Glu Gly Ile Pro Gln Met Ile Pro Ile
    50                  55                  60

```
Gly Gly Ser Val Ile Tyr Ile Gly Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Val Pro Glu Asp Thr Ala Thr Tyr Tyr Cys Ala Thr Asp Ser Gly Gly
            100                 105                 110

Leu Cys Ser His Arg Glu Arg Asp Tyr Asp Ile Trp Gly Gln Gly Thr
        115                 120                 125

Gln Val Thr Val Cys Ser Gly Val Val Tyr Val Gly Asn Pro Gln Glu
    130                 135                 140

Ala
145

<210> SEQ ID NO 150
<211> LENGTH: 434
<212> TYPE: DNA
<213> ORGANISM: artificial sequence
<220> FEATURE:
<223> OTHER INFORMATION: mub insertion site 2 antibody J

<400> SEQUENCE: 150
acgccagatt caaaagacat tgtcaagacg agatgtgcac ctgcaggatt cgggagaagg    60
ctgggggcac gctggaggct ccctgaccct ctcttgttta atgtcgggtc atacgtatta   120
tggaccttgt gggggtgggt tcccccagcc cccaggaaaa gcccgtgagg gaatcccaca   180
aatgattcct attggtggga gtgttattta cattggtggc gtgaagggcc gattcaccat   240
ttcccgagac aactccaaga atactattgc tctcataatg aacgaccctcg tgcctgaaga   300 cacggccact tattattgcg caacagattc aggggggactc tgcagccatc gtgagcgcga   360
ctatgacatt tggggccagg ggacccaggt caccgtctgc ggccgtcgtt tatgttggga   420
atcctcaaga agct                                                    434

<210> SEQ ID NO 151
<211> LENGTH: 144
<212> TYPE: PRT
<213> ORGANISM: artificial sequence
<220> FEATURE:
<223> OTHER INFORMATION: mub insertion site 2 antibody K

<400> SEQUENCE: 151

Thr Pro Asp Ser Lys Asp Ile Val Lys Thr Asp Val His Leu Gln Asp
1               5                   10                  15

Ser Gly Gly Gly Ser Val His Ala Gly Gly Ser Leu Thr Leu Ser Cys
                20                  25                  30

Leu Met Ser Gly His Thr Tyr Tyr Gly Pro Cys Gly Gly Phe Pro
            35                  40                  45

Arg Pro Pro Gly Lys Gly Arg Glu Gly Ile Ala Gln Ile Ile Pro Ile
        50                  55                  60

Gly Gly Ser Val Ile Tyr Ile Gly Gly Val Lys Gly Arg Phe Thr Ile
65                  70                  75                  80

Ser Arg Tyr Asn Ser Lys Asn Thr Ile Ala Leu Ile Met Asn Asp Leu
                85                  90                  95

Val Pro Glu Asp Thr Ala Thr Tyr Cys Ala Thr Asp Ser Gly Gly Leu
            100                 105                 110

Cys Ser His Arg Glu Arg Asp Tyr Asp Ile Trp Gly Gln Gly Thr Gln
        115                 120                 125

Val Thr Val Cys Ser Gly Val Val Tyr Val Gly Asn Pro Gln Glu Ala
```

<210> SEQ ID NO 152
<211> LENGTH: 437
<212> TYPE: DNA
<213> ORGANISM: artificial sequence
<220> FEATURE:
<223> OTHER INFORMATION: mub insertion site 2 antibody K

<400> SEQUENCE: 152

```
acgccagatt caaaagacat tgtcaagacg agatgtgcac ctgcaggatt ctggaggagg      60
ctcggtgcac gctgggggct ccctgacgct ctcttgttta atgtcgggtc atacgtatta    120
tggaccttgt gggggtgggt tcccccggcc cccaggaaaa gggcgtgagg gaatcgcaca    180
aattattcct attggtggga gtgttattta cattggtggc gtgaagggcc gattcaccat    240
ttcccgatac aactccaaga atactattgc tctcataatg aacgacctcg tgcctgaaga    300
cacggccact tattattgcg caacagattc agggggactc tgcagccatc gtgagcgcga    360
ctatgacatt tggggccagg ggacccaggt caccgtctgc agcggccgtc gtttatgttg    420
ggaatcctca agaagct                                                   437
```

<210> SEQ ID NO 153
<211> LENGTH: 144
<212> TYPE: PRT
<213> ORGANISM: artificial sequence
<220> FEATURE:
<223> OTHER INFORMATION: mub insertion site 2 antibody L

<400> SEQUENCE: 153

Thr Pro Asp Ser Lys Asp Ile Val Lys Thr Asp Val His Leu Gln Asp
1               5                   10                  15

Ser Gly Gly Gly Ser Val Gln Ala Gly Gly Ser Leu Thr Leu Ser Cys
            20                  25                  30

Leu Met Ser Gly His Thr Tyr Tyr Gly Pro Cys Val Gly Trp Phe Pro
        35                  40                  45

Gln Arg Pro Gly Lys Ala Arg Glu Gly Ile Ala Gln Met Ile Pro Ile
    50                  55                  60

Gly Gly Ser Val Ser Tyr Ser Gly Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Val Pro Glu Asp Thr Ala Thr Tyr Tyr Cys Ala Thr Asp Ser Gly Gly
            100                 105                 110

Leu Cys Ser His Arg Glu Arg Asp Tyr Asp Ile Trp Gly Gln Gly Thr
        115                 120                 125

Gln Val Thr Val Cys Ser Val Val Tyr Val Gly Asn Pro Gln Glu Ala
    130                 135                 140

<210> SEQ ID NO 154
<211> LENGTH: 433
<212> TYPE: DNA
<213> ORGANISM: artificial sequence
<220> FEATURE:
<223> OTHER INFORMATION: mub insertion site 2 antibody L

<400> SEQUENCE: 154

```
acgccagatt caaaagacat tgtcaagacg agatgtgcac ctgcaggatt ctggaggagg      60
ctcggtgcag gctggaggct ccctgaccct ctcttgttta atgtcgggtc atacgtatta    120
```

```
tggaccttgt gtgggttggt tcccccagcg tccagggaaa gcgcgtgagg gaatcgcaca    180
aatgattcct attggtggga gtgttagtta cagtggtggc gtgaagggcc gattcaccat    240
ttcccgagac aactccaaga atactattgc tctcataatg aacgacctcg tgcctgaaga    300
cacggccact tattattgcg caacagattc aggggactc tgcagccatc gtgagcgcga     360
ctatgacatt tggggccagg ggacccaggt caccgtctgc agcgtcgttt atgttgggaa    420
tcctcaagaa gct                                                      433
```

<210> SEQ ID NO 155
<211> LENGTH: 147
<212> TYPE: PRT
<213> ORGANISM: artificial sequence
<220> FEATURE:
<223> OTHER INFORMATION: mub insertion site 2 antibody M

<400> SEQUENCE: 155

```
Thr Pro Asp Ser Lys Asp Ile Val Lys Thr Asp Val Gln Leu Gln Glu
1               5                   10                  15

Ser Gly Gly Gly Ser Val Gln Glu Gly Gly Ser Leu Arg Leu Ser Cys
            20                  25                  30

Ala Ala Ser Glu Tyr Thr Ala Ile Thr Tyr Cys Met Ala Trp Phe Arg
        35                  40                  45

Gln Ala Pro Gly Lys Glu Arg Glu Gly Val Ala Ala Ile Asn Arg Gly
    50                  55                  60

Gly Gly Ser Thr Tyr Tyr Ala Asp Ser Val Lys Gly Arg Phe Thr Ile
65                  70                  75                  80

Ser Gln Asp Asn Ala Lys Asn Thr Val Tyr Leu Leu Met Asn Ser Leu
                85                  90                  95

Lys Pro Glu Asp Thr Gly Met Tyr Tyr Cys Ala Tyr Lys Gln Thr Gly
            100                 105                 110

Asp Cys Gly Ile Phe Gln Phe Phe Gly Asn Tyr Gly Gln Gly Thr Gln
        115                 120                 125

Val Thr Val Ser Ser Gly Arg Thr His Val Val Tyr Val Gly Asn Pro
    130                 135                 140

Gln Glu Ala
145
```

<210> SEQ ID NO 156
<211> LENGTH: 439
<212> TYPE: DNA
<213> ORGANISM: artificial sequence
<220> FEATURE:
<223> OTHER INFORMATION: mub insertion site 2 antibody M

<400> SEQUENCE: 156

```
acgccagatt caaaagacat tgtcaagacg gatccagatg tgcagctgca ggagtctggg    60
ggaggctcgg tgcaggaggg agggtctctg agactctcct gtgcagcctc tgaatacacc    120
gctattacct actgtatggc ctggttccgc caggctccag gaaggagcg tgaggggtc     180 gcggctatca atcgcggtgg tggtagtaca tattacgccg actccgtgaa gggccgattc    240
accatctccc aggacaacgc caagaacacg gtgtatctcc taatgaacag cctgaaacct    300
gaggacactg gcatgtacta ctgtgcgtac aaacagaccg gtgattgtgg gatcttccaa    360
ttctttggaa actatggcca ggggacccag gtcaccgtct ccagcggccg tcgtttatgt    420
tgggaatcct caagaagct                                                439
```

<210> SEQ ID NO 157
<211> LENGTH: 148
<212> TYPE: PRT
<213> ORGANISM: artificial sequence
<220> FEATURE:
<223> OTHER INFORMATION: mub insertion site 2 antibody N

<400> SEQUENCE: 157

Thr Pro Asp Ser Lys Asp Ile Val Lys Thr Asp Val Gln Leu Gln Glu
1               5                   10                  15
Ser Gly Gly Gly Ser Val Gln Thr Gly Gly Ser Leu Arg Leu Ser Cys
            20                  25                  30
Ala Ala Ser Gly Asp Ser Ile Thr Thr Tyr His Met Ala Trp Phe Arg
        35                  40                  45
Gln Thr Pro Gly Lys Glu Arg Glu Glu Val Ala Val Ile Asn Asp Asp
    50                  55                  60
Ala Asn Ser Arg Ile Tyr Val Asp Ser Val Lys Gly Arg Phe Thr Ile
65                  70                  75                  80
Ser Gln Asp Lys Ala Lys Asn Thr Val Tyr Leu Gln Met Asn Tyr Leu
                85                  90                  95
Thr Pro Glu Asp Thr Ala Ile Tyr Tyr Cys Ala Ala Asp Leu Arg Cys
            100                 105                 110
Val Pro Gly Thr Asp Ser Gly His Pro Tyr Ser Tyr Asn Tyr Trp Gly
        115                 120                 125
Gln Gly Thr Gln Val Thr Ala Ser Ser Gly Val Val Tyr Val Gly Asn
    130                 135                 140
Pro Gln Glu Ala
145

<210> SEQ ID NO 158
<211> LENGTH: 446
<212> TYPE: DNA
<213> ORGANISM: artificial sequence
<220> FEATURE:
<223> OTHER INFORMATION: mub insertion site 2 antibody N

<400> SEQUENCE: 158
acgccagatt caaaagacat tgtcaagacg agatgtgcag ctgcaggagt ctggaggagg      60
ttcggtgcag actggaggat ctctgagact ctcctgtgca gcctctggag attccatcac     120
tacctaccac atggcctggt tccgccagac tccaggaaag gagcgtgagg aggtcgcagt     180
tataaatgat gatgctaatt cgagaatcta tgtcgactcc gtgaagggcc gattcaccat     240
ctcccaagac aaggccaaga acaccgtgta tctgcaaatg aactacctga cgcctgagga     300
cacggccatc tactactgtg cggcagattt gaggtgcgtc cctgggaccg actctggtca     360
tccttattcg tataactact ggggccaggg gacccaggtc accgcctcca gcggccgtcg     420
tttatgttgg gaatcctcaa gaagct                                          446

<210> SEQ ID NO 159
<211> LENGTH: 149
<212> TYPE: PRT
<213> ORGANISM: artificial sequence
<220> FEATURE:
<223> OTHER INFORMATION: mub insertion site 2 antibody O

<400> SEQUENCE: 159

Thr Pro Asp Ser Lys Asp Ile Val Lys Thr Asp Val Gln Leu Gln Glu
1               5                   10                  15
Ser Gly Gly Gly Ser Val Gln Thr Gly Gly Ser Leu Arg Leu Ser Cys

```
                    20                  25                  30

Ala Ala Ser Gly Asp Ser Ile Thr Thr Tyr His Met Ala Trp Phe Arg
        35                  40                  45

Gln Thr Pro Gly Lys Glu Arg Glu Val Ala Val Ile Asn Asp Asp
    50                  55                  60

Ala Asn Ser Arg Ile Tyr Val Asp Ser Val Lys Gly Arg Phe Thr Ile
65                  70                  75                  80

Ser Gln Asp Lys Ala Lys Asn Thr Val Tyr Leu Gln Met Asn Tyr Leu
                85                  90                  95

Thr Pro Glu Asp Thr Ala Ile Tyr Tyr Cys Ala Ala Asp Leu Arg Cys
            100                 105                 110

Val Pro Gly Thr Asp Ser Gly His Pro Tyr Ser Tyr Asn Tyr Trp Gly
        115                 120                 125

Gln Gly Thr Gln Val Thr Ala Ser Ser Gly Arg Val Val Tyr Val Gly
            130                 135                 140

Asn Pro Gln Glu Ala
145

<210> SEQ ID NO 160
<211> LENGTH: 446
<212> TYPE: DNA
<213> ORGANISM: artificial sequence
<220> FEATURE:
<223> OTHER INFORMATION: mub insertion site 2 antibody O

<400> SEQUENCE: 160
acgccagatt caaaagacat tgtcaagacg agatgtgcag ctgcaggagt ctggaggagg     60
ttcggtgcag actggaggat ctctgagact ctcctgtgca gcctctggag attccatcac    120
tacctaccac atggcctggt tccgccagac tccaggaaag gagcgtgagg aggtcgcagt    180
tataaatgat gatgctaatt cgagaatcta tgtcgactcc gtgaagggcc gattcaccat    240
ctcccaagac aaggccaaga acacggtgta tctgcaaatg aactacctga cgcctgagga    300
cacggccatc tactactgtg cggcagattt gaggtgcgtc cctgggaccg actctggtca    360
tccttattcg tataactact ggggccaggg gacccaggtc accgcctcca gcggccgtcg    420
tttatgttgg aatcctcaa gaagct                                          446

<210> SEQ ID NO 161
<211> LENGTH: 150
<212> TYPE: PRT
<213> ORGANISM: artificial sequence
<220> FEATURE:
<223> OTHER INFORMATION: mub insertion site 2 antibody P

<400> SEQUENCE: 161

Thr Pro Asp Ser Lys Asp Ile Val Lys Thr Asp Val Gln Leu Gln Glu
1               5                   10                  15

Ser Gly Gly Gly Ser Ala Gln Pro Gly Gly Ser Leu Arg Leu Ser Cys
            20                  25                  30

Ala Val Ser Gly Ser Thr Ala Ser Met Tyr Cys Leu Ala Trp Phe Arg
        35                  40                  45

Gln Ala Pro Gly Lys Glu Pro Glu Gly Val Ala Ala Ile Ser Gly Asp
    50                  55                  60

Asp Lys Gly Phe Thr Asn Tyr Ala Asp Ser Val Lys Gly Arg Phe Thr
65                  70                  75                  80

Ile Ser Gln Asn Lys Ala Asn Lys Thr Val Asn Leu Gln Met Asn Ser
                85                  90                  95
```

Leu Lys Pro Glu Asp Thr Ala Ile Tyr Tyr Cys Ala Val Asp Ala Arg
            100                 105                 110

Ala Thr Thr Thr Gly Glu Arg Leu His Ala Arg Thr Tyr Glu Phe Trp
            115                 120                 125

Gly Gln Gly Thr Gln Val Thr Val Cys Ser Arg Val Val Tyr Val
        130                 135                 140

Gly Asn Pro Gln Glu Ala
145             150

<210> SEQ ID NO 162
<211> LENGTH: 450
<212> TYPE: DNA
<213> ORGANISM: artificial sequence
<220> FEATURE:
<223> OTHER INFORMATION: mub insertion site 2 antibody P

<400> SEQUENCE: 162
acgccagatt caaaagacat tgtcaagacg gatgtgcagc tgcaggagtc tgggggaggc        60
tcggcgcagc ctggagggtc tctgagactc tcctgtgcag tctctggatc gaccgccagt       120
atgtactgct tggcctggtt ccgccaggct ccagggaagg agcctgaggg ggttgctgct       180
attagtggag atgataaagg gtttacgaat tacgccgact ccgtgaaggg ccggttcacc       240
atctcccaaa acaaggccaa taaaacggtg aatctgcaaa tgaacagcct gaaacctgaa       300
gacacggcca tttattactg tgccgttgat gcgcgagcga caacaactgg tgaacgtcta       360 cacgccccgga cgtacgaatt ctggggccag gggacccagg tcaccgtctc cagcggccgc      420
gtcgtttatg ttgggaatcc tcaagaagct                                       450

<210> SEQ ID NO 163
<211> LENGTH: 148
<212> TYPE: PRT
<213> ORGANISM: artificial sequence
<220> FEATURE:
<223> OTHER INFORMATION: mub insertion site 2 antibody Q

<400> SEQUENCE: 163

Thr Pro Asp Ser Lys Asp Ile Val Lys Thr Asp Val Gln Met Gln Glu
1               5                   10                  15

Ser Gly Gly Gly Ser Val Gln Ala Gly Gly Ser Leu Arg Leu Ser Cys
            20                  25                  30

Ala Ala Ser Gly Asp Thr Leu Ser Thr Tyr Cys Met Gly Trp Phe Arg
        35                  40                  45

Gln Val Pro Gly Lys Asp Arg Glu Gly Val Ala Ala Ile Tyr Arg Leu
    50                  55                  60

Arg Asp Met Thr Phe Tyr Ala Asp Ser Val Lys Gly Arg Phe Thr Ile
65                  70                  75                  80

Ser Arg Asp Asn Ala Asn Asp Thr Val Asp Leu Gln Met Asn Ser Leu
                85                  90                  95

Lys Pro Glu Asp Thr Ala Val Tyr Tyr Cys Ala Ala Arg Cys Val Arg
            100                 105                 110

Leu Phe Gly Thr Cys Gln Leu Val Glu Asp Phe Glu Leu Trp Gly Gln
        115                 120                 125

Gly Thr Gln Val Thr Val Ser Ser Gly Leu Val Val Tyr Val Gly Asn
    130                 135                 140

Pro Gln Glu Ala
145

<210> SEQ ID NO 164
<211> LENGTH: 442
<212> TYPE: DNA
<213> ORGANISM: artificial sequence
<220> FEATURE:
<223> OTHER INFORMATION: mub insertion site 2 antibody Q

<400> SEQUENCE: 164

```
acgccagatt caaaagacat tgtcaagacg agatgtgcag atgcaggagt ctgggggagg    60
gtcggtgcag gctggagggt ctctgagact ctcctgtgca gcctctggag atacccctcag  120
tacctactgc atgggctggt ccgccaagt tccagggaag gaccgtgagg gggtcgcagc    180
gatttatcgt cttagggata tgacgttcta tgccgactcc gtgaagggcc gattcaccat   240
ttcccgtgac aacgccaacg acacggtaga tctgcaaatg aacagcctga acctgaggacacagccgtg  300
cacagccgtg tactactgtg cagcaagatg tgtgcgacta ttcggtactt gtcagctagt   360
cgaagatttt gaactatggg gccaggggac ccaggtcacc gtctccagcg cgtcgttta    420
tgttgggaat cctcaagaag ct                                            442
```

<210> SEQ ID NO 165
<211> LENGTH: 149
<212> TYPE: PRT
<213> ORGANISM: artificial sequence
<220> FEATURE:
<223> OTHER INFORMATION: mub insertion site 2 antibody R

<400> SEQUENCE: 165

```
Thr Pro Asp Ser Lys Asp Ile Val Lys Thr Asp Val Gln Met Gln Glu
1               5                   10                  15
Ser Gly Gly Gly Ser Val Gln Ala Gly Gly Ser Leu Arg Leu Ser Cys
            20                  25                  30
Ala Ala Ser Gly Asp Thr Leu Ser Thr Tyr Cys Met Gly Trp Phe Arg
        35                  40                  45
Gln Ala Pro Gly Lys Asp Arg Glu Gly Val Ala Ala Ile Tyr Arg Leu
    50                  55                  60
Arg Asp Met Thr Phe Tyr Ala Asp Ser Val Lys Gly Arg Phe Thr Ile
65                  70                  75                  80
Ser Arg Asp Asn Ala Asn Asp Thr Val Asp Leu Gln Met Asn Ser Leu
                85                  90                  95
Lys Pro Glu Asp Thr Ala Val Tyr Tyr Cys Ala Ala Arg Cys Val Arg
            100                 105                 110
Leu Phe Gly Thr Cys Gln Leu Val Glu Asp Phe Glu Leu Trp Gly Gln
        115                 120                 125
Gly Thr Gln Val Thr Val Ser Ser Gly Leu Thr Val Val Tyr Val Gly
    130                 135                 140
Asn Pro Gln Glu Ala
145
```

<210> SEQ ID NO 166
<211> LENGTH: 442
<212> TYPE: DNA
<213> ORGANISM: artificial sequence
<220> FEATURE:
<223> OTHER INFORMATION: mub insertion site 2 antibody R

<400> SEQUENCE: 166

```
acgccagatt caaaagacat tgtcaagacg agatgtgcag atgcaggagt ctgggggagg    60
gtcggtgcag gctggagggt ctctgagact ctcctgtgca gcctctggag atacccctcag  120
```

```
tacctactgc atgggctggt tccgccaagt tccagggaag gaccgtgagg gggtcgcagc    180
gatttatcgt cttagggata tgacgttcta tgccgactcc gtgaagggcc gattcaccat    240
ttcccgtgac aacgccaacg acacggtaga tctgcaaatg aacagcctga aacctgagga    300
cacagccgtg tactactgtg cagcaagatg tgtgcgacta ttcggtactt gtcagctagt    360
cgaagatttt gaactatggg gccaggggac ccaggtcacc gtctccagcg gcgtcgttta    420
tgttgggaat cctcaagaag ct                                             442
```

<210> SEQ ID NO 167
<211> LENGTH: 149
<212> TYPE: PRT
<213> ORGANISM: artificial sequence
<220> FEATURE:
<223> OTHER INFORMATION: mub insertion site 2 antibody S

<400> SEQUENCE: 167

```
Thr Pro Asp Ser Lys Asp Ile Val Lys Thr Asp Val Gln Met Gln Glu
 1               5                  10                  15

Ser Gly Gly Gly Ser Val Gln Ala Gly Gly Ser Leu Arg Leu Ser Cys
            20                  25                  30

Ala Ala Ser Gly Asp Thr Leu Ser Thr Tyr Cys Met Gly Trp Phe Arg
        35                  40                  45

Gln Val Pro Gly Lys Asp Arg Glu Gly Val Ala Ala Ile Tyr Arg Leu
    50                  55                  60

Arg Asp Met Thr Phe Tyr Ala Asp Ser Val Lys Gly Arg Phe Thr Ile
65                  70                  75                  80

Ser Arg Asp Asn Ala Asn Asp Thr Val Asp Leu Gln Met Asn Ser Leu
                85                  90                  95

Lys Pro Glu Asp Thr Ala Val Tyr Tyr Cys Ala Ala Arg Cys Val Arg
            100                 105                 110

Leu Phe Gly Thr Cys Gln Leu Val Glu Asp Phe Glu Leu Trp Gly Gln
        115                 120                 125

Gly Thr Gln Val Thr Val Ser Ser Gly Leu Thr Val Val Tyr Val Gly
    130                 135                 140

Asn Pro Gln Glu Ala
145
```

<210> SEQ ID NO 168
<211> LENGTH: 443
<212> TYPE: DNA
<213> ORGANISM: artificial sequence
<220> FEATURE:
<223> OTHER INFORMATION: mub insertion site 2 antibody S

<400> SEQUENCE: 168

```
acgccagatt caaaagacat tgtcaagacg agatgtgcag atgcaggagt ctggggagg     60 gtcggtgcag gctggagggt ctctgagact tcctgtgca gcctctggag atacccctcag    120 tacctactgc atgggctggt tccgccaagt tccagggaag gaccgtgagg gggtcgcagc    180
gatttatcgt cttagggata tgacgttcta tgccgactcc gtgaagggcc gattcaccat    240
ttcccgtgac aacgccaacg acacggtaga tctgcaaatg aacagcctga aacctgagga    300
cacagccgtg tactactgtg cagcaagatg tgtgcgacta ttcggtactt gtcagctagt    360
cgaagatttt gaactatggg gccaggggac ccaggtcacc gtctccagcg gccgtcgttt    420
atgttgggaa tcctcaagaa gct                                            443
```

<210> SEQ ID NO 169
<211> LENGTH: 146
<212> TYPE: PRT
<213> ORGANISM: artificial sequence
<220> FEATURE:
<223> OTHER INFORMATION: mub insertion site 3 antibody A

<400> SEQUENCE: 169

Asp Glu Thr Ile Ser Phe Ala Lys Asp Pro Asp Val Gln Leu Gln Glu
1               5                   10                  15

Ser Gly Gly Gly Ser Val Gln Ala Gly Gly Ser Leu Thr Leu Ser Cys
            20                  25                  30

Leu Met Ser Gly His Thr Tyr Tyr Gly Pro Cys Val Gly Trp Phe Arg
        35                  40                  45

Gln Arg Pro Gly Lys Ala Arg Glu Gly Ile Ala Gln Ile Ser Pro Ser
    50                  55                  60

Gly Gly Ser Val Ser Tyr Ser Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Val Pro Glu Asp Thr Ala Thr Tyr Tyr Cys Ala Ala Ser Gly Gly
            100                 105                 110

Leu Cys Ser His Arg Glu Arg Asp Tyr Asp Ile Trp Gly Gln Gly Thr
        115                 120                 125

Gln Val Thr Val Cys Ser Gly Arg Asn Glu Val Val Lys Glu Leu Glu
    130                 135                 140

Lys Gln
145

<210> SEQ ID NO 170
<211> LENGTH: 439
<212> TYPE: DNA
<213> ORGANISM: artificial sequence
<220> FEATURE:
<223> OTHER INFORMATION: mub insertion site 3 antibody A

<400> SEQUENCE: 170
gaaacgatca gctttgccaa ggatccaaat atgtgcagct gcaggagtct gggggaggct      60
cggtgcaggc tggaggctcc ctgacgctct cttgtttaat gtctggtcat acgtattatg     120
gaccttgtgt gggttggttc cgccagcgtc cagggaaagc gcgtgaggga atcgcacaga     180
ttagtcctag tggtgggagt gttagttaca gtggtggcgt gaagggccga ttcaccattt     240
cccgagacaa ctccaagaat actattgctc tcataatgaa cgacctcgtg cctgaagaca     300
cggccactta ttattgcgca gcagattcag ggggactctg cagccatcgt gagcgcgact     360
atgacatttg gggccagggg acccaggtca ccgtctgcag cggccgcacg aagtcgtcaa     420
ggaactcgaa aagcagggt                                                  439

<210> SEQ ID NO 171
<211> LENGTH: 145
<212> TYPE: PRT
<213> ORGANISM: artificial sequence
<220> FEATURE:
<223> OTHER INFORMATION: mub insertion site 3 antibody B

<400> SEQUENCE: 171

Asp Glu Thr Ile Ser Phe Ala Lys Asp Pro Asp Pro Asp Val His Leu
1               5                   10                  15

Gln Asp Ser Gly Gly Gly Trp Val His Pro Gly Ser Leu Thr Leu
            20                  25                  30

Ser Cys Leu Met Ser Gly Ser Glu Tyr Tyr Gly Ser Pro Val Gly Trp
        35                  40                  45

Phe Pro Gln Pro Pro Gly Lys Gly Arg Glu Glu Ile Ala Glu Ile Val
50                  55                  60

Pro Ile Gly Gly Ser Val Ile Tyr Ile Gly Val Glu Gly Arg Phe
65                  70                  75                  80

Thr Ile Ser Arg Asp Asn Ser Lys Asn Thr Ile Ala Leu Ile Met Asn
                85                  90                  95

Asp Leu Leu Pro Glu Asp Thr Ala Thr Tyr Tyr Cys Ala Ala Asp Ser
            100                 105                 110

Gly Gly Leu Cys Ser His Arg Glu Arg Asp Tyr Asp Ile Trp Gly Gln
        115                 120                 125

Gly Thr Gln Val Thr Val Cys Asn Glu Val Val Lys Glu Leu Glu Lys
    130                 135                 140

Gln
145

<210> SEQ ID NO 172
<211> LENGTH: 435
<212> TYPE: DNA
<213> ORGANISM: artificial sequence
<220> FEATURE:
<223> OTHER INFORMATION: mub insertion site 3 antibody B

<400> SEQUENCE: 172
gaaacgatca gctttgccaa ggatccaaat gatccagatg tgcacctgca ggattcggga      60
ggaggctggg tgcacccggg gggctccctg accctctctt gtttaatgtc gggttccgaa     120
tattatggtt cccctgtggg ttggttcccc cagcccccag gaaagggcg tgaggaaatc      180 gcggaaattg ttcctattgg tgggagtgtt atttacattg gtggcgtgga gggccgattc     240
accatttccc gagacaactc caagaatact attgctctca atgaacga cctcctgcct      300 gaagacacgg ccacttatta ttgcgcagca gattcagggg gactctgcag ccatcgtgag     360
cgcgactatg acatttgggg ccaggggacc caggtcaccg tctgcgaagt cgtcaaggaa     420
ctcgaaaagc agggt                                                     435

<210> SEQ ID NO 173
<211> LENGTH: 139
<212> TYPE: PRT
<213> ORGANISM: artificial sequence
<220> FEATURE:
<223> OTHER INFORMATION: mub insertion site 3 antibody C

<400> SEQUENCE: 173

Asp Glu Thr Ile Ser Phe Ala Lys Asp Pro Asp Val Gln Leu Pro Glu
1               5                   10                  15

Ser Gly Arg Thr Leu Val Pro Pro Gly Gly Ser Leu Lys Leu Ser Trp
            20                  25                  30

Ala Thr His Gly Phe Gly Ile Gly Ser Phe Pro Met Leu Trp Val Pro
        35                  40                  45

Pro Ala Pro Gly Lys Gly Leu Glu Tyr Ile Ala Gly Ile Gly Ser Asp
    50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Leu

```
                    85                  90                  95

Pro Glu Asp Thr Ala Asn Tyr Tyr Cys Ala Lys Asp Val Leu Asp Tyr
            100                 105                 110

His Pro Asp Leu Trp Gly Arg Gly Thr Gln Val Thr Val Cys Arg Gly
        115                 120                 125

Arg Asn Glu Val Val Lys Glu Leu Glu Lys Gln
    130                 135

<210> SEQ ID NO 174
<211> LENGTH: 419
<212> TYPE: DNA
<213> ORGANISM: artificial sequence
<220> FEATURE:
<223> OTHER INFORMATION: mub insertion site 3 antibody C

<400> SEQUENCE: 174
gaaacgatca gctttgccaa ggatccaaat agatgtgcag ctgccagaat ccggaagaac      60
gttggtgcca cccggggggt ccctgaagct ctcctgggca acgacggat tcggaatcgg      120 tagtttcccc atgctgtggg tccccccggc ccccggaaaa gggctcgaat atattgcggg     180
cattggtagt gattatacga cacactattc aaattccctc tcgggccgct tcaccatctc     240
taaagacatt gccaagaata cactagatct gcgcatggac gacctactgc ctgaagacac     300
ggccaattat tattgtgcga aagacgtact tgactaccac ccagatttgt ggggccgggg     360
aacccaggtc accgtctgca ggggccgcag aagtcgtcaa ggaactcgaa aagcagggt     419

<210> SEQ ID NO 175
<211> LENGTH: 145
<212> TYPE: PRT
<213> ORGANISM: artificial sequence
<220> FEATURE:
<223> OTHER INFORMATION: mub insertion site 3 antibody D

<400> SEQUENCE: 175

Asp Glu Thr Ile Ser Phe Ala Lys Asp Pro Val Gln Leu Gln Glu Ser
1               5                   10                  15

Gly Gly Gly Ser Val Gln Asp Gly Gly Thr Leu Gln Leu Ser Cys Glu
            20                  25                  30

Asp Ser Lys Trp Ser Tyr Thr Tyr Cys Met Gly Trp Phe Arg Gln
        35                  40                  45

Ala Pro Gly Lys Glu Arg Glu Pro Val Ala His Ile Asp Ser Glu Gly
    50                  55                  60

Thr Val Ala Tyr Ala Asp Thr Val Lys Gly Arg Phe Thr Ile Ser Arg
65                  70                  75                  80

Gly Asp Ala Lys His Arg Val Tyr Leu Gln Met Asn Asn Leu Lys Ala
                85                  90                  95

Asp Asp Thr Ala Ile Tyr Tyr Cys Ala Ala Asn Gly Gly Tyr Cys Leu
            100                 105                 110

Arg Pro Arg Gln Leu Ala Ala Asp Tyr Glu Tyr Trp Gly Gln Gly Ala
        115                 120                 125

Gln Val Thr Val Ser Ser Gly Asn Glu Val Val Lys Glu Leu Glu Lys
    130                 135                 140

Gln
145

<210> SEQ ID NO 176
<211> LENGTH: 441
<212> TYPE: DNA
```

<213> ORGANISM: artificial sequence
<220> FEATURE:
<223> OTHER INFORMATION: mub insertion site 3 antibody D

<400> SEQUENCE: 176

```
gaaacgatca gctttgccaa ggatccaaat aagtgcagct gcaggagtct ggggggaggct    60
cggtgcagga tggagggact ttacaactct cttgtgaaga ctctaaatgg agctacacgt   120
actattgtat gggtggttc cgccaggctc cagggaagga gcgagagccg gtcgcgcaca   180
ttgatagtga aggcactgtc gcttacgccg acaccgtgaa gggccgattc accatctccc   240
gggggggacgc caagcatagg gtttacctgc aaatgaataa cttgaaggct gatgacacgg   300
ccatctatta ttgtgcggcc aatggtggtt attgcctcag accccgtcaa ctcgccgcgg   360
attatgagta ttggggccag ggggcccagg tcaccgtctc cagcggccgc agaagtcgtc   420
aaggaactcg aaaagcaggg t                                             441
```

<210> SEQ ID NO 177
<211> LENGTH: 139
<212> TYPE: PRT
<213> ORGANISM: artificial sequence
<220> FEATURE:
<223> OTHER INFORMATION: mub insertion site 3 antibody E

<400> SEQUENCE: 177

Asp Glu Thr Ile Ser Phe Ala Lys Asp Pro Asp Val Gln Leu Gln Glu
1               5                   10                  15

Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
        35                  40                  45

Gln Ala Pro Gly Lys Gly Leu Glu Tyr Ile Ala Gly Ile Gly Ser Asp
    50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Val
                85                  90                  95

Pro Glu Asp Thr Ala Asn Tyr Tyr Cys Ala Lys Asp Val Leu Asp Tyr
            100                 105                 110

His Pro Asp Leu Trp Gly Gln Gly Thr Gln Val Thr Val Cys Ser Gly
        115                 120                 125

Arg Asn Glu Val Val Lys Glu Leu Glu Lys Gln
    130                 135

<210> SEQ ID NO 178
<211> LENGTH: 421
<212> TYPE: DNA
<213> ORGANISM: artificial sequence
<220> FEATURE:
<223> OTHER INFORMATION: mub insertion site 3 antibody E

<400> SEQUENCE: 178

```
gaaacgatca gctttgccaa ggatccaaat agatgtgcag ctgcaggagt ctggaggaac    60
attggtgcag cccggggggt ctctgacgct ctcctgtgca gcgcatggat cggaatcgg   120
tagtttcgcc atgctgtggg tccgccaggc cccaggaaag gggctcgagt atattgcggg   180
cattggtagt gattatacga cacactattc aaattccctc tcgggccgct tcaccatctc   240
taaagacatt gccaagaata cactagatct gcgcatggac gacctagtgc ctgaagacac   300
```

```
ggccaattat tattgtgcga aagacgtact tgactaccac ccagatttgt ggggccaggg      360
aacccaggtc accgtctgca gcggccgcac tgaagtcgtc aaggaactcg aaaagcaggg      420
t                                                                      421
```

<210> SEQ ID NO 179
<211> LENGTH: 139
<212> TYPE: PRT
<213> ORGANISM: artificial sequence
<220> FEATURE:
<223> OTHER INFORMATION: mub insertion site 3 antibody F

<400> SEQUENCE: 179

```
Asp Glu Thr Ile Ser Phe Ala Lys Asp Pro Asp Val Gln Leu Gln Glu
1               5                   10                  15

Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
        35                  40                  45

Gln Ala Pro Gly Lys Gly Leu Glu Tyr Ile Ala Gly Ile Gly Ser Asp
    50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Val
                85                  90                  95

Pro Glu Asp Thr Ala Asn Tyr Tyr Cys Ala Lys Asp Val Leu Asp Tyr
            100                 105                 110

His Pro Asp Leu Trp Gly Gln Gly Thr Gln Val Thr Val Cys Ser Gly
        115                 120                 125

Arg Asn Glu Val Val Lys Glu Leu Glu Lys Gln
    130                 135
```

<210> SEQ ID NO 180
<211> LENGTH: 418
<212> TYPE: DNA
<213> ORGANISM: artificial sequence
<220> FEATURE:
<223> OTHER INFORMATION: mub insertion site 3 antibody F

<400> SEQUENCE: 180

```
gaaacgatca gctttgccaa ggatccaaat agatgtgcag ctgcaggagt ctggaggaac       60
attggtgcag cccggggggt ctctgacgct ctcctgtgca gcgcatggat tcggaatcgg      120
tagtttcgcc atgctgtggg tccgccaggc cccaggaaag gggctcgagt atattgcggg      180
cattggtagt gattatacga cacactattc aaattccctc tcgggccgct tcaccatctc      240
taaagacatt gccaagaata cactagatct gcgcatggac gacctagtgc ctgaagacac      300
ggccaattat tattgtgcga aagacgtact tgactaccac ccagatttgt ggggccaggg      360
aacccaggtc accgtctgca gcggccgcga agtcgtcaag gaactcgaaa agcaggg t      418
```

<210> SEQ ID NO 181
<211> LENGTH: 139
<212> TYPE: PRT
<213> ORGANISM: artificial sequence
<220> FEATURE:
<223> OTHER INFORMATION: mub insertion site 3 antibody G

<400> SEQUENCE: 181

```
Asp Glu Thr Ile Ser Phe Ala Lys Asp Pro Asp Val Gln Leu Gln Glu
1               5                   10                  15
```

```
Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
            35                  40                  45

Gln Ala Pro Gly Lys Gly Leu Glu Tyr Ile Ala Gly Ile Gly Ser Asp
    50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Val
                85                  90                  95

Pro Glu Asp Thr Ala Asn Tyr Tyr Cys Ala Lys Asp Val Leu Asp Tyr
            100                 105                 110

His Pro Asp Leu Trp Gly Gln Gly Thr Gln Val Thr Val Cys Ser Gly
        115                 120                 125

Arg Asn Glu Val Val Lys Glu Leu Glu Lys Gln
    130                 135
```

<210> SEQ ID NO 182
<211> LENGTH: 421
<212> TYPE: DNA
<213> ORGANISM: artificial sequence
<220> FEATURE:
<223> OTHER INFORMATION: mub insertion site 3 antibody G

<400> SEQUENCE: 182

```
gaaacgatca gctttgccaa ggatccaaat agatgtgcag ctgcaggagt ctggaggaac      60
attggtgcag cccgggggt ctctgacgct ctcctgtgca gcgcatggat tcggaatcgg     120
tagtttcgcc atgctgtggg tccgccaggc cccaggaaag gggctcgagt atattgcggg     180
cattggtagt gattatacga cacactattc aaattccctc tcgggccgct tcaccatctc     240
taaagacatt gccaagaata cactagatct gcgcatggac gacctagtgc ctgaagacac     300
ggccaattat tattgtgcga agacgtact tgactaccac ccagatttgt ggggccaggg     360
aacccaggtc accgtctgca gcggccgcac tgaagtcgtc aaggaactcg aaaagcaggg     420
t                                                                     421
```

<210> SEQ ID NO 183
<211> LENGTH: 148
<212> TYPE: PRT
<213> ORGANISM: artificial sequence
<220> FEATURE:
<223> OTHER INFORMATION: mub insertion site 3 antibody H

<400> SEQUENCE: 183

```
Asp Glu Thr Ile Ser Phe Ala Lys Asp Pro Asp Val Gln Leu Gln Glu
1               5                   10                  15

Ser Gly Gly Gly Ser Val Gln Thr Gly Gly Ser Leu Arg Leu Ser Cys
            20                  25                  30

Ala Ala Ser Gly Asp Ser Ile Thr Thr Tyr His Met Ala Trp Phe Arg
            35                  40                  45

Gln Thr Pro Gly Lys Glu Arg Glu Val Ala Val Ile Asn Asp Asp
    50                  55                  60

Ala Asn Ser Arg Ile Tyr Val Asp Ser Val Lys Gly Arg Phe Thr Ile
65                  70                  75                  80

Ser Gln Asp Lys Ala Lys Asn Thr Val Tyr Leu Gln Met Asn Tyr Leu
                85                  90                  95
```

```
Thr Pro Glu Asp Thr Ala Ile Tyr Tyr Cys Ala Ala Asp Leu Arg Cys
            100                 105                 110

Val Pro Gly Thr Asp Ser Gly His Pro Tyr Ser Tyr Asn Tyr Trp Gly
        115                 120                 125

Gln Gly Thr Gln Val Thr Val Cys Ser Gly Asn Glu Val Val Lys Glu
    130                 135                 140

Leu Glu Lys Gln
145

<210> SEQ ID NO 184
<211> LENGTH: 446
<212> TYPE: DNA
<213> ORGANISM: artificial sequence
<220> FEATURE:
<223> OTHER INFORMATION: mub insertion site 3 antibody H

<400> SEQUENCE: 184
gaaacgatca gctttgccaa ggatccaaat agatgtgcag ctgcaggagt ctggaggagg      60
ttcggtgcag actggaggat ctctgagact ctcctgtgca gcctctggag attccatcac     120
tacctaccac atggcctggt tccgccagac tccagggaag gagcgtgagg aggtcgcagt     180
tataaatgat gatgctaatt cgagaatcta tgtcgactcc gtgaagggcc gattcaccat     240
ctcccaagac aaggccaaga acacggtgta tctgcaaatg aactacctga cgcctgagga     300
cacggccatc tactactgtg cggcagattt gaggtgcgtc cctgggaccg actctggtca     360
tccttattcg tataactact ggggccaggg gacccaggtc accgtctgca gcggccgaag     420
tcgtcaagga actcgaaaag cagggt                                          446

<210> SEQ ID NO 185
<211> LENGTH: 145
<212> TYPE: PRT
<213> ORGANISM: artificial sequence
<220> FEATURE:
<223> OTHER INFORMATION: mub insertion site 3 antibody I

<400> SEQUENCE: 185

Asp Glu Thr Ile Ser Phe Ala Lys Asp Pro Asp Val His Leu Gln Asp
1               5                   10                  15

Ser Gly Gly Gly Ser Val Gln Ala Gly Gly Ser Leu Thr Leu Ser Trp
            20                  25                  30

Leu Met Ser Gly His Thr Tyr Tyr Gly Pro Cys Val Gly Trp Phe Arg
        35                  40                  45

Gln Pro Pro Gly Lys Ala Arg Glu Gly Ile Pro Gln Ile Ser Pro Ile
    50                  55                  60

Gly Gly Ser Val Ile Tyr Ile Gly Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Leu Pro Glu Asp Thr Ala Thr Tyr Tyr Cys Ala Ala Ser Gly Gly
            100                 105                 110

Leu Cys Ser His Arg Glu Arg Asp Tyr Asp Ile Trp Gly Gln Gly Thr
        115                 120                 125

Gln Val Thr Val Cys Ser Gly Asn Glu Val Val Lys Glu Leu Glu Lys
    130                 135                 140

Gln
145
```

<210> SEQ ID NO 186
<211> LENGTH: 434
<212> TYPE: DNA
<213> ORGANISM: artificial sequence
<220> FEATURE:
<223> OTHER INFORMATION: mub insertion site 3 antibody I

<400> SEQUENCE: 186

```
gaaacgatca gctttgccaa ggatccaaat agatgtgcac ctgcaggatt ctggaggagg      60
ctcggtgcag gctggaggct ccctgacgct ctcttggtta atgtcgggtc atacgtatta     120
tggaccttgt gtgggttggt tccgccagcc cccagggaaa gcgcgtgagg gaatcccaca     180
gattagtcct attggtggga gtgttattta cattggtggc gtgaagggcc gattcaccat     240
ttcccgagac aactccaaga atactattgc tctcataatg aacgacctcc tgcctgaaga     300
cacggccact tattattgcg cagcagattc aggggggactc tgcagccatc gtgagcgcga     360
ctatgacatt tggggccagg ggacccaggt caccgtctgc ggccgaagtc gtcaaggaac     420
tcgaaaagca gggt                                                       434
```

<210> SEQ ID NO 187
<211> LENGTH: 145
<212> TYPE: PRT
<213> ORGANISM: artificial sequence
<220> FEATURE:
<223> OTHER INFORMATION: mub insertion site 3 antibody J

<400> SEQUENCE: 187

```
Asp Glu Thr Ile Ser Phe Ala Lys Asp Pro Asp Val His Leu Gln Asp
1               5                   10                  15
Ser Gly Glu Gly Trp Gly His Ala Gly Gly Ser Leu Thr Leu Ser Cys
            20                  25                  30
Leu Met Ser Gly His Thr Tyr Tyr Gly Pro Cys Gly Gly Gly Phe Pro
        35                  40                  45
Gln Pro Pro Gly Lys Ala Arg Glu Gly Ile Pro Gln Met Ile Pro Ile
    50                  55                  60
Gly Gly Ser Val Ile Tyr Ile Gly Gly Val Lys Gly Arg Phe Thr Ile
65                  70                  75                  80
Ser Arg Asp Asn Ser Lys Asn Thr Ile Ala Leu Ile Met Asn Asp Leu
                85                  90                  95
Val Pro Glu Asp Thr Ala Thr Tyr Tyr Cys Ala Thr Ser Gly Gly
            100                 105                 110
Leu Cys Ser His Arg Glu Arg Asp Tyr Asp Ile Trp Gly Gln Gly Thr
        115                 120                 125
Gln Val Thr Val Cys Ser Gly Asn Glu Val Val Lys Glu Leu Glu Lys
    130                 135                 140
Gln
145
```

<210> SEQ ID NO 188
<211> LENGTH: 434
<212> TYPE: DNA
<213> ORGANISM: artificial sequence
<220> FEATURE:
<223> OTHER INFORMATION: mub insertion site 3 antibody J

<400> SEQUENCE: 188

```
gaaacgatca gctttgccaa ggatccaaat agatgtgcac ctgcaggatt cgggagaagg      60
ctggggggcac gctggaggct ccctgaccct ctcttgttta atgtcgggtc atacgtatta    120
```

```
tggaccttgt gggggtgggt tcccccagcc cccagggaaa gcccgtgagg gaatcccaca    180
aatgattcct attggtggga gtgttatttta cattggtggc gtgaagggcc gattcaccat   240
ttcccgagac aactccaaga atactattgc tctcataatg aacgacctcg tgcctgaaga    300
cacggccact tattattgcg caacagattc aggggggactc tgcagccatc gtgagcgcga   360
ctatgacatt tggggccagg ggacccaggt caccgtctgc ggccgaagtc gtcaaggaac    420
tcgaaaagca gggt                                                      434
```

<210> SEQ ID NO 189
<211> LENGTH: 143
<212> TYPE: PRT
<213> ORGANISM: artificial sequence
<220> FEATURE:
<223> OTHER INFORMATION: mub insertion site 3 antibody K

<400> SEQUENCE: 189

```
Asp Glu Thr Ile Ser Phe Ala Lys Asp Asp Val His Leu Gln Asp Ser
1               5                   10                  15

Gly Gly Gly Ser Val His Ala Gly Gly Ser Leu Thr Leu Ser Cys Leu
            20                  25                  30

Met Ser Gly His Thr Tyr Tyr Gly Pro Cys Gly Gly Gly Phe Pro Arg
        35                  40                  45

Pro Pro Gly Lys Gly Arg Glu Gly Ile Ala Gln Ile Pro Ile Gly
    50                  55                  60

Gly Ser Val Ile Tyr Ile Gly Gly Val Lys Gly Arg Phe Thr Ile Ser
65                  70                  75                  80

Arg Tyr Asn Ser Lys Asn Thr Ile Ala Leu Ile Met Asn Asp Leu Val
                85                  90                  95

Pro Glu Asp Thr Ala Thr Tyr Cys Ala Thr Asp Ser Gly Gly Leu Cys
            100                 105                 110

Ser His Arg Glu Arg Asp Tyr Asp Ile Trp Gly Gln Gly Thr Gln Val
        115                 120                 125

Thr Val Cys Ser Gly Asn Glu Val Val Lys Glu Leu Glu Lys Gln
    130                 135                 140
```

<210> SEQ ID NO 190
<211> LENGTH: 437
<212> TYPE: DNA
<213> ORGANISM: artificial sequence
<220> FEATURE:
<223> OTHER INFORMATION: mub insertion site 3 antibody K

<400> SEQUENCE: 190

```
gaaacgatca gctttgccaa ggatccaaat agatgtgcac ctgcaggatt ctggaggagg    60
ctcggtgcac gctgggggct ccctgacgct ctcttgttta atgtcgggtc atacgtatta   120
tggaccttgt gggggtgggt tcccccggcc cccaggaaaa gggcgtgagg gaatcgcaca    180
aattattcct attggtggga gtgttatttta cattggtggc gtgaagggcc gattcaccat   240
ttcccgatac aactccaaga atactattgc tctcataatg aacgacctcg tgcctgaaga    300
cacggccact tattattgcg caacagattc aggggggactc tgcagccatc gtgagcgcga   360
ctatgacatt tggggccagg ggacccaggt caccgtctgc agcggccgaa gtcgtcaagg    420
aactcgaaaa gcagggt                                                   437
```

<210> SEQ ID NO 191
<211> LENGTH: 143
<212> TYPE: PRT

```
<213> ORGANISM: artificial sequence
<220> FEATURE:
<223> OTHER INFORMATION: mub insertion site 3 antibody L

<400> SEQUENCE: 191
```

Asp Glu Thr Ile Ser Phe Ala Lys Asp Asp Val His Leu Gln Asp Ser
1               5                   10                  15

Gly Gly Gly Ser Val Gln Ala Gly Gly Ser Leu Thr Leu Ser Cys Leu
            20                  25                  30

Met Ser Gly His Thr Tyr Tyr Gly Pro Cys Val Gly Trp Phe Pro Gln
        35                  40                  45

Arg Pro Gly Lys Ala Arg Glu Gly Ile Ala Gln Met Ile Pro Ile Gly
    50                  55                  60

Gly Ser Val Ser Tyr Ser Gly Gly Val Lys Gly Arg Phe Thr Ile Ser
65                  70                  75                  80

Arg Asp Asn Ser Lys Asn Thr Ile Ala Leu Ile Met Asn Asp Leu Val
                85                  90                  95

Pro Glu Asp Thr Ala Thr Tyr Tyr Cys Ala Thr Asp Ser Gly Gly Leu
            100                 105                 110

Cys Ser His Arg Glu Arg Asp Tyr Asp Ile Trp Gly Gln Gly Thr Gln
        115                 120                 125

Val Thr Val Cys Ser Asn Glu Val Val Lys Glu Leu Glu Lys Gln
    130                 135                 140

```
<210> SEQ ID NO 192
<211> LENGTH: 433
<212> TYPE: DNA
<213> ORGANISM: artificial sequence
<220> FEATURE:
<223> OTHER INFORMATION: mub insertion site 3 antibody L
<400> SEQUENCE: 192
gaaacgatca gctttgccaa ggatccaaat agatgtgcac ctgcaggatt ctggaggagg    60
ctcggtgcag gctggaggct ccctgaccct ctcttgttta atgtcgggtc atacgtatta   120
tggaccttgt gtgggttggt tcccccagcg tccagggaaa gcgcgtgagg gaatcgcaca   180
aatgattcct attggtggga gtgttagtta cagtggtggc gtgaagggcc gattcaccat   240
ttcccgagac aactccaaga atactattgc tctcataatg aacgacctcg tgcctgaaga   300
cacggccact tattattgcg caacagattc agggggactc tgcagccatc gtgagcgcga   360
ctatgacatt tggggccagg ggacccaggt caccgtctgc agcgaagtcg tcaaggaact   420
cgaaaagcag ggt                                                      433

<210> SEQ ID NO 193
<211> LENGTH: 146
<212> TYPE: PRT
<213> ORGANISM: artificial sequence
<220> FEATURE:
<223> OTHER INFORMATION: mub insertion site 3 antibody M

<400> SEQUENCE: 193
```

Asp Glu Thr Ile Ser Phe Ala Lys Asp Asp Val Gln Leu Gln Glu Ser
1               5                   10                  15

Gly Gly Gly Ser Val Gln Glu Gly Gly Ser Leu Arg Leu Ser Cys Ala
            20                  25                  30

Ala Ser Glu Tyr Thr Ala Ile Thr Tyr Cys Met Ala Trp Phe Arg Gln
        35                  40                  45

Ala Pro Gly Lys Glu Arg Glu Gly Val Ala Ala Ile Asn Arg Gly Gly

```
            50                  55                  60
Gly Ser Thr Tyr Tyr Ala Asp Ser Val Lys Gly Arg Phe Thr Ile Ser
 65                  70                  75                  80

Gln Asp Asn Ala Lys Asn Thr Val Tyr Leu Leu Met Asn Ser Leu Lys
                 85                  90                  95

Pro Glu Asp Thr Gly Met Tyr Tyr Cys Ala Tyr Lys Gln Thr Gly Asp
                100                 105                 110

Cys Gly Ile Phe Gln Phe Phe Gly Asn Tyr Gln Gly Thr Gln Val
                115                 120                 125

Thr Val Ser Ser Gly Arg Thr His Asn Glu Val Val Lys Glu Leu Glu
                130                 135                 140

Lys Gln
145

<210> SEQ ID NO 194
<211> LENGTH: 439
<212> TYPE: DNA
<213> ORGANISM: artificial sequence
<220> FEATURE:
<223> OTHER INFORMATION: mub insertion site 3 antibody M

<400> SEQUENCE: 194
gaaacgatca gctttgccaa ggatccaaat gatccagatg tgcagctgca ggagtctggg      60
ggaggctcgg tgcaggaggg agggtctctg agactctcct gtgcagcctc tgaatacacc     120
gctattacct actgtatggc ctggttccgc caggctccag ggaaggagcg tgaggggtc     180 gcggctatca atcgcggtgg tggtagtaca tattacgccg actccgtgaa gggccgattc     240
accatctccc aggacaacgc caagaacacg gtgtatctcc taatgaacag cctgaaacct     300
gaggacactg gcatgtacta ctgtgcgtac aaacagaccg gtgattgtgg gatcttccaa     360
ttctttggaa actatggcca ggggacccag gtcaccgtct ccagcggccg aagtcgtcaa     420
ggaactcgaa aagcagggt                                                  439

<210> SEQ ID NO 195
<211> LENGTH: 147
<212> TYPE: PRT
<213> ORGANISM: artificial sequence
<220> FEATURE:
<223> OTHER INFORMATION: mub insertion site 3 antibody N

<400> SEQUENCE: 195

Asp Glu Thr Ile Ser Phe Ala Lys Asp Asp Val Gln Leu Gln Glu Ser
 1               5                  10                  15

Gly Gly Gly Ser Val Gln Thr Gly Gly Ser Leu Arg Leu Ser Cys Ala
                20                  25                  30

Ala Ser Gly Asp Ser Ile Thr Thr Tyr His Met Ala Trp Phe Arg Gln
                35                  40                  45

Thr Pro Gly Lys Glu Arg Glu Glu Val Ala Val Ile Asn Asp Asp Ala
                50                  55                  60

Asn Ser Arg Ile Tyr Val Asp Ser Val Lys Gly Arg Phe Thr Ile Ser
 65                  70                  75                  80

Gln Asp Lys Ala Lys Asn Thr Val Tyr Leu Gln Met Asn Tyr Leu Thr
                85                  90                  95

Pro Glu Asp Thr Ala Ile Tyr Tyr Cys Ala Ala Asp Leu Arg Cys Val
                100                 105                 110

Pro Gly Thr Asp Ser Gly His Pro Tyr Ser Tyr Asn Tyr Trp Gly Gln
                115                 120                 125
```

Gly Thr Gln Val Thr Ala Ser Ser Gly Asn Glu Val Val Lys Glu Leu
        130                 135                 140

Glu Lys Gln
145

<210> SEQ ID NO 196
<211> LENGTH: 446
<212> TYPE: DNA
<213> ORGANISM: artificial sequence
<220> FEATURE:
<223> OTHER INFORMATION: mub insertion site 3 antibody N

<400> SEQUENCE: 196
gaaacgatca gctttgccaa ggatccaaat agatgtgcag ctgcaggagt ctggaggagg      60
ttcggtgcag actggaggat ctctgagact ctcctgtgca gcctctggag attccatcac     120
tacctaccac atggcctggt tccgccagac tccagggaag gagcgtgagg aggtcgcagt     180
tataaatgat gatgctaatt cgagaatcta tgtcgactcc gtgaagggcc gattcaccat     240
ctcccaagac aaggccaaga acacggtgta tctgcaaatg aactacctga cgcctgagga     300
cacggccatc tactactgtg cggcagattt gaggtgcgtc cctgggaccg actctggtca     360
tccttattcg tataactact ggggccaggg gacccaggtc accgcctcca gcggccgaag     420
tcgtcaagga actcgaaaag cagggt                                          446

<210> SEQ ID NO 197
<211> LENGTH: 148
<212> TYPE: PRT
<213> ORGANISM: artificial sequence
<220> FEATURE:
<223> OTHER INFORMATION: mub insertion site 3 antibody O

<400> SEQUENCE: 197

Asp Glu Thr Ile Ser Phe Ala Lys Asp Asp Val Gln Leu Gln Glu Ser
1               5                   10                  15

Gly Gly Gly Ser Val Gln Thr Gly Gly Ser Leu Arg Leu Ser Cys Ala
            20                  25                  30

Ala Ser Gly Asp Ser Ile Thr Thr Tyr His Met Ala Trp Phe Arg Gln
        35                  40                  45

Thr Pro Gly Lys Glu Arg Glu Glu Val Ala Val Ile Asn Asp Asp Ala
    50                  55                  60

Asn Ser Arg Ile Tyr Val Asp Ser Val Lys Gly Arg Phe Thr Ile Ser
65                  70                  75                  80

Gln Asp Lys Ala Lys Asn Thr Val Tyr Leu Gln Met Asn Tyr Leu Thr
                85                  90                  95

Pro Glu Asp Thr Ala Ile Tyr Tyr Cys Ala Ala Asp Leu Arg Cys Val
            100                 105                 110

Pro Gly Thr Asp Ser Gly His Pro Tyr Ser Tyr Asn Tyr Trp Gly Gln
        115                 120                 125

Gly Thr Gln Val Thr Ala Ser Ser Gly Arg Asn Glu Val Val Lys Glu
    130                 135                 140

Leu Glu Lys Gln
145

<210> SEQ ID NO 198
<211> LENGTH: 446
<212> TYPE: DNA
<213> ORGANISM: artificial sequence
<220> FEATURE:

<223> OTHER INFORMATION: mub insertion site 3 antibody O

<400> SEQUENCE: 198

```
gaaacgatca gctttgccaa ggatccaaat agatgtgcag ctgcaggagt ctggaggagg      60
ttcggtgcag actggaggat ctctgagact ctcctgtgca gcctctggag attccatcac     120
tacctaccac atggcctggt ccgccagac tccagggaag gagcgtgagg aggtcgcagt     180
tataaatgat gatgctaatt cgagaatcta tgtcgactcc gtgaagggcc gattcaccat     240
ctcccaagac aaggccaaga cacggtgta tctgcaaatg aactacctga cgcctgagga     300
cacggccatc tactactgtg cggcagattt gaggtgcgtc cctgggaccg actctggtca     360
tccttattcg tataactact ggggccaggg gacccaggtc accgcctcca gcggccgaag     420
tcgtcaagga actcgaaaag cagggt                                          446
```

<210> SEQ ID NO 199
<211> LENGTH: 149
<212> TYPE: PRT
<213> ORGANISM: artificial sequence
<220> FEATURE:
<223> OTHER INFORMATION: mub insertion site 3 antibody P

<400> SEQUENCE: 199

```
Asp Glu Thr Ile Ser Phe Ala Lys Asp Asp Val Gln Leu Gln Glu Ser
1               5                  10                  15

Gly Gly Gly Ser Ala Gln Pro Gly Gly Ser Leu Arg Leu Ser Cys Ala
            20                  25                  30

Val Ser Gly Ser Thr Ala Ser Met Tyr Cys Leu Ala Trp Phe Arg Gln
        35                  40                  45

Ala Pro Gly Lys Glu Pro Glu Gly Val Ala Ala Ile Ser Gly Asp Asp
    50                  55                  60

Lys Gly Phe Thr Asn Tyr Ala Asp Ser Val Lys Gly Arg Phe Thr Ile
65                  70                  75                  80

Ser Gln Asn Lys Ala Asn Lys Thr Val Asn Leu Gln Met Asn Ser Leu
                85                  90                  95

Lys Pro Glu Asp Thr Ala Ile Tyr Tyr Cys Ala Val Asp Ala Arg Ala
            100                 105                 110

Thr Thr Thr Gly Glu Arg Leu His Ala Arg Thr Tyr Glu Phe Trp Gly
        115                 120                 125

Gln Gly Thr Gln Val Thr Val Cys Ser Gly Arg Asn Glu Val Val Lys
    130                 135                 140

Glu Leu Glu Lys Gln
145
```

<210> SEQ ID NO 200
<211> LENGTH: 450
<212> TYPE: DNA
<213> ORGANISM: artificial sequence
<220> FEATURE:
<223> OTHER INFORMATION: mub insertion site 3 antibody P

<400> SEQUENCE: 200

```
gaaacgatca gctttgccaa ggatccaaat gatgtgcagc tgcaggagtc tgggggaggc      60
tcggcgcagc ctggagggtc tctgagactc tcctgtgcag tctctggatc gaccgccagt     120
atgtactgct tggcctggtt ccgccaggct ccagggaagg agcctgaggg ggttgctgct     180
attagtggag atgataaagg gtttacgaat tacgccgact ccgtgaaggg ccggttcacc     240
atctcccaaa acaaggccaa taaaacggtg aatctgcaaa tgaacagcct gaaacctgaa     300
```

```
gacacggcca tttattactg tgccgttgat gcgcgagcga caacaactgg tgaacgtcta      360
cacgcccgga cgtacgaatt ctggggccag gggacccagg tcaccgtctg cagcggccgc      420
gaagtcgtca aggaactcga aaagcagggt                                       450
```

<210> SEQ ID NO 201
<211> LENGTH: 147
<212> TYPE: PRT
<213> ORGANISM: artificial sequence
<220> FEATURE:
<223> OTHER INFORMATION: mub insertion site 3 antibody Q

<400> SEQUENCE: 201

```
Asp Glu Thr Ile Ser Phe Ala Lys Asp Asp Val Gln Met Gln Glu Ser
1               5                   10                  15

Gly Gly Gly Ser Val Gln Ala Gly Gly Ser Leu Arg Leu Ser Cys Ala
            20                  25                  30

Ala Ser Gly Asp Thr Leu Ser Thr Tyr Cys Met Gly Trp Phe Arg Gln
        35                  40                  45

Val Pro Gly Lys Asp Arg Glu Gly Val Ala Ala Ile Tyr Arg Leu Arg
    50                  55                  60

Asp Met Thr Phe Tyr Ala Asp Ser Val Lys Gly Arg Phe Thr Ile Ser
65                  70                  75                  80

Arg Asp Asn Ala Asn Asp Thr Val Asp Leu Gln Met Asn Ser Leu Lys
                85                  90                  95

Pro Glu Asp Thr Ala Val Tyr Tyr Cys Ala Ala Arg Cys Val Arg Leu
            100                 105                 110

Phe Gly Thr Cys Gln Leu Val Glu Asp Phe Glu Leu Trp Gly Gln Gly
        115                 120                 125

Thr Gln Val Thr Val Ser Ser Gly Leu Asn Glu Val Val Lys Glu Leu
    130                 135                 140

Glu Lys Gln
145
```

<210> SEQ ID NO 202
<211> LENGTH: 442
<212> TYPE: DNA
<213> ORGANISM: artificial sequence
<220> FEATURE:
<223> OTHER INFORMATION: mub insertion site 3 antibody Q

<400> SEQUENCE: 202

```
gaaacgatca gctttgccaa ggatccaaat agatgtgcag atgcaggagt ctggggagg        60 gtcggtgcag gctggagggt ctctgagact ctcctgtgca gcctctggag atacccccag      120
tacctactgc atgggctggt tccgccaagt tccaggaaag gaccgtgagg gggtcgcagc      180
gatttatcgt cttagggata tgacgttcta tgccgactcc gtgaagggcc gattcaccat      240
ttcccgtgac aacgccaacg acacggtaga tctgcaaatg aacagcctga acctgaggga      300
cacagccgtg tactactgtg cagcaagatg tgtgcgacta ttcggtactt gtcagctagt      360
cgaagatttt gaactatggg gccaggggac ccaggtcacc gtctccagcg gcgaagtcgt      420
caaggaactc gaaaagcagg gt                                              442
```

<210> SEQ ID NO 203
<211> LENGTH: 148
<212> TYPE: PRT
<213> ORGANISM: artificial sequence
<220> FEATURE:

<223> OTHER INFORMATION: mub insertion site 3 antibody R

<400> SEQUENCE: 203

Asp Glu Thr Ile Ser Phe Ala Lys Asp Asp Val Gln Met Gln Glu Ser
1               5                   10                  15

Gly Gly Gly Ser Val Gln Ala Gly Gly Ser Leu Arg Leu Ser Cys Ala
            20                  25                  30

Ala Ser Gly Asp Thr Leu Ser Thr Tyr Cys Met Gly Trp Phe Arg Gln
        35                  40                  45

Ala Pro Gly Lys Asp Arg Glu Gly Val Ala Ala Ile Tyr Arg Leu Arg
    50                  55                  60

Asp Met Thr Phe Tyr Ala Asp Ser Val Lys Gly Arg Phe Thr Ile Ser
65                  70                  75                  80

Arg Asp Asn Ala Asn Asp Thr Val Asp Leu Gln Met Asn Ser Leu Lys
                85                  90                  95

Pro Glu Asp Thr Ala Val Tyr Tyr Cys Ala Ala Arg Cys Val Arg Leu
            100                 105                 110

Phe Gly Thr Cys Gln Leu Val Glu Asp Phe Glu Leu Trp Gly Gln Gly
        115                 120                 125

Thr Gln Val Thr Val Ser Ser Gly Leu Thr Asn Glu Val Val Lys Glu
    130                 135                 140

Leu Glu Lys Gln
145

<210> SEQ ID NO 204
<211> LENGTH: 442
<212> TYPE: DNA
<213> ORGANISM: artificial sequence
<220> FEATURE:
<223> OTHER INFORMATION: mub insertion site 3 antibody R

<400> SEQUENCE: 204

```
gaaacgatca gctttgccaa ggatccaaat agatgtgcag atgcaggagt ctggggagg      60
gtcggtgcag gctggagggt ctctgagact ctcctgtgca gcctctggag ataccctcag    120
tacctactgc atgggctggt tccgccaagt tccaggaaag gaccgtgagg gggtcgcagc    180
gatttatcgt cttagggata tgacgttcta tgccgactcc gtgaagggcc gattcaccat    240
ttcccgtgac aacgccaacg acacggtaga tctgcaaatg aacagcctga acctgaggga    300
cacagccgtg tactactgtg cagcaagatg tgtgcgacta ttcggtactt gtcagctagt    360
cgaagatttt gaactatggg gccaggggac ccaggtcacc gtctccagcg gcgaagtcgt    420
caaggaactc gaaaagcagg gt                                             442
```

<210> SEQ ID NO 205
<211> LENGTH: 148
<212> TYPE: PRT
<213> ORGANISM: artificial sequence
<220> FEATURE:
<223> OTHER INFORMATION: mub insertion site 3 antibody S

<400> SEQUENCE: 205

Asp Glu Thr Ile Ser Phe Ala Lys Asp Asp Val Gln Met Gln Glu Ser
1               5                   10                  15

Gly Gly Gly Ser Val Gln Ala Gly Gly Ser Leu Arg Leu Ser Cys Ala
            20                  25                  30

Ala Ser Gly Asp Thr Leu Ser Thr Tyr Cys Met Gly Trp Phe Arg Gln
        35                  40                  45

Val Pro Gly Lys Asp Arg Glu Gly Val Ala Ala Ile Tyr Arg Leu Arg
        50                  55                  60

Asp Met Thr Phe Tyr Ala Asp Ser Val Lys Gly Arg Phe Thr Ile Ser
65                  70                  75                  80

Arg Asp Asn Ala Asn Asp Thr Val Asp Leu Gln Met Asn Ser Leu Lys
                85                  90                  95

Pro Glu Asp Thr Ala Val Tyr Tyr Cys Ala Ala Arg Cys Val Arg Leu
            100                 105                 110

Phe Gly Thr Cys Gln Leu Val Glu Asp Phe Glu Leu Trp Gly Gln Gly
        115                 120                 125

Thr Gln Val Thr Val Ser Ser Gly Leu Thr Asn Glu Val Val Lys Glu
    130                 135                 140

Leu Glu Lys Gln
145

<210> SEQ ID NO 206
<211> LENGTH: 443
<212> TYPE: DNA
<213> ORGANISM: artificial sequence
<220> FEATURE:
<223> OTHER INFORMATION: mub insertion site 3 antibody S

<400> SEQUENCE: 206
gaaacgatca gctttgccaa ggatccaaat agatgtgcag atgcaggagt ctggggagg      60 gtcggtgcag gctggagggt ctctgagact ctcctgtgca gcctctggag ataccctcag     120
tacctactgc atgggctggt ccgccaagt tccagggaag gaccgtgagg gggtcgcagc      180
gatttatcgt cttagggata tgacgttcta tgccgactcc gtgaagggcc gattcaccat     240
ttcccgtgac aacgccaacg acacggtaga tctgcaaatg aacagcctga acctgaggga    300
cacagccgtg tactactgtg cagcaagatg tgtgcgacta ttcggtactt gtcagctagt    360
cgaagatttt gaactatggg gccagggac ccaggtcacc gtctccagcg gccgaagtcg     420
tcaaggaact cgaaaagcag ggt                                            443

<210> SEQ ID NO 207
<211> LENGTH: 146
<212> TYPE: PRT
<213> ORGANISM: artificial sequence
<220> FEATURE:
<223> OTHER INFORMATION: cnbp insertion site antibody A

<400> SEQUENCE: 207

Asn Lys Ala Leu Lys Glu Leu Gln Gln Asp Asp Val Gln Leu Gln Glu
1               5                   10                  15

Ser Gly Gly Gly Ser Val Gln Ala Gly Gly Ser Leu Thr Leu Ser Cys
            20                  25                  30

Leu Met Ser Gly His Thr Tyr Tyr Gly Pro Cys Val Gly Trp Phe Arg
        35                  40                  45

Gln Arg Pro Gly Lys Ala Arg Glu Gly Ile Ala Gln Ile Ser Pro Ser
    50                  55                  60

Gly Gly Ser Val Ser Tyr Ser Gly Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Val Pro Glu Asp Thr Ala Thr Tyr Tyr Cys Ala Ala Asp Ser Gly Gly
            100                 105                 110

Leu Cys Ser His Arg Glu Arg Asp Tyr Asp Ile Trp Gly Gln Gly Thr

```
                115                 120                 125
Gln Val Thr Val Cys Ser Gly Arg Gly Thr Val Lys Lys Leu Ser Glu
            130                 135                 140
Lys Tyr
145

<210> SEQ ID NO 208
<211> LENGTH: 439
<212> TYPE: DNA
<213> ORGANISM: artificial sequence
<220> FEATURE:
<223> OTHER INFORMATION: cnbp insertion site antibody A

<400> SEQUENCE: 208
cttcaacaag atggaacagt caagaagcta atgtgcagct gcaggagtct gggggaggct      60
cggtgcaggc tggaggctcc ctgacgctct cttgtttaat gtctggtcat acgtattatg     120
gaccttgtgt gggttggttc cgccagcgtc cagggaaagc gcgtgaggga atcgcacaga     180
ttagtcctag tggtgggagt gttagttaca gtggtggcgt gaagggccga ttcaccattt     240
cccgagacaa ctccaagaat actattgctc tcataatgaa cgacctcgtg cctgaagaca     300
cggccactta ttattgcgca gcagattcag ggggactctg cagccatcgt gagcgcgact     360
atgacatttg ggccagggga acccaggtca ccgtctgcag cggccgcact ctgaaaagta     420
cttcggtgca gatattact                                                  439

<210> SEQ ID NO 209
<211> LENGTH: 145
<212> TYPE: PRT
<213> ORGANISM: artificial sequence
<220> FEATURE:
<223> OTHER INFORMATION: cnbp insertion site antibody B

<400> SEQUENCE: 209

Asn Lys Ala Leu Lys Glu Leu Gln Gln Asp Asp Pro Asp Val His Leu
1               5                   10                  15

Gln Asp Ser Gly Gly Gly Trp Val His Pro Gly Gly Ser Leu Thr Leu
            20                  25                  30

Ser Cys Leu Met Ser Gly Ser Glu Tyr Tyr Gly Ser Pro Val Gly Trp
        35                  40                  45

Phe Pro Gln Pro Pro Gly Lys Gly Arg Glu Glu Ile Ala Glu Ile Val
    50                  55                  60

Pro Ile Gly Gly Ser Val Ile Tyr Ile Gly Gly Val Glu Gly Arg Phe
65                  70                  75                  80

Thr Ile Ser Arg Asp Asn Ser Lys Asn Thr Ile Ala Leu Ile Met Asn
                85                  90                  95

Asp Leu Leu Pro Glu Asp Thr Ala Thr Tyr Tyr Cys Ala Ala Asp Ser
            100                 105                 110

Gly Gly Leu Cys Ser His Arg Glu Arg Asp Tyr Asp Ile Trp Gly Gln
        115                 120                 125

Gly Thr Gln Val Thr Val Cys Gly Thr Val Lys Lys Leu Ser Glu Lys
    130                 135                 140

Tyr
145

<210> SEQ ID NO 210
<211> LENGTH: 435
<212> TYPE: DNA
<213> ORGANISM: artificial sequence
```

<220> FEATURE:
<223> OTHER INFORMATION: cnbp insertion site antibody B

<400> SEQUENCE: 210

```
cttcaacaag atgaacagt caagaagcta gatccagatg tgcacctgca ggattcggga    60
ggaggctggg tgcacccggg gggctccctg accctctctt gtttaatgtc gggttccgaa  120
tattatggtt ccctgtggg ttggttcccc cagcccccag gaaagggcg tgaggaaatc   180
gcggaaattg ttcctattgg tgggagtgtt atttacattg gtggcgtgga gggccgattc  240
accatttccc gagacaactc caagaatact attgctctca atgaacga cctcctgcct   300
gaagacacgg ccacttatta ttgcgcagca gattcagggg gactctgcag ccatcgtgag  360
cgcgactatg acatttgggg ccaggggacc caggtcaccg tctgctctga aaagtacttc  420
ggtgcagata ttact                                                    435
```

<210> SEQ ID NO 211
<211> LENGTH: 139
<212> TYPE: PRT
<213> ORGANISM: artificial sequence
<220> FEATURE:
<223> OTHER INFORMATION: cnbp insertion site antibody C

<400> SEQUENCE: 211

```
Asn Lys Ala Leu Lys Glu Leu Gln Gln Asp Asp Val Gln Leu Pro Glu
 1               5                  10                  15
Ser Gly Arg Thr Leu Val Pro Pro Gly Gly Ser Leu Lys Leu Ser Trp
            20                  25                  30
Ala Thr His Gly Phe Gly Ile Gly Ser Phe Pro Met Leu Trp Val Pro
        35                  40                  45
Pro Ala Pro Gly Lys Gly Leu Glu Tyr Ile Ala Gly Ile Gly Ser Asp
    50                  55                  60
Tyr Thr Thr His Tyr Ser Asn Ser Leu Ser Gly Arg Phe Thr Ile Ser
65                  70                  75                  80
Lys Asp Ile Ala Lys Asn Thr Leu Asp Leu Arg Met Asp Asp Leu Leu
                85                  90                  95
Pro Glu Asp Thr Ala Asn Tyr Tyr Cys Ala Lys Asp Val Leu Asp Tyr
            100                 105                 110
His Pro Asp Leu Trp Gly Arg Gly Thr Gln Val Thr Val Cys Arg Gly
        115                 120                 125
Arg Gly Thr Val Lys Lys Leu Ser Glu Lys Tyr
    130                 135
```

<210> SEQ ID NO 212
<211> LENGTH: 419
<212> TYPE: DNA
<213> ORGANISM: artificial sequence
<220> FEATURE:
<223> OTHER INFORMATION: cnbp insertion site antibody C

<400> SEQUENCE: 212

```
cttcaacaag atgaacagt caagaagcta agatgtgcag ctgccagaat ccggaagaac    60
gttggtgcca cccgggggt ccctgaagct ctcctgggca acgcacggat tcggaatcgg  120
tagtttcccc atgctgtggg tccccccggc cccggaaaa gggctcgaat atattgcggg  180
cattggtagt gattatacga cacactattc aaattccctc tcggccgct tcaccatctc   240
taaagacatt gccaagaata cactagatct gcgcatggac gacctactgc ctgaagacac  300
ggccaattat tattgtgcga aagacgtact tgactaccac ccagatttgt ggggccgggg  360
```

```
aacccaggtc accgtctgca ggggccgcat ctgaaaagta cttcggtgca gatattact      419
```

<210> SEQ ID NO 213
<211> LENGTH: 145
<212> TYPE: PRT
<213> ORGANISM: artificial sequence
<220> FEATURE:
<223> OTHER INFORMATION: cnbp insertion site antibody D

<400> SEQUENCE: 213

```
Asn Lys Ala Leu Lys Glu Leu Gln Gln Asp Val Gln Leu Gln Glu Ser
1               5                   10                  15
Gly Gly Gly Ser Val Gln Asp Gly Gly Thr Leu Gln Leu Ser Cys Glu
            20                  25                  30
Asp Ser Lys Trp Ser Tyr Thr Tyr Tyr Cys Met Gly Trp Phe Arg Gln
        35                  40                  45
Ala Pro Gly Lys Glu Arg Glu Pro Val Ala His Ile Asp Ser Glu Gly
    50                  55                  60
Thr Val Ala Tyr Ala Asp Thr Val Lys Gly Arg Phe Thr Ile Ser Arg
65                  70                  75                  80
Gly Asp Ala Lys His Arg Val Tyr Leu Gln Met Asn Asn Leu Lys Ala
                85                  90                  95
Asp Asp Thr Ala Ile Tyr Tyr Cys Ala Ala Asn Gly Gly Tyr Cys Leu
            100                 105                 110
Arg Pro Arg Gln Leu Ala Ala Asp Tyr Glu Tyr Trp Gly Gln Gly Ala
        115                 120                 125
Gln Val Thr Val Ser Ser Gly Gly Thr Val Lys Lys Leu Ser Glu Lys
    130                 135                 140
Tyr
145
```

<210> SEQ ID NO 214
<211> LENGTH: 441
<212> TYPE: DNA
<213> ORGANISM: artificial sequence
<220> FEATURE:
<223> OTHER INFORMATION: cnbp insertion site antibody D

<400> SEQUENCE: 214

```
cttcaacaag atggaacagt caagaagcta aagtgcagct gcaggagtct gggggaggct      60
cggtgcagga tggagggact ttacaactct cttgtgaaga ctctaaatgg agctacacgt     120
actattgtat ggggtggttc cgccaggctc cagggaagga gcgagagccg gtcgcgcaca     180
ttgatagtga aggcactgtc gcttacgccg acaccgtgaa gggccgattc accatctccc     240
gggggacgc caagcatagg gtttacctgc aaatgaataa cttgaaggct gatgacacgg     300
ccatctatta ttgtgcggcc aatggtggtt attgcctcag accccgtcaa ctcgccgcgg     360
attatgagta ttggggccag ggggcccagg tcaccgtctc cagcggccgc atctgaaaag     420
tacttcggtg cagatattac t                                              441
```

<210> SEQ ID NO 215
<211> LENGTH: 138
<212> TYPE: PRT
<213> ORGANISM: artificial sequence
<220> FEATURE:
<223> OTHER INFORMATION: cnbp insertion site antibody E

<400> SEQUENCE: 215

Asn Lys Ala Leu Lys Glu Leu Gln Gln Asp Val Gln Leu Gln Glu
1               5                   10                  15

Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
            35                  40                  45

Gln Ala Pro Gly Lys Gly Leu Glu Tyr Ile Ala Gly Ile Gly Ser Asp
        50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Val
                85                  90                  95

Pro Glu Asp Thr Ala Asn Tyr Tyr Cys Ala Lys Asp Val Leu Asp Tyr
            100                 105                 110

His Pro Asp Leu Trp Gly Gln Gly Thr Gln Val Thr Val Cys Ser Gly
            115                 120                 125

Gly Thr Val Lys Lys Leu Ser Glu Lys Tyr
        130                 135

<210> SEQ ID NO 216
<211> LENGTH: 421
<212> TYPE: DNA
<213> ORGANISM: artificial sequence
<220> FEATURE:
<223> OTHER INFORMATION: cnbp insertion site antibody E

<400> SEQUENCE: 216
cttcaacaag atggaacagt caagaagcta agatgtgcag ctgcaggagt ctggaggaac     60
attggtgcag cccgggggt ctctgacgct ctcctgtgca gcgcatggat tcggaatcgg    120
tagtttcgcc atgctgtggg tccgccaggc cccaggaaag gggctcgagt atattgcggg    180
cattggtagt gattatacga cacactattc aaattccctc tcgggccgct tcaccatctc    240
taaagacatt gccaagaata cactagatct gcgcatggac gacctagtgc ctgaagacac    300
ggccaattat tattgtgcga aagacgtact tgactaccac ccagatttgt ggggccaggg    360
aacccaggtc accgtctgca gcggccgcac ttctgaaaag tacttcggtg cagatattac    420
t                                                                    421

<210> SEQ ID NO 217
<211> LENGTH: 139
<212> TYPE: PRT
<213> ORGANISM: artificial sequence
<220> FEATURE:
<223> OTHER INFORMATION: cnbp insertion site antibody F

<400> SEQUENCE: 217

Asn Lys Ala Leu Lys Glu Leu Gln Gln Asp Val Gln Leu Gln Glu
1               5                   10                  15

Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
            35                  40                  45

Gln Ala Pro Gly Lys Gly Leu Glu Tyr Ile Ala Gly Ile Gly Ser Asp
        50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Val

```
                    85                  90                  95
Pro Glu Asp Thr Ala Asn Tyr Tyr Cys Ala Lys Asp Val Leu Asp Tyr
        100                 105                 110

His Pro Asp Leu Trp Gly Gln Gly Thr Gln Val Thr Val Cys Ser Gly
        115                 120                 125

Arg Gly Thr Val Lys Lys Leu Ser Glu Lys Tyr
        130                 135

<210> SEQ ID NO 218
<211> LENGTH: 418
<212> TYPE: DNA
<213> ORGANISM: artificial sequence
<220> FEATURE:
<223> OTHER INFORMATION: cnbp insertion site antibody F

<400> SEQUENCE: 218
cttcaacaag atggaacagt caagaagcta agatgtgcag ctgcaggagt ctggaggaac    60
attggtgcag cccgggggtc tctgacgct ctcctgtgca gcgcatggat tcggaatcgg   120
tagtttcgcc atgctgtggg tccgccaggc cccaggaaag gggctcgagt atattgcggg   180
cattggtagt gattatacga cacactattc aaattccctc tcgggccgct tcaccatctc   240
taaagacatt gccaagaata cactagatct gcgcatggac gacctagtgc ctgaagacac   300
ggccaattat tattgtgcga aagacgtact tgactaccac ccagatttgt ggggccaggg   360
aacccaggtc accgtctgca gcggccgctc tgaaaagtac ttcggtgcag atattact    418

<210> SEQ ID NO 219
<211> LENGTH: 138
<212> TYPE: PRT
<213> ORGANISM: artificial sequence
<220> FEATURE:
<223> OTHER INFORMATION: cnbp insertion site antibody G

<400> SEQUENCE: 219

Asn Lys Ala Leu Lys Glu Leu Gln Gln Asp Asp Val Gln Leu Gln Glu
1               5                   10                  15

Ser Gly Gly Thr Leu Val Gln Pro Gly Gly Ser Leu Thr Leu Ser Cys
            20                  25                  30

Ala Ala His Gly Phe Gly Ile Gly Ser Phe Ala Met Leu Trp Val Arg
        35                  40                  45

Gln Ala Pro Gly Lys Gly Leu Glu Tyr Ile Ala Gly Ile Gly Ser Asp
    50                  55                  60

Tyr Thr Thr His Tyr Ser Asn Ser Leu Ser Gly Arg Phe Thr Ile Ser
65                  70                  75                  80

Lys Asp Ile Ala Lys Asn Thr Leu Asp Leu Arg Met Asp Asp Leu Val
                85                  90                  95

Pro Glu Asp Thr Ala Asn Tyr Tyr Cys Ala Lys Asp Val Leu Asp Tyr
        100                 105                 110

His Pro Asp Leu Trp Gly Gln Gly Thr Gln Val Thr Val Cys Ser Gly
        115                 120                 125

Gly Thr Val Lys Lys Leu Ser Glu Lys Tyr
        130                 135

<210> SEQ ID NO 220
<211> LENGTH: 421
<212> TYPE: DNA
<213> ORGANISM: artificial sequence
<220> FEATURE:
<223> OTHER INFORMATION: cnbp insertion site antibody G
```

<400> SEQUENCE: 220

```
cttcaacaag atggaacagt caagaagcta agatgtgcag ctgcaggagt ctggaggaac       60
attggtgcag cccgggggt ctctgacgct ctcctgtgca gcgcatggat tcggaatcgg      120
tagtttcgcc atgctgtggg tccgccaggc cccaggaaag gggctcgagt atattgcggg      180
cattggtagt gattatacga cacactattc aaattccctc tcgggccgct tcaccatctc      240
taaagacatt gccaagaata cactagatct gcgcatggac gacctagtgc ctgaagacac      300
ggccaattat tattgtgcga agacgtact tgactaccac ccagatttgt ggggccaggg      360
aacccaggtc accgtctgca gcggccgcac ttctgaaaag tacttcggtg cagatattac      420
t                                                                     421
```

<210> SEQ ID NO 221
<211> LENGTH: 148
<212> TYPE: PRT
<213> ORGANISM: artificial sequence
<220> FEATURE:
<223> OTHER INFORMATION: cnbp insertion site antibody H

<400> SEQUENCE: 221

```
Asn Lys Ala Leu Lys Glu Leu Gln Gln Asp Val Gln Leu Gln Glu
1               5                   10                  15

Ser Gly Gly Gly Ser Val Gln Thr Gly Gly Ser Leu Arg Leu Ser Cys
            20                  25                  30

Ala Ala Ser Gly Asp Ser Ile Thr Thr Tyr His Met Ala Trp Phe Arg
        35                  40                  45

Gln Thr Pro Gly Lys Glu Arg Glu Glu Val Ala Val Ile Asn Asp Asp
    50                  55                  60

Ala Asn Ser Arg Ile Tyr Val Asp Ser Val Lys Gly Arg Phe Thr Ile
65                  70                  75                  80

Ser Gln Asp Lys Ala Lys Asn Thr Val Tyr Leu Gln Met Asn Tyr Leu
                85                  90                  95

Thr Pro Glu Asp Thr Ala Ile Tyr Tyr Cys Ala Ala Asp Leu Arg Cys
            100                 105                 110

Val Pro Gly Thr Asp Ser Gly His Pro Tyr Ser Tyr Asn Tyr Trp Gly
        115                 120                 125

Gln Gly Thr Gln Val Thr Val Cys Ser Gly Gly Thr Val Lys Lys Leu
    130                 135                 140

Ser Glu Lys Tyr
145
```

<210> SEQ ID NO 222
<211> LENGTH: 446
<212> TYPE: DNA
<213> ORGANISM: artificial sequence
<220> FEATURE:
<223> OTHER INFORMATION: cnbp insertion site antibody H

<400> SEQUENCE: 222

```
cttcaacaag atggaacagt caagaagcta agatgtgcag ctgcaggagt ctggaggagg       60
ttcggtgcag actggaggat ctctgagact ctcctgtgca gcctctggag attccatcac      120
tacctaccac atggcctggt tccgccagac tccaggaaag gagcgtgagg aggtcgcagt      180
tataaatgat gatgctaatt cgagaatcta tgtcgactcc gtgaagggcc gattcaccat      240
ctcccaagac aaggccaaga acacggtgta tctgcaaatg aactacctga cgcctgagga      300
```

```
cacggccatc tactactgtg cggcagattt gaggtgcgtc cctgggaccg actctggtca      360
tccttattcg tataactact ggggccaggg gacccaggtc accgtctgca gcggcctctg      420
aaaagtactt cggtgcagat attact                                          446
```

<210> SEQ ID NO 223
<211> LENGTH: 145
<212> TYPE: PRT
<213> ORGANISM: artificial sequence
<220> FEATURE:
<223> OTHER INFORMATION: cnbp insertion site antibody I

<400> SEQUENCE: 223

```
Asn Lys Ala Leu Lys Glu Leu Gln Gln Asp Asp Val His Leu Gln Asp
 1               5                  10                  15

Ser Gly Gly Gly Ser Val Gln Ala Gly Gly Ser Leu Thr Leu Ser Trp
            20                  25                  30

Leu Met Ser Gly His Thr Tyr Tyr Gly Pro Cys Val Gly Trp Phe Arg
        35                  40                  45

Gln Pro Pro Gly Lys Ala Arg Glu Gly Ile Pro Gln Ile Ser Pro Ile
    50                  55                  60

Gly Gly Ser Val Ile Tyr Ile Gly Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Leu Pro Glu Asp Thr Ala Thr Tyr Tyr Cys Ala Ala Asp Ser Gly Gly
            100                 105                 110

Leu Cys Ser His Arg Glu Arg Asp Tyr Asp Ile Trp Gly Gln Gly Thr
        115                 120                 125

Gln Val Thr Val Cys Ser Gly Gly Thr Val Lys Lys Leu Ser Glu Lys
    130                 135                 140

Tyr
145
```

<210> SEQ ID NO 224
<211> LENGTH: 434
<212> TYPE: DNA
<213> ORGANISM: artificial sequence
<220> FEATURE:
<223> OTHER INFORMATION: cnbp insertion site antibody I

<400> SEQUENCE: 224

```
cttcaacaag atggaacagt caagaagcta agatgtgcac ctgcaggatt ctggaggagg       60
ctcggtgcag gctggaggct ccctgacgct ctcttggtta atgtcgggtc atacgtatta      120
tggaccttgt gtgggttggt tccgccagcc cccagggaaa gcgcgtgagg gaatcccaca      180
gattagtcct attggtggga gtgttattta cattggtggc gtgaagggcc gattcaccat      240
ttcccgagac aactccaaga atactattgc tctcataatg aacgacctcc tgcctgaaga      300
cacggccact tattattgcg cagcagattc agggggactc tgcagccatc gtgagcgcga      360
ctatgacatt tggggccagg ggacccaggt caccgtctgc ggcctctgaa aagtacttcg      420
gtgcagatat tact                                                        434
```

<210> SEQ ID NO 225
<211> LENGTH: 145
<212> TYPE: PRT
<213> ORGANISM: artificial sequence
<220> FEATURE:
<223> OTHER INFORMATION: cnbp insertion site antibody J -continued

<400> SEQUENCE: 225

Asn Lys Ala Leu Lys Glu Leu Gln Gln Asp Asp Val His Leu Gln Asp
1               5                   10                  15

Ser Gly Glu Gly Trp Gly His Ala Gly Gly Ser Leu Thr Leu Ser Cys
            20                  25                  30

Leu Met Ser Gly His Thr Tyr Tyr Gly Pro Cys Gly Gly Phe Pro
        35                  40                  45

Gln Pro Pro Gly Lys Ala Arg Glu Gly Ile Pro Gln Met Ile Pro Ile
    50                  55                  60

Gly Gly Ser Val Ile Tyr Ile Gly Gly Val Lys Gly Arg Phe Thr Ile
65                  70                  75                  80

Ser Arg Asp Asn Ser Lys Asn Thr Ile Ala Leu Ile Met Asn Asp Leu
                85                  90                  95

Val Pro Glu Asp Thr Ala Thr Tyr Tyr Cys Ala Thr Asp Ser Gly Gly
            100                 105                 110

Leu Cys Ser His Arg Glu Arg Asp Tyr Asp Ile Trp Gly Gln Gly Thr
        115                 120                 125

Gln Val Thr Val Cys Ser Gly Gly Thr Val Lys Lys Leu Ser Glu Lys
    130                 135                 140

Tyr
145

<210> SEQ ID NO 226
<211> LENGTH: 434
<212> TYPE: DNA
<213> ORGANISM: artificial sequence
<220> FEATURE:
<223> OTHER INFORMATION: cnbp insertion site antibody J

<400> SEQUENCE: 226
cttcaacaag atggaacagt caagaagcta agatgtgcac ctgcaggatt cgggagaagg      60
ctggggcac gctggaggct ccctgaccct ctcttgttta atgtcgggtc atacgtatta     120
tggaccttgt gggggtgggt tcccccagcc cccagggaaa gcccgtgagg gaatcccaca     180
aatgattcct attggtggga gtgttattta cattggtggc gtgaagggcc gattcaccat     240
ttcccgagac aactccaaga atactattgc tctcataatg aacgacctcg tgcctgaaga     300
cacggccact tattattgcg caacagattc aggggggactc tgcagccatc gtgagcgcga     360
ctatgacatt tggggccagg ggacccaggt caccgtctgc ggcctctgaa agtacttcg     420
gtgcagatat tact                                                         434

<210> SEQ ID NO 227
<211> LENGTH: 144
<212> TYPE: PRT
<213> ORGANISM: artificial sequence
<220> FEATURE:
<223> OTHER INFORMATION: cnbp insertion site antibody K

<400> SEQUENCE: 227

Asn Lys Ala Leu Lys Glu Leu Gln Gln Asp Asp Val His Leu Gln Asp
1               5                   10                  15

Ser Gly Gly Gly Ser Val His Ala Gly Gly Ser Leu Thr Leu Ser Cys
            20                  25                  30

Leu Met Ser Gly His Thr Tyr Tyr Gly Pro Cys Gly Gly Phe Pro
        35                  40                  45

Arg Pro Pro Gly Lys Gly Arg Glu Gly Ile Ala Gln Ile Ile Pro Ile

```
              50                  55                  60
Gly Gly Ser Val Ile Tyr Ile Gly Gly Val Lys Gly Arg Phe Thr Ile
 65                  70                  75                  80

Ser Arg Tyr Asn Ser Lys Asn Thr Ile Ala Leu Ile Met Asn Asp Leu
                 85                  90                  95

Val Pro Glu Asp Thr Ala Thr Tyr Cys Ala Thr Asp Ser Gly Gly Leu
             100                 105                 110

Cys Ser His Arg Glu Arg Asp Tyr Asp Ile Trp Gly Gln Gly Thr Gln
         115                 120                 125

Val Thr Val Cys Ser Gly Gly Thr Val Lys Lys Leu Ser Glu Lys Tyr
     130                 135                 140
```

<210> SEQ ID NO 228
<211> LENGTH: 437
<212> TYPE: DNA
<213> ORGANISM: artificial sequence
<220> FEATURE:
<223> OTHER INFORMATION: cnbp insertion site antibody K

<400> SEQUENCE: 228

```
cttcaacaag atggaacagt caagaagcta agatgtgcac ctgcaggatt ctggaggagg    60
ctcggtgcac gctgggggct ccctgacgct ctcttgttta atgtcgggtc atacgtatta   120
tggaccttgt gggggtgggt tcccccggcc cccaggaaaa gggcgtgagg gaatcgcaca   180
aattattcct attggtggga gtgttattta cattggtggc gtgaagggcc gattcaccat   240
ttcccgatac aactccaaga atactattgc tctcataatg aacgacctcg tgcctgaaga   300
cacggccact tattattgcg caacagattc agggggactc tgcagccatc gtgagcgcga   360
ctatgacatt tggggccagg ggacccaggt caccgtctgc agcggcctct gaaaagtact   420
tcggtgcaga tattact                                                  437
```

<210> SEQ ID NO 229
<211> LENGTH: 144
<212> TYPE: PRT
<213> ORGANISM: artificial sequence
<220> FEATURE:
<223> OTHER INFORMATION: cnbp insertion site antibody L

<400> SEQUENCE: 229

```
Asn Lys Ala Leu Lys Glu Leu Gln Gln Asp Asp Val His Leu Gln Asp
  1               5                  10                  15

Ser Gly Gly Gly Ser Val Gln Ala Gly Gly Ser Leu Thr Leu Ser Cys
             20                  25                  30

Leu Met Ser Gly His Thr Tyr Tyr Gly Pro Cys Val Gly Trp Phe Pro
         35                  40                  45

Gln Arg Pro Gly Lys Ala Arg Glu Gly Ile Ala Gln Met Ile Pro Ile
     50                  55                  60

Gly Gly Ser Val Ser Tyr Ser Gly Gly Val Lys Gly Arg Phe Thr Ile
 65                  70                  75                  80

Ser Arg Asp Asn Ser Lys Asn Thr Ile Ala Leu Ile Met Asn Asp Leu
                 85                  90                  95

Val Pro Glu Asp Thr Ala Thr Tyr Cys Ala Thr Asp Ser Gly Gly
             100                 105                 110

Leu Cys Ser His Arg Glu Arg Asp Tyr Asp Ile Trp Gly Gln Gly Thr
         115                 120                 125

Gln Val Thr Val Cys Ser Gly Val Lys Lys Leu Ser Glu Lys Tyr
     130                 135                 140
```

<210> SEQ ID NO 230
<211> LENGTH: 433
<212> TYPE: DNA
<213> ORGANISM: artificial sequence
<220> FEATURE:
<223> OTHER INFORMATION: cnbp insertion site antibody L

<400> SEQUENCE: 230

```
cttcaacaag atggaacagt caagaagcta agatgtgcac ctgcaggatt ctggaggagg      60
ctcggtgcag gctggaggct ccctgaccct ctcttgttta atgtcgggtc atacgtatta     120
tggaccttgt gtgggttggt tcccccagcg tccaggaaaa gcgcgtgagg gaatcgcaca     180
aatgattcct attggtggga gtgttagtta cagtggtggc gtgaagggcc gattcaccat     240
ttcccgagac aactccaaga atactattgc tctcataatg aacgacctcg tgcctgaaga     300
cacggccact tattattgcg caacagattc aggggggactc tgcagccatc gtgagcgcga     360
ctatgacatt tggggccagg ggacccaggt caccgtctgc agctctgaaa agtacttcgg     420
tgcagatatt act                                                        433
```

<210> SEQ ID NO 231
<211> LENGTH: 147
<212> TYPE: PRT
<213> ORGANISM: artificial sequence
<220> FEATURE:
<223> OTHER INFORMATION: cnbp insertion site antibody M

<400> SEQUENCE: 231

```
Asn Lys Ala Leu Lys Glu Leu Gln Gln Asp Asp Val Gln Leu Gln Glu
1               5                   10                  15

Ser Gly Gly Gly Ser Val Gln Glu Gly Gly Ser Leu Arg Leu Ser Cys
            20                  25                  30

Ala Ala Ser Glu Tyr Thr Ala Ile Thr Tyr Cys Met Ala Trp Phe Arg
        35                  40                  45

Gln Ala Pro Gly Lys Glu Arg Glu Gly Val Ala Ala Ile Asn Arg Gly
    50                  55                  60

Gly Gly Ser Thr Tyr Tyr Ala Asp Ser Val Lys Gly Arg Phe Thr Ile
65                  70                  75                  80

Ser Gln Asp Asn Ala Lys Asn Thr Val Tyr Leu Leu Met Asn Ser Leu
                85                  90                  95

Lys Pro Glu Asp Thr Gly Met Tyr Tyr Cys Ala Tyr Lys Gln Thr Gly
            100                 105                 110

Asp Cys Gly Ile Phe Gln Phe Phe Gly Asn Tyr Gly Gln Gly Thr Gln
        115                 120                 125

Val Thr Val Ser Ser Gly Arg Thr His Gly Thr Val Lys Lys Leu Ser
    130                 135                 140

Glu Lys Tyr
145
```

<210> SEQ ID NO 232
<211> LENGTH: 439
<212> TYPE: DNA
<213> ORGANISM: artificial sequence
<220> FEATURE:
<223> OTHER INFORMATION: cnbp insertion site antibody M

<400> SEQUENCE: 232

```
cttcaacaag atggaacagt caagaagcta gatccagatg tgcagctgca ggagtctggg      60
```

```
ggaggctcgg tgcaggaggg agggtctctg agactctcct gtgcagcctc tgaatacacc    120
gctattacct actgtatggc ctggttccgc caggctccag ggaaggagcg tgaggggtc     180 gcggctatca atcgcggtgg tggtagtaca tattacgccg actccgtgaa gggccgattc    240
accatctccc aggacaacgc caagaacacg gtgtatctcc taatgaacag cctgaaacct    300
gaggacactg gcatgtacta ctgtgcgtac aaacagaccg gtgattgtgg gatcttccaa    360
ttctttggaa actatggcca ggggacccag gtcaccgtct ccagcggcct ctgaaaagta    420
cttcggtgca gatattact                                                 439
```

<210> SEQ ID NO 233  
<211> LENGTH: 148  
<212> TYPE: PRT  
<213> ORGANISM: artificial sequence  
<220> FEATURE:  
<223> OTHER INFORMATION: cnbp insertion site antibody N

<400> SEQUENCE: 233

```
Asn Lys Ala Leu Lys Glu Leu Gln Gln Asp Asp Val Gln Leu Gln Glu
 1               5                  10                  15

Ser Gly Gly Gly Ser Val Gln Thr Gly Gly Ser Leu Arg Leu Ser Cys
            20                  25                  30

Ala Ala Ser Gly Asp Ser Ile Thr Thr Tyr His Met Ala Trp Phe Arg
        35                  40                  45

Gln Thr Pro Gly Lys Glu Arg Glu Glu Val Ala Val Ile Asn Asp Asp
    50                  55                  60

Ala Asn Ser Arg Ile Tyr Val Asp Ser Val Lys Gly Arg Phe Thr Ile
65                  70                  75                  80

Ser Gln Asp Lys Ala Lys Asn Thr Val Tyr Leu Gln Met Asn Tyr Leu
                85                  90                  95

Thr Pro Glu Asp Thr Ala Ile Tyr Tyr Cys Ala Ala Asp Leu Arg Cys
            100                 105                 110

Val Pro Gly Thr Asp Ser Gly His Pro Tyr Ser Tyr Asn Tyr Trp Gly
        115                 120                 125

Gln Gly Thr Gln Val Thr Ala Ser Ser Gly Gly Thr Val Lys Lys Leu
    130                 135                 140

Ser Glu Lys Tyr
145
```

<210> SEQ ID NO 234  
<211> LENGTH: 446  
<212> TYPE: DNA  
<213> ORGANISM: artificial sequence  
<220> FEATURE:  
<223> OTHER INFORMATION: cnbp insertion site antibody N

<400> SEQUENCE: 234

```
cttcaacaag atggaacagt caagaagcta agatgtgcag ctgcaggagt ctggaggagg    60
ttcggtgcag actggaggat ctctgagact ctcctgtgca gcctctggag attccatcac    120
tacctaccac atggcctggt tccgccagac tccaggaag gagcgtgagg aggtcgcagt     180
tataaatgat gatgctaatt cgagaatcta tgtcgactcc gtgaagggcc gattcaccat    240
ctcccaagac aaggccaaga acacggtgta tctgcaaatg aactacctga cgcctgagga    300
cacggccatc tactactgtg cggcagattt gaggtgcgtc cctgggaccg actctggtca    360
tccttattcg tataactact ggggccaggg gacccaggtc accgcctcca gcggcctctg    420
aaaagtactt cggtgcagat attact                                         446
```

<210> SEQ ID NO 235
<211> LENGTH: 149
<212> TYPE: PRT
<213> ORGANISM: artificial sequence
<220> FEATURE:
<223> OTHER INFORMATION: cnbp insertion site antibody O

<400> SEQUENCE: 235

Asn Lys Ala Leu Lys Glu Leu Gln Gln Asp Asp Val Gln Leu Gln Glu
1               5                   10                  15
Ser Gly Gly Gly Ser Val Gln Thr Gly Gly Ser Leu Arg Leu Ser Cys
            20                  25                  30
Ala Ala Ser Gly Asp Ser Ile Thr Thr Tyr His Met Ala Trp Phe Arg
        35                  40                  45
Gln Thr Pro Gly Lys Glu Arg Glu Val Ala Val Ile Asn Asp Asp
    50                  55                  60
Ala Asn Ser Arg Ile Tyr Val Asp Ser Val Lys Gly Arg Phe Thr Ile
65                  70                  75                  80
Ser Gln Asp Lys Ala Lys Asn Thr Val Tyr Leu Gln Met Asn Tyr Leu
                85                  90                  95
Thr Pro Glu Asp Thr Ala Ile Tyr Tyr Cys Ala Ala Asp Leu Arg Cys
            100                 105                 110
Val Pro Gly Thr Asp Ser Gly His Pro Tyr Ser Tyr Asn Tyr Trp Gly
        115                 120                 125
Gln Gly Thr Gln Val Thr Ala Ser Ser Gly Arg Gly Thr Val Lys Lys
    130                 135                 140
Leu Ser Glu Lys Tyr
145

<210> SEQ ID NO 236
<211> LENGTH: 446
<212> TYPE: DNA
<213> ORGANISM: artificial sequence
<220> FEATURE:
<223> OTHER INFORMATION: cnbp insertion site antibody O

<400> SEQUENCE: 236
cttcaacaag atggaacagt caagaagcta agatgtgcag ctgcaggagt ctggaggagg      60
ttcggtgcag actggaggat ctctgagact ctcctgtgca gcctctggag attccatcac     120
tacctaccac atggcctggt tccgccagac tccagggaag gagcgtgagg aggtcgcagt     180
tataaatgat gatgctaatt cgagaatcta tgtcgactcc gtgaagggcc gattcaccat     240
ctcccaagac aaggccaaga acacggtgta tctgcaaatg aactacctga cgcctgagga     300
cacggccatc tactactgtg cggcagattt gaggtgcgtc cctgggaccg actctggtca     360
tccttattcg tataactact ggggccaggg gacccaggtc accgcctcca gcggcctctg     420
aaaagtactt cggtgcagat attact                                          446

<210> SEQ ID NO 237
<211> LENGTH: 150
<212> TYPE: PRT
<213> ORGANISM: artificial sequence
<220> FEATURE:
<223> OTHER INFORMATION: cnbp insertion site antibody P

<400> SEQUENCE: 237

Asn Lys Ala Leu Lys Glu Leu Gln Gln Asp Asp Val Gln Leu Gln Glu
1               5                   10                  15

Ser Gly Gly Gly Ser Ala Gln Pro Gly Gly Ser Leu Arg Leu Ser Cys
            20                  25                  30

Ala Val Ser Gly Ser Thr Ala Ser Met Tyr Cys Leu Ala Trp Phe Arg
            35                  40                  45

Gln Ala Pro Gly Lys Glu Pro Glu Gly Val Ala Ala Ile Ser Gly Asp
    50                  55                  60

Asp Lys Gly Phe Thr Asn Tyr Ala Asp Ser Val Lys Gly Arg Phe Thr
65                  70                  75                  80

Ile Ser Gln Asn Lys Ala Asn Lys Thr Val Asn Leu Gln Met Asn Ser
                85                  90                  95

Leu Lys Pro Glu Asp Thr Ala Ile Tyr Tyr Cys Ala Val Asp Ala Arg
            100                 105                 110

Ala Thr Thr Thr Gly Glu Arg Leu His Ala Arg Thr Tyr Glu Phe Trp
            115                 120                 125

Gly Gln Gly Thr Gln Val Thr Val Cys Ser Arg Gly Thr Val Lys
    130                 135                 140

Lys Leu Ser Glu Lys Tyr
145                 150

<210> SEQ ID NO 238
<211> LENGTH: 450
<212> TYPE: DNA
<213> ORGANISM: artificial sequence
<220> FEATURE:
<223> OTHER INFORMATION: cnbp insertion site antibody P

<400> SEQUENCE: 238
cttcaacaag atggaacagt caagaagcta gatgtgcagc tgcaggagtc tgggggaggc      60
tcggcgcagc ctggagggtc tctgagactc tcctgtgcag tctctggatc gaccgccagt     120
atgtactgct tggcctggtt ccgccaggct ccagggaagg agcctgaggg ggttgctgct     180
attagtggag atgataaagg gtttacgaat tacgccgact ccgtgaaggg ccggttcacc     240
atctcccaaa acaaggccaa taaaacggtg aatctgcaaa tgaacagcct gaaacctgaa     300
gacacggcca tttattactg tgccgttgat gcgcgagcga caacaactgg tgaacgtcta     360
cacgcccgga cgtacgaatt ctggggccag gggacccagg tcaccgtctg cagcggccgc     420
tctgaaaagt acttcggtgc agatattact                                      450

<210> SEQ ID NO 239
<211> LENGTH: 148
<212> TYPE: PRT
<213> ORGANISM: artificial sequence
<220> FEATURE:
<223> OTHER INFORMATION: cnbp insertion site antibody Q

<400> SEQUENCE: 239

Asn Lys Ala Leu Lys Glu Leu Gln Gln Asp Asp Val Gln Met Gln Glu
1               5                   10                  15

Ser Gly Gly Gly Ser Val Gln Ala Gly Gly Ser Leu Arg Leu Ser Cys
            20                  25                  30

Ala Ala Ser Gly Asp Thr Leu Ser Thr Tyr Cys Met Gly Trp Phe Arg
            35                  40                  45

Gln Val Pro Gly Lys Asp Arg Glu Gly Val Ala Ala Ile Tyr Arg Leu
    50                  55                  60

Arg Asp Met Thr Phe Tyr Ala Asp Ser Val Lys Gly Arg Phe Thr Ile
65                  70                  75                  80

Ser Arg Asp Asn Ala Asn Asp Thr Val Asp Leu Gln Met Asn Ser Leu
            85                  90                  95

Lys Pro Glu Asp Thr Ala Val Tyr Tyr Cys Ala Ala Arg Cys Val Arg
            100                 105                 110

Leu Phe Gly Thr Cys Gln Leu Val Glu Asp Phe Glu Leu Trp Gly Gln
            115                 120                 125

Gly Thr Gln Val Thr Val Ser Ser Gly Leu Gly Thr Val Lys Lys Leu
        130                 135                 140

Ser Glu Lys Tyr
145

<210> SEQ ID NO 240
<211> LENGTH: 442
<212> TYPE: DNA
<213> ORGANISM: artificial sequence
<220> FEATURE:
<223> OTHER INFORMATION: cnbp insertion site antibody Q

<400> SEQUENCE: 240
cttcaacaag atggaacagt caagaagcta agatgtgcag atgcaggagt ctgggggagg     60
gtcggtgcag ctggagggt ctctgagact ctcctgtgca gcctctggag atacccctcag   120 tacctactgc atgggctggt ccgccaagt tccagggaag gaccgtgagg gggtcgcagc    180
gatttatcgt cttagggata tgacgttcta tgccgactcc gtgaagggcc gattcaccat    240
ttcccgtgac aacgccaacg acacggtaga tctgcaaatg aacagcctga acctgagga     300 cacagccgtg tactactgtg cagcaagatg tgtgcgacta ttcggtactt gtcagctagt    360
cgaagatttt gaactatggg gccaggggac ccaggtcacc gtctccagcg gctctgaaaa    420
gtacttcggt gcagatatta ct                                              442

<210> SEQ ID NO 241
<211> LENGTH: 149
<212> TYPE: PRT
<213> ORGANISM: artificial sequence
<220> FEATURE:
<223> OTHER INFORMATION: cnbp insertion site antibody R

<400> SEQUENCE: 241

Asn Lys Ala Leu Lys Glu Leu Gln Gln Asp Asp Val Gln Met Gln Glu
1               5                   10                  15

Ser Gly Gly Gly Ser Val Gln Ala Gly Gly Ser Leu Arg Leu Ser Cys
            20                  25                  30

Ala Ala Ser Gly Asp Thr Leu Ser Thr Tyr Cys Met Gly Trp Phe Arg
        35                  40                  45

Gln Ala Pro Gly Lys Asp Arg Glu Gly Val Ala Ala Ile Tyr Arg Leu
    50                  55                  60

Arg Asp Met Thr Phe Tyr Ala Asp Ser Val Lys Gly Arg Phe Thr Ile
65                  70                  75                  80

Ser Arg Asp Asn Ala Asn Asp Thr Val Asp Leu Gln Met Asn Ser Leu
            85                  90                  95

Lys Pro Glu Asp Thr Ala Val Tyr Tyr Cys Ala Ala Arg Cys Val Arg
            100                 105                 110

Leu Phe Gly Thr Cys Gln Leu Val Glu Asp Phe Glu Leu Trp Gly Gln
            115                 120                 125

Gly Thr Gln Val Thr Val Ser Ser Gly Leu Gly Thr Val Lys Lys
        130                 135                 140

Leu Ser Glu Lys Tyr

<210> SEQ ID NO 242
<211> LENGTH: 442
<212> TYPE: DNA
<213> ORGANISM: artificial sequence
<220> FEATURE:
<223> OTHER INFORMATION: cnbp insertion site antibody R

<400> SEQUENCE: 242

```
cttcaacaag atggaacagt caagaagcta agatgtgcag atgcaggagt ctgggggagg      60
gtcggtgcag gctggagggt ctctgagact ctcctgtgca gcctctggag atacccctcag   120
tacctactgc atgggctggt tccgccaagt tccagggaag gaccgtgagg gggtcgcagc    180
gatttatcgt cttagggata tgacgttcta tgccgactcc gtgaagggcc gattcaccat    240
ttcccgtgac aacgccaacg acacggtaga tctgcaaatg aacagcctga acctgagga     300
cacagccgtg tactactgtg cagcaagatg tgtgcgacta ttcggtactt gtcagctagt    360
cgaagatttt gaactatggg gccaggggac ccaggtcacc gtctccagcg gctctgaaaa   420
gtacttcggt gcagatatta ct                                             442
```

<210> SEQ ID NO 243
<211> LENGTH: 149
<212> TYPE: PRT
<213> ORGANISM: artificial sequence
<220> FEATURE:
<223> OTHER INFORMATION: cnbp insertion site antibody S

<400> SEQUENCE: 243

Asn Lys Ala Leu Lys Glu Leu Gln Gln Asp Asp Val Gln Met Gln Glu
1               5                   10                  15

Ser Gly Gly Gly Ser Val Gln Ala Gly Gly Ser Leu Arg Leu Ser Cys
            20                  25                  30

Ala Ala Ser Gly Asp Thr Leu Ser Thr Tyr Cys Met Gly Trp Phe Arg
        35                  40                  45

Gln Val Pro Gly Lys Asp Arg Glu Gly Val Ala Ala Ile Tyr Arg Leu
    50                  55                  60

Arg Asp Met Thr Phe Tyr Ala Asp Ser Val Lys Gly Arg Phe Thr Ile
65                  70                  75                  80

Ser Arg Asp Asn Ala Asn Asp Thr Val Asp Leu Gln Met Asn Ser Leu
                85                  90                  95

Lys Pro Glu Asp Thr Ala Val Tyr Tyr Cys Ala Ala Arg Cys Val Arg
            100                 105                 110

Leu Phe Gly Thr Cys Gln Leu Val Glu Asp Phe Glu Leu Trp Gly Gln
        115                 120                 125

Gly Thr Gln Val Thr Val Ser Ser Gly Leu Thr Gly Thr Val Lys Lys
    130                 135                 140

Leu Ser Glu Lys Tyr
145

<210> SEQ ID NO 244
<211> LENGTH: 443
<212> TYPE: DNA
<213> ORGANISM: artificial sequence
<220> FEATURE:
<223> OTHER INFORMATION: cnbp insertion site antibody S

<400> SEQUENCE: 244

```
cttcaacaag atggaacagt caagaagcta agatgtgcag atgcaggagt ctgggggagg      60
```

```
gtcggtgcag gctggagggt ctctgagact ctcctgtgca gcctctggag atacccctcag    120 tacctactgc atgggctggt tccgccaagt tccagggaag gaccgtgagg gggtcgcagc    180
gatttatcgt cttagggata tgacgttcta tgccgactcc gtgaagggcc gattcaccat    240
ttcccgtgac aacgccaacg acacggtaga tctgcaaatg aacagcctga aacctgagga    300
cacagccgtg tactactgtg cagcaagatg tgtgcgacta ttcggtactt gtcagctagt    360
cgaagatttt gaactatggg gccaggggac ccaggtcacc gtctccagcg gcctctgaaa    420
agtacttcgg tgcagatatt act                                            443
```

<210> SEQ ID NO 245
<211> LENGTH: 20
<212> TYPE: DNA
<213> ORGANISM: artificial sequence
<220> FEATURE:
<223> OTHER INFORMATION: lactobacillus identification forward

<400> SEQUENCE: 245

```
agagtttgat cctggctcag                                                  20
```

<210> SEQ ID NO 246
<211> LENGTH: 20
<212> TYPE: DNA
<213> ORGANISM: artificial sequence
<220> FEATURE:
<223> OTHER INFORMATION: lactobacillus identification reverse

<400> SEQUENCE: 246

```
ccgtcaattc ctttgagttt                                                  20
```

<210> SEQ ID NO 247
<211> LENGTH: 21
<212> TYPE: DNA
<213> ORGANISM: artificial sequence
<220> FEATURE:
<223> OTHER INFORMATION: l reuteri identification forward

<400> SEQUENCE: 247

```
gccgcctaag gtgggacaga t                                                21
```

<210> SEQ ID NO 248
<211> LENGTH: 20
<212> TYPE: DNA
<213> ORGANISM: artificial sequence
<220> FEATURE:
<223> OTHER INFORMATION: l reuteri identification reverse

<400> SEQUENCE: 248

```
aacactcaag gattgtctga                                                  20
```

<210> SEQ ID NO 249
<211> LENGTH: 32
<212> TYPE: DNA
<213> ORGANISM: artificial sequence
<220> FEATURE:
<223> OTHER INFORMATION: MuB partial gene forward

<400> SEQUENCE: 249

```
gctctagaac ggttcactac aagtacgcag at                                    32
```

<210> SEQ ID NO 250
<211> LENGTH: 34
<212> TYPE: DNA

```
<213> ORGANISM: artificial sequence
<220> FEATURE:
<223> OTHER INFORMATION: MuB partial gene reverse

<400> SEQUENCE: 250
cgagctctgc gaaaaaagac aaaaaggctc aacc                               34

<210> SEQ ID NO 251
<211> LENGTH: 27
<212> TYPE: DNA
<213> ORGANISM: artificial sequence
<220> FEATURE:
<223> OTHER INFORMATION: CnBP complete forward

<400> SEQUENCE: 251
gctctagaac tcataatatg gtctttg                                       27

<210> SEQ ID NO 252
<211> LENGTH: 28
<212> TYPE: DNA
<213> ORGANISM: artificial sequence
<220> FEATURE:
<223> OTHER INFORMATION: CnBP complete reverse

<400> SEQUENCE: 252
cgagctcata atttaacatt aatttgtg                                      28

<210> SEQ ID NO 253
<211> LENGTH: 22
<212> TYPE: DNA
<213> ORGANISM: artificial sequence
<220> FEATURE:
<223> OTHER INFORMATION: VHH large insert forward

<400> SEQUENCE: 253
gtcctggatc ccttctacaa gg                                            22

<210> SEQ ID NO 254
<211> LENGTH: 23
<212> TYPE: DNA
<213> ORGANISM: artificial sequence
<220> FEATURE:
<223> OTHER INFORMATION: VHH large insert reverse

<400> SEQUENCE: 254
gggacgtcct gttgaactgt tcc                                           23

<210> SEQ ID NO 255
<211> LENGTH: 24
<212> TYPE: DNA
<213> ORGANISM: artificial sequence
<220> FEATURE:
<223> OTHER INFORMATION: MuB inverse forward

<400> SEQUENCE: 255
gacgacttca tttggatcct tggt                                          24

<210> SEQ ID NO 256
<211> LENGTH: 37
<212> TYPE: DNA
<213> ORGANISM: artificial sequence
<220> FEATURE:
<223> OTHER INFORMATION: MuB inverse reverse

<400> SEQUENCE: 256
acgcgtcgac catatggaag tcgtcaagga actcgaa                            37
```

<210> SEQ ID NO 257
<211> LENGTH: 38
<212> TYPE: DNA
<213> ORGANISM: artificial sequence
<220> FEATURE:
<223> OTHER INFORMATION: VHH insert for MuB forward

<400> SEQUENCE: 257
cgggatccag atgtgcagct gcaggagtct ggaggagg                             38

<210> SEQ ID NO 258
<211> LENGTH: 43
<212> TYPE: DNA
<213> ORGANISM: artificial sequence
<220> FEATURE:
<223> OTHER INFORMATION: VHH insert for MuB reverse

<400> SEQUENCE: 258
ggaattccat atgagtgcgg ccgctggaga cggtgacctg ggt                       43

<210> SEQ ID NO 259
<211> LENGTH: 24
<212> TYPE: DNA
<213> ORGANISM: artificial sequence
<220> FEATURE:
<223> OTHER INFORMATION: L reuteri MuB gene without restriction sites

<400> SEQUENCE: 259
acggttcact acaagtacgc agat                                            24

<210> SEQ ID NO 260
<211> LENGTH: 27
<212> TYPE: DNA
<213> ORGANISM: artificial sequence
<220> FEATURE:
<223> OTHER INFORMATION: l reuteri MuB gene without restriction sites

<400> SEQUENCE: 260
tgcgaaaaaa gacaaaaagg ctcaacc                                         27

<210> SEQ ID NO 261
<211> LENGTH: 31
<212> TYPE: DNA
<213> ORGANISM: artificial sequence
<220> FEATURE:
<223> OTHER INFORMATION: CnBP inverse forward

<400> SEQUENCE: 261
ggaattccat atgtctgaaa agtacttcgg t                                    31

<210> SEQ ID NO 262
<211> LENGTH: 21
<212> TYPE: DNA
<213> ORGANISM: artificial sequence
<220> FEATURE:
<223> OTHER INFORMATION: CnBP inverse reverse

<400> SEQUENCE: 262
tagcttcttg acggatccat c                                               21

<210> SEQ ID NO 263
<211> LENGTH: 37
<212> TYPE: DNA
<213> ORGANISM: artificial sequence
<220> FEATURE:

<223> OTHER INFORMATION: VHH insert for CnBP forward

<400> SEQUENCE: 263
cgggatccga tgtgcagctg caggagtctg gaggagg        37

<210> SEQ ID NO 264
<211> LENGTH: 43
<212> TYPE: DNA
<213> ORGANISM: artificial sequence
<220> FEATURE:
<223> OTHER INFORMATION: VHH insert for CnBP reverse

<400> SEQUENCE: 264
ggaattccat atgagtgcgg ccgctggaga cggtgacctg ggt        43

<210> SEQ ID NO 265
<211> LENGTH: 21
<212> TYPE: DNA
<213> ORGANISM: artificial sequence
<220> FEATURE:
<223> OTHER INFORMATION: CnBP phos oligos forward

<400> SEQUENCE: 265
actctagata tggtctttgc g        21

<210> SEQ ID NO 266
<211> LENGTH: 21
<212> TYPE: DNA
<213> ORGANISM: artificial sequence
<220> FEATURE:
<223> OTHER INFORMATION: CnBP phospho oligos reverse

<400> SEQUENCE: 266
ataatttaac actagtttgt g        21

<210> SEQ ID NO 267
<211> LENGTH: 27
<212> TYPE: DNA
<213> ORGANISM: artificial sequence
<220> FEATURE:
<223> OTHER INFORMATION: salmonella FimH forward

<400> SEQUENCE: 267
ggaattccat atgaaaatat actcagc        27

<210> SEQ ID NO 268
<211> LENGTH: 30
<212> TYPE: DNA
<213> ORGANISM: artificial sequence
<220> FEATURE:
<223> OTHER INFORMATION: salmonella FimH reverse

<400> SEQUENCE: 268
ccgctcgagt tactaatcat aatcgactcg        30

<210> SEQ ID NO 269
<211> LENGTH: 29
<212> TYPE: DNA
<213> ORGANISM: artificial sequence
<220> FEATURE:
<223> OTHER INFORMATION: salmonella OmPD forward

<400> SEQUENCE: 269
ggaattccat atgaaactta agttagtgg        29

-continued

```
<210> SEQ ID NO 270
<211> LENGTH: 32
<212> TYPE: DNA
<213> ORGANISM: artificial sequence
<220> FEATURE:
<223> OTHER INFORMATION: salmonella OmPD reverse

<400> SEQUENCE: 270
ccgctcgagt tactagaact ggtagttcag ac                                  32

<210> SEQ ID NO 271
<211> LENGTH: 696
<212> TYPE: DNA
<213> ORGANISM: artificial sequence
<220> FEATURE:
<223> OTHER INFORMATION: L.reuteri FimH seq

<400> SEQUENCE: 271
atgggcagca gccatcatca tcatcatcac agcagcggcc tggtgccgcg cggcagccat     60
atgaaaatat actcagcgct attgctggcg gggaccgcgc tcttttttcac ccatcccgcg   120 ctggcgacgg tttgccgtaa ttcaaacggg acggcgaccg atatctttta cgacctgtca   180
gatgttttca ccagtggcaa taatcagccg gacaggtgg ttacgctgcc ggaaaaatct    240
ggttgggtcg gcgtaaacgc gacgtgcccg gcggggacaa cggtaaatta tatctaccga   300
agctatgtat cagaattacc ggtacaaagc accgaaggaa attttaaata cctcaagctg   360
aatgactacc ttctgggcgc gatgagcatc accgatagtg tcgctggcgt attttatccg   420
ccccgtaact atattcgcat gggcgtcgac tctaacgtgt cgcagcaaat gccgtttggc   480
gtgcaggact caaagctggt ttttaaatta aaagtgatac ggccttttat taatatggtg   540
acgatccctc gccagacaat gtttactgtc tatgtgacga cctctaccgg cgacgcgttg   600
agcacgccgg tatataccat tagctacagc ggcaaagtgg aagtgccgca aaactgcgaa   660
gtgaatgccg acaggtcgt ggagtttgat ttcggc                              696

<210> SEQ ID NO 272
<211> LENGTH: 1089
<212> TYPE: DNA
<213> ORGANISM: artificial sequence
<220> FEATURE:
<223> OTHER INFORMATION: L.reuteri OmPD seq

<400> SEQUENCE: 272
atgaaactta agttagtagc agtggcagtg acttccctgt tggcagcagg cgttgtaaat     60
gcagccgagg tatataacaa agacggcaat aaactggatc tgtacggtaa agttcacgct   120
cagcattatt tctctgatga taacggaagt gatggtgaca aaacttacgc gcgtctgggc   180
tttaaaggcg aaactcagat caacgatcag ttaaccggtt ttggccagtg gaatatgaa    240 ttcaaaggca accgtactga agccagggc gctgacaaag acaaaacccg tctggcgttt   300
gctggtctga attcgctga ctacggttct ttcgactacg tcgtaacta cggcgttgct    360 tacgacatcg gcgcatggac cgacgttcta ccagagttcg gtggcgatac ctggactcag   420
actgacgtct tcatgactgg ccgtactact ggtgttgcca cctaccgtaa cactgacttc   480
tttggcctgt tgaaggtct gaactttgcc gcgcagtacc agggcaaaaa cgaccgtgac   540
ggcgcgtacg agtctaacgg cgacggttc ggtctgtccg caacgtatga gtacgaaggt   600
tttggcgtag gtgcggccta tgcgaagtct gaccgtacta caaccaggt gaaagcagcg   660 agcaacctga atgctgcggg taaaaacgct gaagtctggg ctgctggtct gaaatatgat   720
```

| | | | | | |
|---|---|---|---|---|---|
| gcgaacaaca | tctacctggc | gaccacctac | tccgaaacgc | tgaacatgac | cacctttggt | 780 |
| gaagattcag | cgggtgatgc | gtttatcgcg | aataaaaccc | agaactttga | agcagttgct | 840 |
| cagtatcagt | ccgacttcgg | tctgcgtccg | tccatcgctt | acctgaaatc | caaaggtaaa | 900 |
| aacctgggta | cttacggcga | ccaggatctg | gttgagtaca | tcgatgtcgg | tgctacctac | 960 |
| tacttcaaca | aaaacatgtc | caccttcgtt | gattacaaaa | tcaacctgct | ggacgacagc | 1020 |
| gacttcacca | aagcggctaa | agtgtctacc | gacaacatcg | ttgctgttgg | tctgaactac | 1080 |
| cagttctaa | | | | | | 1089 |